US008436173B2

(12) United States Patent
Murakami et al.

(10) Patent No.: US 8,436,173 B2
(45) Date of Patent: May 7, 2013

(54) BORON COMPOUNDS, THEIR PRODUCTION PROCESSES, AND FUNCTIONAL ELECTRONIC DEVICES USING SAME

(75) Inventors: Masahiro Murakami, Kyoto (JP); Naoki Ishida, Kyoto (JP); Mizuna Narumi, Kyoto (JP); Yoichi Arimoto, Suita (JP); Munehiro Hasegawa, Suita (JP); Tomoya Arai, Suita (JP); Tsuyoshi Goya, Suita (JP)

(73) Assignees: Kyoto University, Kyoto (JP); Nippon Shokubai Co., Ltd., Osaka (JP)

( * ) Notice: Subject to any disclaimer, the term of this patent is extended or adjusted under 35 U.S.C. 154(b) by 381 days.

(21) Appl. No.: 12/734,961

(22) PCT Filed: Dec. 4, 2008

(86) PCT No.: PCT/JP2008/072096
§ 371 (c)(1),
(2), (4) Date: Jun. 4, 2010

(87) PCT Pub. No.: WO2009/072582
PCT Pub. Date: Jun. 11, 2009

(65) Prior Publication Data
US 2011/0046372 A1 Feb. 24, 2011

(30) Foreign Application Priority Data

Dec. 6, 2007 (JP) .................................. 2007-315945
Dec. 2, 2008 (JP) .................................. 2008-307846

(51) Int. Cl.
*C07F 5/02* (2006.01)
(52) U.S. Cl.
USPC ........................................................ 546/13
(58) Field of Classification Search ...................... 546/13
See application file for complete search history.

(56) References Cited

FOREIGN PATENT DOCUMENTS

| JP | 2006-096934 | 4/2006 |
| JP | 2007-035791 | 2/2007 |
| JP | 2007-070282 | 3/2007 |
| JP | 2007-077033 | 3/2007 |
| WO | 2005/062675 | 7/2005 |
| WO | 2005/062676 | 7/2005 |
| WO | 2006/070817 | 7/2006 |

OTHER PUBLICATIONS

Ishida, et al., Synthesis of Amine-Borane Intramolecular Complexes through Palladium-Catalyzed Rearrangement of Ammonioalkynyltriarylborates, Organic Letters, 10 (6), 1279-1281 (2008).*
Hagelee, et al., Boron Compounds XLIV The Influence of Silicon on the Formulation of (Z/E)-Tetrasubstituted Ethylenes Via 1-Alkynylborates, Synthesis and Reactivity in Inorganic and Metal-lorganicchemistry, vol. 1, No. 7, pp. 53-67 (1977).*
International Search Report issued Jan. 20, 2009 in International (PCT) Application No. PCT/JP2008/072096.
Naoki Ishida et al., "Synthesis of Amine-Borane Intramolecular Complexes through Palladium-Catalyzed Rearrangement of Ammonioalkynyltriarylborates", Organic Letters, Feb. 14, 2008, vol. 10, No. 6, pp. 1279-1281.
A. S. Balueva et al., "Synthesis and Properties of 1-diphenylboryl-2-diphenylphosphinoethene", Izvestiya Akademii Nauk, Seriya Khimicheskaya, 1993, No. 2, pp. 378-380, particularly, compounds 4 to 7.
P. J. Grisdale et al., "A Boron Containing Analog of the Norbornene Ring System", Journal of Organometallic Chemistry, 1970, vol. 22, No. 2, pp. C19-C21.

(Continued)

*Primary Examiner* — Erich A Leeser
(74) *Attorney, Agent, or Firm* — Wenderoth, Lind & Ponack, L.L.P.

(57) ABSTRACT

The present invention provides novel boron compounds which are useful, depending on their characteristics, as light-emitting materials, electron-transport materials, electron-injection materials, hole-blocking materials, or organic semiconductor materials, and which have new molecular structures quite different from those of the heretofore known boron compounds; their production processes; and functional electronic devices using the same. The novel boron compounds are, for example, those of the following formula (1):

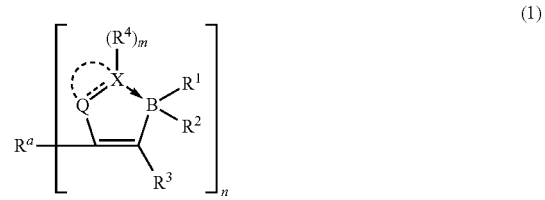

These boron compounds can be produced by, for example, reacting boron compounds of the following formula (4):

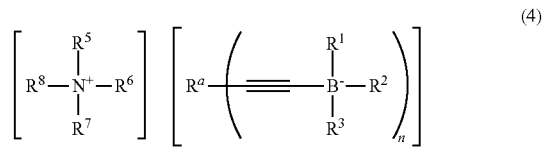

with compounds of the following formula (5):

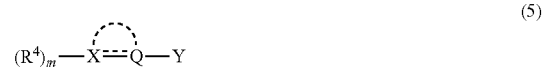

in the presence of a catalyst containing at least one metal element selected from the group consisting of palladium, platinum, and nickel. These boron compounds are used for the functional electronic devices.

16 Claims, 1 Drawing Sheet

OTHER PUBLICATIONS

Atsushi Wakamiya et al., "Intramolecular B—N Coordination as a Scaffold for Electron-Transporting Materials: Synthesis and Properties of Boryl-Substituted Thienylthiazoles", Angew. Chem. Int. Ed. 2006, 45, 3170-3173.

Dietmar Seyferth and Michael A. Weiner, "The Preparation of Organolithium Compounds by the Transmetalation Reaction I. Vinyllithium", J. Am. Chem., Soc., 1961, 83(17), pp. 3583-3586.

Laurent Deloux and Morris Srebnik, "Stereospecific Synthesis of Temarotene, Its Structural Isomers, and Mixed Triaryl Alkenes from *gem*-Borazirconocene Alkenes", J. Org. Chem., 1995, pp. 3276-3277.

Ei-ichi Negishi and Tamotsu Takahashi, "On the Origin of the Configurational Instability of (1-Silyl-1-alkenyl)lithiums and Related Alkenylmetals", J. Am. Chem. Soc., 1986, pp. 3402-3408.

European Office Action issued Aug. 22, 2012 in corresponding European Application No. 08857568.3.

Supplementary European Search Report issued Feb. 22, 2012 in corresponding European Application No. 08857568.3.

Leon A. Hagelee et al., "Boron Compounds XLIV: The Influence of Silicon on the Formation of (Z/E)-Tetrasubstituted Ethylenes via 1-Alkynylborates", Syn. React. Inorg. Metal-Org. Chem., vol. 1, No. 7. Jan. 1, 1997, pp. 53-67.

\* cited by examiner

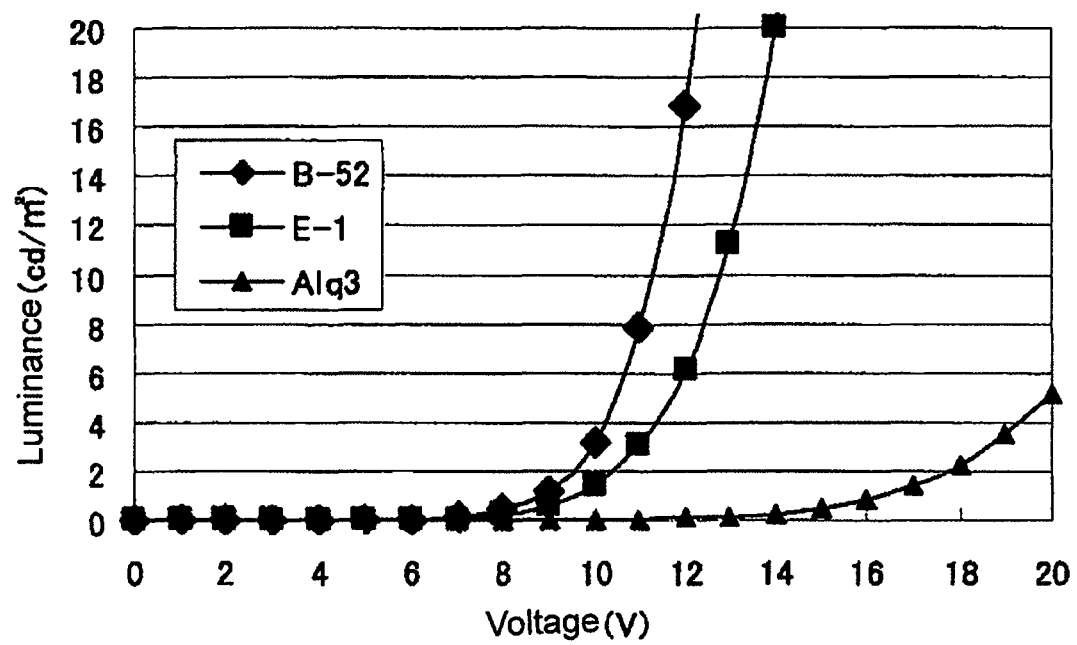

BORON COMPOUNDS, THEIR PRODUCTION PROCESSES, AND FUNCTIONAL ELECTRONIC DEVICES USING SAME

TECHNICAL FIELD

The present invention relates to novel boron compounds, their production processes, and functional electronic devices using the same.

BACKGROUND ART

Various boron compounds have recently been attracting attention as light-emitting materials, electron-transport materials, electron-injection materials, and hole-blocking materials for use in organic light-emitting diode (OLED) devices, or organic semiconductor materials for use in organic thin-film transistors. For example, Japanese Patent Laid-Open Publication No. 2006-96934 discloses a boron compound which has three aromatic groups or heterocyclic groups and which forms a complex with an amine compound or a phosphine compound. Japanese Patent Laid-Open Publication No. 2007-70282 discloses a triaryl boron derivative which has three aryl groups to each of which a heteroaryl group is bonded through an arylene group. Japanese Patent Laid-Open Publication No. 2007-77033 discloses a triaryl boron compound which has three aryl groups including one to which a triazine group having two carbazole groups is bonded. International Publication WO 2005/062675 discloses a triaryl boron compound which has three aromatic carbocyclic groups or heterocyclic groups. These boron compounds are all triaryl boron compounds in which three aryl groups or heteroaryl groups are bonded to a boron atom. In the past, most boron compounds have been limited to those having such a bonding pattern.

In contrast, coordination compounds of boron have been studied. For example, Japanese Patent Laid-Open Publication No. 2007-35791 discloses a boron compound in which the fourth group is coordinated to a boron atom having three substituent groups. International Publication WO 2005/062676 discloses a boron compound in which the fourth group is coordinated to a boron atom having two substituent groups and one aromatic carbocyclic group or heterocyclic group. Angew. Chem. Int. Ed. 2006, 45, 3170-3173 discloses a boron compound in which a thienylthiazole group is bonded to a boron atom having two aryl groups, and further, the nitrogen atom of the thiazole ring is coordinated to the boron atom. These boron compounds are a new group of compounds which utilize the electron acceptability of boron, and are extremely interesting. In particular, Angew. Chem. Int. Ed. 2006, 45, 3170-3173 describes that the boron compound disclosed therein may be preferred as an electronic material, because the nitrogen atom of the thiazole ring is coordinated to the boron atom, and therefore, the lowest unoccupied molecular orbital (LUMO) is lowered. However, from the viewpoint that three aryl groups or heteroaryl groups are bonded to a boron atom, all these boron compounds fall into the same category as that of the triaryl boron compounds disclosed in Japanese Patent Laid-Open Publications Nos. 2006-96934, 2007-70282, and 2007-77033, and International Publication WO 2005/062675.

DISCLOSURE OF THE INVENTION

Problems to be Solved by the Invention

Under the above circumstances, the problems to be solved by the present invention are to provide novel boron compounds which are useful, depending on their characteristics, as light-emitting materials, electron-transport materials, electron-injection materials, hole-blocking materials, or organic semiconductor materials, and which have new molecular structures quite different from those of the heretofore known boron compounds; their production processes; and functional electronic devices using the same.

Means for Solving the Problems

The present inventors have extensively studied and, as a result, they have found that the rearrangement reaction of an acetylene compound which has an electron-donating site capable of coordinating to boron on one side and which has a triarylboron group on the side opposite thereto, proceeds stereoselectively by the use of a catalyst containing at least one metal element selected from the group consisting of palladium, platinum, and nickel, so that the boron atom coordinates to an atom donating an unshared electron pair in the molecule to form a cyclic structure containing the boron atom, resulting in a novel boron compound, thereby completing the present invention.

Thus, the present invention provides boron compounds of the following formula (1):

[Chemical Formula 1]

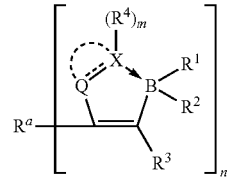

(1)

wherein $R^1$, $R^2$, and $R^3$ are the same or different from each other and are each independently an aryl group or a heterocyclic group, each of which optionally has at least one substituent group, or any two of $R^1$, $R^2$, and $R^3$ are combined with each other to form a ring; $R^4$ is a hydrogen atom or a substituent group; m is an integer of from 0 to 2; when m is 2, plurally occurring $R^4$'s are the same or different from each other; Q is a linking group; X is a nitrogen atom, an oxygen atom, a sulfur atom, a phosphorus atom, or, a selenium atom; a dashed half arc indicates that Q and X may be part of a common ring; dashed and solid lines between Q and X indicate a single or double bond; an arrow directed from X to B indicates a coordinate bond; $R^a$ is hydrogen or a monovalent, divalent, trivalent, or tetravalent organic framework; n is an integer of from 1 to 4; and when n is an integer of from 2 to 4, plurally occurring $R^1$'s, $R^2$'s, $R^3$'s, m's, Q's, X's, dashed half arcs, and dashed and solid lines between Q and X are the same or different from each other, respectively.

Among the boron compounds of the above formula (1), there may be preferred boron compounds of the following formula (2):

[Chemical Formula 2]

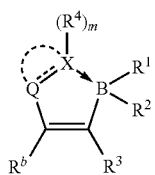

(2)

wherein $R^1$, $R^2$, $R^3$, $R^4$, m, Q, X, a dashed half arc, dashed and solid lines between Q and X, and an arrow directed from X to B have the same meanings in the above formula (1); when m is 2, plurally occurring $R^4$'s are the same or different from each other; and $R^b$ is hydrogen or a monovalent organic framework, and boron compounds of the following formula (3):

[Chemical Formula 3]

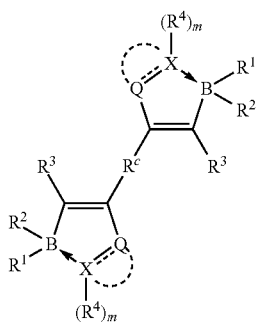

(3)

wherein $R^1$, $R^2$, $R^3$, $R^4$, m, Q, X, a dashed half arc, dashed and solid lines between Q and X, and an arrow directed from X to B have the same meanings in the above formula (1); $R^c$ is a divalent organic framework; and plurally occurring $R^1$'s, $R^2$'s, $R^3$'s, $R^4$'s, m's, Q's, X's, dashed half arcs, and dashed and solid lines between Q and X are the same or different from each other, respectively.

In the above formula (1), (2), or (3), Q and X may preferably be part of a common ring, and it may be more preferred that the above common ring is a pyridine ring, a quinoline ring, or a thiophene ring, X is the nitrogen atom of the pyridine ring or the quinoline ring, or the sulfur atom of the thiophene ring, and m is 0. Also in the formula (1), (2), or (3), it may be preferred that Q is a methylene group, X is a nitrogen atom, and m is 2. Further in the formula (1), (2), or (3), it may be preferred that Q is a methylene group, X is an oxygen atom, and m is 1.

The present invention further provides a process for producing a boron compound of the following formula (1):

[Chemical Formula 4]

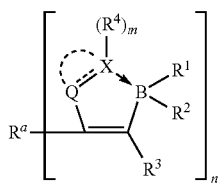

(1)

wherein $R^1$, $R^2$, and $R^3$ are the same or different from each other and are each independently an aryl group or a heterocyclic group, each of which optionally has at least one substituent group, or any two of $R^1$, $R^2$, and $R^3$ are combined with each other to form a ring; $R^4$ is a hydrogen atom or a substituent group; m is an integer of from 0 to 2; when m is 2, plurally occurring $R^4$'s are the same or different from each other; Q is a linking group; X is a nitrogen atom, an oxygen atom, a sulfur atom, a phosphorus atom, or a selenium atom; a dashed half arc indicates that Q and X may be part of a common ring;

dashed and solid lines between Q and X indicate a single or double bond; an arrow directed from X to B indicates a coordinate bond; $R^a$ is hydrogen or a monovalent, divalent, trivalent, or tetravalent organic framework; n is an integer of from 1 to 4; and when n is an integer of from 2 to 4, plurally occurring $R^1$'s, $R^2$'s, $R^3$'s, $R^4$'s, m's, Q's, X's, dashed half arcs, and dashed and solid lines between Q and X are the same or different from each other, respectively, the process comprising reacting a boron compound of the following formula (4):

[Chemical Formula 5]

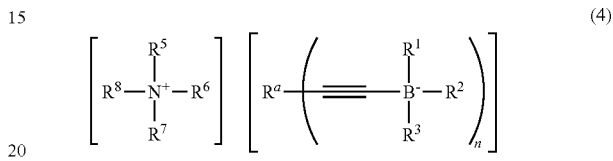

(4)

wherein $R^1$, $R^2$, $R^3$, $R^a$, and n have the same meanings as in the above formula (1); when n is an integer of from 2 to 4, plurally occurring $R^1$'s, $R^2$'s, and $R^3$'s are the same or different from each other, respectively; and $R^5$, $R^6$, $R^7$, and $R^8$ are the same or different from each other and are each independently a hydrogen atom or a substituent group, with a compound of the following formula (5):

[Chemical Formula 6]

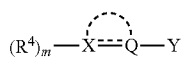

(5)

wherein $R^4$, m, Q, X, a dashed half arc, and dashed and solid lines between Q and X have the same meanings as in the above formula (1); when m is 2, plurally occurring $R^4$'s are the same or different from each other; and Y is a fluorine atom, a chlorine atom, a bromine atom, or an iodine atom, in the presence of a catalyst containing at least one metal element selected from the group consisting of palladium, platinum, and nickel.

In the above formulas (1) and (5), Q and X may preferably be part of a common ring, and it may be more preferred that the above common ring is a pyridine ring, a quinoline ring, or a thiophene ring, X is the nitrogen atom of the pyridine ring or the quinoline ring, or the sulfur atom of the thiophene ring, and m is 0. Also in the formulas (1) and (5), there may be preferred that Q is a methylene group, X is a nitrogen atom, and m is 2. Further in the formulas (1) and (5), there may be preferred that Q is a methylene group, X is an oxygen atom, and m is 1.

The present invention further provides a process for producing a boron compound of the following formula (6):

[Chemical Formula 7]

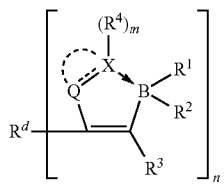

(6)

wherein $R^1$, $R^2$, and $R^3$ are the same or different from each other and are each independently an aryl group or a heterocyclic group, each of which optionally has at least one substituent group, or any two of $R^1$, $R^2$, and $R^3$, are combined with each other to form a ring; $R^4$ is a hydrogen atom or a substituent group; m is an integer of from 0 to 2; when m is 2, plurally occurring $R^4$'s are the same or different from each other; Q is a linking group; X is a nitrogen atom, an oxygen atom, a sulfur atom, a phosphorus atom, or a selenium atom; a dashed half arc indicates that Q and X may be part of a common ring; dashed and solid lines between Q and X indicate a single or double bond; an arrow directed from X to B indicates a coordinate bond; $R^d$ is a monovalent, divalent, trivalent, or tetravalent organic framework; n is an integer of from 1 to 4; and when n is an integer of from 2 to 4, plurally occurring $R^1$'s, $R^2$'s, $R^3$'s, $R^4$'s, m's, Q's, X's, dashed half arcs, and dashed and solid lines between Q and X are the same or different from each other, respectively, the process comprising reacting a boron compound of the following formula (7):

[Chemical Formula 8]

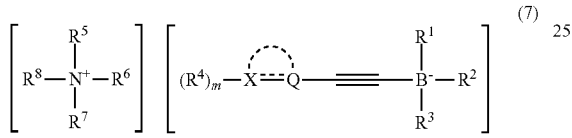

(7)

wherein $R^1$, $R^2$, $R^3$, $R^4$, m, Q, X, a dashed half arc, and dashed and sold lines between Q and X have the same meanings as in the above formula (6); when m is 2, plurally occurring $R^4$'s are the same or different from each other; and $R^5$, $R^6$, $R^7$, and $R^8$ are the same or different from each other and are each independently a hydrogen atom or a substituent group, with a compound of the following formula (8):

[Chemical Formula 9]

$$R^d—(Y)_n \quad (8)$$

wherein $R^d$ and n have the same meanings as in the above formula (6); Y is a fluorine atom, a chlorine atom, a bromine atom, or an iodine atom; and when n is an integer of from 2 to 4, plurally occurring Y's are the same or different from each other, in the presence of a catalyst containing at least one metal element selected from the group consisting of palladium, platinum, and nickel.

Among the boron compounds of the above formula (6), boron compounds of the following formula (9):

[Chemical Formula 10]

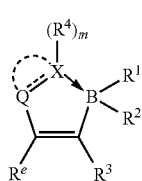

(9)

wherein $R^1$, $R^2$, $R^3$, $R^4$, m, Q, X, a dashed half arc, dashed and solid lines between Q and X, and an arrow directed from X to B have the same meanings as in the above formula (6); when m is 2, plurally occurring $R^4$'s are the same or different from each other; and $R^e$ is a monovalent organic framework, can be produced by reacting the boron compound of the above formula (7) with the compound of the above formula (8) wherein $R^d$ is $R^e$ which indicates a monovalent organic framework and n is 1, in the presence of a catalyst containing at least one metal element selected from the group consisting of palladium, platinum, and nickel.

Also among the boron compounds of the above formula (6), boron compounds of the following formula (10):

[Chemical Formula 11]

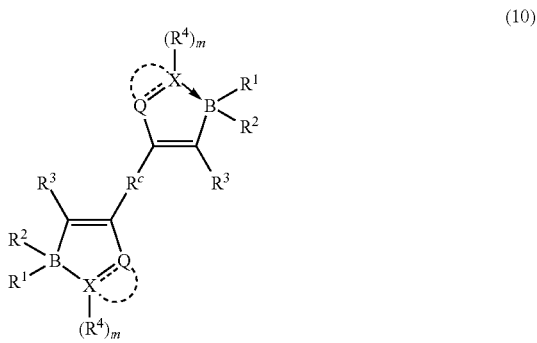

(10)

wherein $R^1$, $R^2$, $R^3$, $R^4$, m, Q, X, a dashed half arc, dashed and solid lines between Q and X, and an arrow directed from X to B have the same meanings as in the above formula (6); $R^c$ is a divalent organic framework; and plurally occurring $R^1$'s, $R^2$'s, $R^3$'s, m's, Q's, X's, dashed half arcs, and dashed and solid lines between Q and X are the same or different from each other, respectively, can be produced by reacting the boron compound of the above formula (7) is reacted with the compound of the above formula (8) wherein $R^d$ is $R^c$ which indicates a divalent organic framework and n is 2, in the presence of a catalyst containing at least one metal element selected from the group consisting of palladium, platinum, and nickel.

In the above formulas (6) and (7), (9), or (10), Q and X may preferably be part of a common ring, and it may be more preferred that the above common ring is a pyridine ring, a quinoline ring, or a thiophene ring, X is the nitrogen atom of the pyridine ring or the quinoline ring, or the sulfur atom of the thiophene ring, and m is 0. Also in the above formulas (6) and (7), (9), or (10), it may be preferred that Q is a methylene group, X is a nitrogen atom, and m is 2. Further in the above formulas (6) and (7), (9), or (10), it may be preferred that Q is a methylene group, X is an oxygen atom, and m is 1.

The present invention further provides a process for producing a boron compound of the following formula (11):

[Chemical Formula 12]

(11)

wherein $R^1$, $R^2$, and $R^3$ are the same or different from each other and are each independently an aryl group or a heterocyclic group, each of which optionally has at least one substituent group, or any two of $R^1$, $R^2$, and $R^3$ are combined with each other to form a ring; $R^4$ is a hydrogen atom or a substituent group; m is an integer of from 0 to 2; when m is 2, plurally occurring $R^4$'s are the same or different from each other; Q is a linking group; X is a nitrogen atom, an oxygen atom, a sulfur atom, a phosphorus atom, or a selenium atom; a dashed half arc indicates that Q and X may be part of a common ring; dashed and solid lines between Q and X indicate a single or double bond; an arrow directed from X to B indicates a coordinate bond; and $R^b$ is hydrogen or a monovalent organic framework, the process comprising reacting a boron compound of the following formula (12):

[Chemical Formula 13]

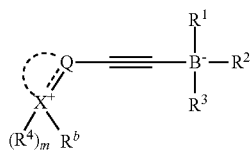

(12)

wherein $R^1$, $R^2$, $R^3$, $R^4$, $R^b$, m, Q, X, a dashed half arc, and dashed and sold lines between Q and X have the same meanings as in the above formula (11); and when m is 2, plurally occurring $R^4$'s are the same or different from each other, in the presence of a catalyst containing at least one metal element selected from the group consisting of palladium, platinum, and nickel.

In the above formulas (11) and (12), Q and X may preferably be part of a common ring, and it may be more preferred that the above common ring is a pyridine ring, a quinoline ring, or a thiophene ring, X is the nitrogen atom of the pyridine ring or the quinoline ring, or the sulfur atom of the thiophene ring, and m is 0.

The present invention further provides a process for producing a boron compound of the following formula (13):

[Chemical Formula 14]

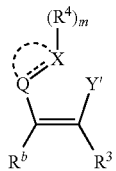

(13)

wherein $R^1$, $R^2$, and $R^3$ are the same or different from each other and are each independently an aryl group or a heterocyclic group, each of which optionally has at least one substituent group, or alternatively, $R^1$ and $R^2$ are combined with each other to form a ring; $R^4$ is a hydrogen atom or a substituent group; m is an integer of from 0 to 2; when m is 2, plurally occurring $R^4$'s are the same or different from each other; Q is a linking group; X is a nitrogen atom, an oxygen atom, a sulfur atom, a phosphorus atom, or a selenium atom; a dashed half arc indicates that Q and X may be part of a common ring; dashed and solid lines between Q and X indicate a single or double bond; an arrow directed from X to B indicates a coordinate bond; and $R^b$ is hydrogen or a monovalent organic framework, the process comprising reacting a lithium compound which is produced from an organic lithium compound acting on a compound of the following formula (14):

[Chemical Formula 15]

(14)

wherein $R^3$, $R^4$, m, Q, X, a dashed half arc, dashed and solid lines between Q and X, and $R^b$ have the same meanings as in the above formula (13); when m is 2, plurally occurring $R^4$'s are the same or different from each other; and Y' is a fluorine atom, a chlorine atom, a bromine atom, or an iodine atom, with a boron compound of the following formula (15):

[Chemical Formula 16]

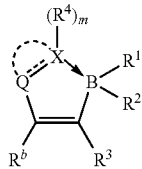

(15)

wherein $R^1$ and $R^2$ have the same meanings as in the above formula (13); W is a fluorine atom, a chlorine atom, a bromine atom, an iodine atom, an alkoxy group, or aryloxy group.

In the above formulas (13) and (14), Q and X may preferably be part of a common ring, and it may be more preferred that the above common ring is a pyridine ring, a quinoline ring, or a thiophene ring, X is the nitrogen atom of the pyridine ring or the quinoline ring, or the sulfur atom of the thiophene ring, and m is 0.

The present invention further provides various functional electronic devices each comprising any of the boron compounds of the above formula (1), (2), or (3), or any of their more specific boron compounds, to be used as a light-emitting material, an electron-transport material, an electron-injection material, a hole-blocking material, or an organic semiconductor material.

The present invention further provides a process for producing a boron compound of the following formula (1):

[Chemical Formula 17]

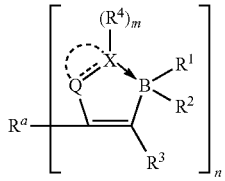

(1)

wherein $R^1$, $R^2$, and $R^3$ are the same or different from each other and are each independently an aryl group or a heterocyclic group, each of which optionally has at least one substituent group, or any two of $R^1$, $R^2$, and $R^3$ are combined with each other to form a ring; $R^4$ is a hydrogen atom or a substituent group; m is an integer of from 0 to 2; when m is 2, plurally occurring $R^4$'s are the same or different from each other; Q is a linking group; X is a nitrogen atom, an oxygen atom, a sulfur atom, a phosphorus atom, or a selenium atom; a dashed half arc indicates that Q and X may be part of a common ring;

dashed and solid lines between Q and X indicate a single or double bond; an arrow directed from X to B indicates a coordinate bond; $R^a$ is hydrogen or a monovalent, divalent, trivalent, or tetravalent organic framework; n is an integer of from 1 to 4; and when n is an integer of from 2 to 4, plurally occurring $R^1$'s, $R^2$'s, $R^3$'s, $R^4$'s, m's, Q's, X's, dashed half arcs, and dashed and solid lines between Q and X are the same or different from each other, respectively, the process comprising reacting a boron compound of the following formula (4):

[Chemical Formula 18]

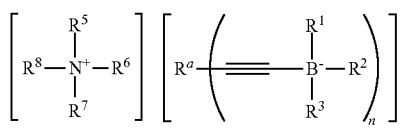

(4)

wherein $R^1$, $R^2$, $R^3$, $R^a$, and n have the same meanings as in the above formula (1); when n is an integer of from 2 to 4, plurally occurring $R^1$'s, $R^2$'s, and $R^3$'s are the same or different from each other, respectively; and $R^5$, $R^6$, $R^7$, and $R^8$ are the same or different from each other and are each independently a hydrogen atom or a substituent group, with a compound of the following formula (16):

[Chemical Formula 19]

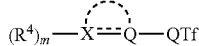

(16)

wherein $R^4$, m, Q, X, a dashed half arc, and dashed and solid lines between Q and X have the same meanings as in the above formula (1); when m is 2, plurally occurring $R^4$'s are the same or different from each other; and Tf is a trifluoromethanesulfonyl group, in the presence of a catalyst containing at least one metal element selected from the group consisting of palladium, platinum, and nickel.

In the above formulas (1) and (16), Q and X may preferably be part of a common ring, and it may be more preferred that the above common ring is a pyridine ring, a quinoline ring, a phenanthridine ring, or a thiophene ring, X is the nitrogen atom of the pyridine ring, the quinoline ring, or the phenanthridine ring, or the sulfur atom of the thiophene ring, and m is 0.

The present invention further provides boron compounds of the following formula (17):

[Chemical Formula 20]

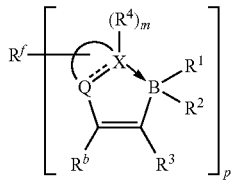

(17)

wherein $R^1$, $R^2$, and $R^3$ are the same or different from each other and are each independently an aryl group or a heterocyclic group, each of which optionally has at least one substituent group, or any two of $R^1$, $R^2$, and $R^3$ are combined with each other to form a ring; $R^4$ is a hydrogen atom or a substituent group; m is an integer of from 0 to 2; when m is 2, plurally occurring $R^4$'s are the same or different from each other; Q is a linking group; X is a nitrogen atom, an oxygen atom, a sulfur atom, a phosphorus atom, or a selenium atom; a solid half arc indicates that Q and X is part of a common ring; dashed and solid lines between Q and X indicate a single or double bond; an arrow directed from X to B indicates a coordinate bond; $R^b$ is hydrogen or a monovalent organic framework; $R^f$ is a p-valent organic framework; p is an integer of from 2 to 6; and plurally occurring $R^1$'s, $R^2$'s, $R^3$'s, m's, Q's, X's, solid half arcs, dashed and solid lines between Q and X, and $R^b$'s are the same or different from each other, respectively.

Among the boron compounds of the above formula (17), there may be preferred boron compounds of the following formula (18):

[Chemical Formula 21]

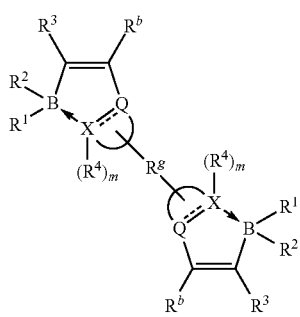

(18)

wherein $R^1$, $R^2$, $R^3$, $R^4$, m, Q, X, a solid half arc, dashed and solid lines between Q and X, an arrow directed from X to B, and $R^b$ have the same meanings as in the above formula (17); $R^g$ is a divalent organic framework; and plurally occurring $R^1$'s, $R^2$'s, $R^3$'s, $R^4$'s, m's, Q's, X's, solid half arcs, dashed lines and solid lines between Q and X, and $R^b$'s are the same or different from each other, respectively, and boron compounds of the following formula (19):

[Chemical Formula 22]

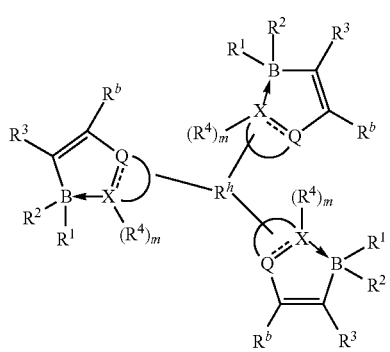

(19)

wherein $R^1$, $R^2$, $R^3$, $R^4$, m, Q, X, a solid half arc, dashed and solid lines between Q and X, an arrow directed from X to B, and $R^b$ have the same meanings as in the above formula (17); $R^h$ is a trivalent organic framework; and plurally occurring $R^1$'s, $R^2$'s, $R^3$'s, m's, Q's, X's, solid half arcs, dashed and solid lines between Q and X, and $R^b$'s are the same or different from each other, respectively.

In the above formula (17), (18), or (19), it may be preferred that the above common ring is a pyridine ring, a quinoline ring, a phenanthridine ring, or a thiophene ring, X is the nitrogen atom of the pyridine ring, the quinoline ring, or the phenanthridine ring, or the sulfur atom of the thiophene ring, and m is 0.

The present invention further provides a process for producing a boron compound of the following formula (17):

[Chemical Formula 23]

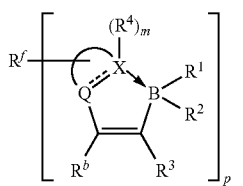

(17)

wherein $R^1$, $R^2$, and $R^3$ are the same or different from each other and are each independently an aryl group or a heterocyclic group, each of which optionally has at least one substituent group, or any two of $R^1$, $R^2$, and $R^3$ are combined with each other to form a ring; $R^4$ is a hydrogen atom or a substituent group; m is an integer of from 0 to 2; when m is 2, plurally occurring $R^4$'s are the same or different from each other; Q is a linking group; X is a nitrogen atom, an oxygen atom, a sulfur atom, a phosphorus atom, or a selenium atom; a solid half arc indicates that Q and X is part of a common ring; dashed and solid lines between Q and X indicate a single or double bond; an arrow directed from X to B indicates a coordinate bond; $R^h$ is hydrogen or a monovalent organic framework; $R^f$ is a p-valent organic framework; p is an integer of from 2 to 6; and plurally occurring $R^1$'s, $R^2$'s, $R^3$'s, m's, Q's, X's, solid half arcs, dashed and solid lines between Q and X, and $R^b$'s are the same or different from each other, respectively, the process comprising reacting a boron compound of the following formula (20):

[Chemical Formula 24]

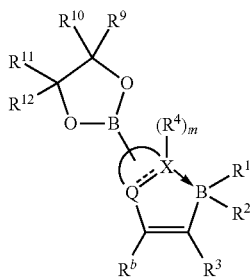

(20)

wherein $R^1$, $R^2$, $R^3$, $R^4$, m, Q, X, a solid half arc, dashed and solid lines between Q and X, an arrow directed from X to B, and $R^b$ have the same meanings as in the above formula (17); when m is 2, plurally occurring $R^4$'s are the same or different from each other; and $R^9$, $R^{10}$, $R^{11}$, and $R^{12}$ are the same or different from each other and are each independently a hydrogen atom or a substituent group, with a compound of the following formula (21):

[Chemical Formula 25]

(21)

wherein $R^f$ and p have the same meanings as in the above formula (17); Y" is a fluorine atom, a chlorine atom, a bromine atom, an iodine atom, or a trifluoromethanesulfonyloxy group; and plurally occurring Y"'s are the same or different from each other, in the presence of a catalyst containing at least one metal element selected from the group consisting of palladium, platinum, and nickel.

Among the boron compounds of the above formula (17), boron compounds of the following formula (18):

[Chemical Formula 26]

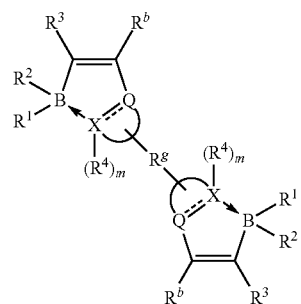

(18)

wherein $R^1$, $R^2$, $R^3$, $R^4$, m, Q, X, a solid half arc, dashed and solid lines between Q and X, an arrow directed from X to B, and $R^b$ have the same meanings as in the above formula (17); $R^g$ is a divalent organic framework; and plurally occurring $R^1$'s, $R^2$'s, $R^3$'s, m's, Q's, X's, solid half arcs, dashed and solid lines between Q and X, arrows directed from X to B, and $R^b$'s are the same or different from each other, respectively, can be produced by reacting a boron compound of the above formula (20) with a compound of the above formula (21) wherein $R^f$ is $R^g$ which indicates a divalent organic framework and p is 2, in the presence of a catalyst containing at least one metal element selected from the group consisting of palladium, platinum, and nickel.

Also among the boron compounds of the above formula (17), boron compounds of the following formula (19):

[Chemical Formula 27]

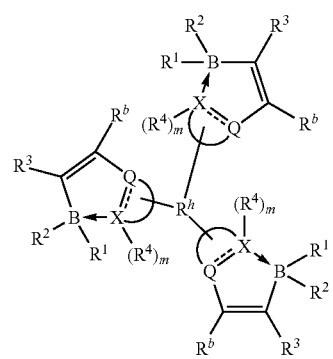

(19)

wherein $R^1$, $R^2$, $R^3$, $R^4$, m, Q, X, a solid half arc, dashed and solid lines between Q and X, an arrow directed from X to B, and $R^b$ have the same meanings as in the above formula (17); $R^h$ is a trivalent organic framework; and plurally occurring $R^1$'s, $R^2$'s, $R^3$'s, $R^4$'s, m's, Q's, X's, solid half arcs, dashed and solid lines between Q and X, and $R^b$'s are the same or different from each other, respectively, can be produced by reacting a boron compound of the above formula (20) with a compound of the above formula (21) wherein $R^f$ is $R^h$ which indicates a trivalent organic framework and p is 3, in the presence of a catalyst containing at least one metal element selected from the group consisting of palladium, platinum, and nickel.

In the above formula (17), (18), or (19), it may be preferred that the above common ring is a pyridine ring, a quinoline ring, a phenanthridine ring, or a thiophene ring, X is the nitrogen atom of the pyridine ring, the quinoline ring, or the phenanthridine ring, or the sulfur atom of the thiophene ring, and m is 0.

The present invention further provides boron compounds of the following formula (22):

[Chemical Formula 28]

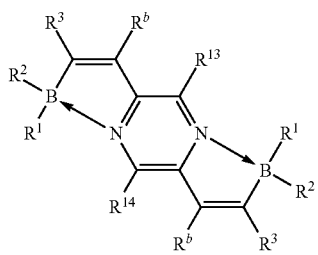

(22)

wherein $R^1$, $R^2$, and $R^3$ are the same or different from each other and are each independently an aryl group or a heterocyclic group, each of which optionally has at least one substituent group, or any two of $R^1$, $R^2$, and $R^3$ are combined with each other to form a ring; an arrow directed from N to B indicates a coordinate bond; $R^b$ is hydrogen or a monovalent organic framework; and $R^{13}$ and $R^{14}$ are the same or different from each other and are each independently a hydrogen atom or a substituent group.

In the above formula (22), $R^{13}$ and $R^{14}$ may preferably be methyl groups. Also in the above formula (22), it may be preferred that $R^1$, $R^2$, and $R^3$ are bipenylyl groups and $R^b$ is a hydrogen atom.

The present invention further provides a process for producing a boron compound of the following formula (22):

[Chemical Formula 29]

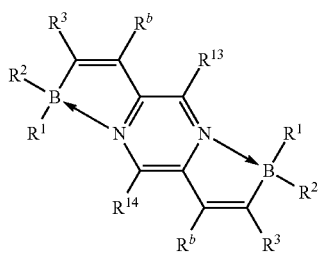

(22)

wherein $R^1$, $R^2$, and $R^3$ are the same or different from each other and are each independently an aryl group or a heterocyclic group, each of which optionally has at least one substituent group, or any two of $R^1$, $R^2$, and $R^3$ are combined with each other to form a ring; an arrow directed from N to B indicates a coordinate bond; $R^b$ is hydrogen or a monovalent organic framework; and $R^{13}$ and $R^{14}$ are the same or different from each other and are each independently a hydrogen atom or a substituent group, the process comprising reacting a boron compound of the formula (23):

[Chemical Formula 30]

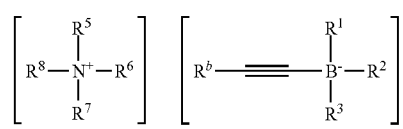

(23)

wherein $R^1$, $R^2$, $R^3$, and $R^b$ have the same meanings as in the above formula (22); and $R^5$, $R^6$, $R^7$, and $R^8$ are the same or different from each other and are each independently a hydrogen atom or a substituent group, with a compound of the following formula (24):

[Chemical Formula 31]

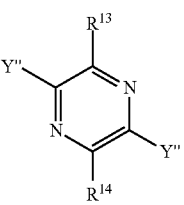

(24)

wherein $R^{13}$ and $R^{14}$ have the same meanings as in the above formula (22); Y''' is a fluorine atom, a chlorine atom, a bromine atom, an iodine atom, or a trifluoromethanesulfonyloxy group; and plurally occurring Y'''s are the same or different from each other, in the presence of a catalyst containing at least one metal element selected from the group consisting of palladium, platinum, and nickel.

In the above formulas (22) and (24), $R^{13}$ and $R^{14}$ may preferably be methyl groups; and in the above formula (24), Y''' may preferably be a bromine atom. Also in the above formulas (22) and (23), it may be preferred that $R^1$, $R^2$, and $R^3$ are biphenylyl groups and $R^b$ is a hydrogen atom.

The present invention further provides boron compounds of the following formula (25):

[Chemical Formula 32]

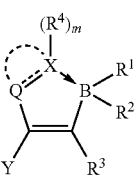

(25)

wherein $R^1$, $R^2$, and $R^3$ are the same or different from each other and are each independently an aryl group or a heterocyclic group, each of which optionally has at least one substituent group, or any two of $R^1$, $R^2$, and $R^3$ are combined with each other to form a ring; $R^4$ is a hydrogen atom or a substituent group; m is an integer of from 0 to 2; when m is 2, plurally occurring $R^4$'s are the same or different from each other; Q is a linking group; X is a nitrogen atom, an oxygen atom, a sulfur atom, a phosphorus atom, or a selenium atom; a dashed half arc indicates that Q and X may be part of a common ring; dashed and solid lines between Q and X indicate a single or double bond; an arrow directed from X to B indicates a coordinate bond; and Y is a fluorine atom, a chlorine atom, a bromine atom, or an iodine atom.

In the above formula (25), Q and X may preferably be part of a common ring, and it may be more preferred that the above common ring is a pyridine ring, a quinoline ring, a phenanthridine ring, or a thiophene ring, X is the nitrogen atom of the pyridine ring, the quinoline ring, or the phenanthridine ring, or the sulfur atom of the thiophene ring, and m is 0. Also in the above formula (25), it may be preferred that Q is a methylene group, X is a nitrogen atom, and m is 2. Further in the above formula (25), there may be preferred that Q is a methylene group, X is an oxygen atom, and m is 1.

The present invention further provides a process for producing a boron compound of the following formula (25):

[Chemical Formula 33]

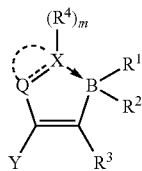

(25)

wherein $R^1$, $R^2$, and $R^3$ are the same or different from each other and are each independently an aryl group or a heterocyclic group, each of which optionally has at least one substituent group, or any two of $R^1$, $R^2$, and $R^3$ are combined with each other to form a ring; $R^4$ is a hydrogen atom or a substituent group; m is an integer of from 0 to 2; when m is 2, plurally occurring $R^4$'s are the same or different from each other; Q is a linking group; X is a nitrogen atom, an oxygen atom, a sulfur atom, a phosphorus atom, or a selenium atom; a dashed half arc indicates that Q and X may be part of a common ring; dashed and solid lines between Q and X indicate a single or double bond; an arrow directed from X to B indicates a coordinate bond; and Y is a fluorine atom, a chlorine atom, a bromine atom, or an iodine atom, the process comprising reacting a boron compound of the following formula (26):

[Chemical Formula 34]

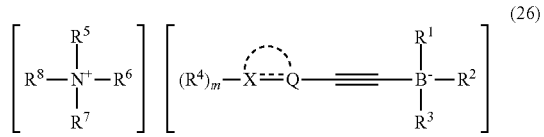

(26)

wherein $R^1$, $R^2$, $R^3$, $R^4$, m, Q, X, a dashed half arc, and dashed and solid lines between Q and X have the same meanings in the above formula (25); when m is 2, plurally occurring $R^4$'s are the same or different from each other; and $R^5$, $R^6$, $R^7$, and $R^8$ are the same or different from each other and are each independently a hydrogen atom or a substituent group, with a halogenating agent.

In the above formulas (25) and (26), Q and X may preferably be part of a common ring, and it may be more preferred that the above common ring is a pyridine ring, a quinoline ring, a phenanthridine ring, or a thiophene ring, X is the nitrogen atom of the pyridine ring, the quinoline ring, or the phenanthridine ring, or the sulfur atom of the thiophene ring, and m is 0. Also in the above formulas (25) and (26), it may be preferred that Q is a methylene group, X is a nitrogen atom, and m is 2. Further in the above formulas (25) and (26), it may be preferred that Q is a methylene group, X is an oxygen atom, and m is 1.

The present invention further provides various functional electronic devices each comprising any of the boron compounds of the above formula (17), (18), (19), (22), or (25), or any of their more specific boron compounds, to be used as a light-emitting material, an electron-transport material, an electron-injection material, a hole-blocking material, or an organic semiconductor material.

EFFECTS OF THE INVENTION

According to the present invention, there can be provided novel boron compounds which are useful, depending on their characteristics, as light-emitting materials, electron-transport materials, electron-injection materials, hole-blocking materials, or organic semiconductor materials, and which have new molecular structures quite different from those of the heretofore known boron compounds; production processes capable of producing these novel boron compounds with high efficiency in a simple and easy manner; and functional electronic devices having excellent electric characteristics, in which these novel boron compounds are used as light-emitting materials, electron-transport materials, electron-injection materials, hole-blocking materials, or organic semiconductor materials.

BRIEF DESCRIPTION OF THE DRAWING

FIG. 1 is a graph showing the relationship between the applied voltage and the emitted light luminance for organic light-emitting diode (OLED) devices using the novel boron compounds of the present invention and for the comparative organic light-emitting diode (OLED) device.

BEST MODE FOR CARRYING OUT THE INVENTION

Novel Boron Compounds I

The novel boron compounds I of the present invention are boron compounds of the following formula (1):

[Chemical Formula 35]

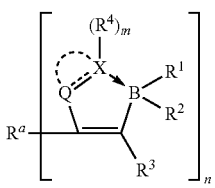

(1)

wherein $R^1$, $R^2$, and $R^3$ are the same or different from each other and are each independently an aryl group or a heterocyclic group, each of which optionally has at least one substituent group, or any two of $R^1$, $R^2$, and $R^3$ are combined with each other to form a ring; $R^4$ is a hydrogen atom or a substituent group; m is an integer of from 0 to 2; when m is 2, plurally occurring $R^4$'s are the same or different from each other; Q is a linking group; X is a nitrogen atom, an oxygen atom, a sulfur atom, a phosphorus atom, or a selenium atom; a dashed half arc indicates that Q and X may be part of a common ring; dashed and solid lines between Q and X indicate a single or double bond; an arrow directed from X to B indicates a coordinate bond; $R^a$ is hydrogen or a monovalent, divalent, trivalent, or tetravalent organic framework; n is an integer of from 1 to 4; and when n is an integer of from 2 to 4, plurally occurring $R^1$'s, $R^2$'s, $R^3$'s, m's, Q's, X's, dashed half arcs, and dashed and solid lines between Q and X are the same or different from each other, respectively.

In the above formula (1), examples of the "aryl group" in the aryl group which optionally has at least one substituent group, as indicated by $R^1$, $R^2$, or $R^3$, may include, but are not limited to, phenyl group, biphenylyl group (e.g., 4-biphenylyl group), naphthyl group (e.g., 2-naphthyl group), tetrahydronaphthyl group (e.g., 5,6,7,8-tetrahydronaphthalen-2-yl group), indenyl group (e.g., 1H-inden-5-yl group), and indanyl group (e.g., indan-5-yl group). Among these aryl groups, phenyl group, biphenylyl group (e.g., 4-biphenylyl group), and naphthyl group (e.g., 2-naphthyl group) may be preferred.

Examples of the "heterocyclic group" in the heterocyclic group which optionally has at least one substituent group, as indicated by $R^1$, $R^2$, or $R^3$, may include, but are not limited to, pyrrolyl group (e.g., 2-pyrrolyl group), pyridyl group (e.g., 2-pyridyl group), quinolyl group (e.g., 2-quinolyl group), piperidinyl group (e.g., 4-piperidinyl group), piperidino group, furyl group (e.g., 2-furyl group), and thienyl group (e.g., 2-thienyl group). Among these heterocyclic groups, pyridyl group (e.g., 2-pyridyl group) and thienyl group (e.g., 2-thienyl group) may be preferred.

Examples of the "substituent group" in the aryl group and in the heterocyclic group, both of which optionally have at least one substituent group, may include, but are not limited to, halogen atom (e.g., fluorine atom, chlorine atom, bromine atom, and iodine atom), haloalkyl group (e.g., fluoromethyl group, difluoromethyl group, trifluoromethyl group), straight or branched chain alkyl group having from 1 to 4 carbon atoms (e.g., methyl group, ethyl group, propyl group, isopropyl group, butyl group, isobutyl group, tert-butyl group), cyclic alkyl group having from 5 to 7 carbon atoms (e.g., cyclopentyl group, cyclohexyl group), straight or branched chain alkoxy group having from 1 to 8 carbon atoms (e.g., methoxy group, ethoxy group, propoxy group, isopropoxy group, butoxy group, isobutoxy group, tert-butoxy group, pentyloxy group, hexyloxy group, heptyloxy group, octyloxy group), hydroxy group, nitro group, cyano group, amino group, mono- or di-alkylamino group in which each alkyl group has from 1 to 4 carbon atoms (e.g., methylamino group, ethylamino group, dimethylamino group, diethylamino group), acyl group (e.g., acetyl group, propionyl group, butyryl group), alkenyl group having from 2 to 6 carbon atoms (e.g., vinyl group, 1-propenyl group, allyl group), alkynyl group having from 2 to 6 carbon atoms (e.g., ethynyl group, 1-propynyl group, propargyl group), phenyl group, substituted phenyl group (e.g., 4-fluorophenyl group, 4-chlorophenyl group, 4-methylphenyl group (i.e., p-tolyl group), 4-methoxyphenyl group, 4-nitrophenyl group), carbamoyl group, and N,N-dialkylcarbamoyl group (e.g., N,N-dimethylcarbamoyl group, N,N-diethylcarbamoyl group, N,N-dipropylcarbamoyl group).

Alternatively, any two of $R^1$, $R^2$, and $R^3$ may be combined with each other to form a ring. Examples of such a ring may include, but are not limited to: as a result of the combination of $R^1$ and $R^2$, borole ring, benzoborole ring, dibenzoborole ring, 1,4-dihydroborinine ring, 1,4-dihydrobenzo[b]borinine ring, 5,10-dihydro-dibenzo[b,e]borinine ring, 4H-1,4-oxaborinine ring, 4H-benzo[b][1,4]oxaborinine ring, 10H-dibenzo[b,e][1,4]oxaborinine ring, 1,4-dihydro-1,4-azaborinine ring, 1,4-dihydrobenzo[b][1,4]azaborinine ring, and 5,10-dihydrodibenzo[b,e][1,4]azaborinine ring; as a result of the combination of $R^1$ and $R^3$, 5,6-dihydrodibenzo[b,d]borinine ring; and these rings having at least one substituent group. In the above formula (1), examples of the substituent group as indicated by $R^4$ may include, but are not limited to, the substituent groups described above as the "substituent group" in the aryl group and in the heterocyclic group, both of which optionally have at least one substituent group.

In the above formula (1), m is the number of substituent groups $R^4$ bonded to X, and is an integer of from 0 to 2, depending on the valence of X, whether the bond between Q and X is a single or double bond, whether or not Q and X are part of a common ring, and others. In this connection, when m is 2, plurally occurring $R^4$'s are the same or different from each other.

In the above formula (1), examples of the linking group as indicated by Q may include, but are not limited to, =C<, =CH—, —CH<, —CH$_2$—, —CH$_2$CH$_2$—, —C$_6$H$_4$— (e.g., -(1,2-C$_6$H$_4$)—), —C$_{10}$H$_6$— (e.g., -(1,2-C$_{10}$H$_6$)—), —CO—, —CS—, —CH$_2$N<, and —CH$_2$N=. Among these linking groups, =C<, —CH$_2$—, and —CH$_2$CH$_2$— may be preferred.

In the above formula (1), X is a nitrogen atom, an oxygen atom, a sulfur atom, a phosphorus atom, or a selenium atom. Among these atoms, a nitrogen atom and an oxygen atom may be preferred.

In the above formula (1), examples of the common ring of Q and X, as indicated by the dashed half arc, may include, but are not limited to, pyrrole ring, pyridine ring, indole ring, isoindole ring, quinoline ring, isoquinoline ring, furan ring, pyran ring, benzofuran ring, isobenzofuran ring, chromene ring, isochromene ring, phosphindole ring, isophosphindole ring, phosphinoline ring, isophosphinoline ring, thiophene ring, thiopyran ring, thiochromene ring, isothiochromene ring, selenophene ring, selenopyran ring, selenochromene ring, and isoselenochromene ring. These rings optionally have at least one substituent group. Among these rings, pyridine ring, quinoline ring, furan ring, and thiophene ring may be preferred.

In the above formula (1), examples of the monovalent organic framework as indicated by $R^a$ may include, but are not limited to, methyl group, ethyl group, propyl group, isopropyl group, cyclohexyl group, phenyl group, 4-methylphenyl group (i.e., p-tolyl group), and naphthyl group (e.g., 2-naphthyl group). Examples of the divalent organic framework as indicated by $R^a$ may include, but are not limited to, methylene group, ethylene group, trimethylene group, propylene group, phenylene group (e.g., 1,4-phenylene group), and naphthylene group (e.g., 2,6-naphthylene group). Examples of the trivalent organic framework as indicated by $R^a$ may include, but are not limited to, methanetriyl group, ethanetriyl group (e.g., ethane-1,1,2-triyl group), propanetriyl group (e.g., propane-1,2,3-triyl group), benzenetriyl group (e.g., benzene-1,3,5-triyl group), and naphthalenetriyl group (e.g., naphthalene-1,4,6-triyl group). Examples of the tetravalent organic framework as indicated by $R^a$ may include, but are not limited to, methanetetrayl group, ethanetetrayl group (e.g., ethane-1,1,2,2-tetrayl group), propanetetrayl group (e.g., propane-1,1,2,3-tetrayl group), benzenetetrayl group (e.g., benzene-1,2,4,5-tetrayl group), and naphthalenetetrayl group (e.g., naphthalene-1,4,5,8-tetrayl group).

In the above formula (1), n is the number of boron-containing ring moieties (i.e., moieties in brackets) which are bonded to the hydrogen or monovalent, divalent, trivalent, or tetravalent organic framework as indicated by $R^a$. When $R^a$ is hydrogen, n is 1. When $R^a$ is the monovalent, divalent, trivalent, or tetravalent organic framework, n is an integer of from 1 to 4. In this connection, when n is an integer of from 2 to 4, plurally occurring $R^1$'s, $R^2$'s, $R^3$'s, m's, Q's, X's, dashed half arcs, and dashed and solid lines between Q and X are the same or different from each other, respectively.

In the above formula (1), Q and X may preferably be part of a common ring, and it may be more preferred that the above common ring is a pyridine ring, a quinoline ring, or a thiophene ring, X is the nitrogen atom of the pyridine ring or the quinoline ring, or the sulfur atom of the thiophene ring, and m is 0. That is, boron compounds of the following formulas (27), (28), and (29) may be preferred:

[Chemical Formula 36]

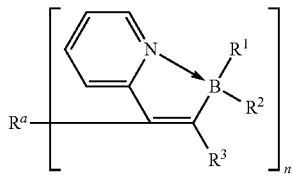

(27)

wherein $R^1$, $R^2$, $R^3$, $R^a$, and n have the same meanings as in the above formula (1); when n is an integer of from 2 to 4, plurally occurring $R^1$'s, $R^2$'s, and $R^3$'s are the same or different from each other, respectively; the pyridine ring optionally has at least one substituent group; and an arrow directed from N to B indicates a coordinate bond;

[Chemical Formula 37]

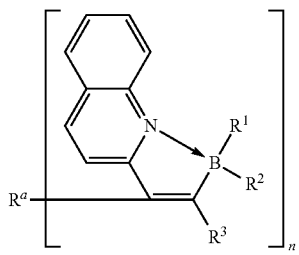

(28)

wherein $R^1$, $R^2$, $R^3$, $R^a$, and n have the same meanings as in the above formula (1); when n is an integer of from 2 to 4, plurally occurring $R^1$'s, $R^2$'s, and $R^3$'s are the same or different from each other, respectively; the quinoline ring optionally has at least one substituent group; and an arrow directed from N to B indicates a coordinate bond; and

[Chemical Formula 38]

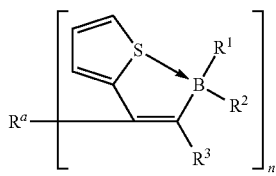

(29)

wherein $R^1$, $R^2$, $R^3$, $R^a$, and n have the same meanings as in the above formula (1); when n is an integer of from 2 to 4, plurally occurring $R^1$'s, $R^2$'s, and $R^3$'s are the same or different from each other, respectively; the thiophene ring optionally has at least one substituent group; and an arrow directed from S to B indicates a coordinate bond.

Also in the above formula (1), it may be preferred that Q is a methylene group, X is a nitrogen atom, and m is 2. That is, a boron compound of the following formula (30) may be preferred:

[Chemical Formula 39]

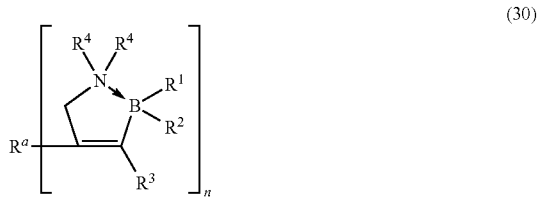

(30)

wherein $R^1$, $R^2$, $R^3$, $R^4$, $R^a$, and n have the same meanings as in the above formula (1); when n is 1, plurally occurring $R^4$'s are the same or different from each other; when n is an integer of from 2 to 4, plurally occurring $R^1$'s, $R^2$'s, $R^3$'s, and $R^4$'s are the same or different from each other, respectively; and an arrow directed from N to B indicates a coordinate bond.

Further in the above formula (1), it may be preferred that Q is a methylene group, X is an oxygen atom, and m is 1. That is, a boron compound of the following formula (31) may be preferred:

[Chemical Formula 40]

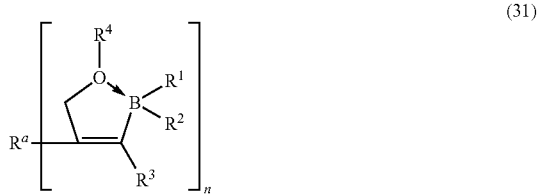

(31)

wherein $R^1$, $R^2$, $R^3$, $R^4$, $R^a$, and n have the same meanings as in the above formula (1); when n is an integer of from 2 to 4, plurally occurring $R^1$'s, $R^2$'s, $R^3$'s, and $R^4$'s are the same or different from each other, respectively; and an arrow directed from O to B indicates a coordinate bond.

The variable n is typically an integer of from 1 to 4, preferably an integer of 1 or 2. That is, among the boron compounds of the above formula (1), boron compounds of the following formulas (2) and (3) may be preferred:

[Chemical Formula 41]

(2)

wherein $R^1$, $R^2$, $R^3$, $R^4$, m, Q, X, a dashed half arc, dashed and solid lines between Q and X, and an arrow directed from X to B have the same meanings as in the above formula (1); when m is 2, plurally occurring $R^4$'s are the same or different from each other; and $R^b$ is hydrogen or a monovalent organic framework; and

[Chemical Formula 42]

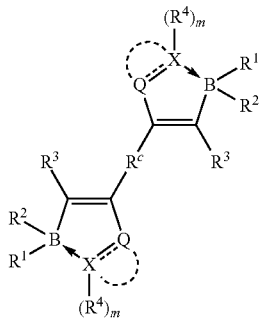

(3)

wherein $R^1$, $R^2$, $R^3$, $R^4$, m's, Q's, X's, a dashed half arc, dashed and solid lines between Q and X, and an arrow directed from X to B have the same meanings as in the above formula (1); $R^c$ is a divalent organic framework; and plurally occurring $R^1$'s, $R^2$'s, $R^3$'s, R4's, m's, Q's, X's, dashed half arcs, and dashed and solid lines between Q and X are the same or different from each other, respectively.

In the above formula (2), examples of the monovalent organic framework as indicated by $R^b$ may include, but are not limited to, methyl group, ethyl group, propyl group, isopropyl group, cyclohexyl group, phenyl group, 4-methylphenyl group (i.e., tolyl group), and naphthyl group (e.g., 2-naphthyl group).

In the above formula (3), examples of the divalent organic framework as indicated by $R^c$ may include, but are not limited to, methylene group, ethylene group, trimethylene group, propylene group, phenylene group (e.g., 1,4-phenylene group), and naphthylene group (e.g., 2,6-naphthylene group).

In the above formula (2), Q and X may preferably be part of a common ring, and it may be more preferred that the above common ring is a pyridine ring, a quinoline ring, or a thiophene ring, X is the nitrogen atom of the pyridine ring or quinoline ring, or the sulfur atom of the thiophene ring, and m is 0. That is, boron compounds of the following formulas (32), (33), and (34) may be preferred:

[Chemical Formula 43]

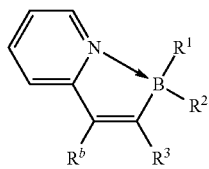

(32)

wherein $R^1$, $R^2$, and $R^3$ have the same meanings as in the above formula (1); the pyridine ring optionally has at least one substituent group; an arrow directed from N to B indicates a coordinate bond; and $R^b$ has the same meaning as in the above formula (2);

[Chemical Formula 44]

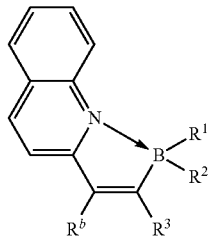

(33)

wherein $R^1$, $R^2$, and $R^3$ have the same meanings as in the above formula (1); the quinoline ring optionally has at least one substituent group; an arrow directed from N to B indicates a coordinate bond; and $R^b$ has the same meaning as in the above formula (2); and

[Chemical Formula 45]

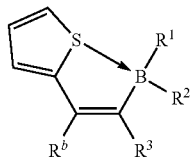

(34)

wherein $R^1$, $R^2$, and $R^3$ have the same meanings as in the above formula (1); the thiophene ring optionally has at least one substituent group; an arrow directed from S to B indicates a coordinate bond; and $R^b$ has the same meaning as in the above formula (2).

In the above formula (3), Q and X may preferably be part of a common ring, and it may be more preferred that the above common ring is a pyridine ring, a quinoline ring, or a thiophene ring, X is the nitrogen atom of the pyridine ring or the quinoline ring, or the sulfur atom of the thiophene ring, and m is 0. That is, boron compounds of the following formula (35), (36), and (37) may be preferred:

[Chemical Formula 46]

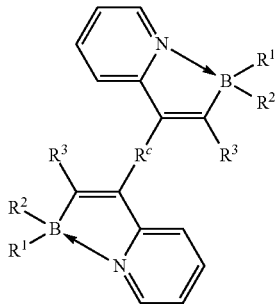

(35)

wherein $R^1$, $R^2$, and $R^3$ have the same meanings as in the above formula (1); plurally occurring $R^1$'s, $R^2$'s, and $R^3$'s are the same or different from each other, respectively; the pyridine ring optionally has at least one substituent group; an arrow directed from N to B indicates a coordinate bond; and $R^c$ has the same meaning as in the above formula (3);

[Chemical Formula 47]

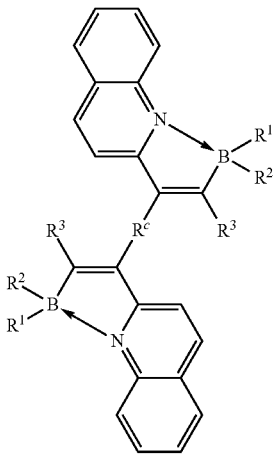
(36)

wherein $R^1$, $R^2$, and $R^3$ have the same meanings as in the above formula (1); plurally occurring $R^1$'s, $R^2$'s, and $R^3$'s are the same or different from each other, respectively; the quinoline ring optionally has at least one substituent group; an arrow directed from N to B indicates a coordinate bond; and $R^c$ has the same meaning as in the above formula (3); and

[Chemical Formula 48]

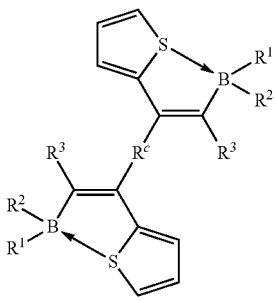
(37)

wherein $R^1$, $R^2$, and $R^3$ have the same meanings as in the above formula (1); plurally occurring $R^1$'s, $R^2$'s, and $R^3$'s are the same or different from each other, respectively; the thiophene ring optionally has at least one substituent group; an arrow directed from S to B indicates a coordinate bond; and $R^c$ has the same meaning as in the above formula (3).

In the above formula (2) or (3), it may be preferred that Q is a methylene group, X is a nitrogen atom, and m is 2. That is, boron compounds of the following formulas (38) and (39) may be preferred:

[Chemical Formula 49]

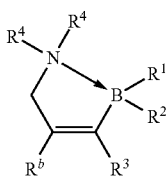
(38)

wherein $R^1$, $R^2$, $R^3$, and $R^4$ have the same meanings as in the above formula (1); plurally occurring $R^4$'s are the same or different from each other; an arrow directed from N to B indicates a coordinate bond; and $R^b$ has the same meaning as in the above formula (2); and

[Chemical Formula 50]

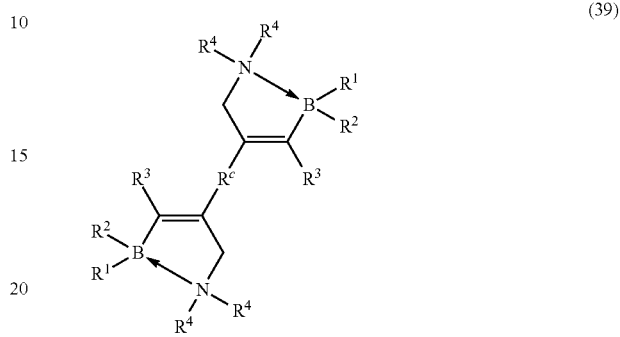
(39)

wherein $R^1$, $R^2$, $R^3$, and $R^4$ have the same meanings as in the above formula (1); plurally occurring $R^1$'s, $R^2$'s, $R^3$'s, and $R^4$'s are the same or different from each other, respectively; an arrow directed from N to B indicates a coordinate bond; and $R^c$ has the same meaning as in the above formula (3).

In the above formula (2) or (3), it may be preferred that Q is a methylene group, X is an oxygen atom, and m is 1. That is, boron compounds of the following formulas (40) and (41) may be preferred:

[Chemical Formula 51]

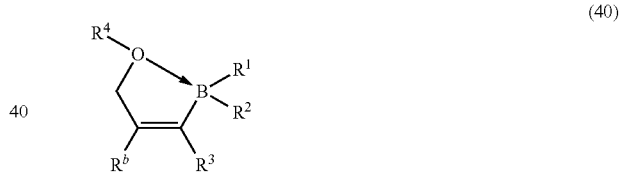
(40)

wherein $R^1$, $R^2$, $R^3$, and $R^4$ have the same meanings as in the above formula (1); an arrow directed from O to B indicates a coordinate bond; and $R^b$ has the same meaning as in the above formula (2); and

[Chemical Formula 52]

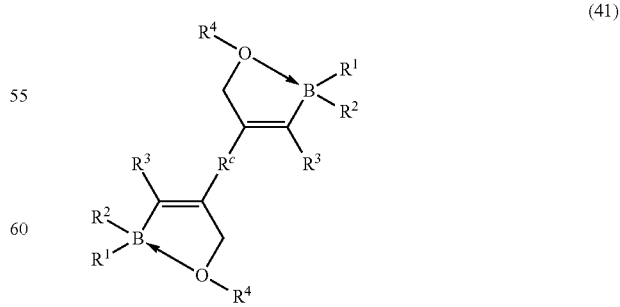
(41)

wherein $R^1$, $R^2$, $R^3$, and $R^4$ have the same meanings as in the above formula (1); plurally occurring $R^1$'s, $R^2$'s, $R^3$'s, and $R^4$'s are the same or different from each other, respectively;

an arrow directed from O to B indicates a coordinate bond; and $R^c$ has the same meaning as in the above formula (3).

Specific examples of the boron compound of the above formula (1) may include, but are not limited to, boron compounds of the following formulas (A-1) to (A-48), (B-1) to (B-53), (C-1) to (C-46), (D-1) to (D-47), (E-1) to (E-3), (F-1) to (F-48), (G-1) to (G-47), (H-1) to (H-47), (I-1) to (I-47), (J-1) to (J-47), (K-1) to (K-48), (L-1) to (L-47), and (M-1) to (M-47). In the following formulas (A-1) to (A-48), (B-1) to (B-53), (C-1) to (C-46), (D-1) to (D-47), (E-1) to (E-3), (F-1) to (F-48), (G-1) to (G-47), (H-1) to (H-47), (I-1) to (I-47), (J-1) to (J-47), (K-1) to (K-48), (L-1) to (L-47), and (M-1) to (M-47), a straight line having no element symbol at one end thereof indicates that a methyl group is attached thereto.

[Chemical Formula 53]

(A-1)
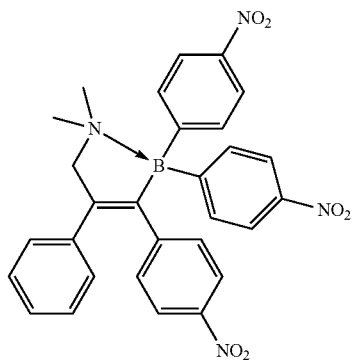

(A-2)
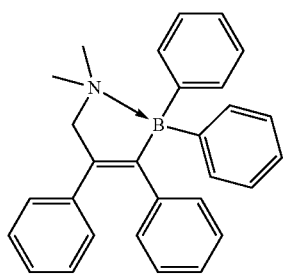

(A-3)
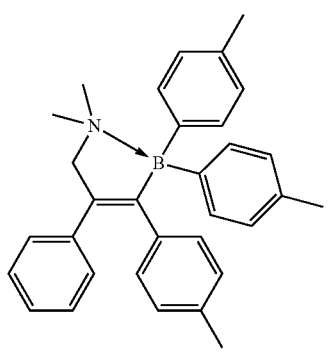

(A-4)
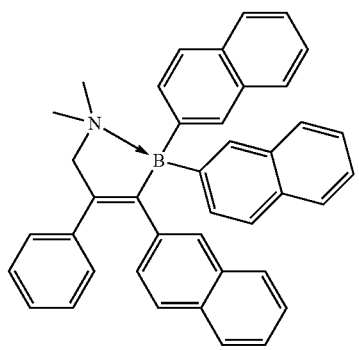

(A-5)
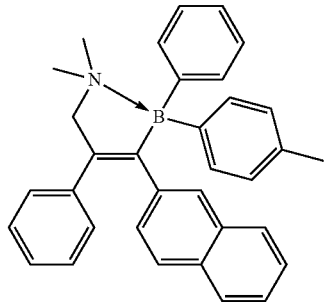

(A-6)
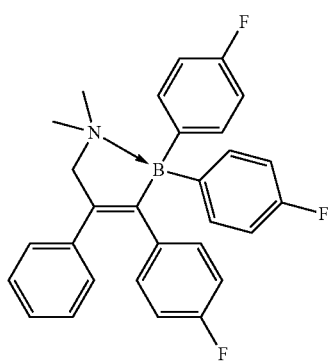

(A-7)
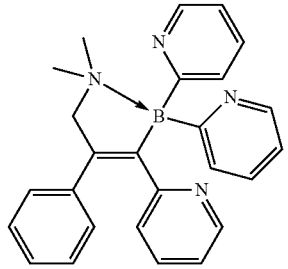

(A-8)
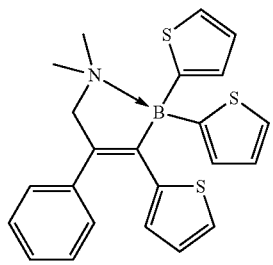

(A-9)
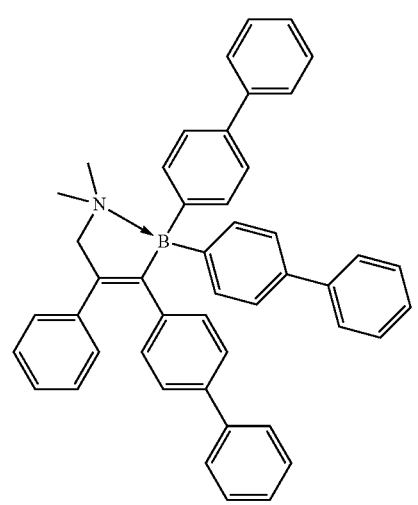
(A-10)
(A-11)
[Chemical Formula 54]
(A-12)
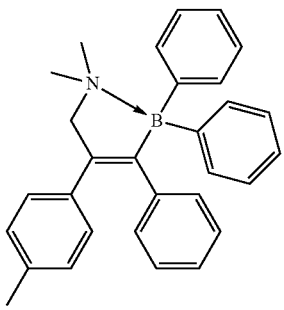
(A-13)
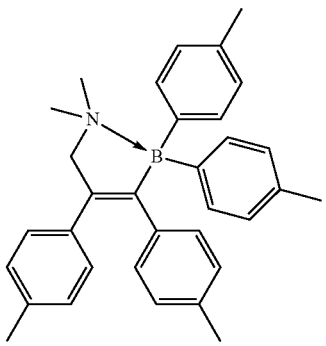
(A-14)
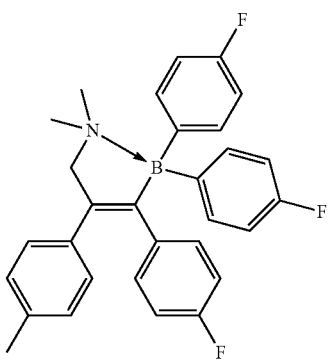
(A-15)

(A-16)
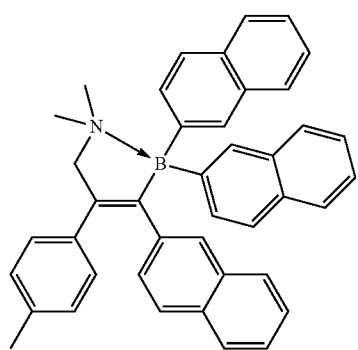
(A-17)
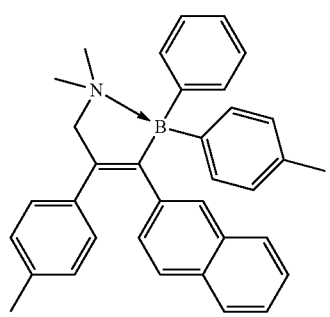
(A-18)
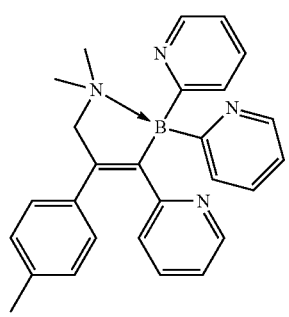
(A-19)
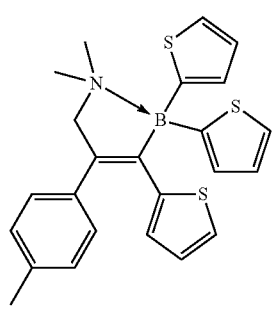
(A-20)
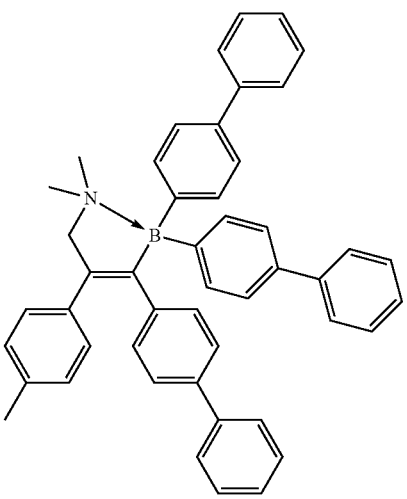
[Chemical Formula 55]
(A-21)
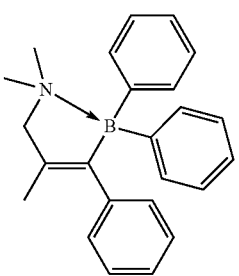
(A-22)
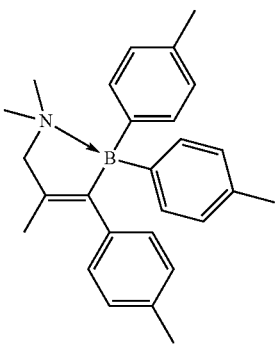
(A-23)
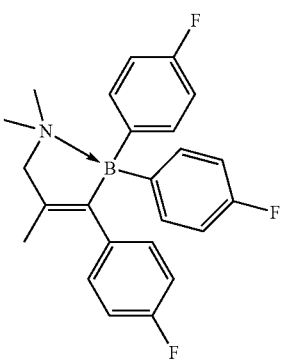

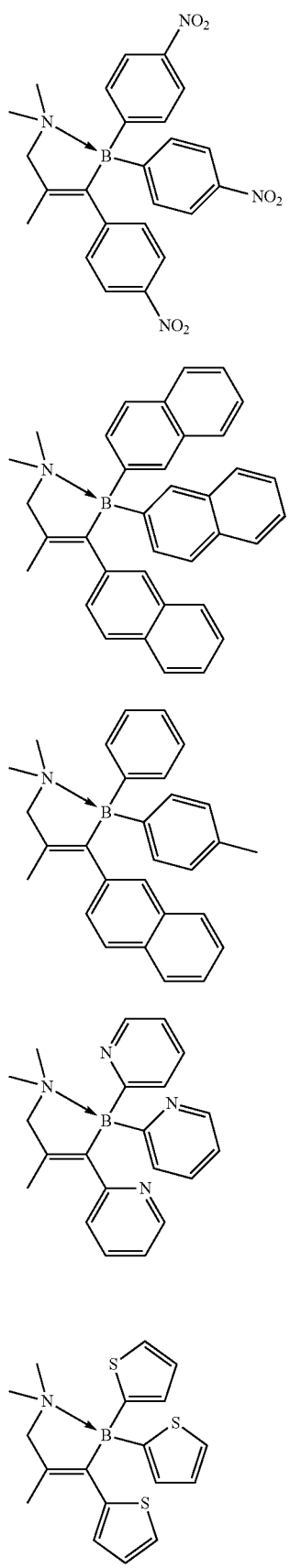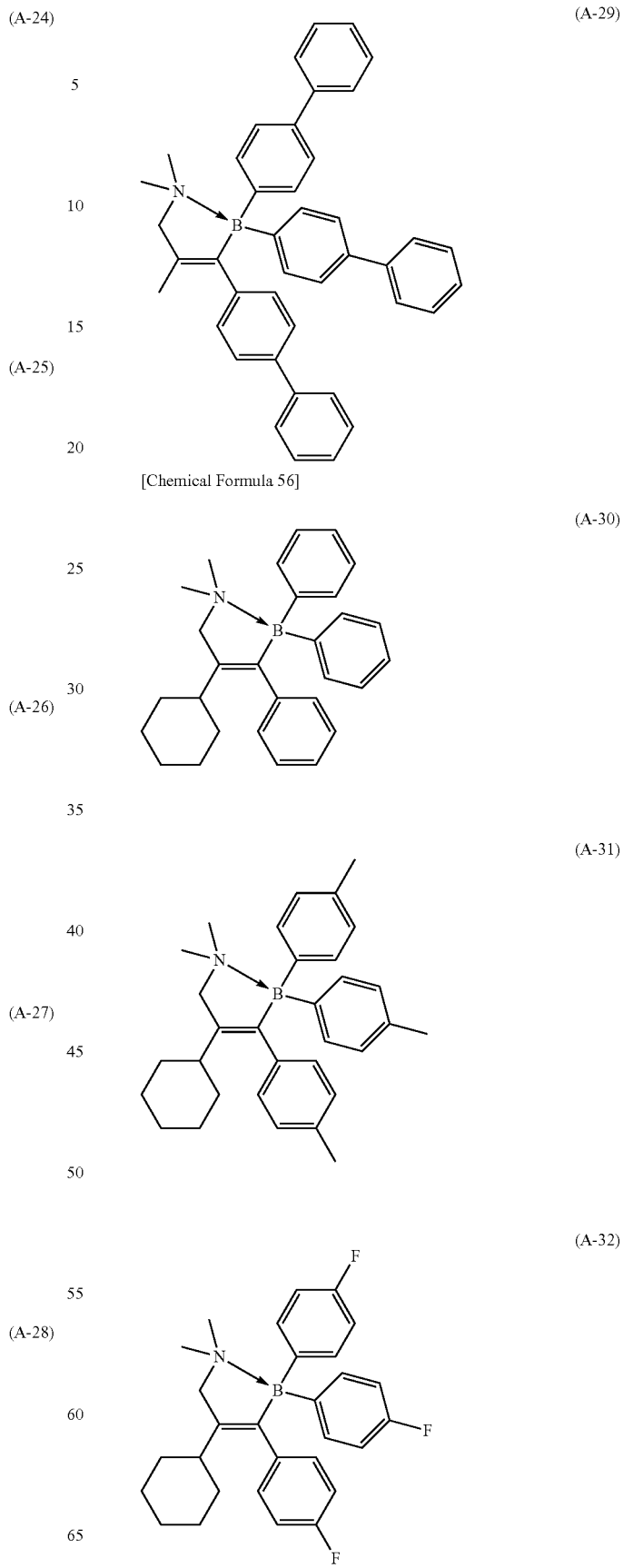

(A-33)
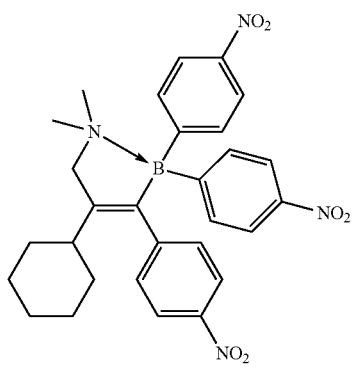
(A-34)
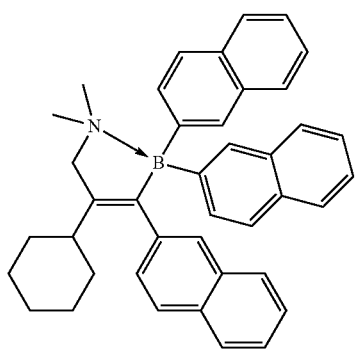
(A-35)
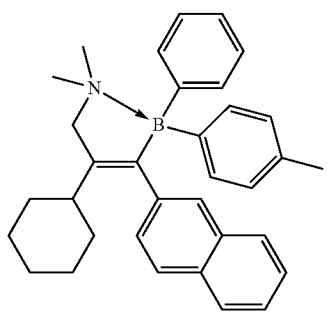
(A-36)
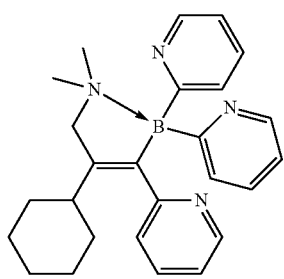
(A-37)
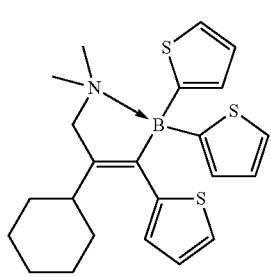
(A-38)
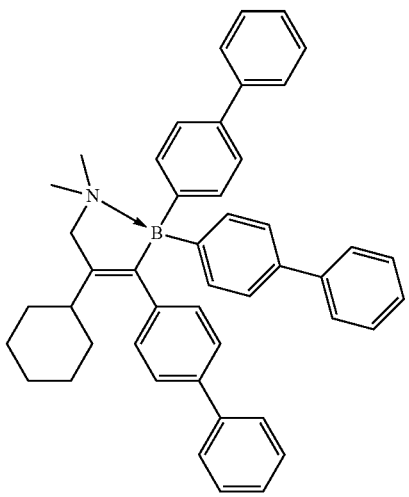
[Chemical Formula 57]
(A-39)
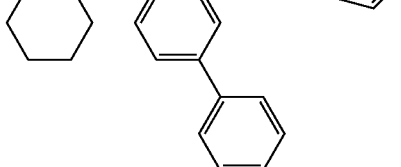
(A-40)
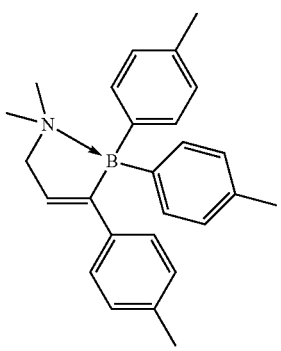
(A-41)
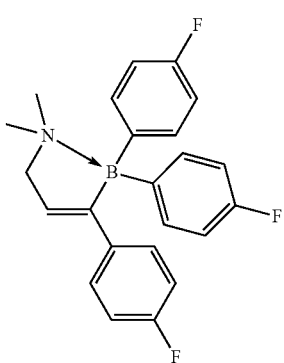

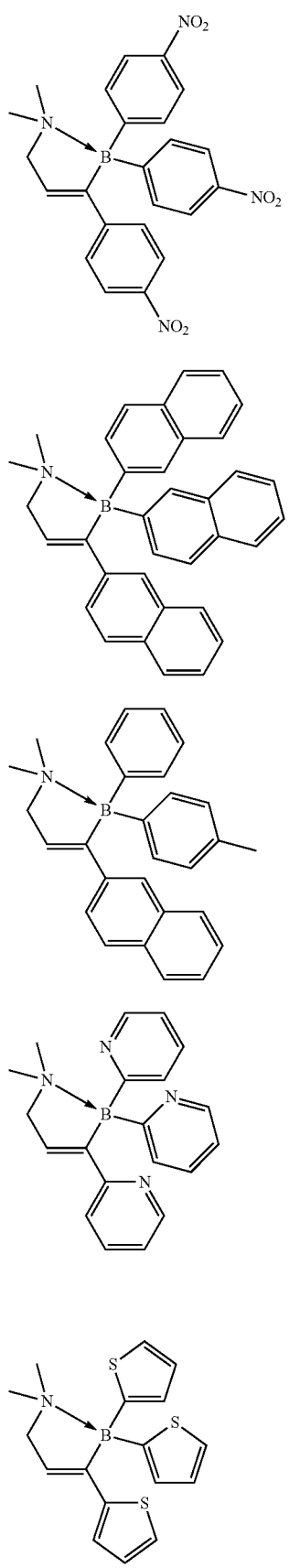
(A-42)
(A-43)
(A-44)
(A-45)
(A-46)
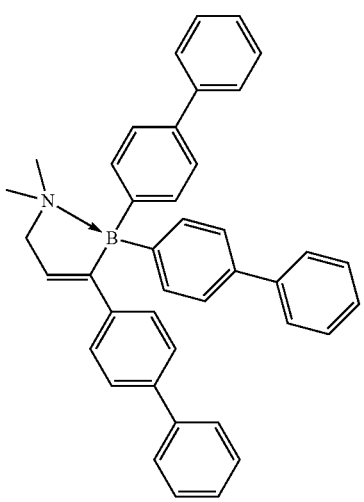
(A-47)
(A-48)
[Chemical Formula 58]
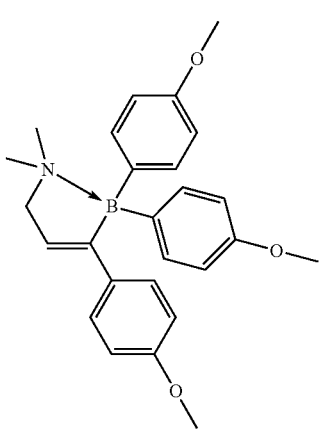
(B-1)
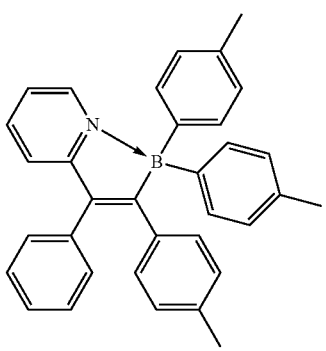
(B-2)

(B-3)
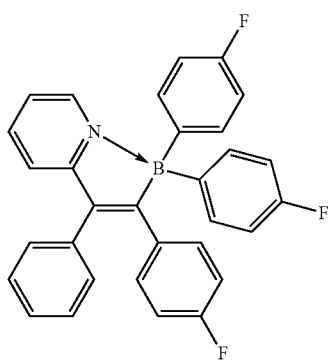
(B-4)
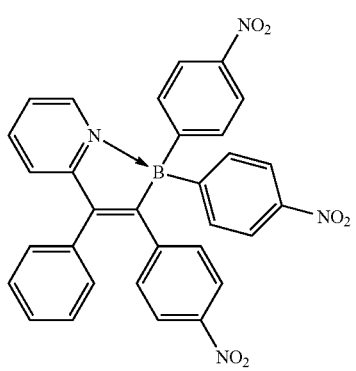
(B-5)
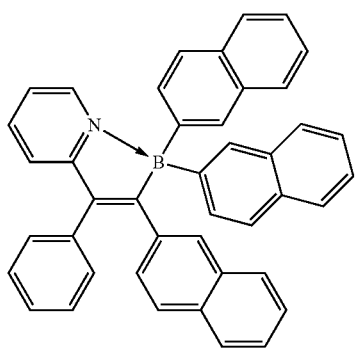
(B-6)
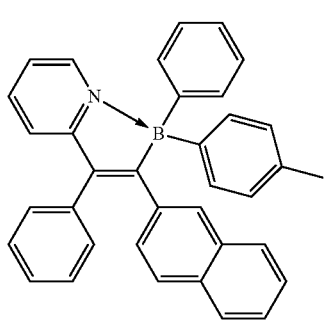
(B-7)
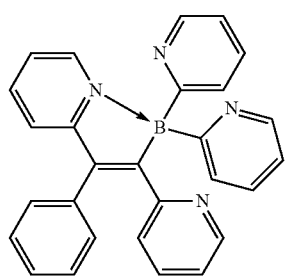
(B-8)
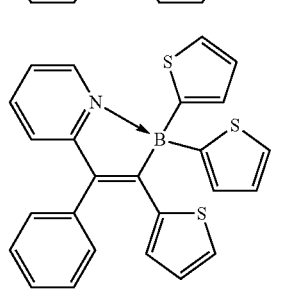
(B-9)
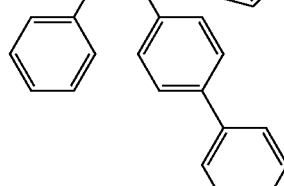
(B-10)
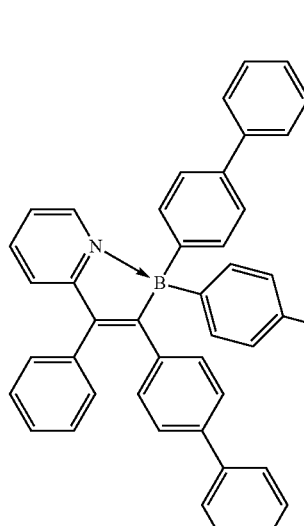

(B-11)
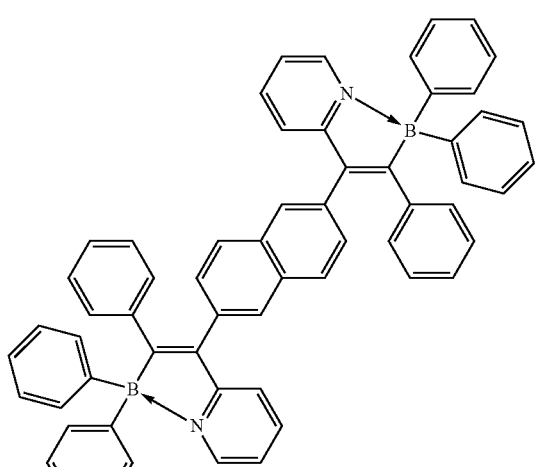
[Chemical Formula 59]
(B-12)
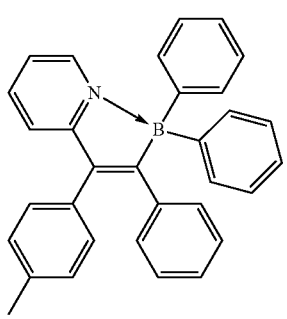
(B-13)
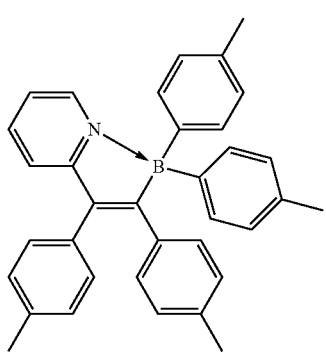
(B-14)
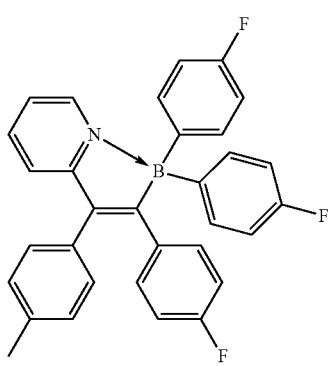
(B-15)
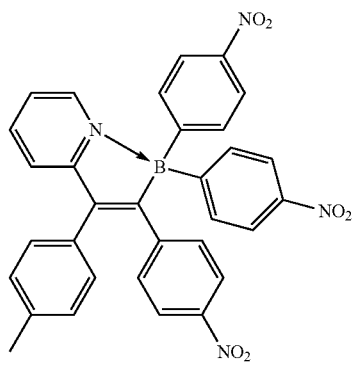
(B-16)
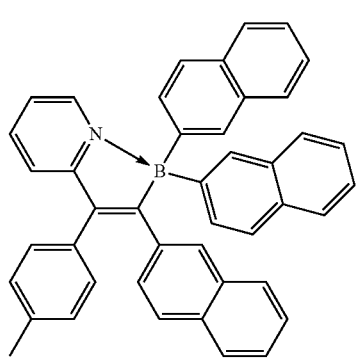
(B-17)
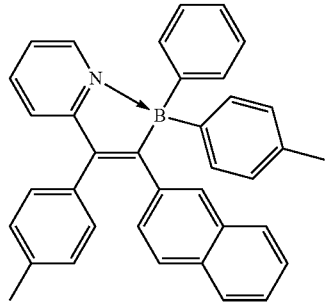
(B-18)
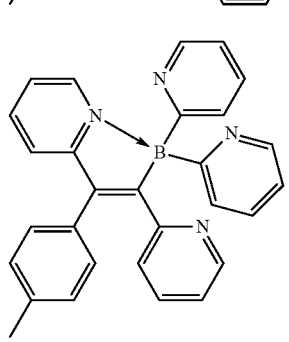
(B-19)
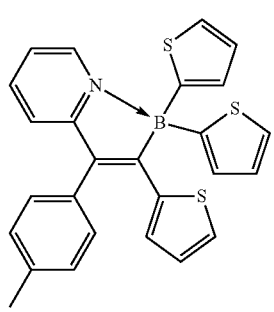

-continued
(B-20)
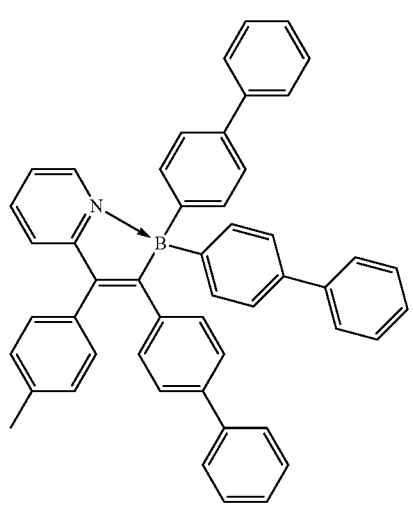
[Chemical Formula 60]
(B-21)
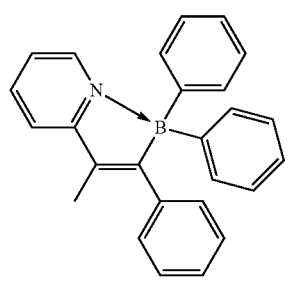
(B-22)
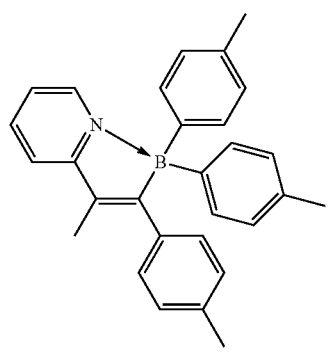
(B-23)
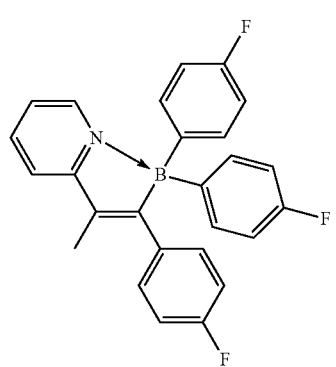
-continued
(B-24)
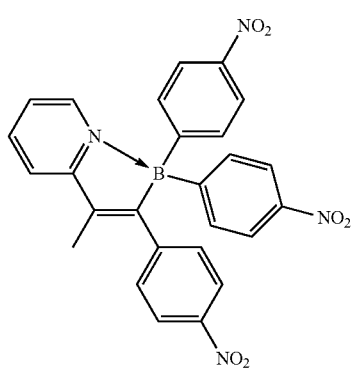
(B-25)
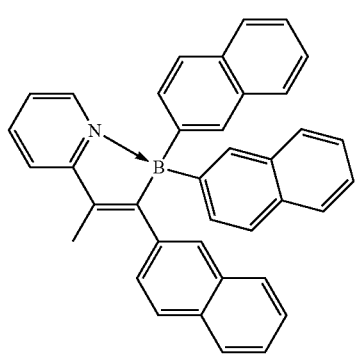
(B-26)
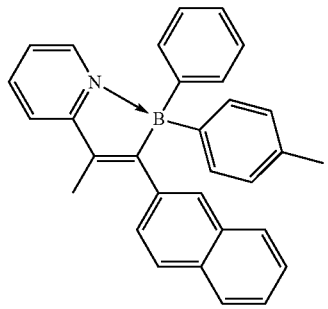
(B-27)
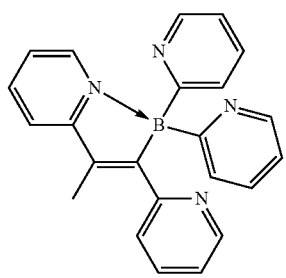
(B-28)
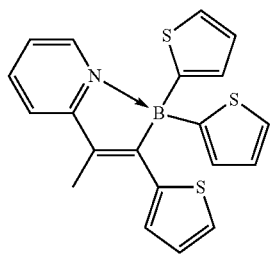

(B-29) 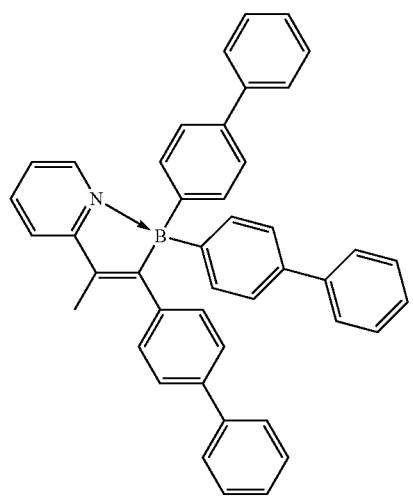
[Chemical Formula 61]
(B-30) 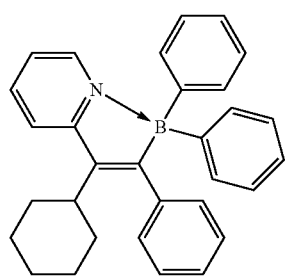
(B-31) 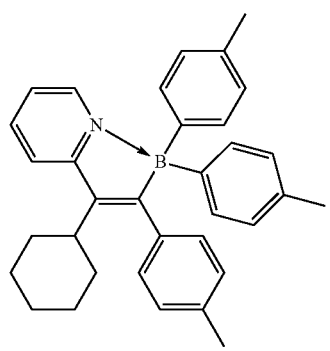
(B-32) 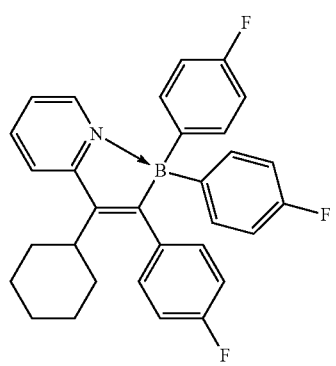
(B-33) 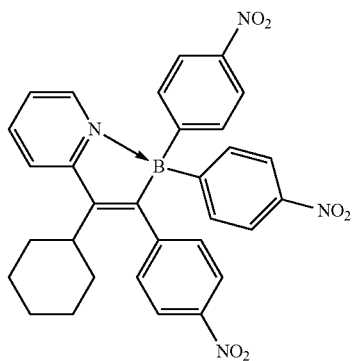
(B-34) 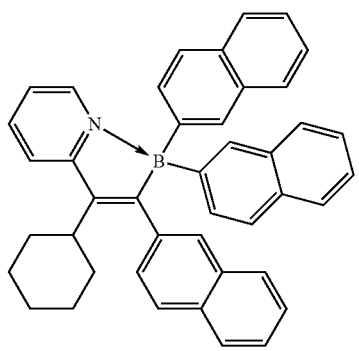
(B-35) 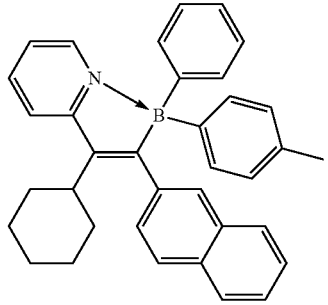
(B-36) 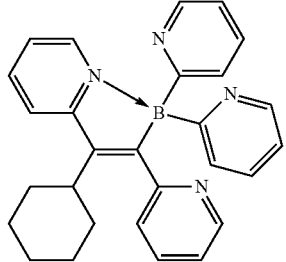
(B-37) 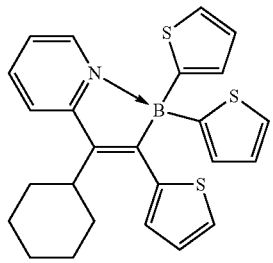

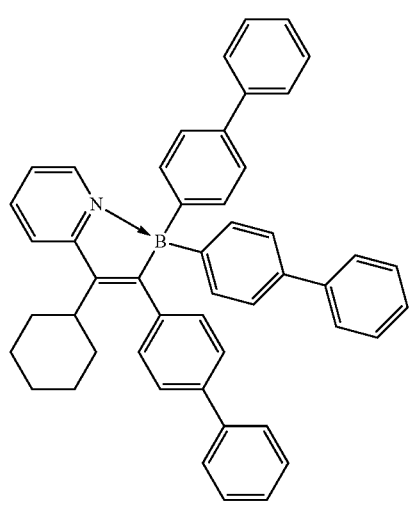
(B-38)
[Chemical Formula 62]
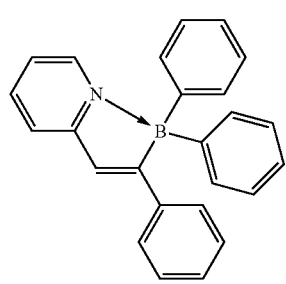
(B-39)
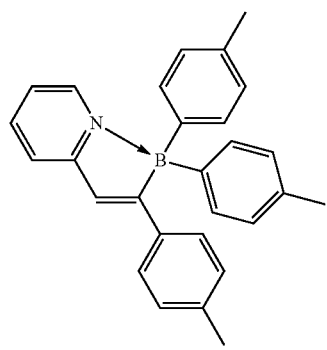
(B-40)
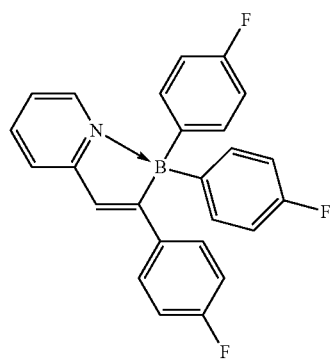
(B-41)
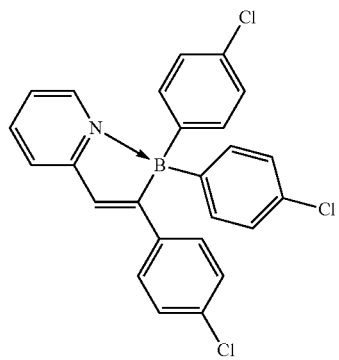
(B-42)
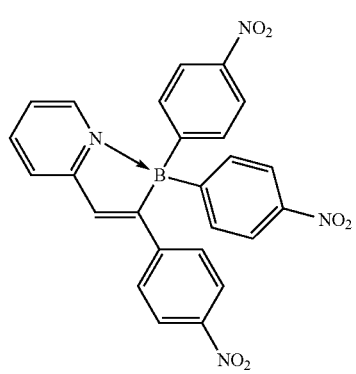
(B-43)
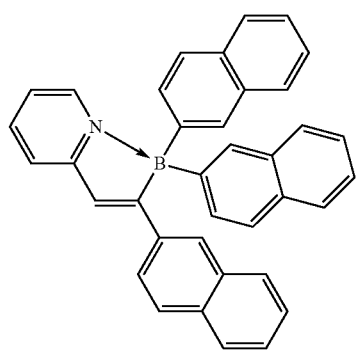
(B-44)
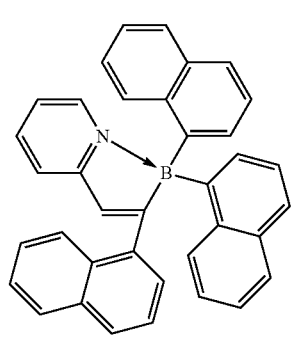
(B-45)

(B-46)
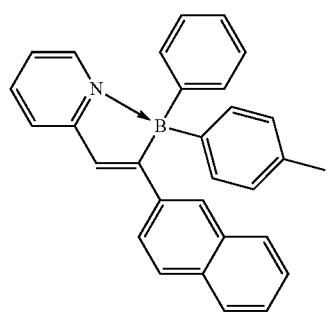
(B-47)
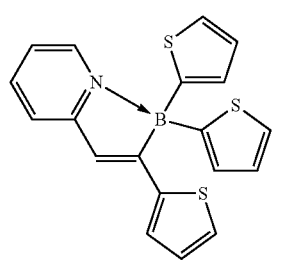
(B-48)
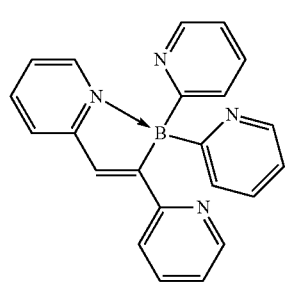
(B-49)
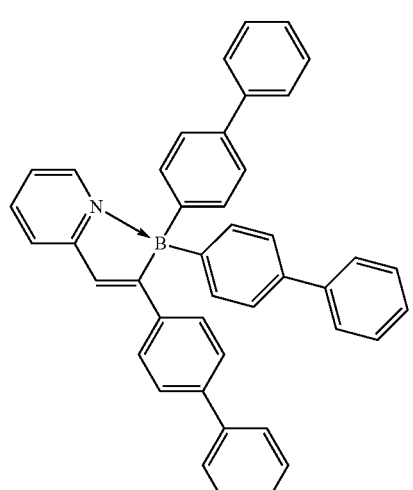
(B-50)
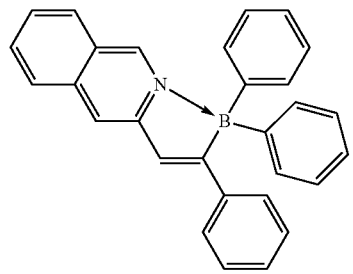
(B-51)
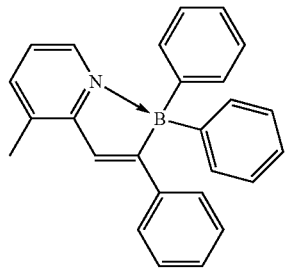
(B-52)
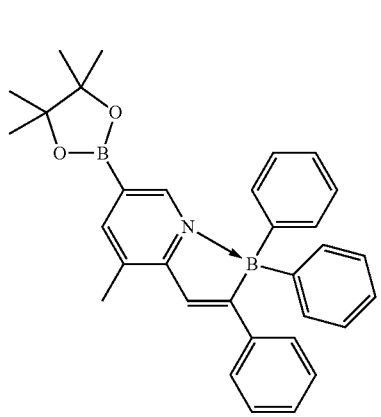
(B-53)
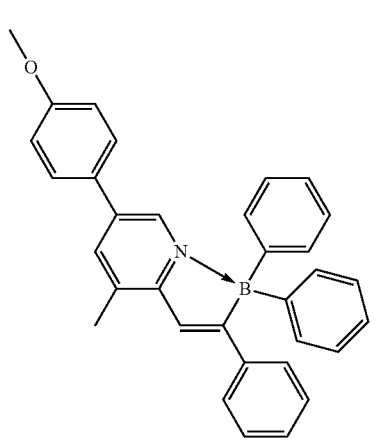
[Chemical Formula 63]
(C-1)
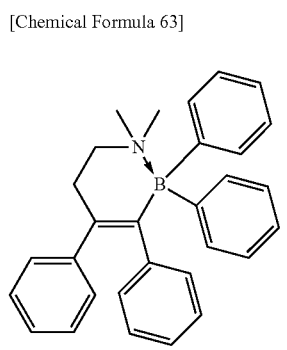

(C-2) 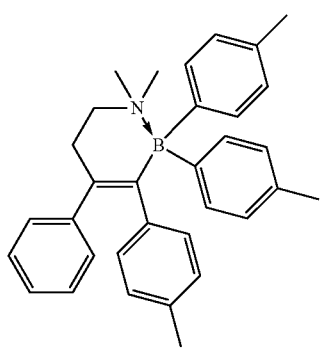
(C-3) 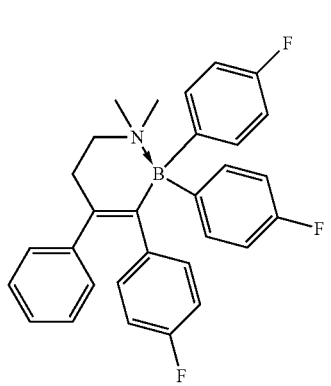
(C-4)
(C-5)
(C-6) 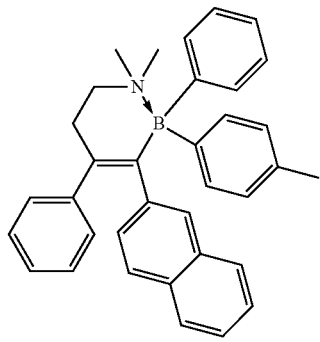
(C-7) 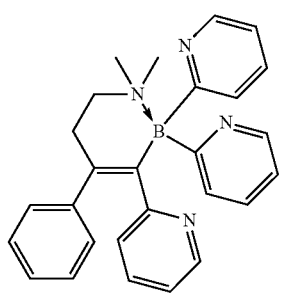
(C-8) 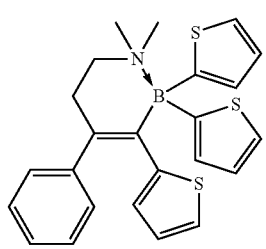
(C-9) 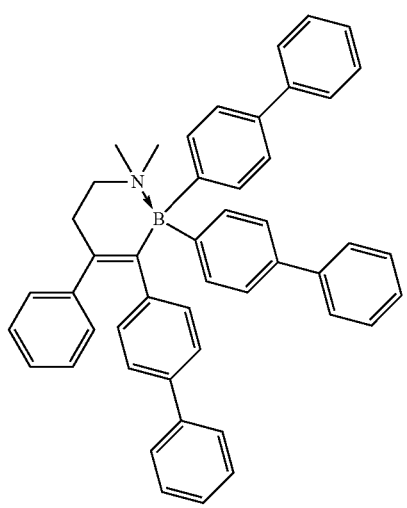

(C-10)
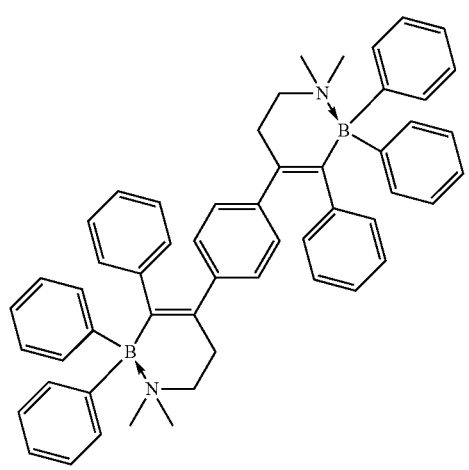
(C-11)
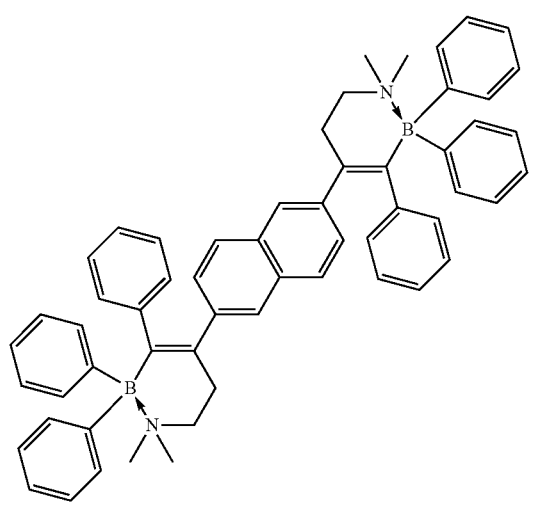
[Chemical Formula 64]
(C-12)
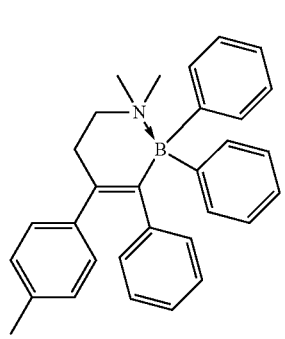
(C-13)
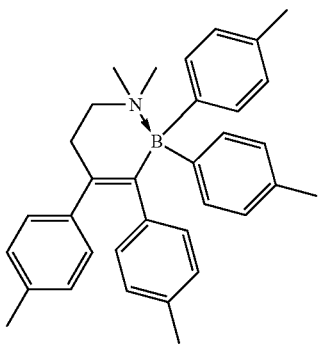
(C-14)
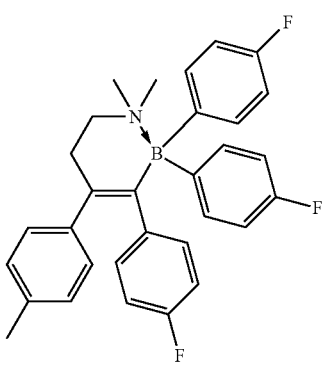
(C-15)
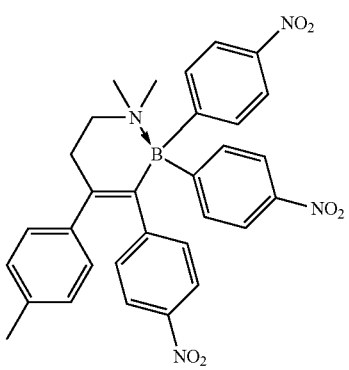
(C-16)
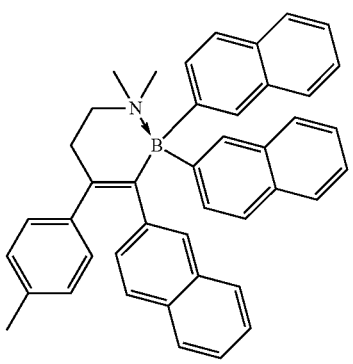

(C-17)
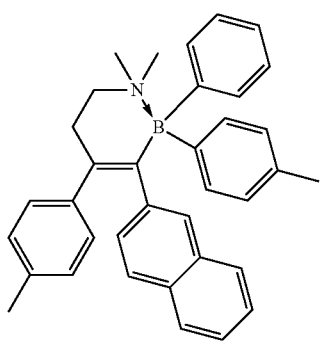
(C-18)
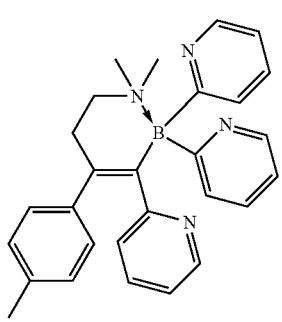
(C-19)
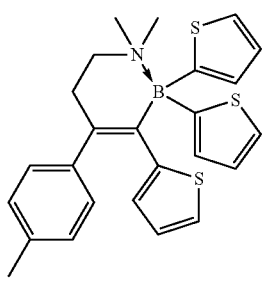
(C-20)
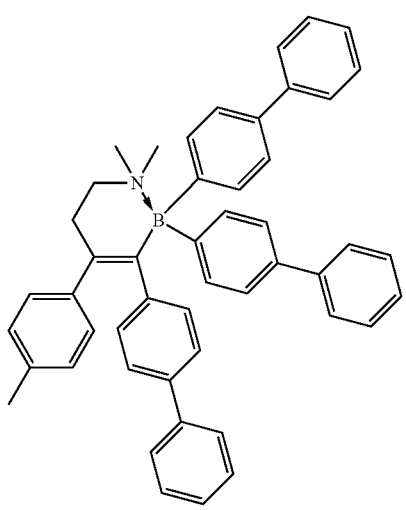
[Chemical Formula 65]
(C-21)
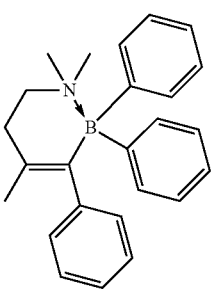
(C-22)
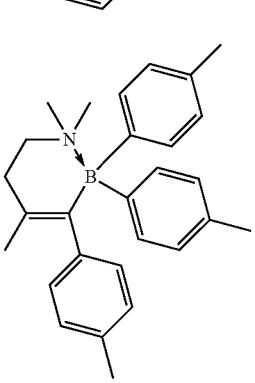
(C-23)
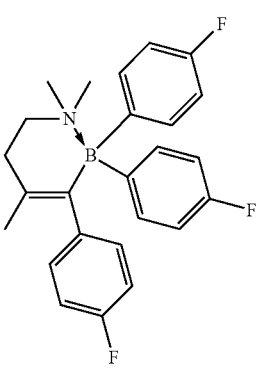
(C-24)
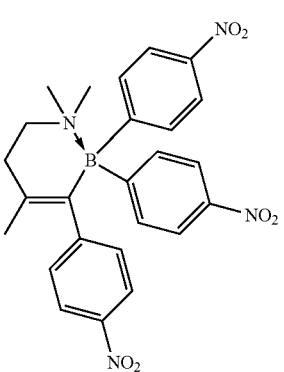

(C-24) 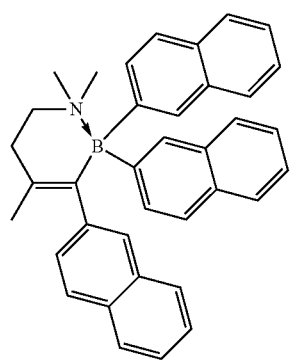
(C-25) 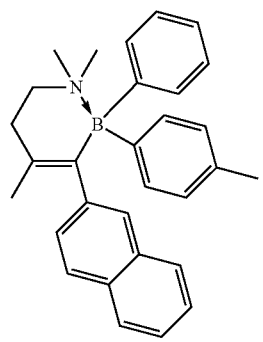
(C-26) 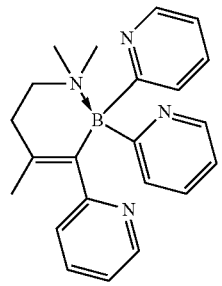
(C-27) 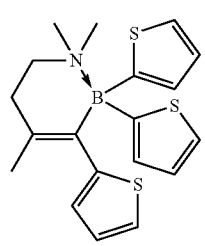
(C-28) 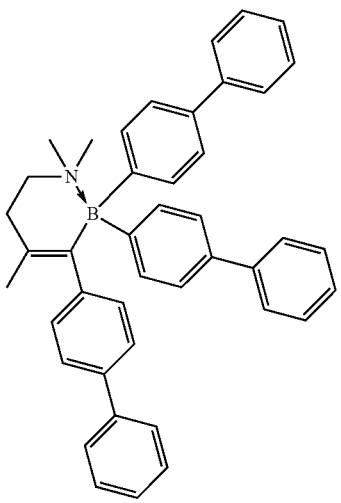
[Chemical Formula 66]
(C-29) 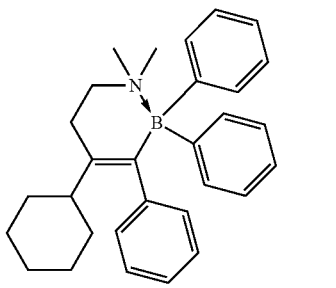
(C-30) 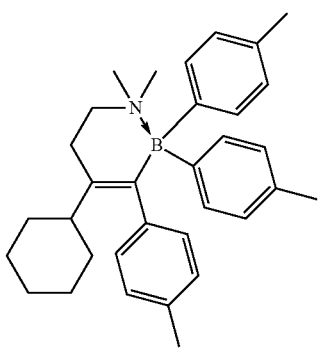
(C-31) 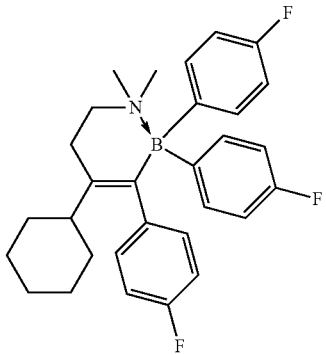

(C-32)
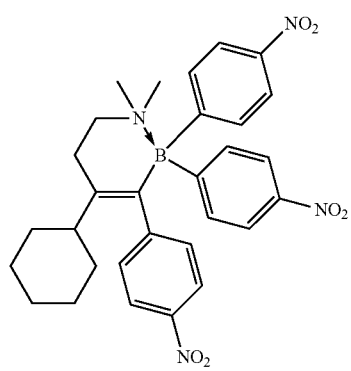
(C-33)
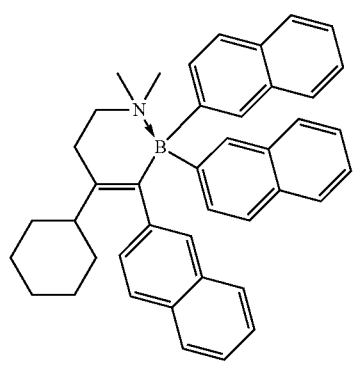
(C-34)
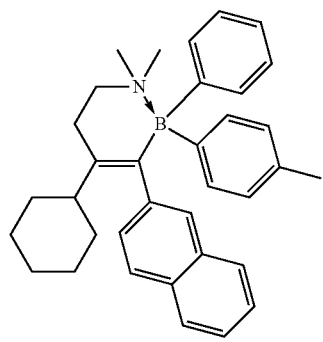
(C-35)
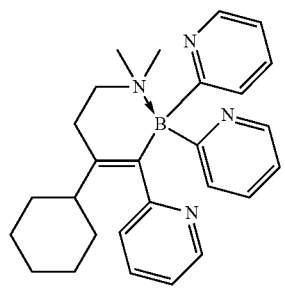
(C-36)
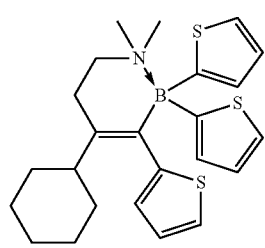
(C-37)
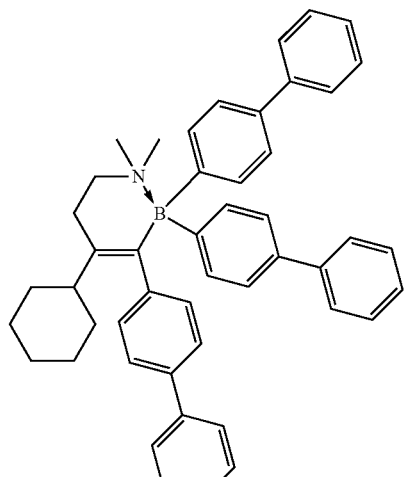
[Chemical Formula 67]
(C-38)
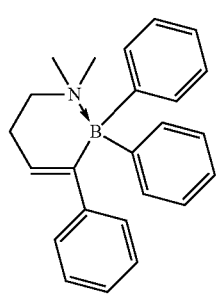
(C-39)
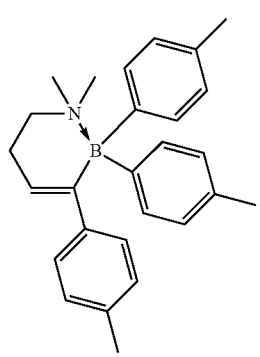
(C-40)
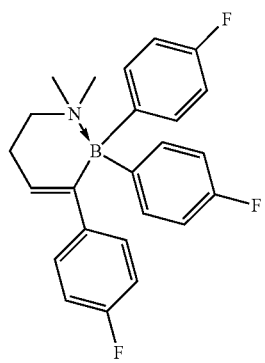

(C-41) 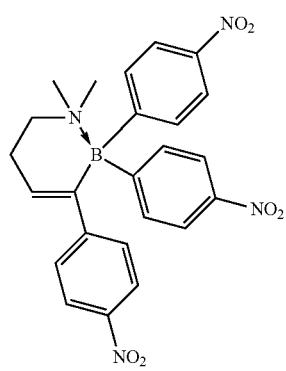
(C-42) 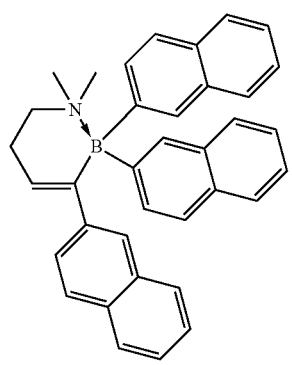
(C-43) 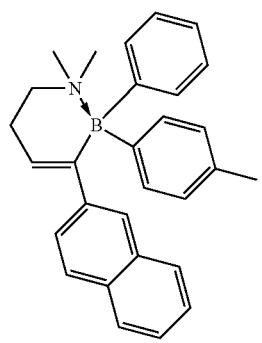
(C-44) 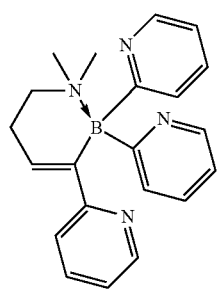
(C-45) 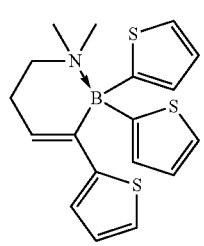
(C-46) 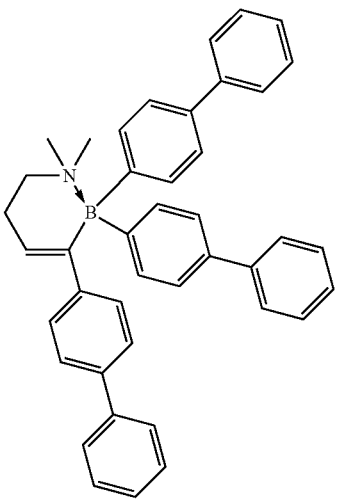
[Chemical Formula 68]
(D-1) 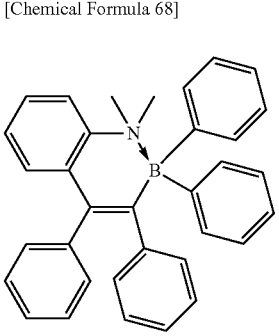
(D-2) 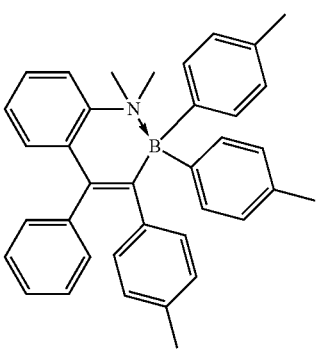
(D-3) 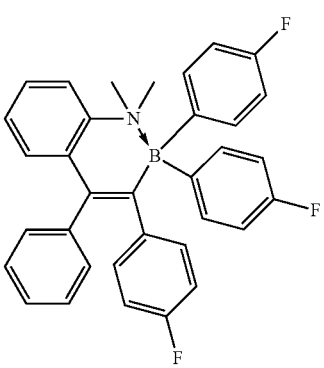

(D-4)
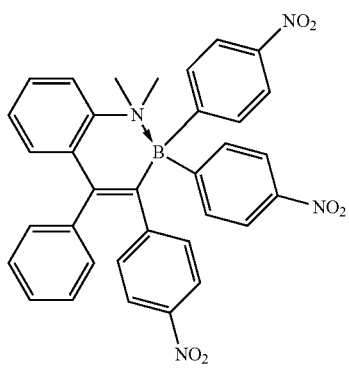
(D-5)
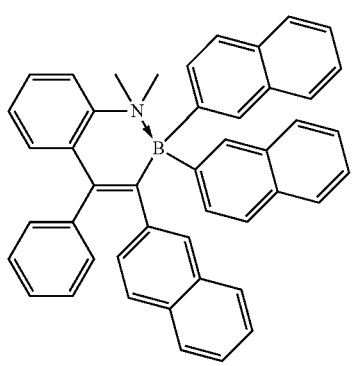
(D-6)
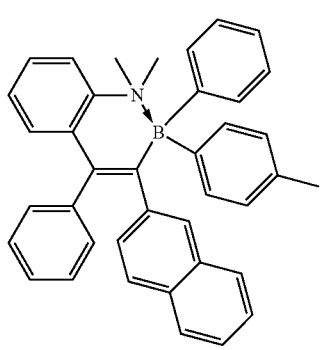
(D-7)
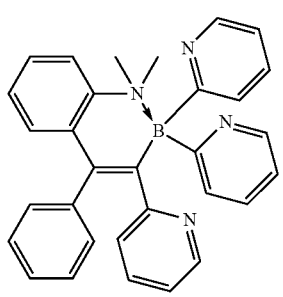
(D-8)
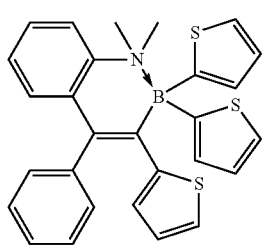
(D-9)
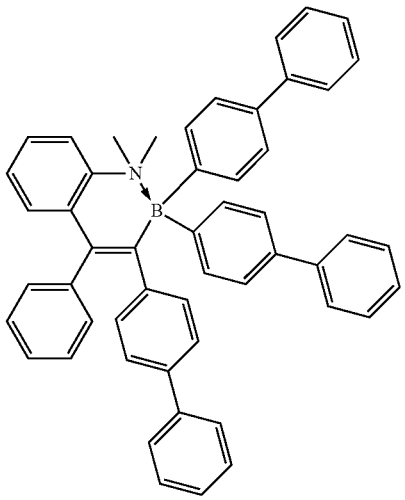
(D-10)
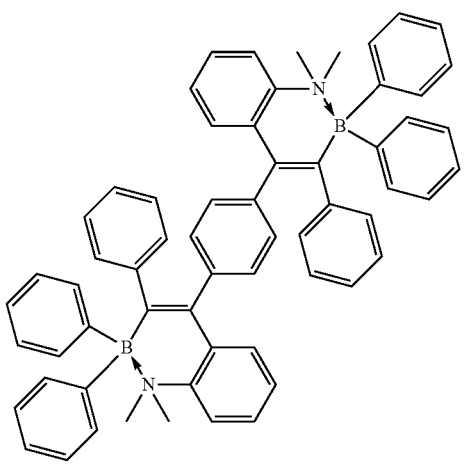
(D-11)
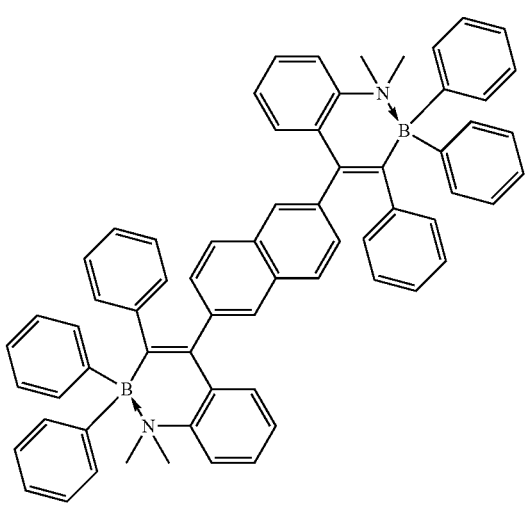

[Chemical Formula 69]
(D-12) 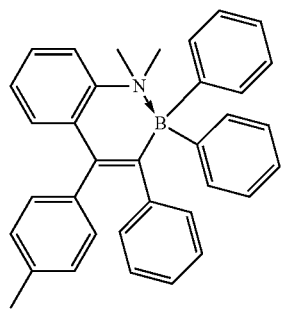
(D-13) 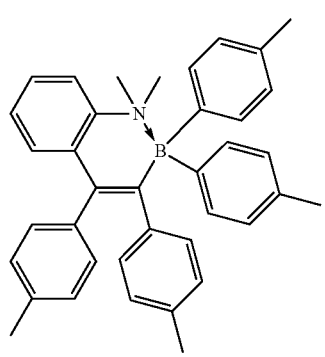
(D-14) 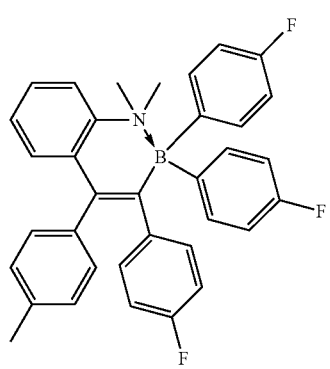
(D-15) 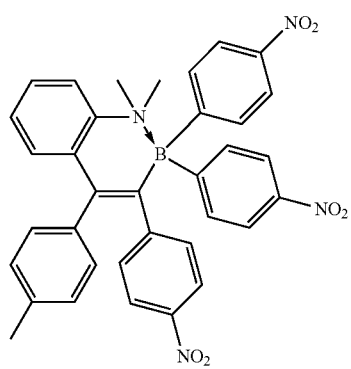
(D-16) 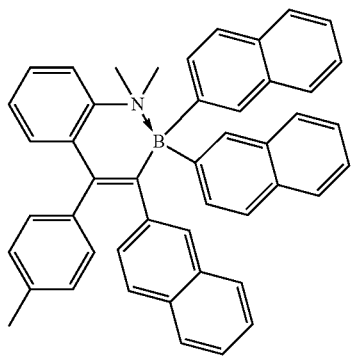
(D-17) 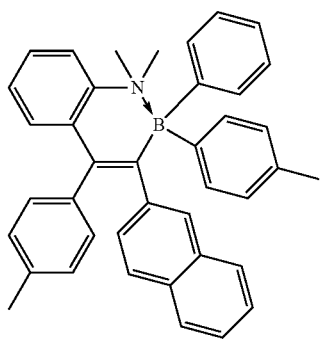
(D-18)
(D-19) 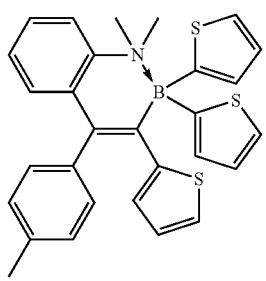

-continued
(D-20)
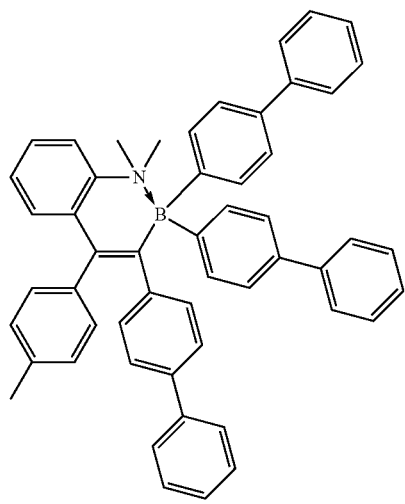
[Chemical Formula 70]
(D-21)
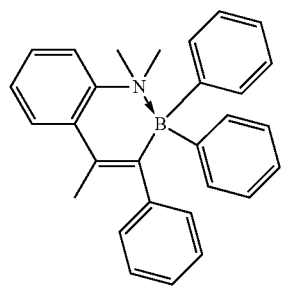
(D-22)
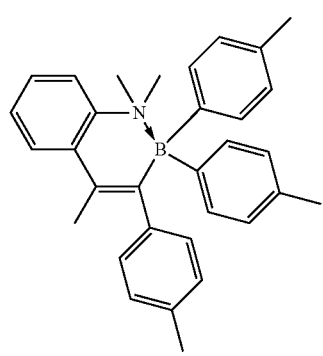
(D-23)
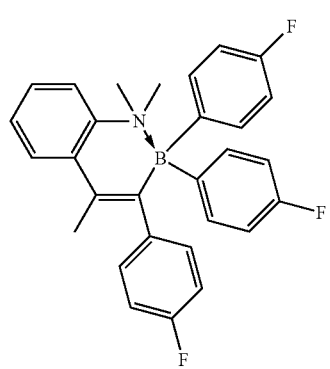
-continued
(D-24)
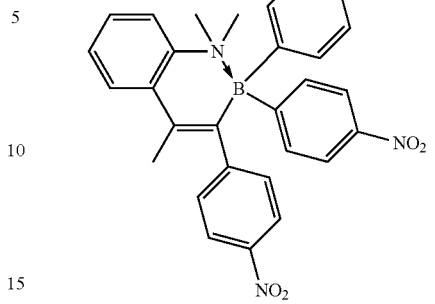
(D-25)
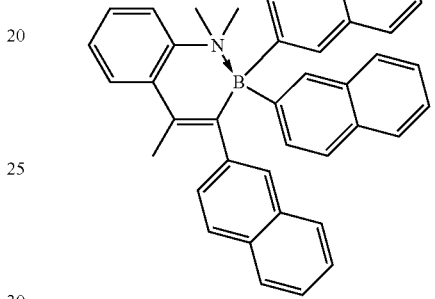
(D-26)
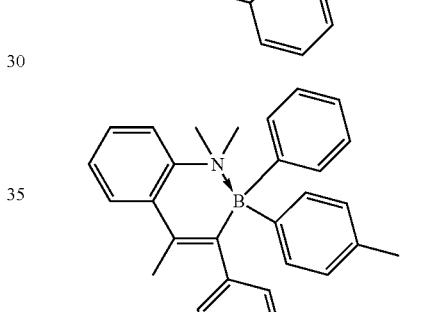
(D-27)
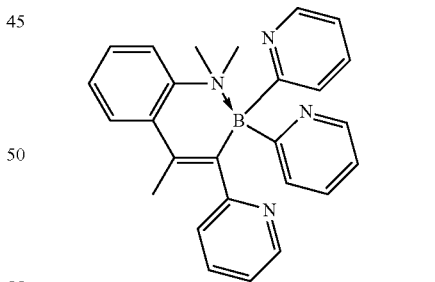
(D-28)
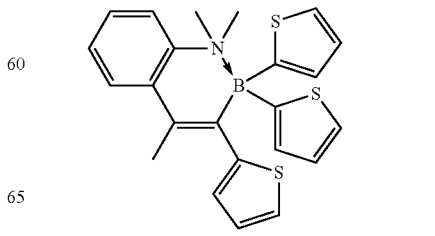

(D-29) 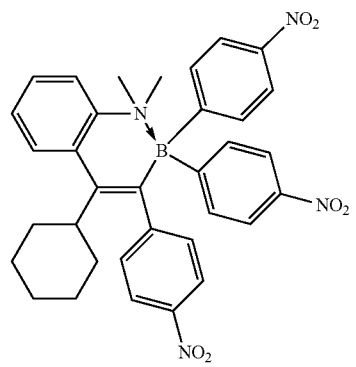
[Chemical Formula 71]
(D-30) 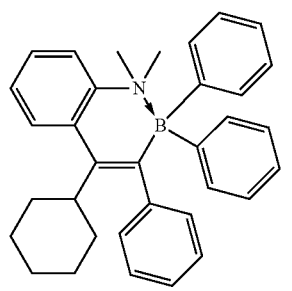
(D-31) 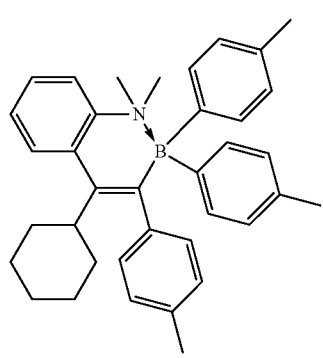
(D-32) 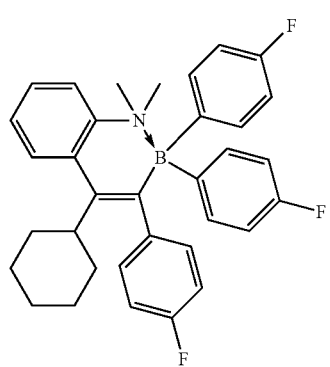
(D-33) 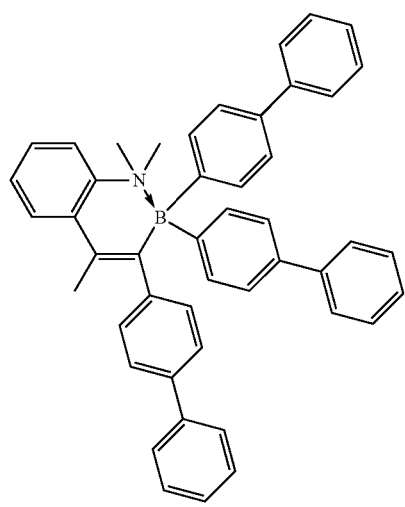
(D-34) 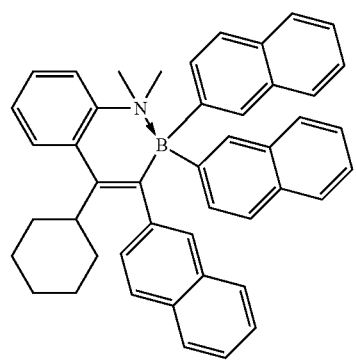
(D-35) 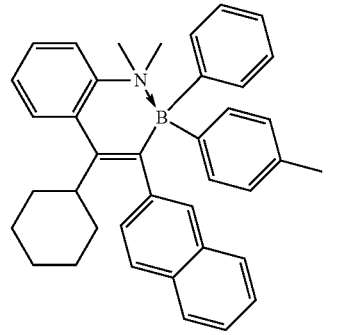
(D-36) 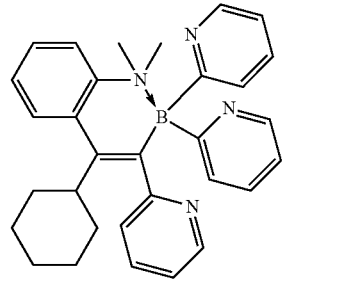
(D-37) 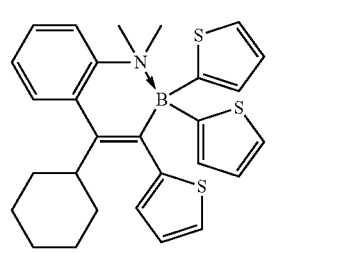

(D-38)
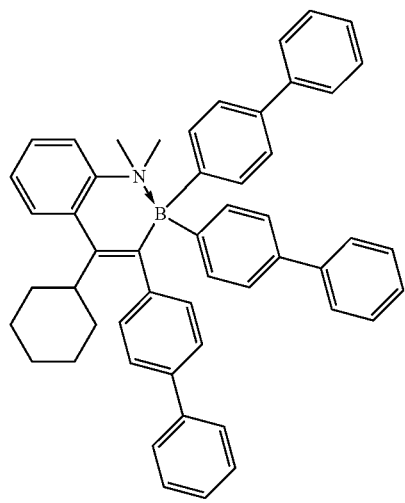
[Chemical Formula 72]
(D-39)
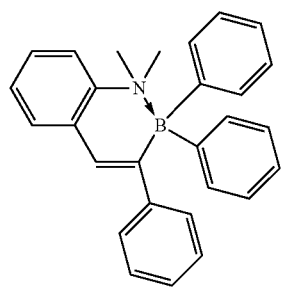
(D-40)
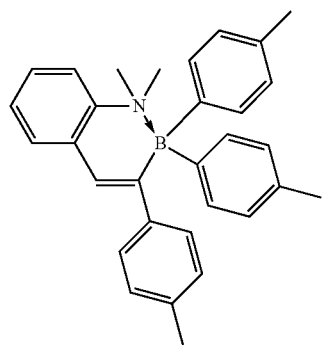
(D-41)
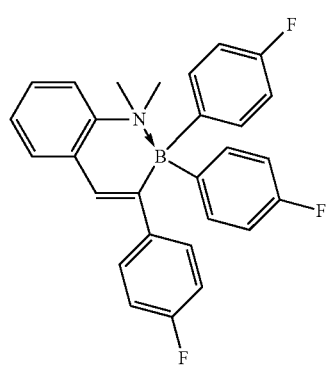
(D-42)
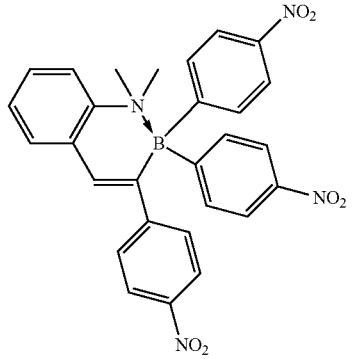
(D-43)
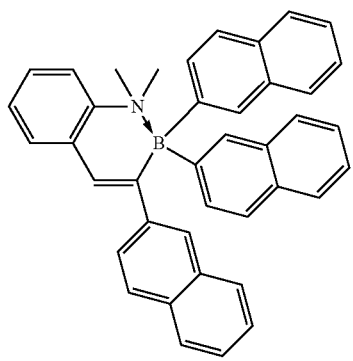
(D-44)
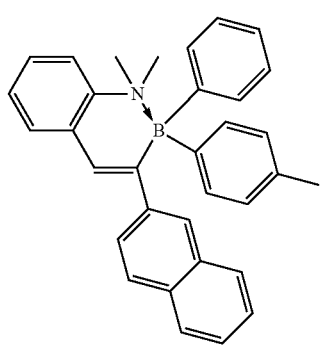
(D-45)
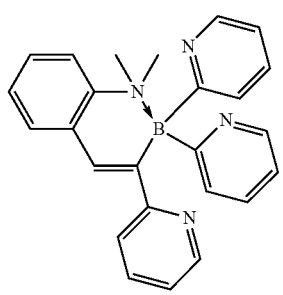
(D-46)
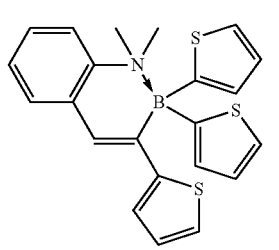

(D-47)
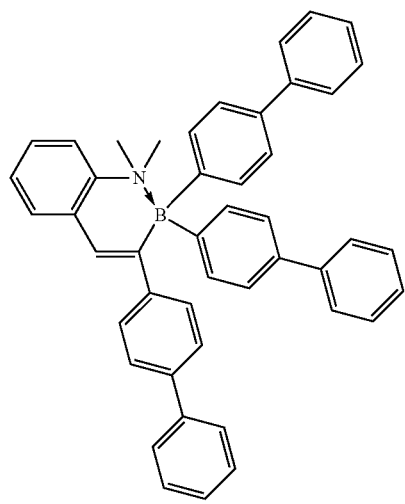
[Chemical Formula 73]
(E-1)
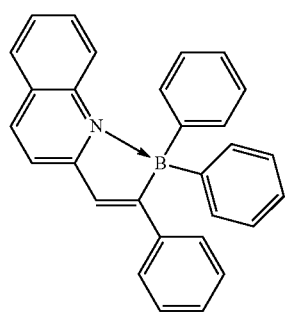
(E-2)
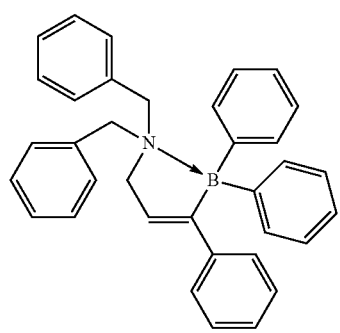
(E-3)
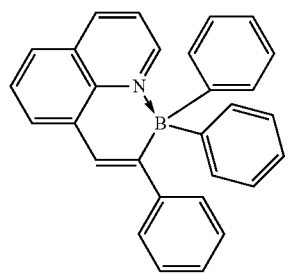
[Chemical Formula 74]
(F-1)
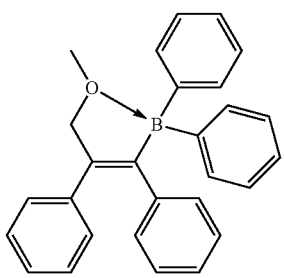
(F-2)
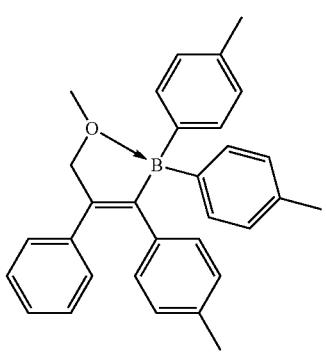
(F-3)
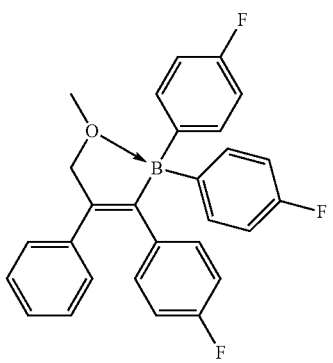
(F-4)
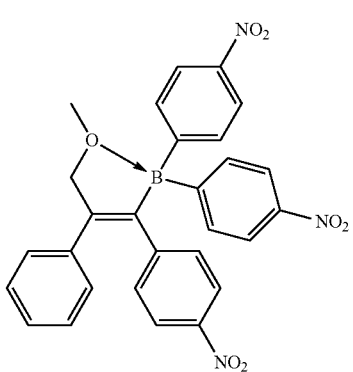

(F-5)
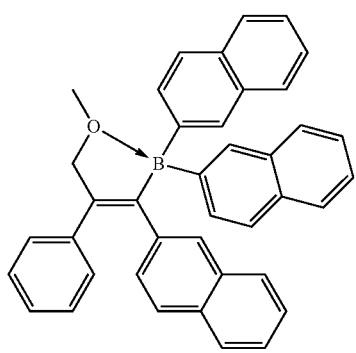
(F-6)
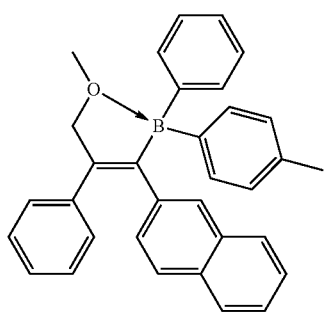
(F-7)
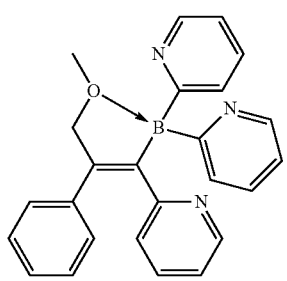
(F-8)
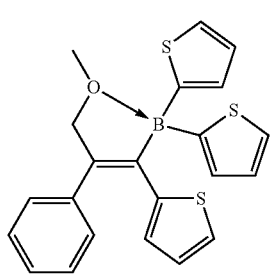
(F-9)
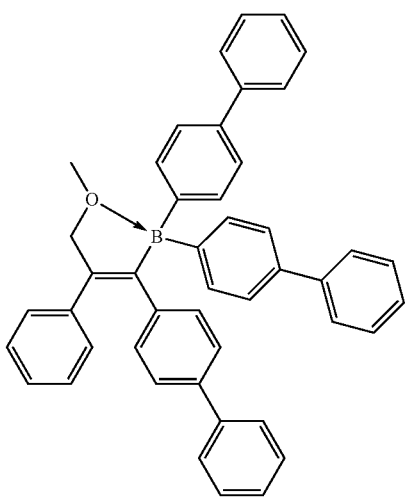
(F-10)
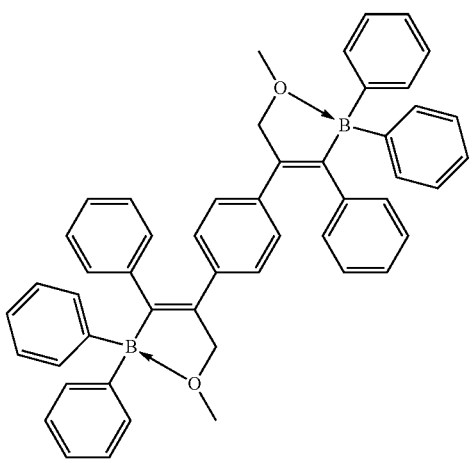
(F-11)
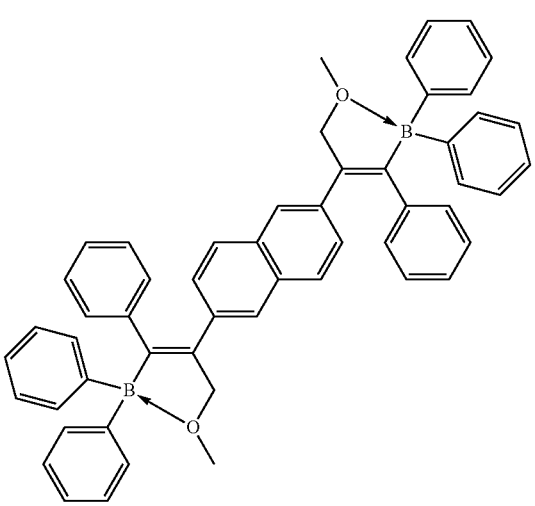

[Chemical Formula 75]
(F-12)
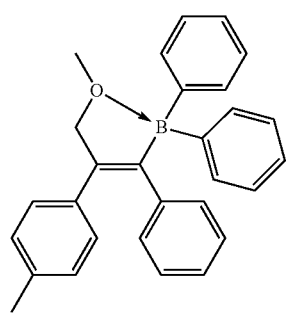
(F-13)
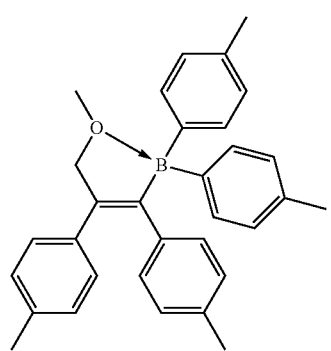
(F-14)
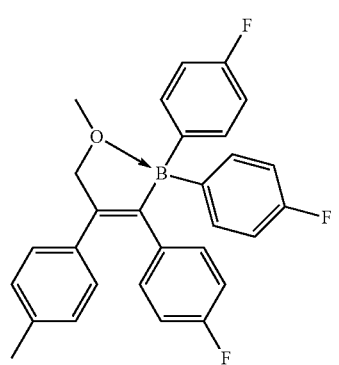
(F-15)
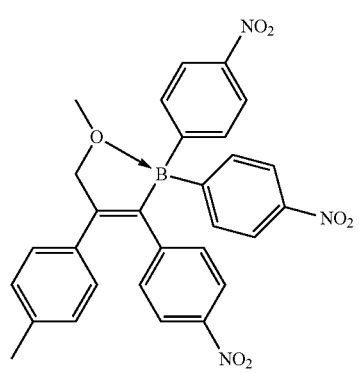
(F-16)
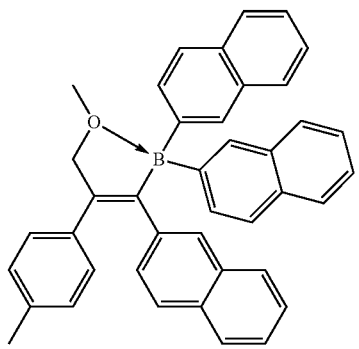
(F-17)
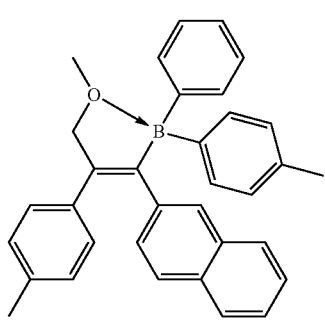
(F-18)
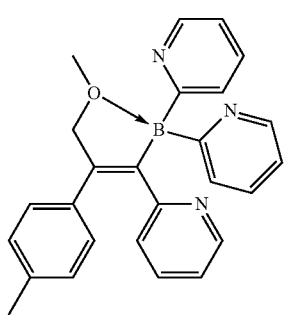
(F-19)
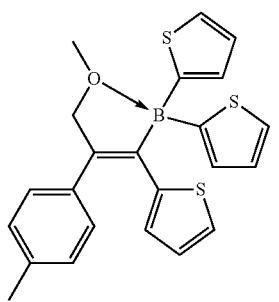

(F-20) 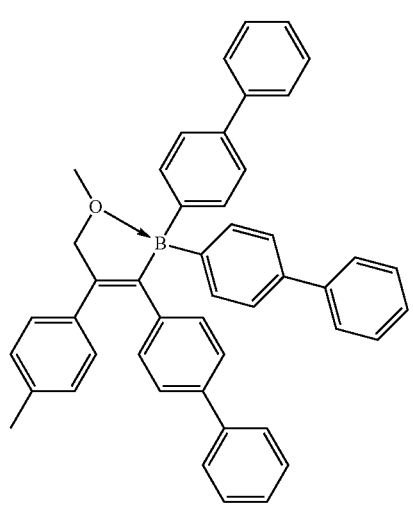
[Chemical Formula 76]
(F-21) 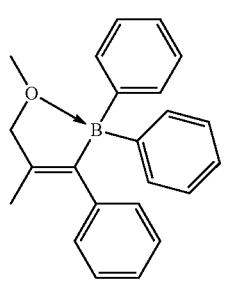
(F-22) 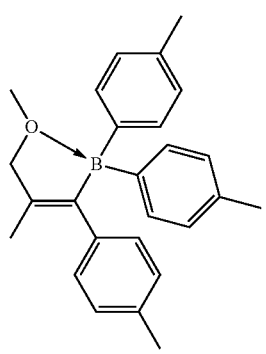
(F-23) 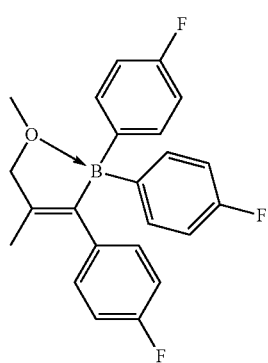
(F-24) 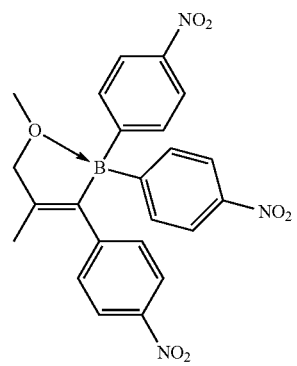
(F-25) 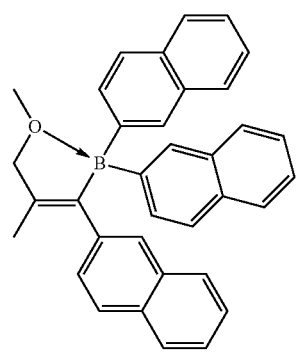
(F-26) 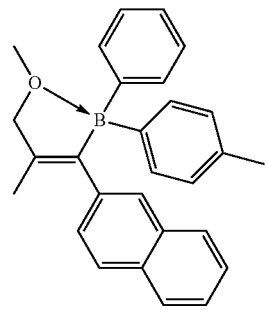
(F-27) 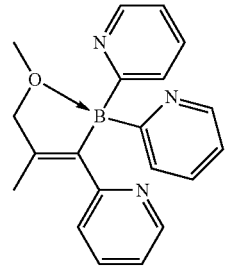
(F-28) 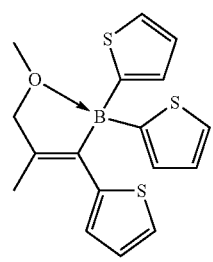

(F-29)
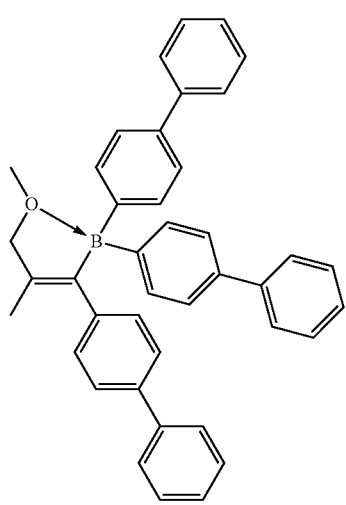
[Chemical Formula 77]
(F-30)
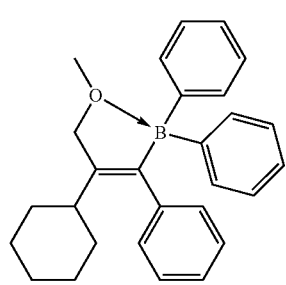
(F-31)
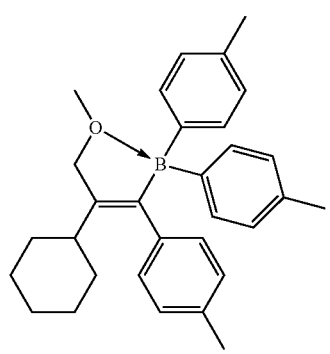
(F-32)
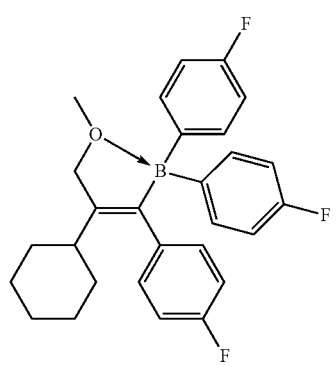
(F-33)
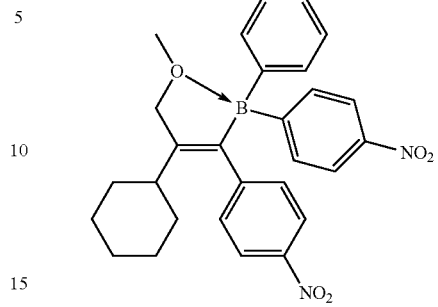
(F-34)
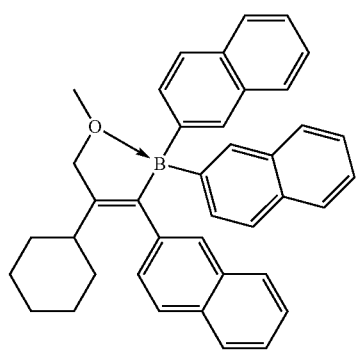
(F-35)
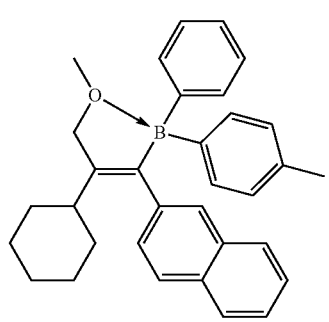
(F-36)
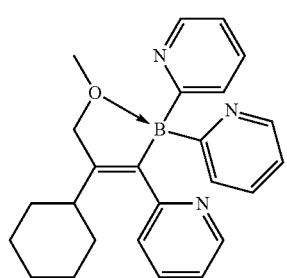
(F-37)
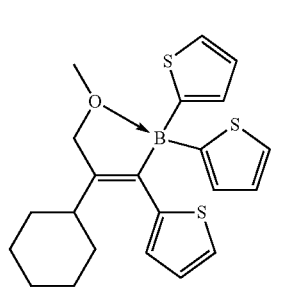

(F-38)
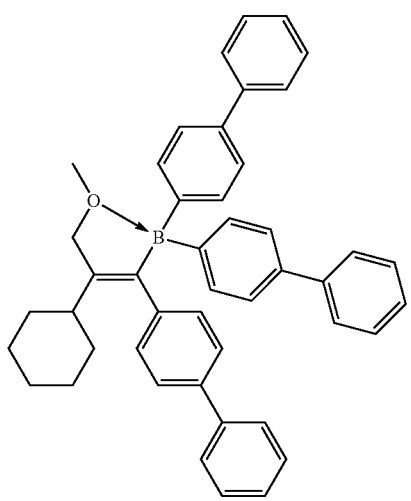
[Chemical Formula 78]
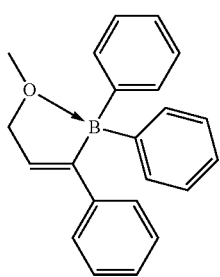
(F-39)
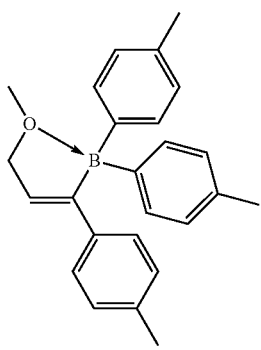
(F-40)
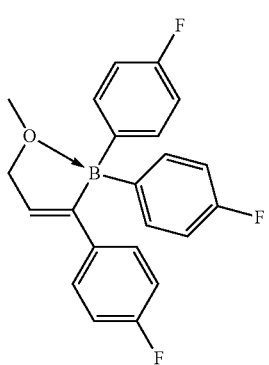
(F-41)
(F-42)
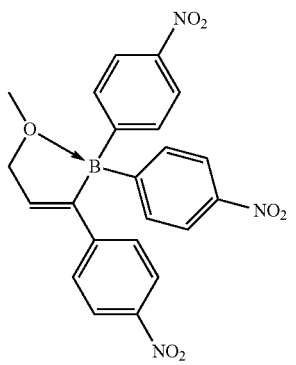
(F-43)
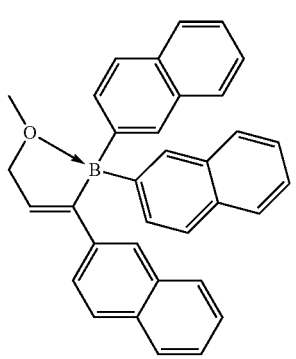
(F-44)
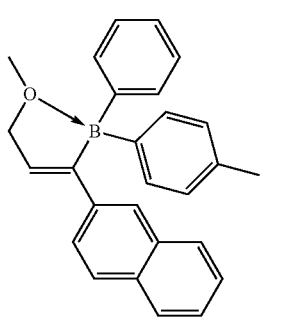
(F-45)
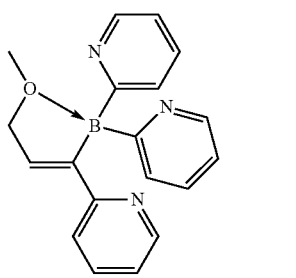
(F-46)
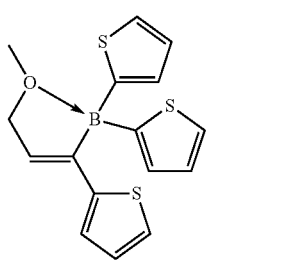

(F-47)
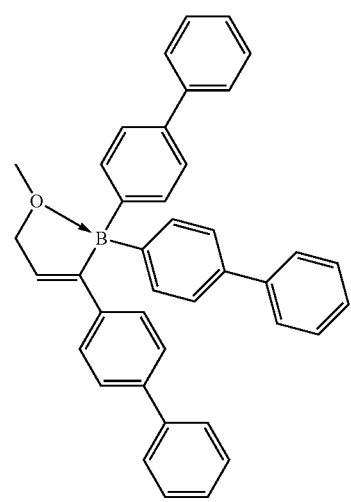
(F-48)
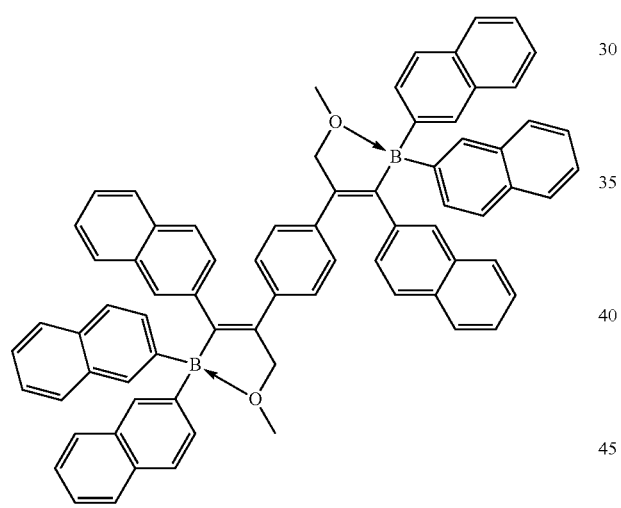
[Chemical Formula 79]
(G-1)
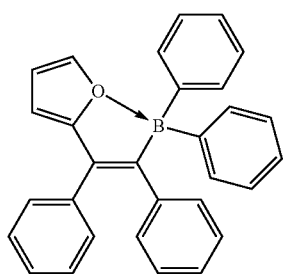
(G-2)
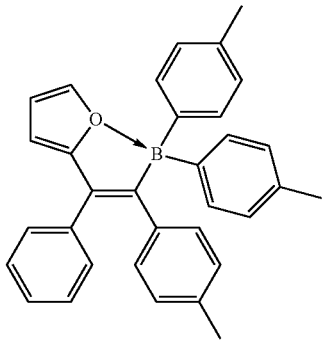
(G-3)
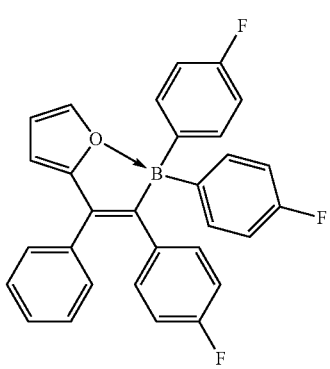
(G-4)
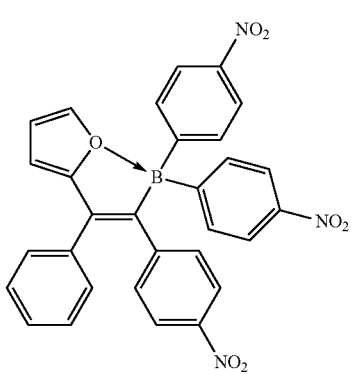
(G-5)
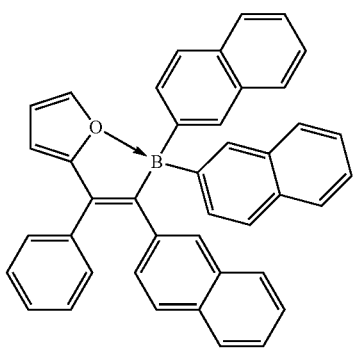

(G-6) 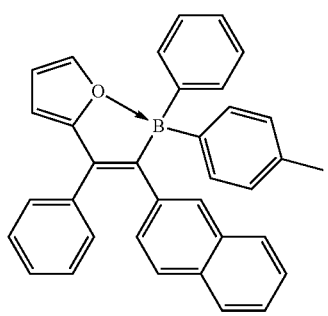
(G-7) 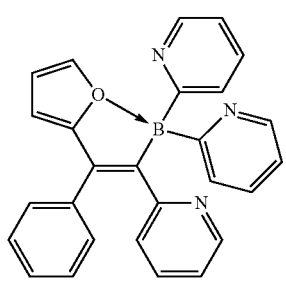
(G-8) 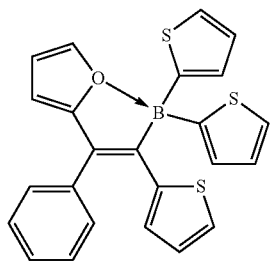
(G-9) 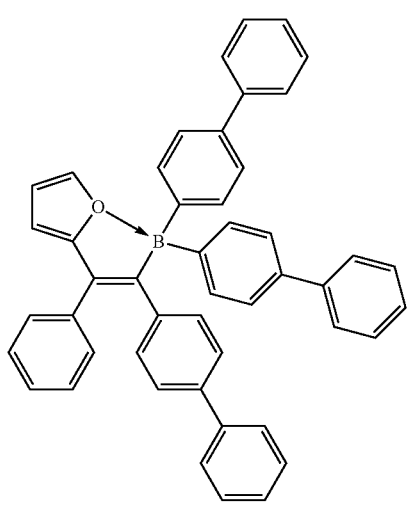
(G-10) 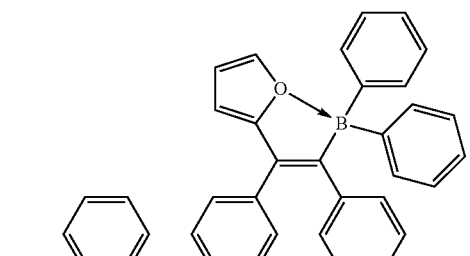
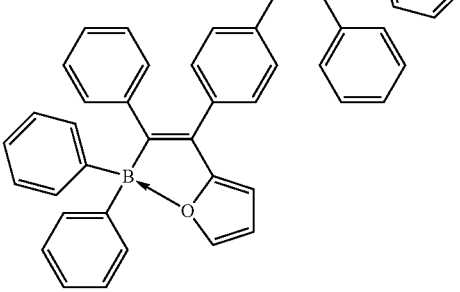
(G-11) 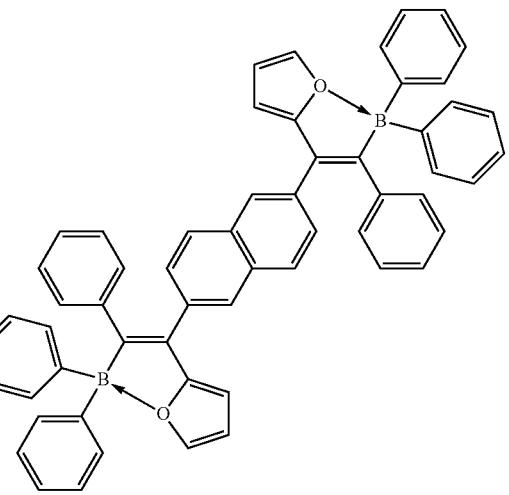
[Chemical Formula 80]
(G-12) 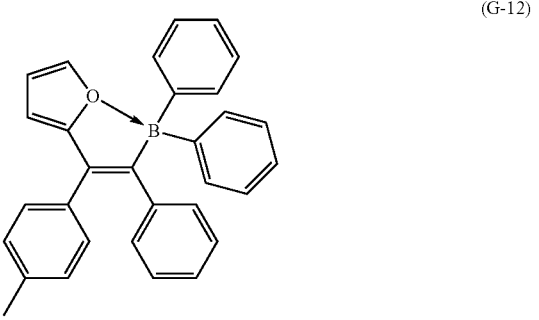

(G-13)
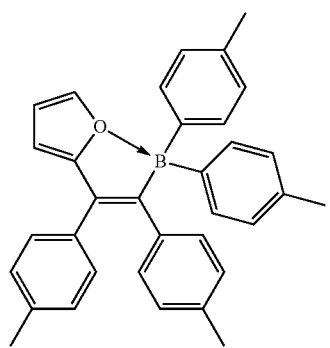
(G-14)
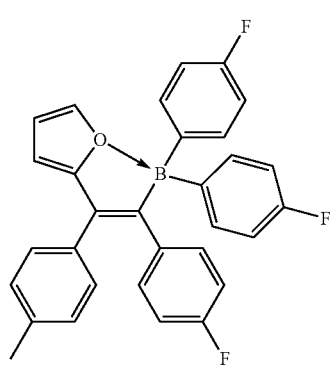
(G-15)
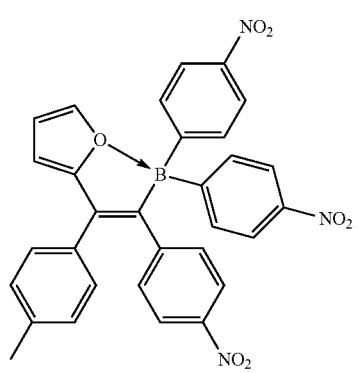
(G-16)
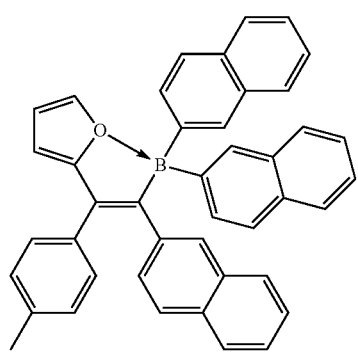
(G-17)
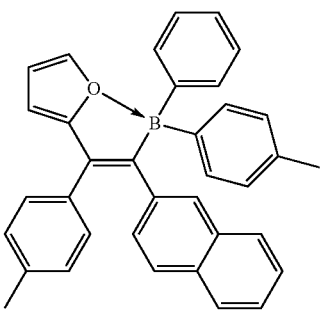
(G-18)
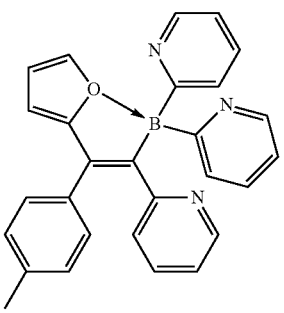
(G-19)
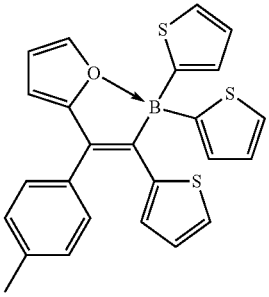
(G-20)
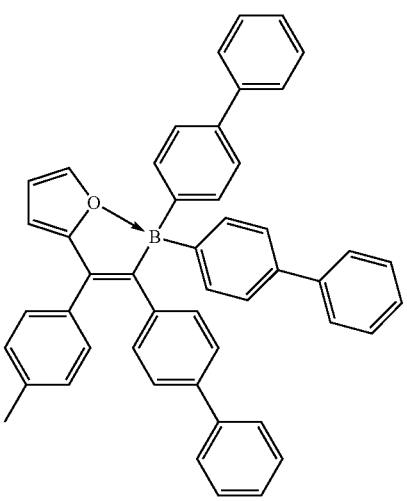

(G-21) 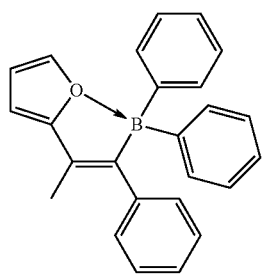
(G-22) 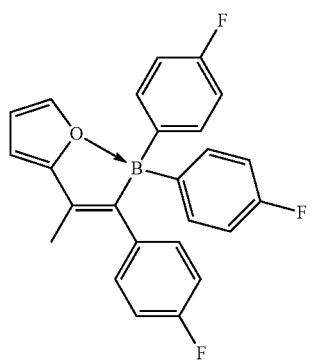
(G-25) 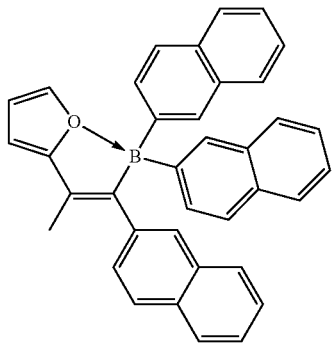
(G-26) 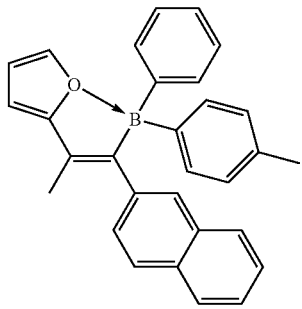
(G-23) 
(G-27) 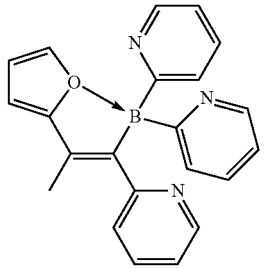
(G-24)
(G-28) 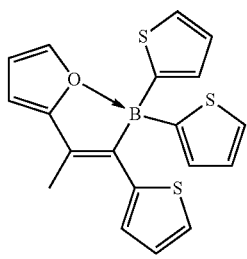

(G-29)
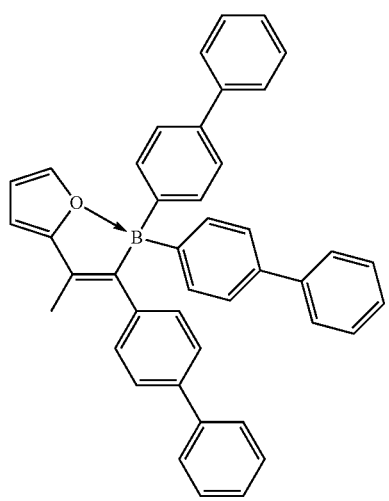
[Chemical Formula 82]
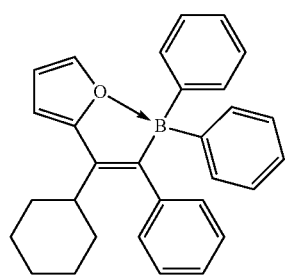
(G-30)
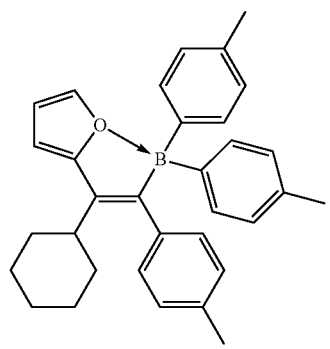
(G-31)
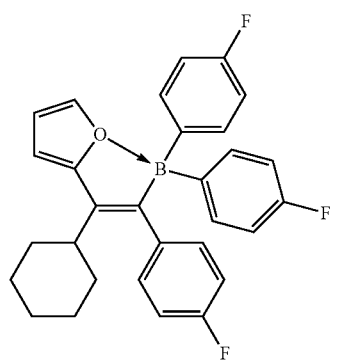
(G-32)
(G-33)
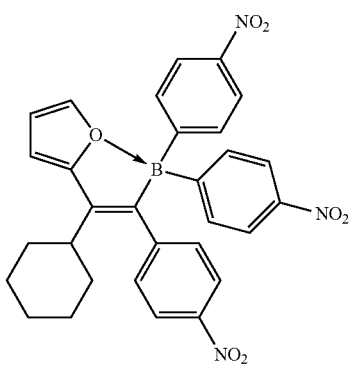
(G-34)
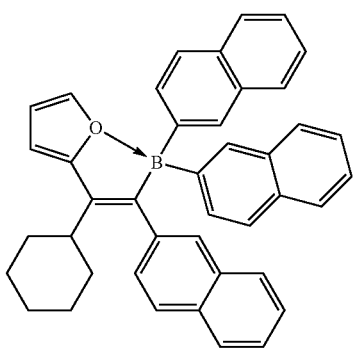
(G-35)
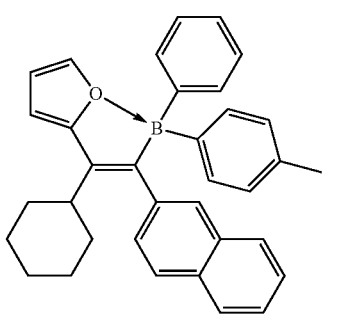
(G-36)
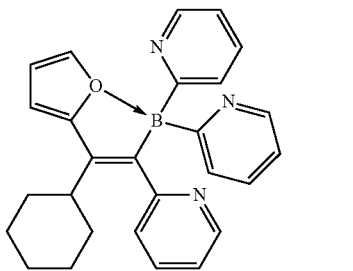
(G-37)
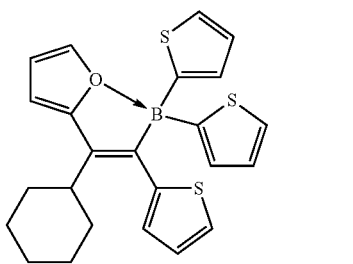

(G-38)
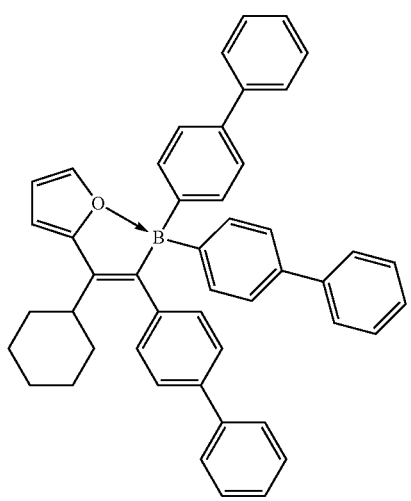
[Chemical Formula 83]
(G-39)
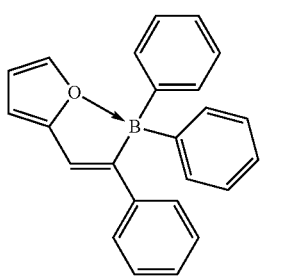
(G-40)
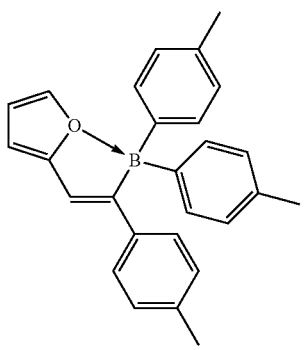
(G-41)
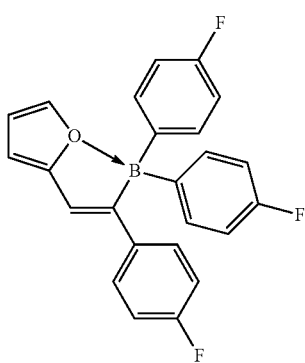
(G-42)
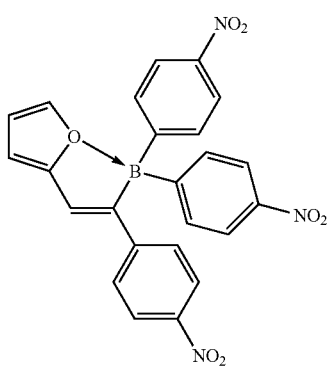
(G-43)
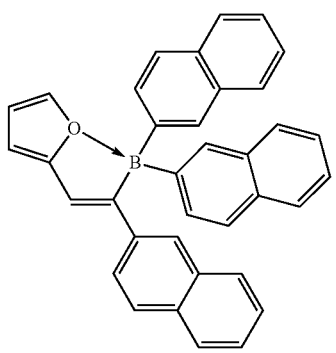
(G-44)
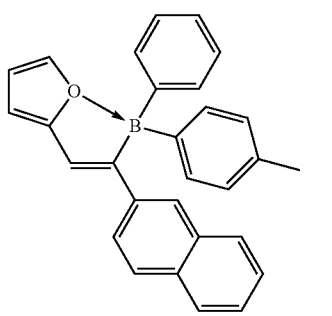
(G-45)
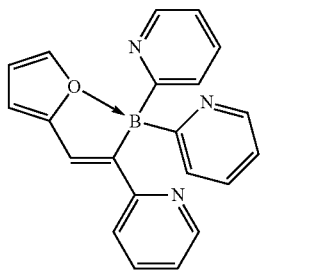
(G-46)
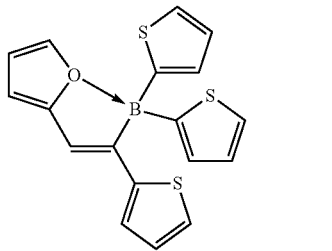

(G-47)
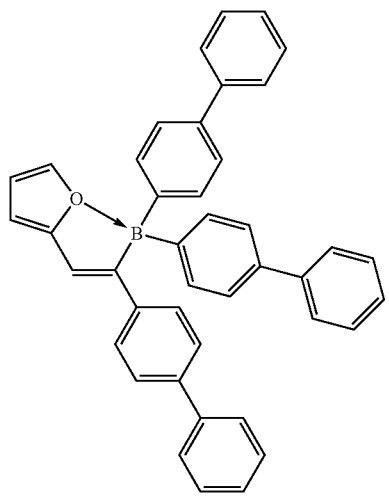
[Chemical Formula 84]
(H-1)
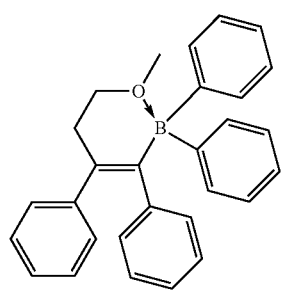
(H-2)
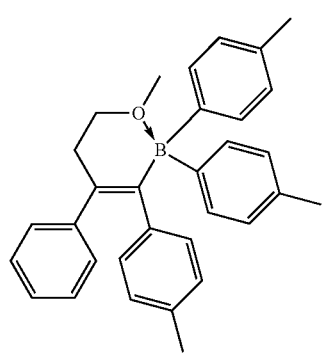
(H-3)
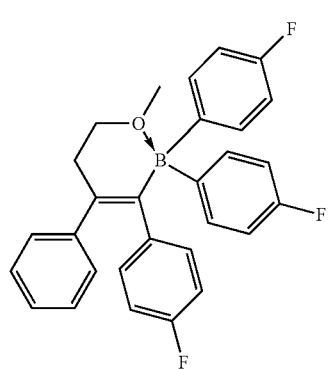
(H-4)
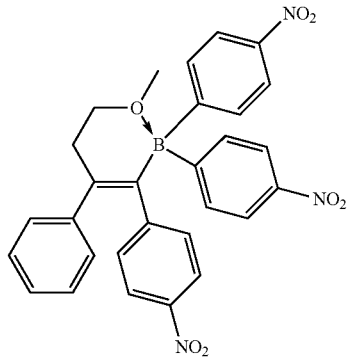
(H-5)
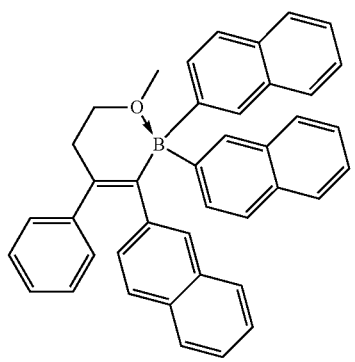
(H-6)
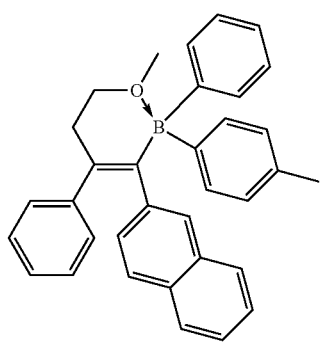
(H-7)
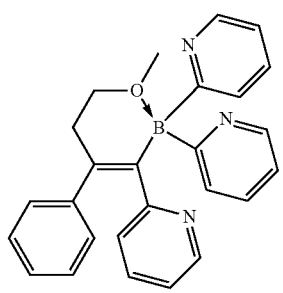
(H-8)
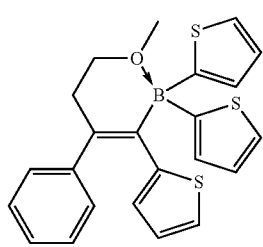

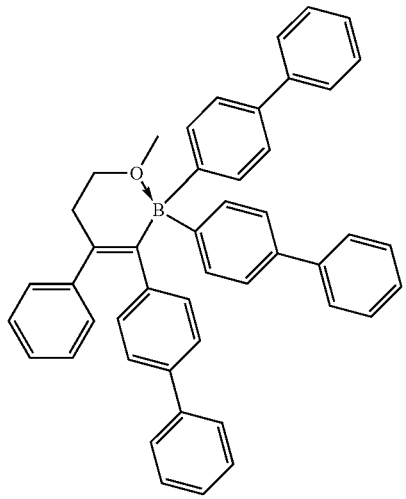
(H-9)
(H-10)
(H-11)
[Chemical Formula 85]
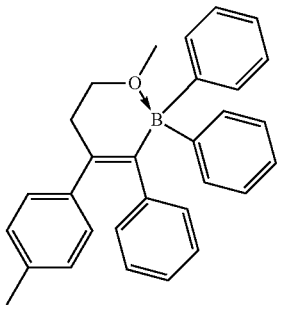
(H-12)
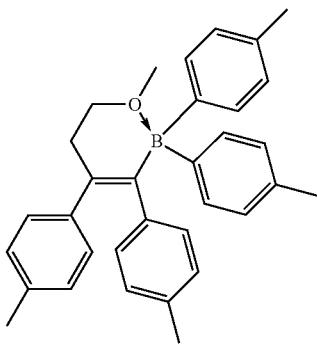
(H-13)
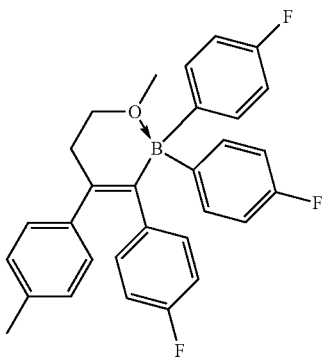
(H-14)
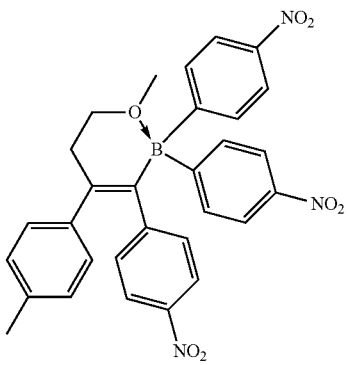
(H-15)

(H-16)
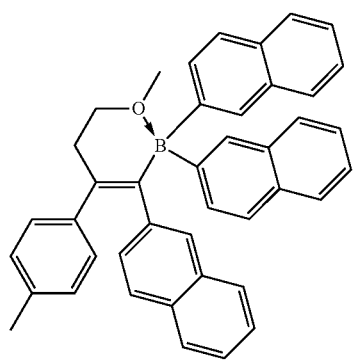
(H-17)
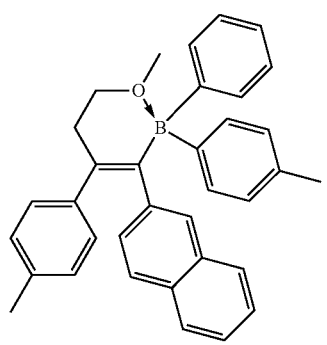
(H-18)
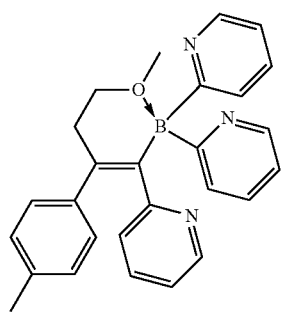
(H-19)
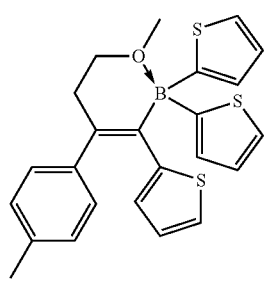
(H-20)
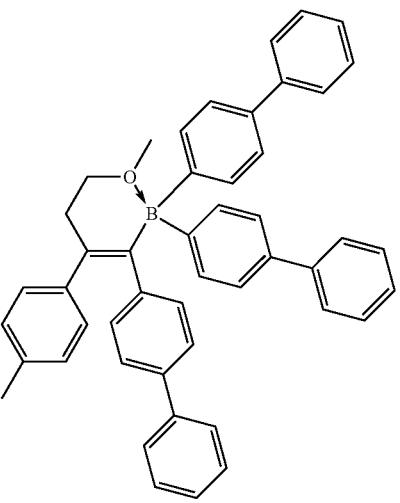
[Chemical Formula 86]
(H-21)
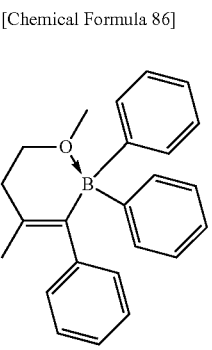
(H-22)
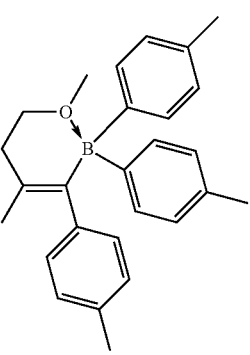
(H-23)
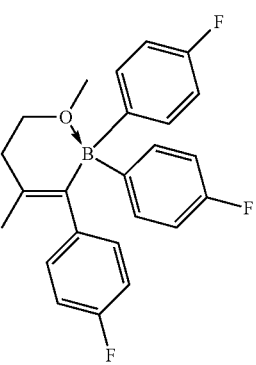

(H-24)
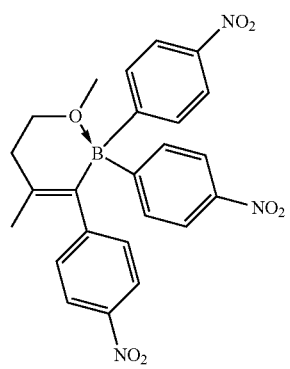
(H-25)
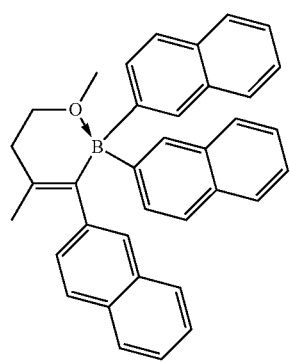
(H-26)
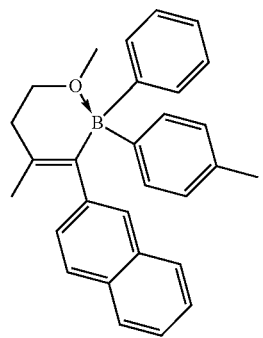
(H-27)
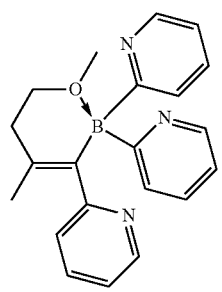
(H-28)
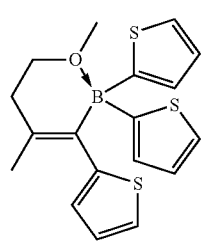
(H-29)
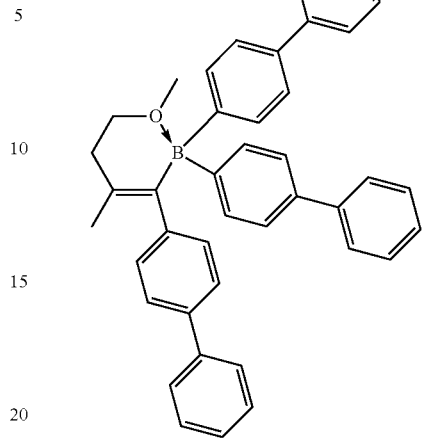
[Chemical Formula 87]
(H-30)
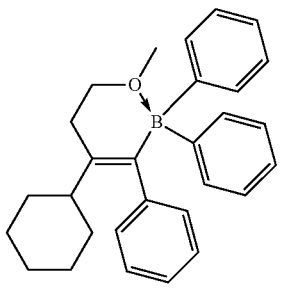
(H-31)
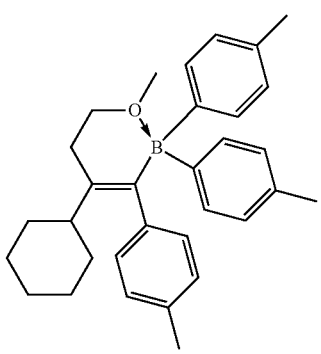
(H-32)
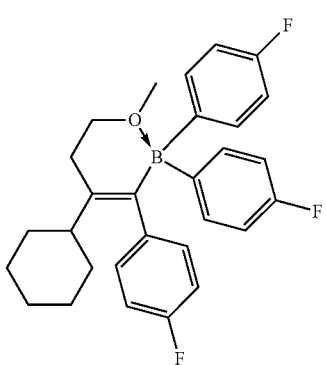

-continued
(H-33)
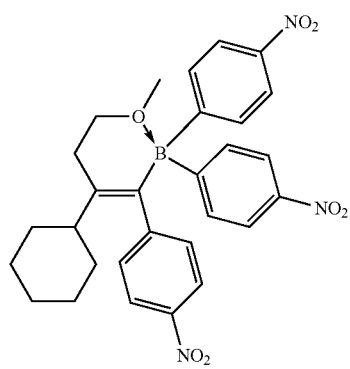
(H-34)
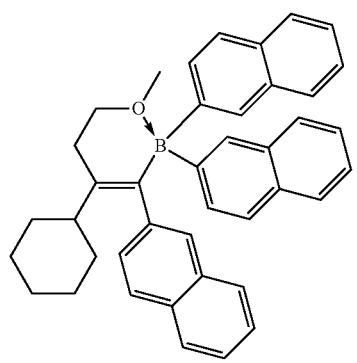
(H-35)
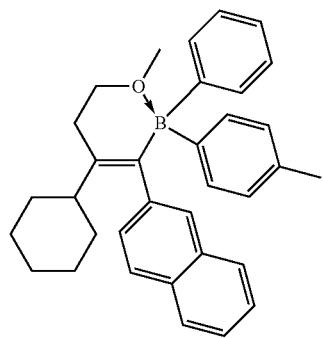
(H-36)
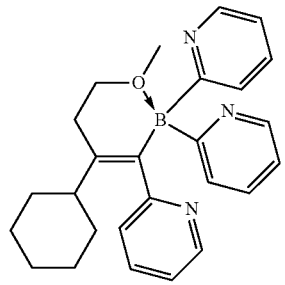
(H-37)
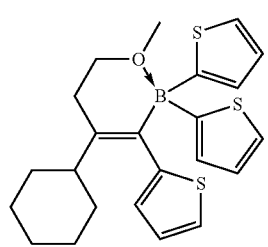
-continued
(H-38)
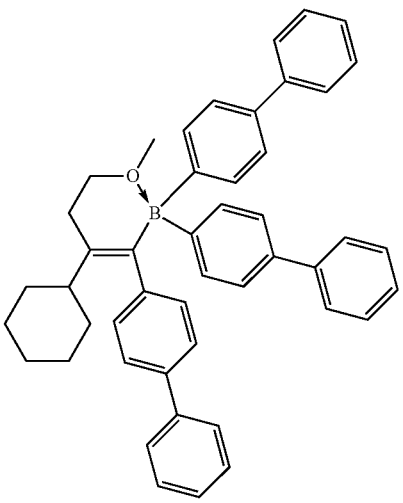
[Chemical Formula 88]
(H-39)
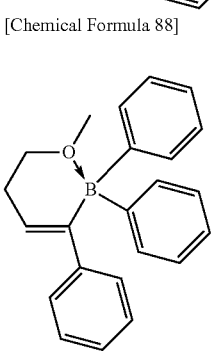
(H-40)
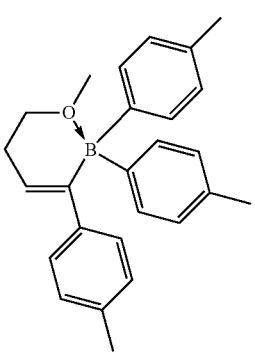
(H-41)
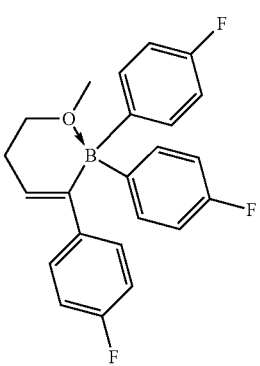

(H-42) 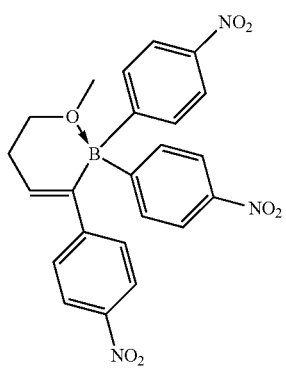
(H-43) 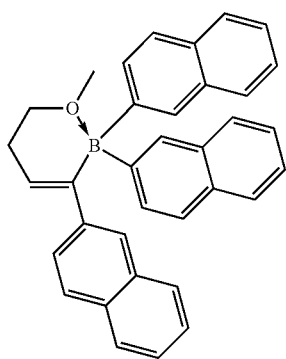
(H-44) 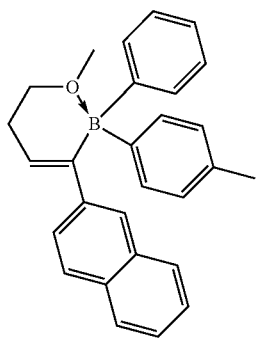
(H-45) 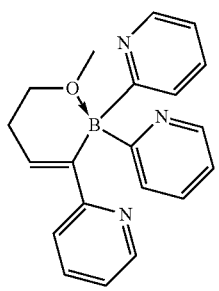
(H-46) 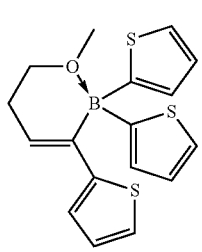
(H-47) 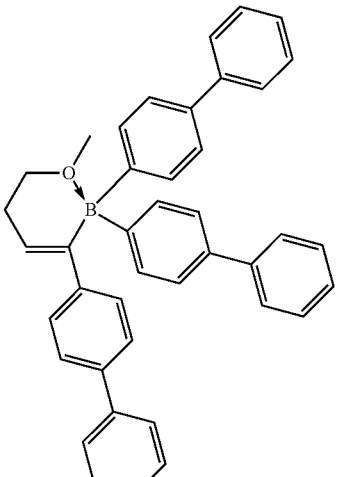
[Chemical Formula 89]
(I-1) 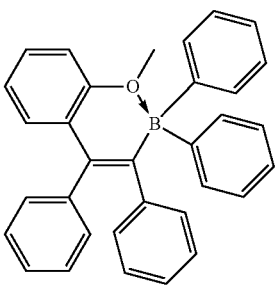
(I-2) 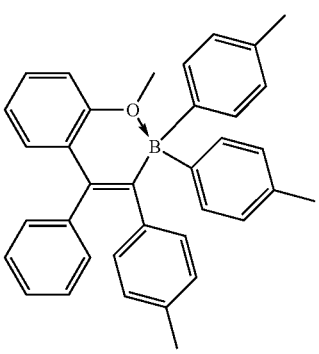
(I-3) 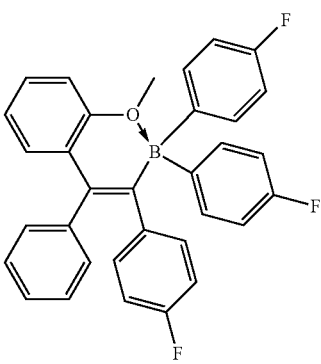

(I-4)
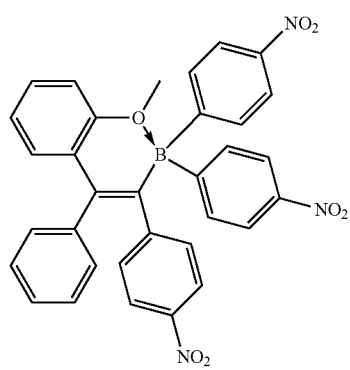
(I-5)
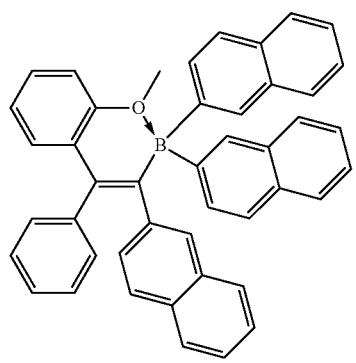
(I-6)
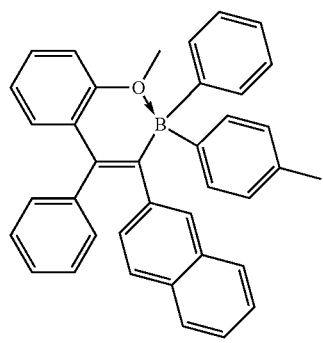
(I-7)
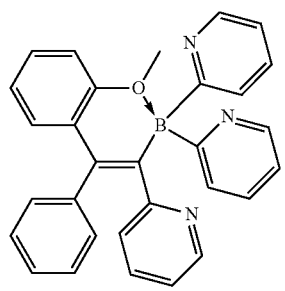
(I-8)
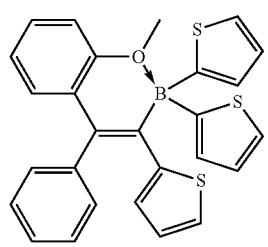
(I-9)
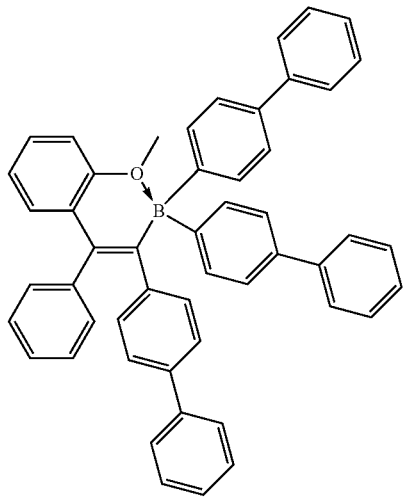
(I-10)
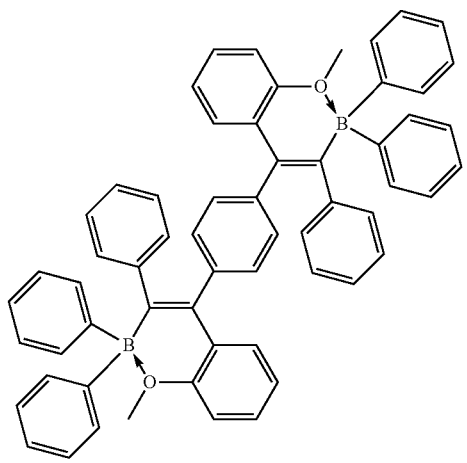
(I-11)
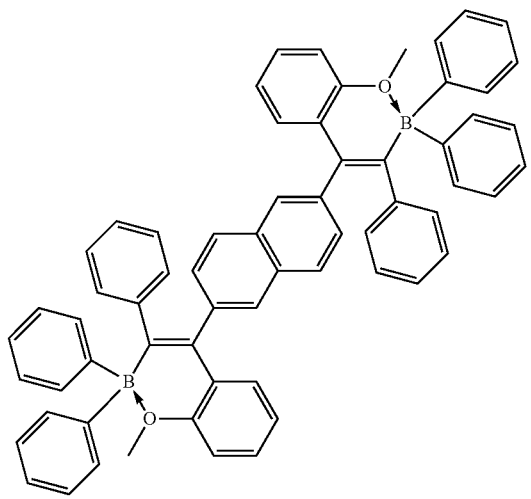

[Chemical Formula 90]
(I-12) 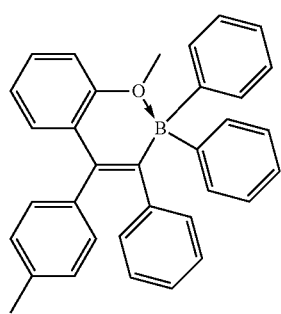
(I-13) 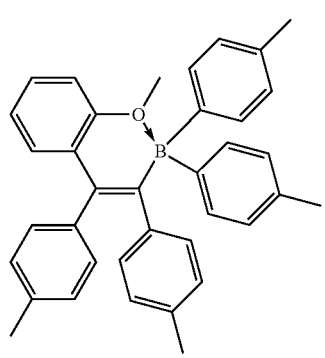
(I-14) 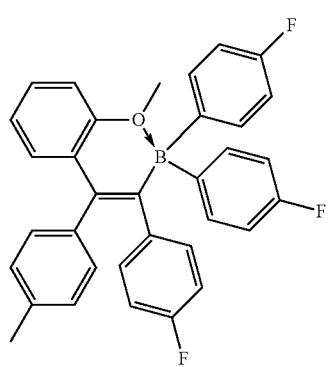
(I-15) 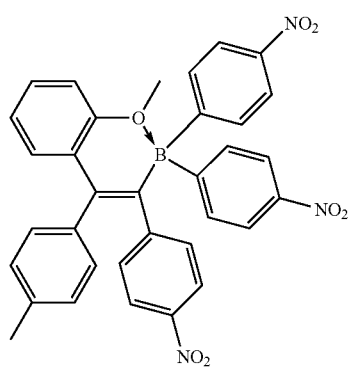
(I-16) 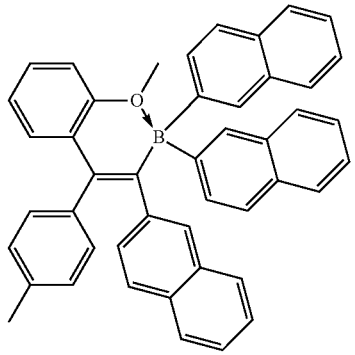
(I-17) 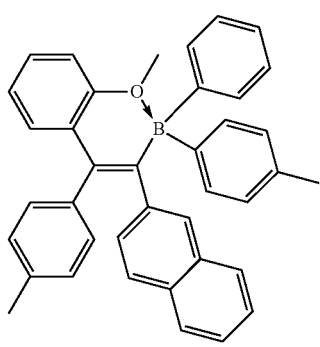
(I-18) 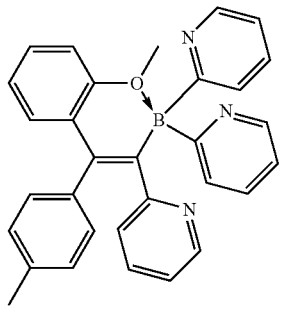
(I-19) 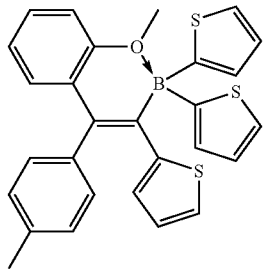

(I-20)
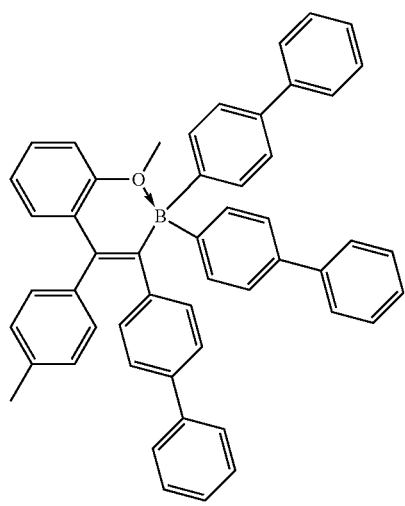
[Chemical Formula 91]
(I-21)
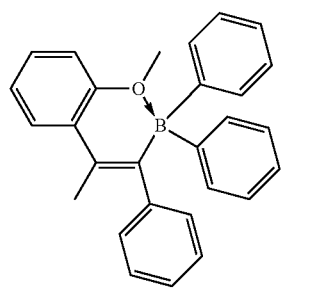
(I-22)
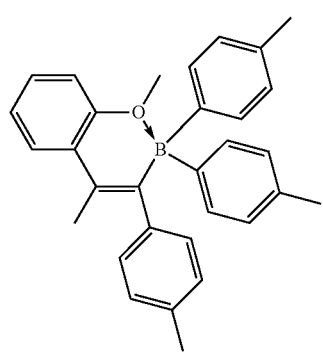
(I-23)
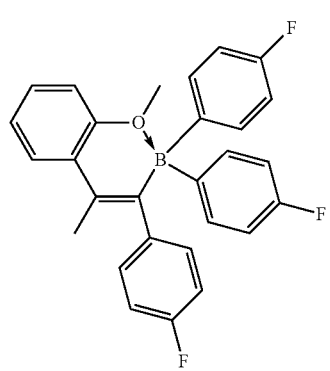
(I-24)
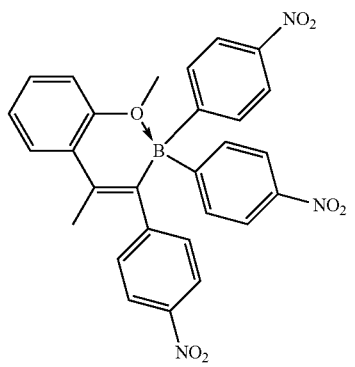
(I-25)
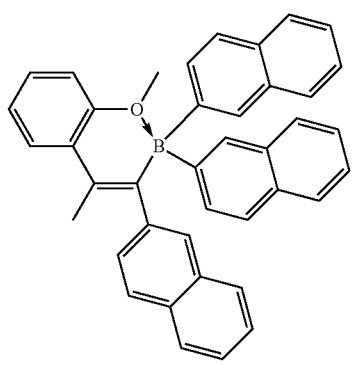
(I-26)
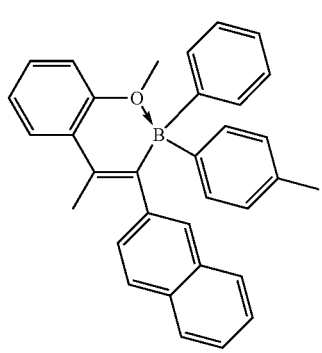
(I-27)
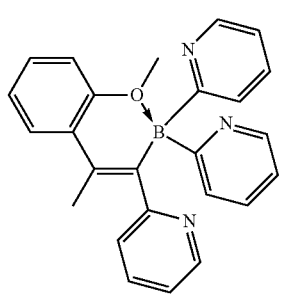
(I-28)
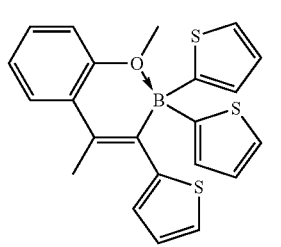

(I-29)
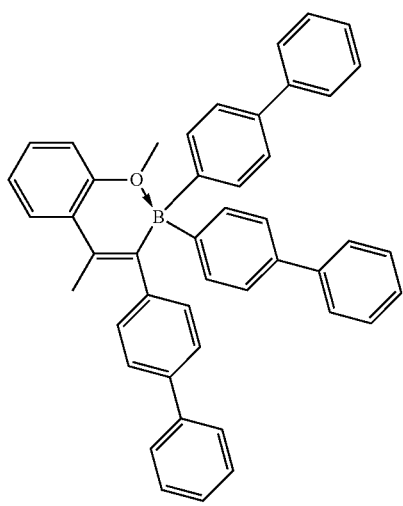
[Chemical Formula 92]
(I-30)
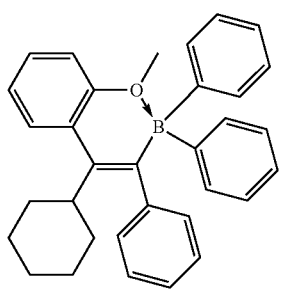
(I-31)
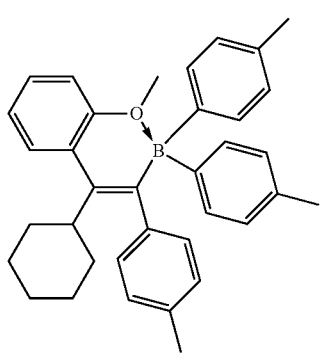
(I-32)
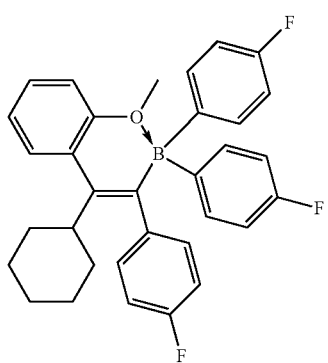
(I-33)
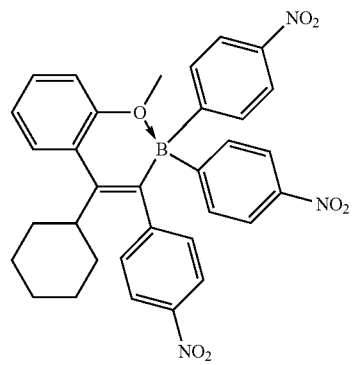
(I-34)
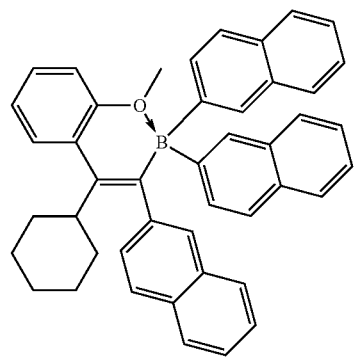
(I-35)
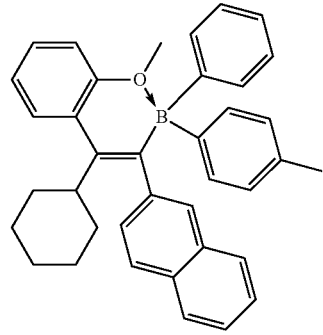
(I-36)
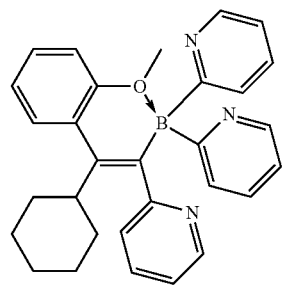
(I-37)
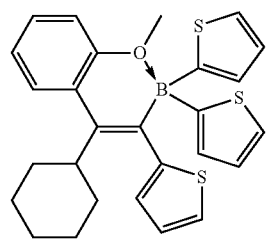

(I-38)
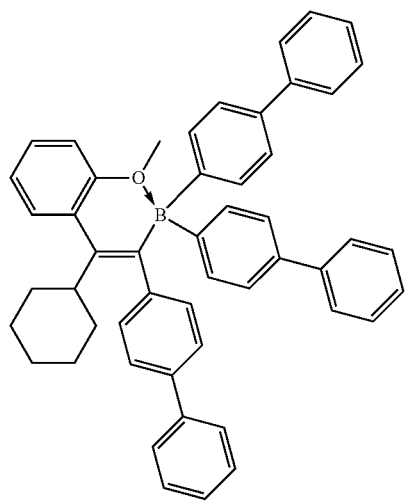
[Chemical Formula 93]
(I-39)
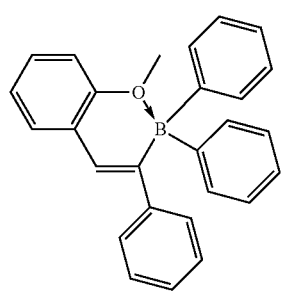
(I-40)
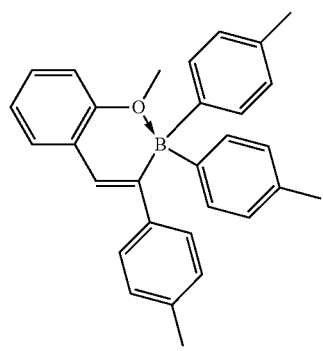
(I-41)
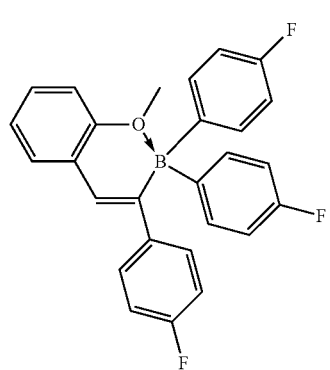
(I-42)
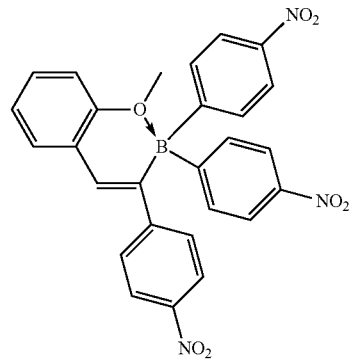
(I-43)
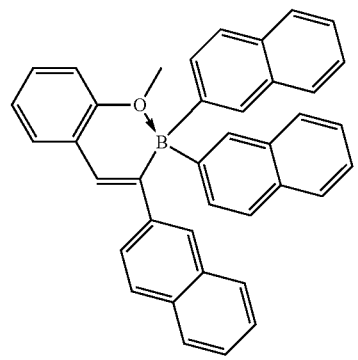
(I-44)
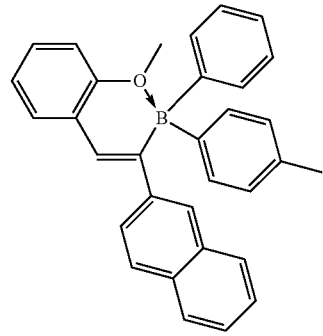
(I-45)
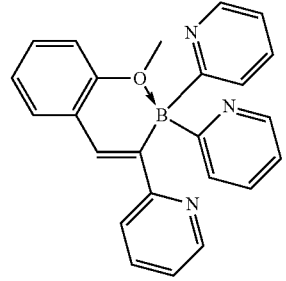
(I-46)
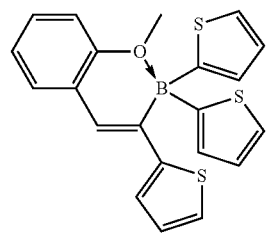

(I-47)
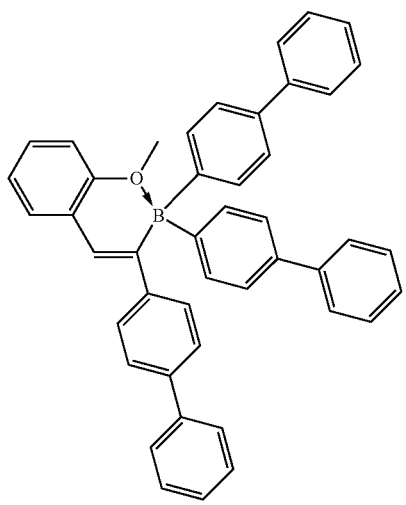
[Chemical Formula 94]
(J-1)
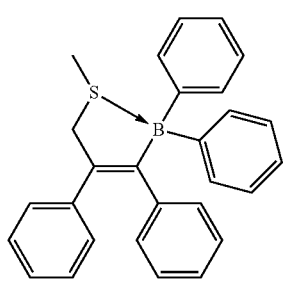
(J-2)
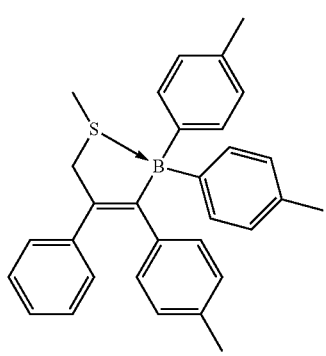
(J-3)
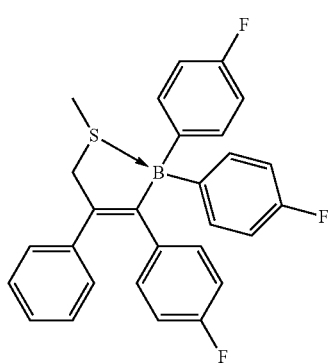
(J-4)
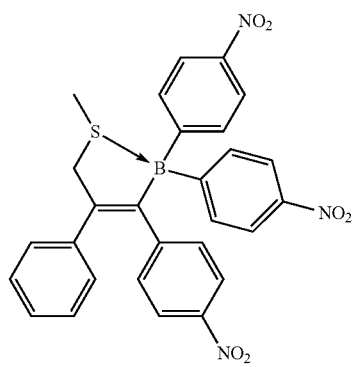
(J-5)
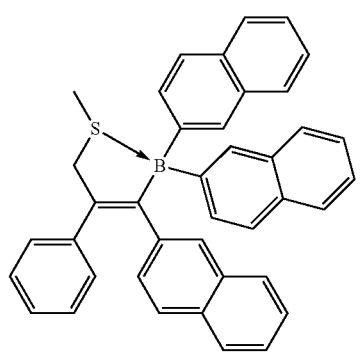
(J-6)
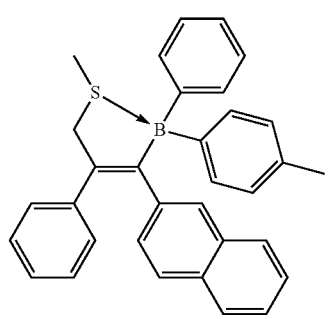
(J-7)
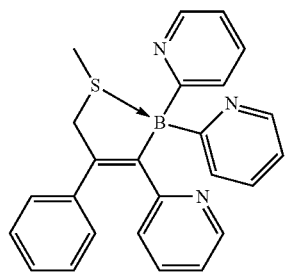
(J-8)
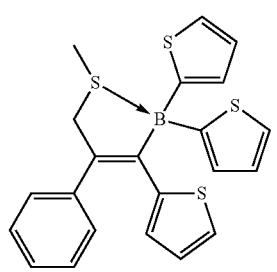

(J-9)
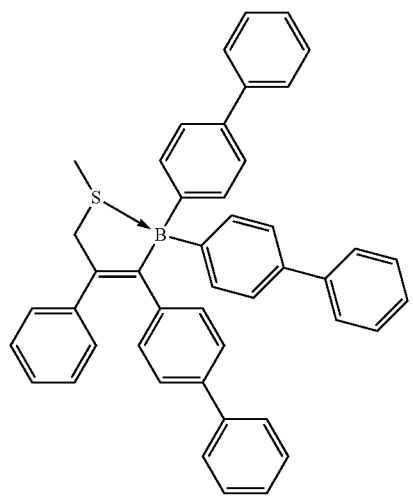
(J-10)
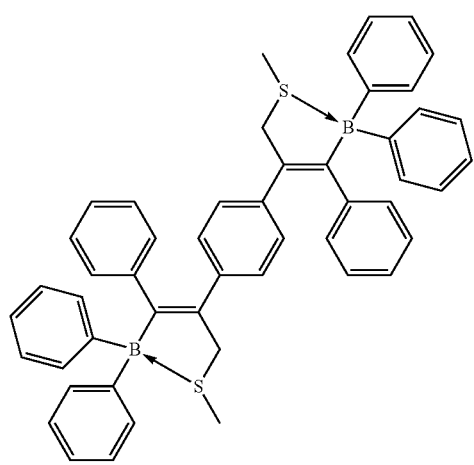
(J-11)
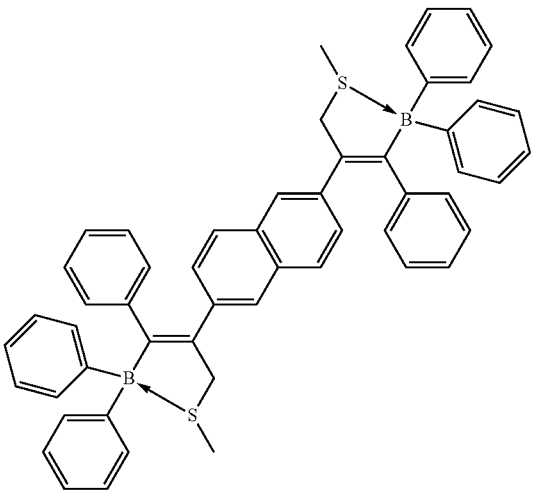
[Chemical Formula 95]
(J-12)
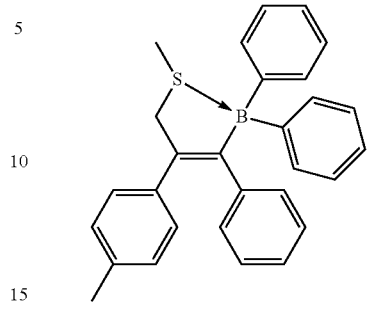
(J-13)
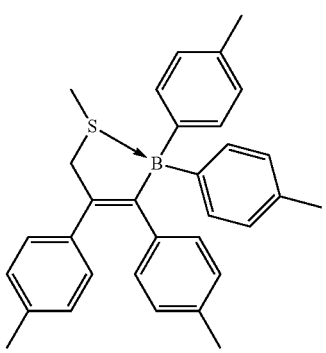
(J-14)
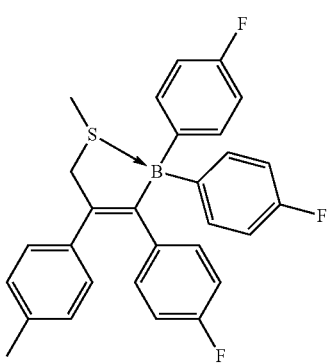
(J-15)
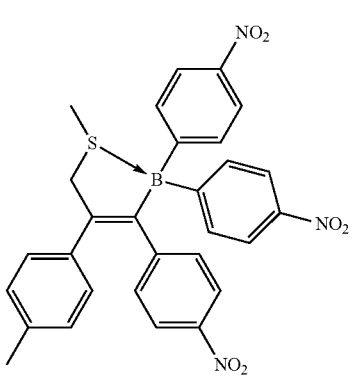

-continued
(J-16)
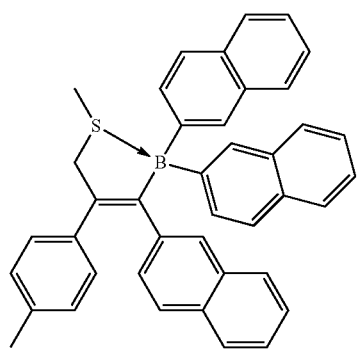
(J-17)
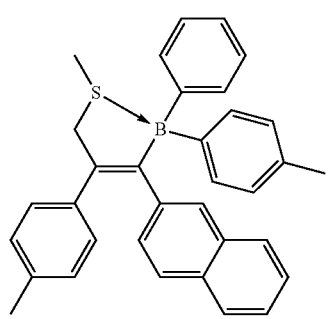
(J-18)
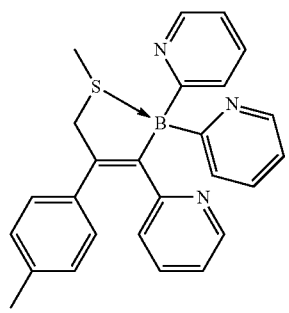
(J-19)
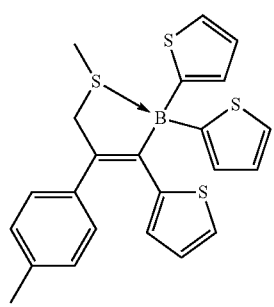
-continued
(J-20)
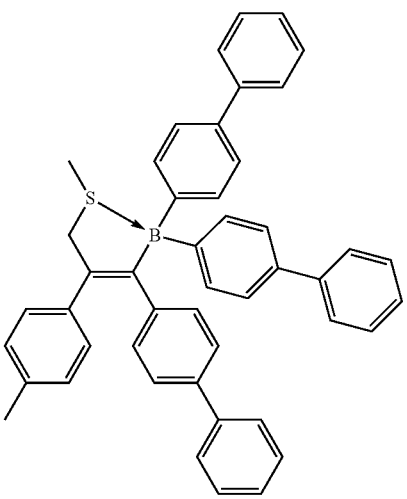
[Chemical Formula 96]
(J-21)
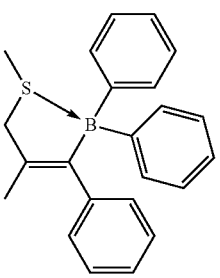
(J-22)
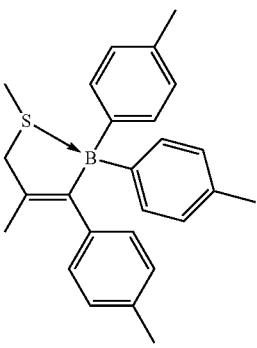
(J-23)
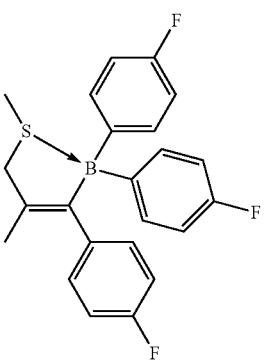

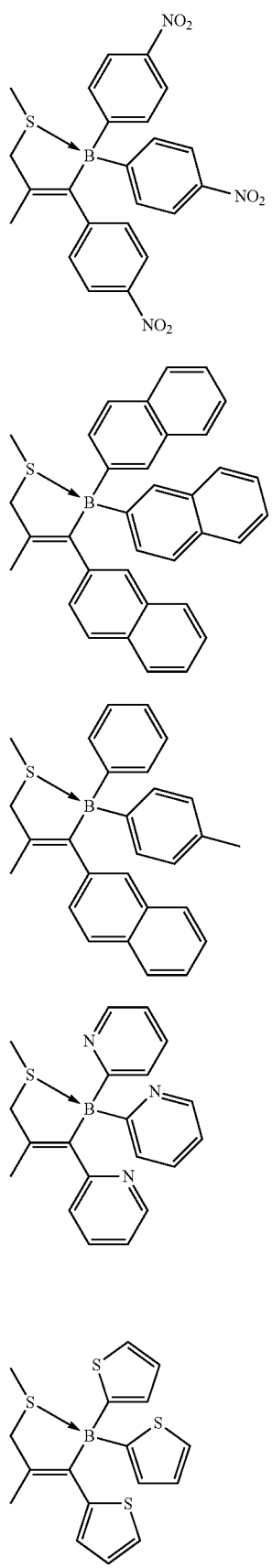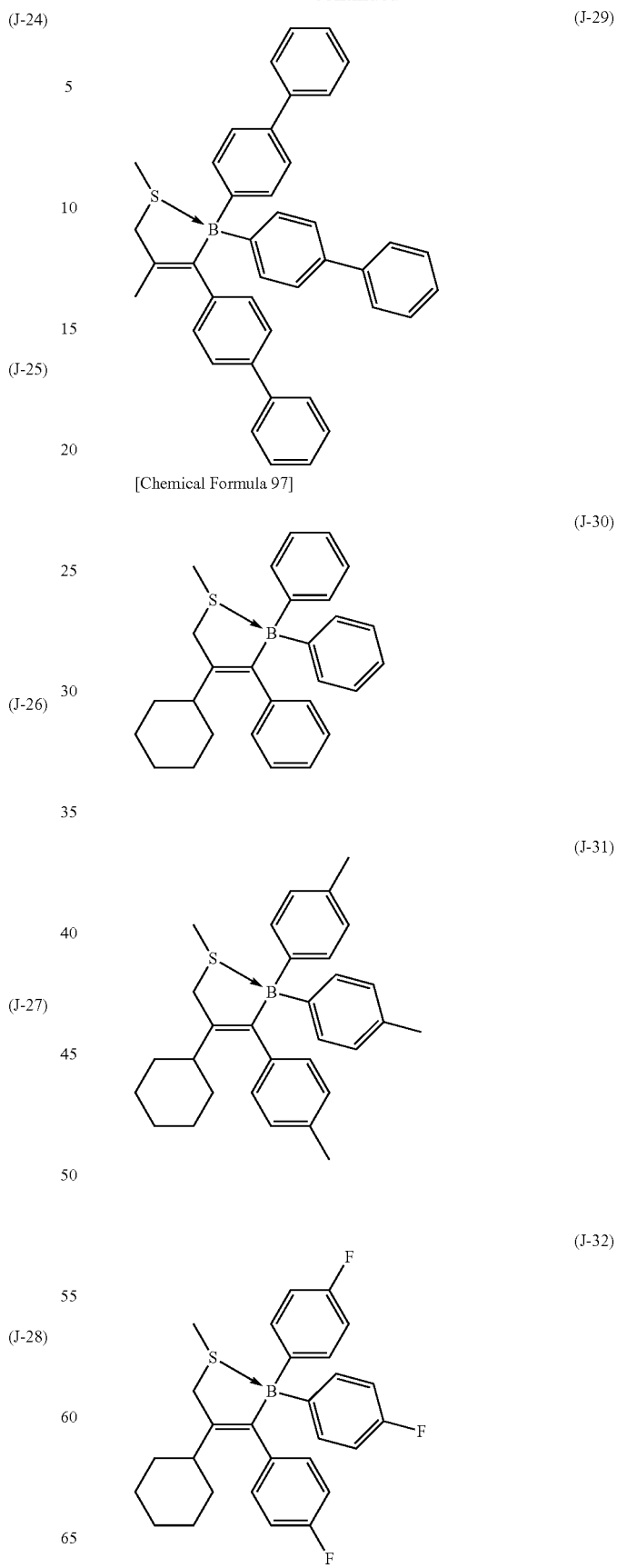
[Chemical Formula 97]

(J-33)
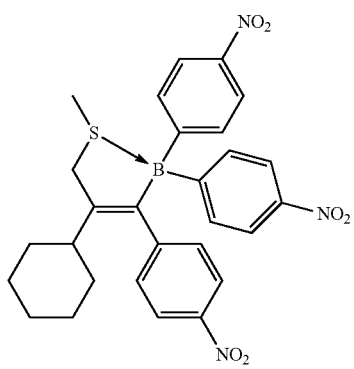
(J-34)
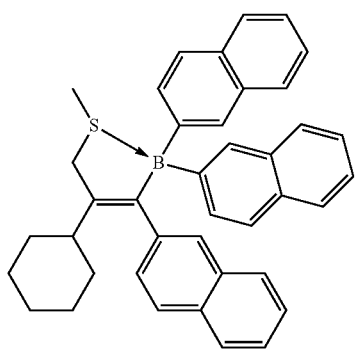
(J-35)
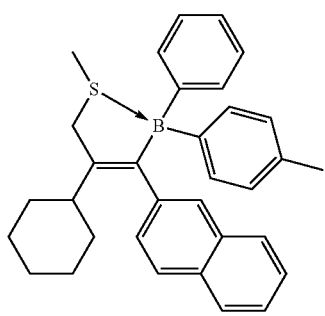
(J-36)
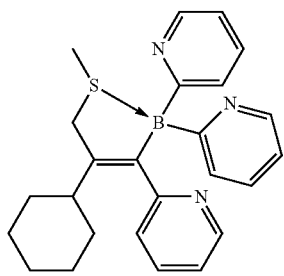
(J-37)
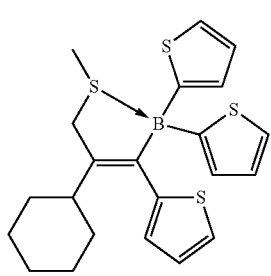
(J-38)
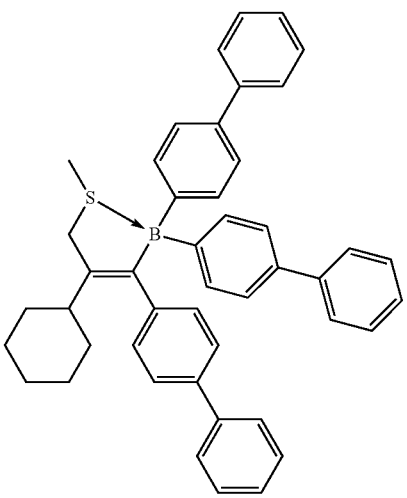
[Chemical Formula 98]
(J-39)
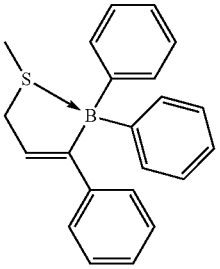
(J-40)
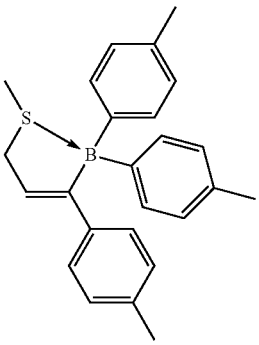
(J-41)
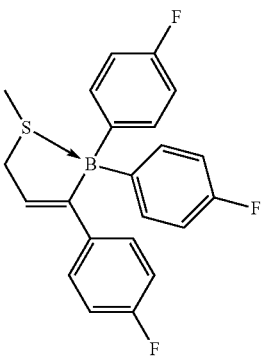

-continued
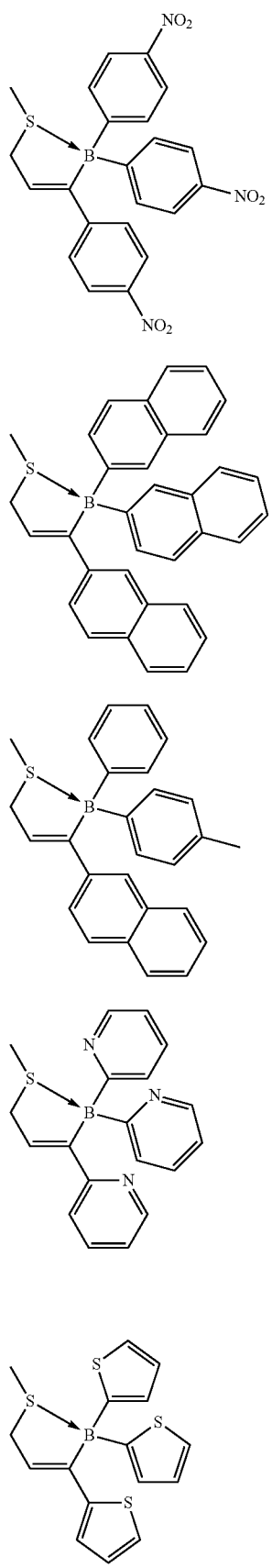
(J-42)
(J-43)
(J-44)
(J-45)
(J-46)
-continued
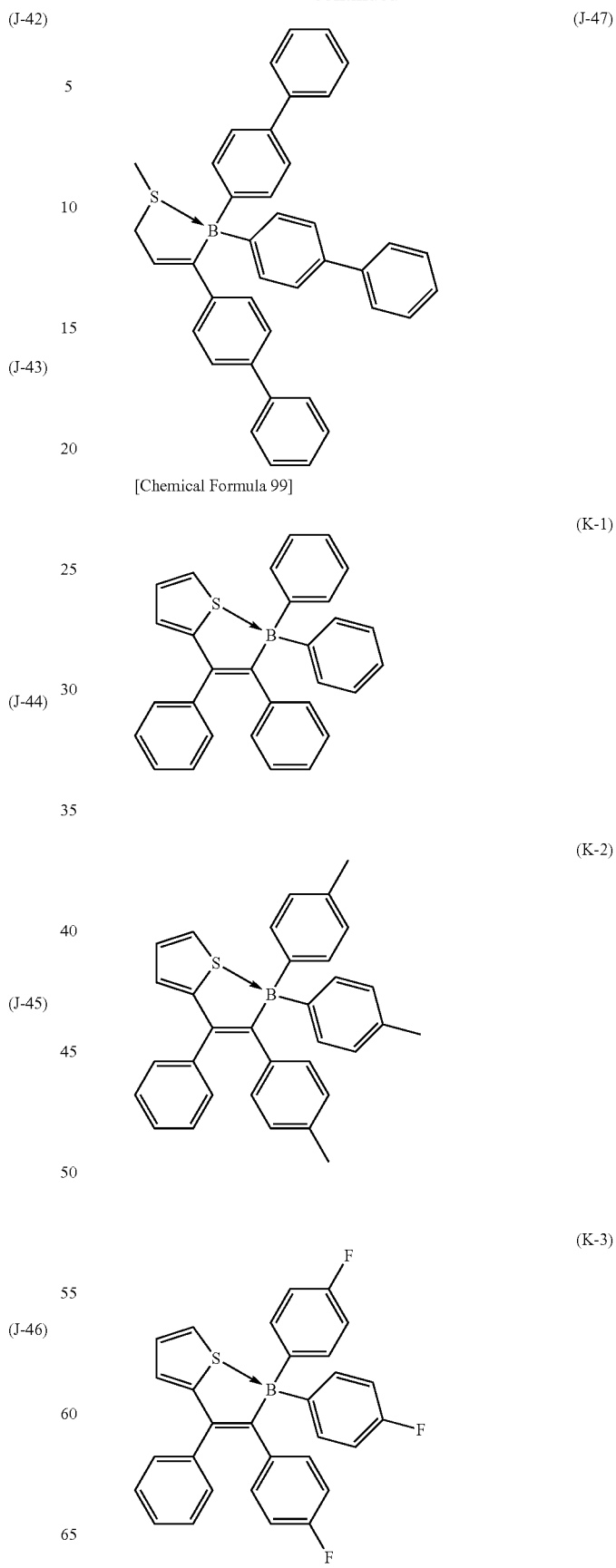
(J-47)
[Chemical Formula 99]
(K-1)
(K-2)
(K-3)

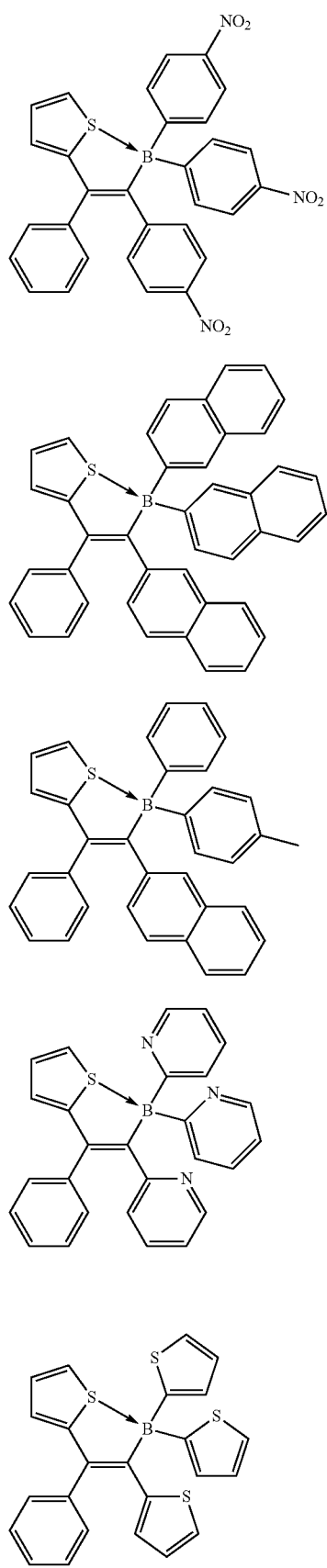
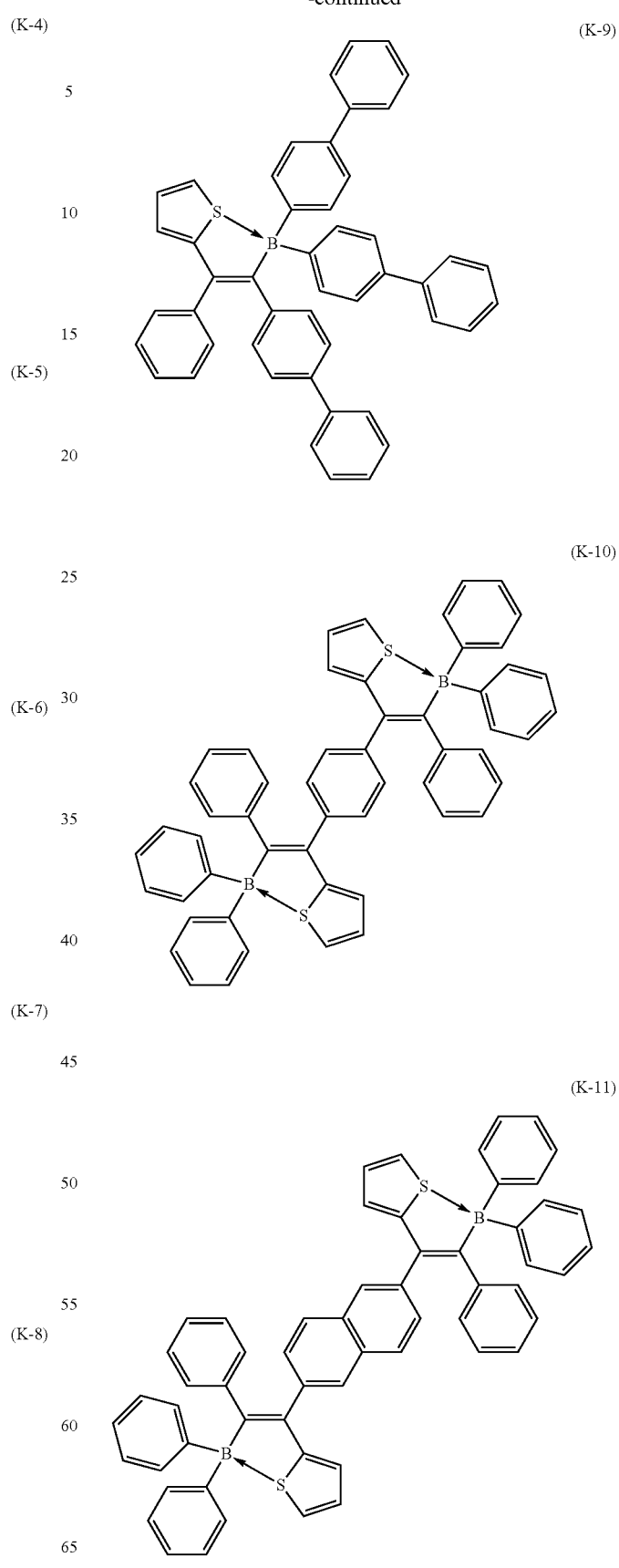

[Chemical Formula 100]
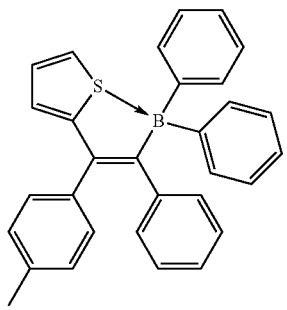 (K-12)
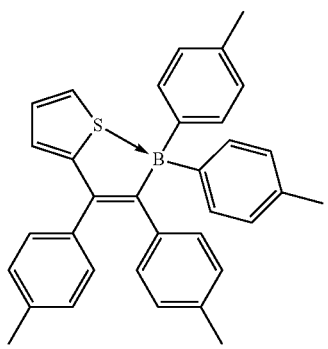 (K-13)
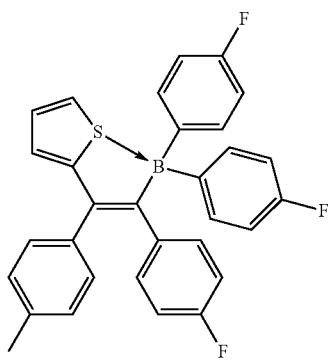 (K-14)
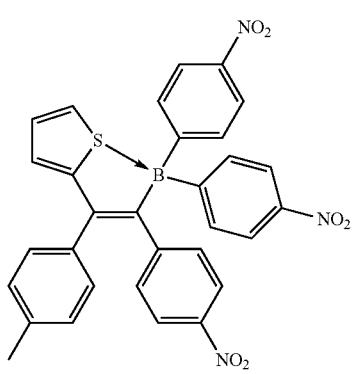 (K-15)
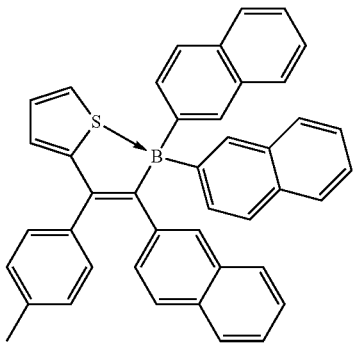 (K-16)
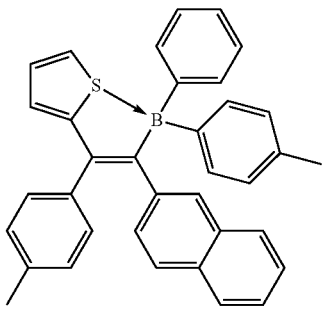 (K-17)
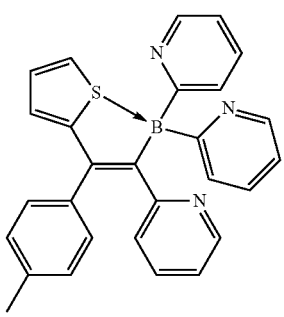 (K-18)
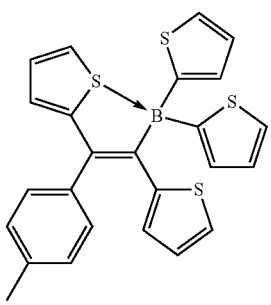 (K-19)

(K-20)
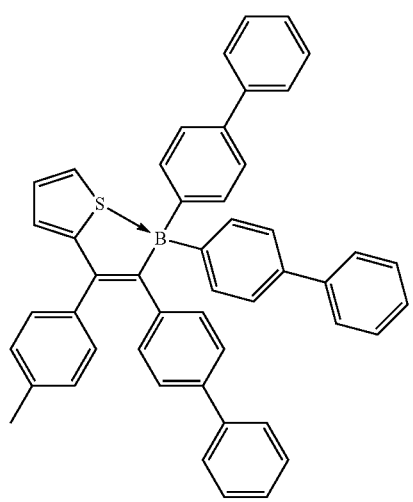
[Chemical Formula 101]
(K-21)
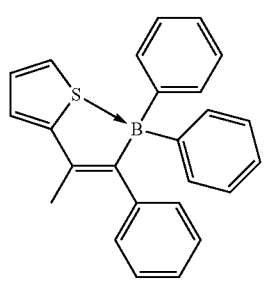
(K-22)
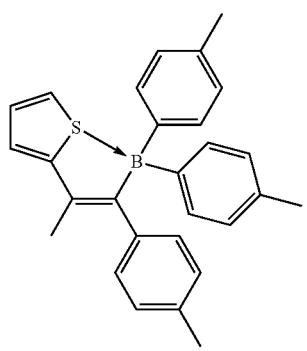
(K-23)
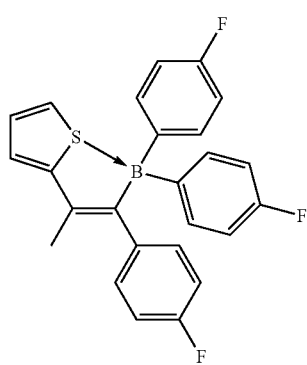
(K-24)
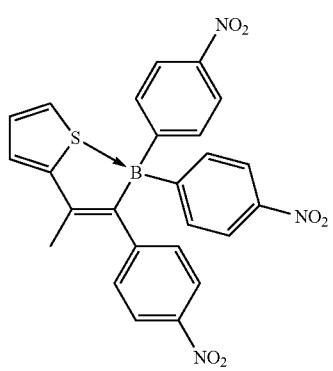
(K-25)
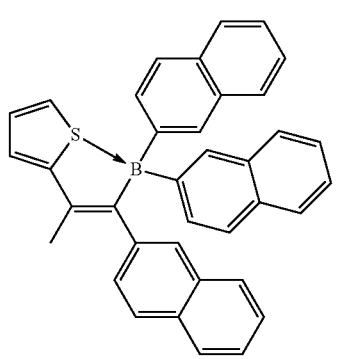
(K-26)
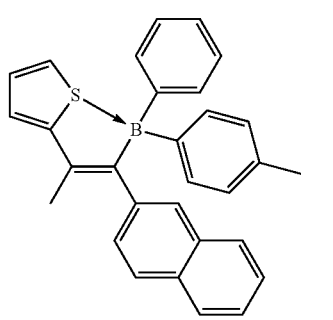
(K-27)
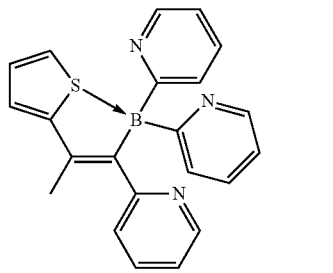
(K-28)
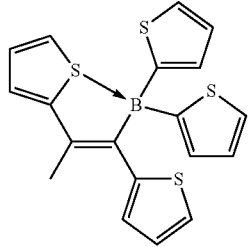

(K-29)
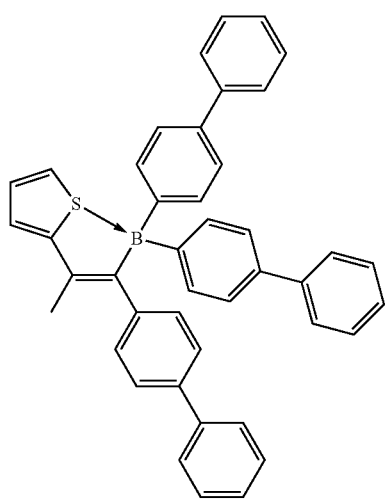
[Chemical Formula 102]
(K-30)
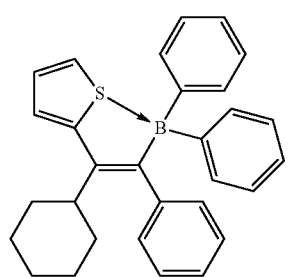
(K-31)
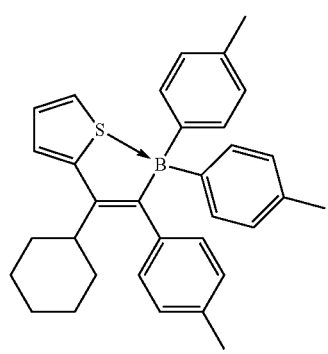
(K-32)
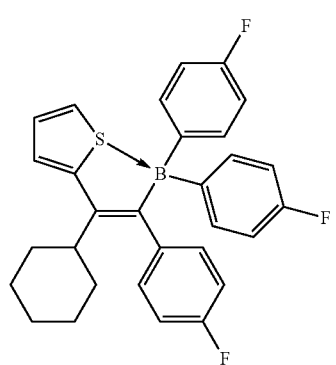
(K-33)
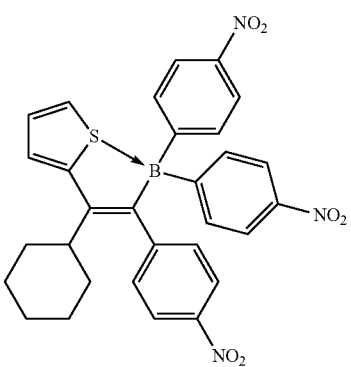
(K-34)
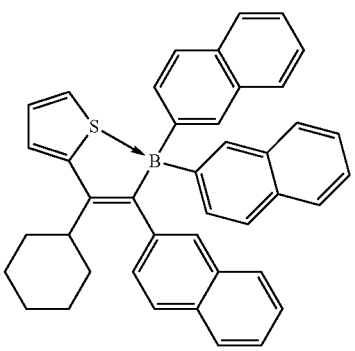
(K-35)
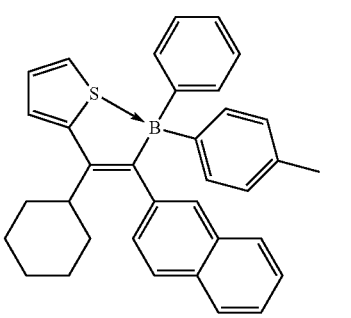
(K-36)
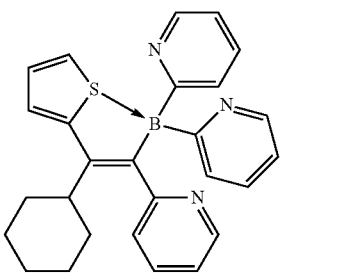
(K-37)
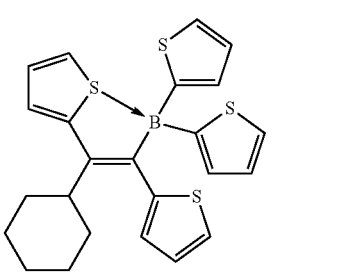

137
-continued
(K-38)
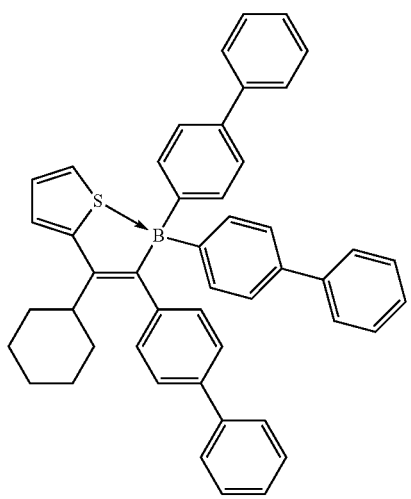
[Chemical Formula 103]
(K-39)
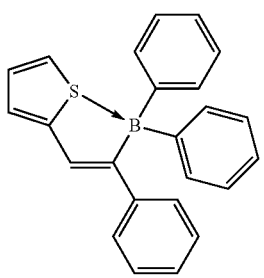
(K-40)
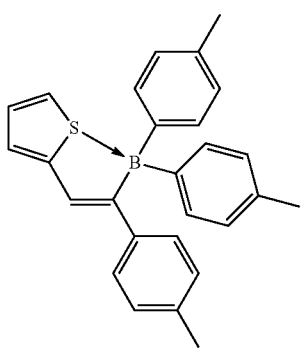
(K-41)
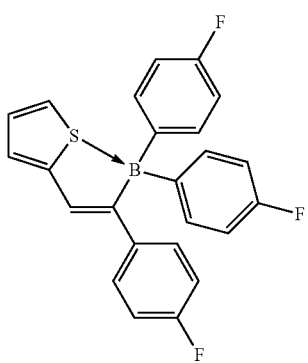
138
-continued
(K-42)
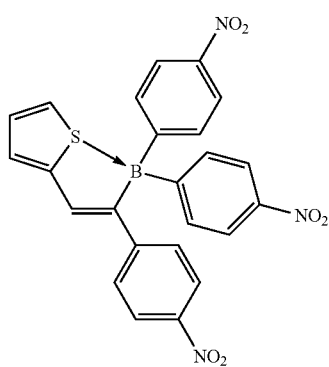
(K-43)
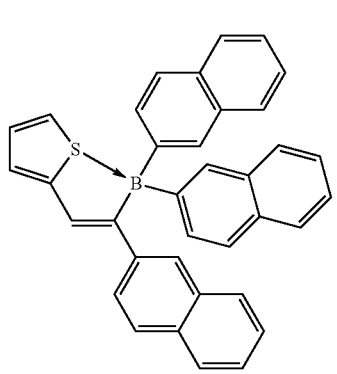
(K-44)
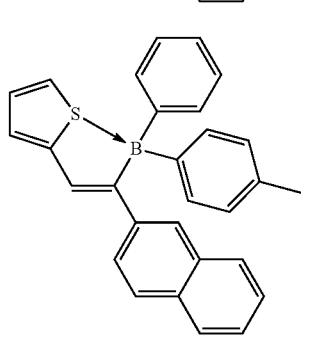
(K-45)
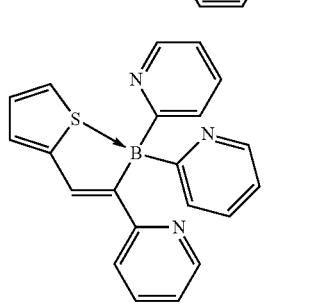
(K-46)
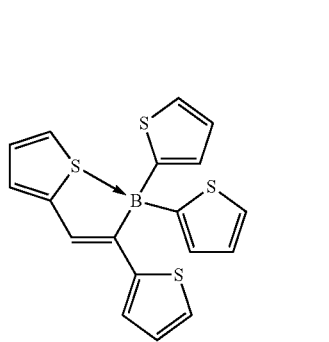

(K-47)
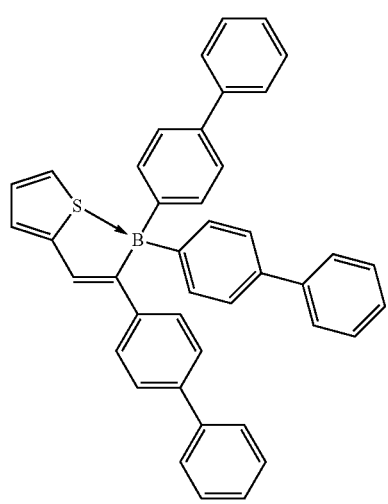
(K-48)
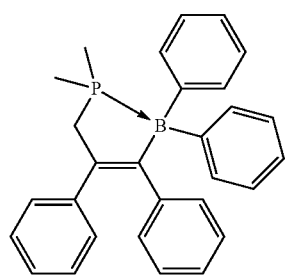
[Chemical Formula 104]
(L-1)
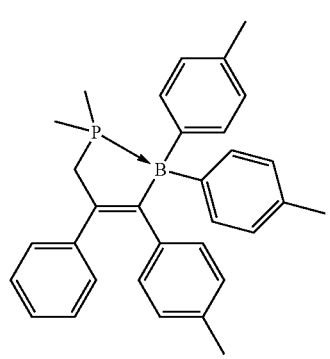
(L-2)
(L-3)
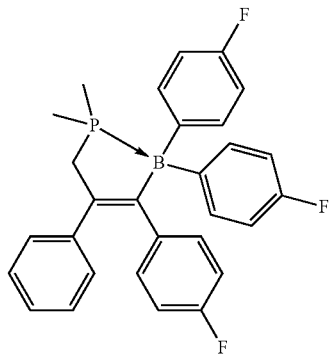
(L-4)
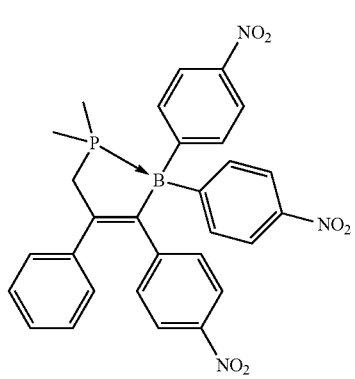
(L-5)
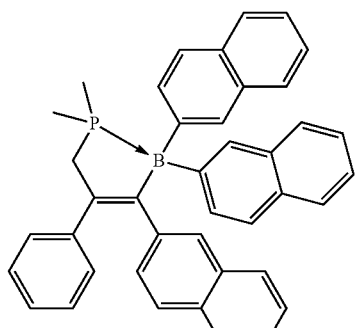
(L-6)
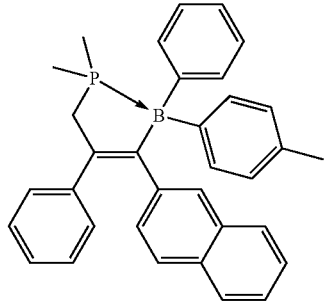
(L-7)
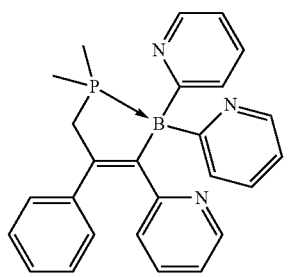

(L-8)
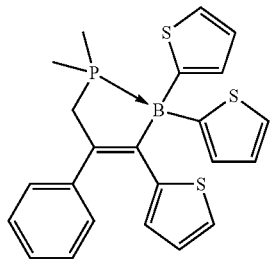
(L-9)
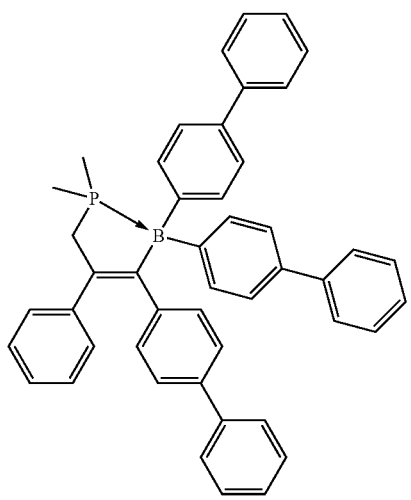
(L-10)
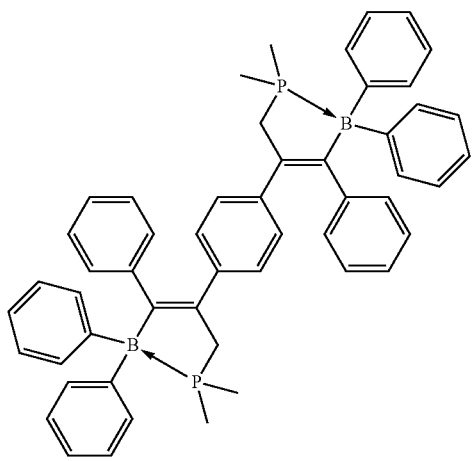
(L-11)
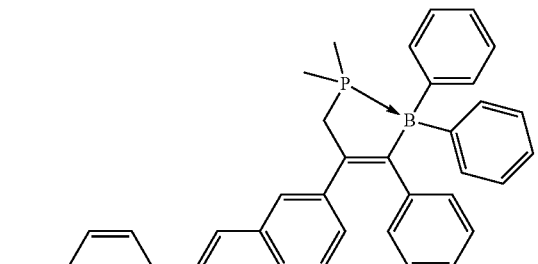
[Chemical Formula 105]
(L-12)
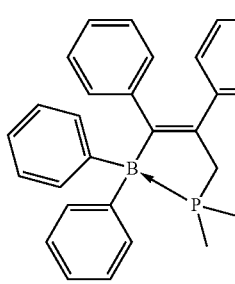
(L-13)
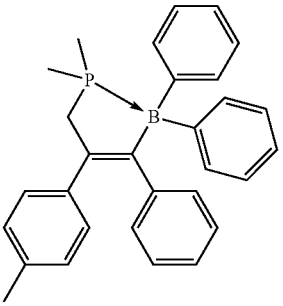
(L-14)
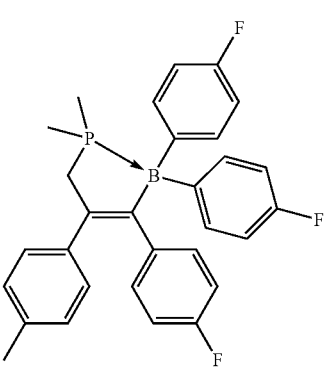

(L-15) 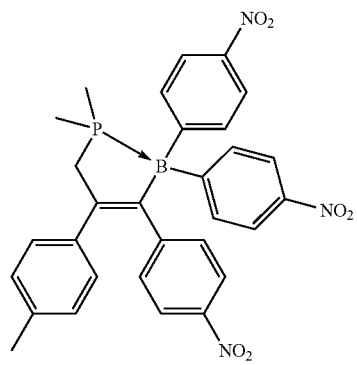
(L-16) 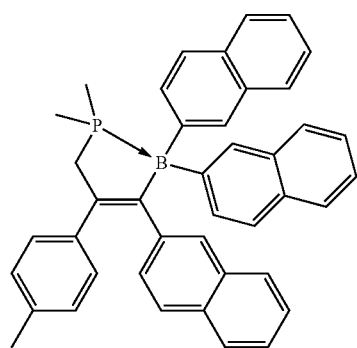
(L-17) 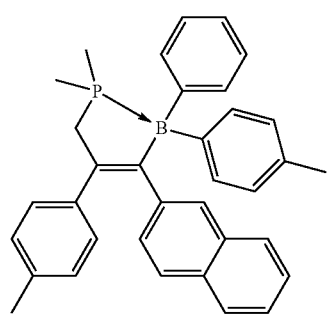
(L-18) 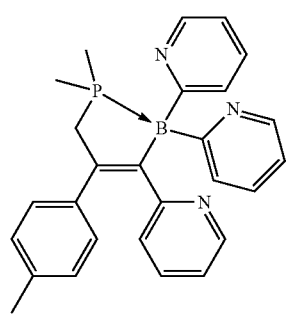
(L-19) 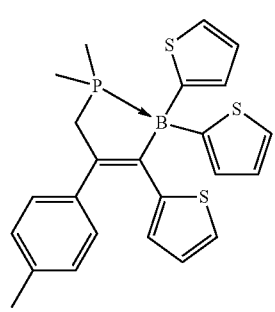
(L-20) 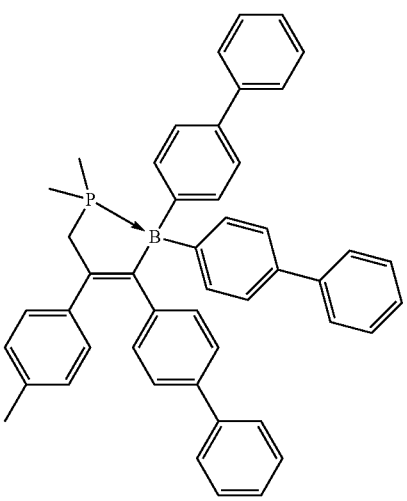
[Chemical Formula 106]
(L-21) 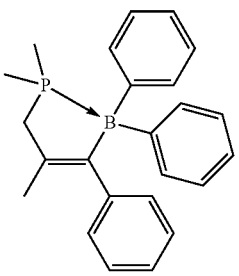
(L-22) 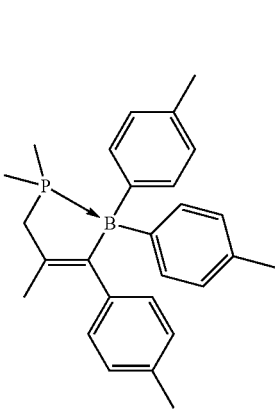
(L-23) 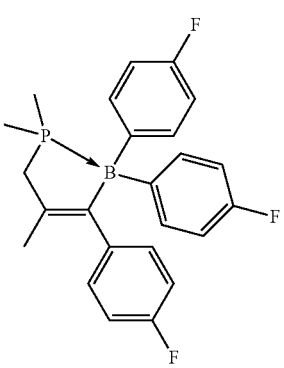

(L-24)
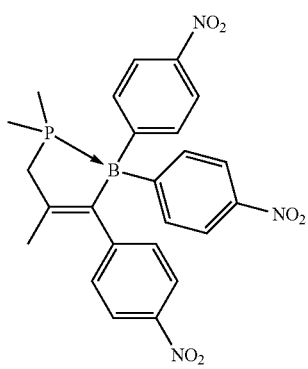
(L-25)
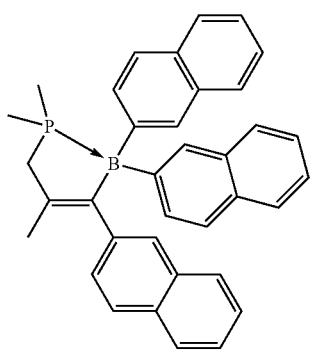
(L-26)
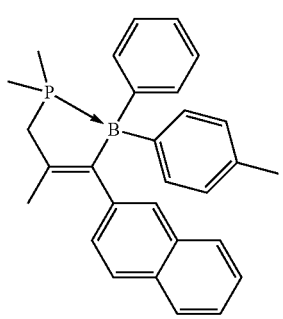
(L-27)
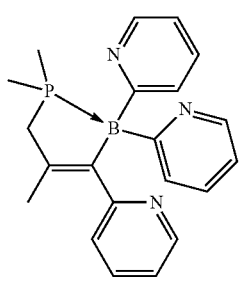
(L-28)
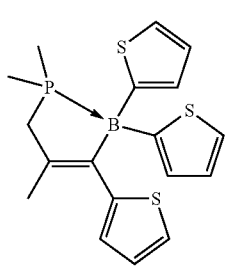
(L-29)
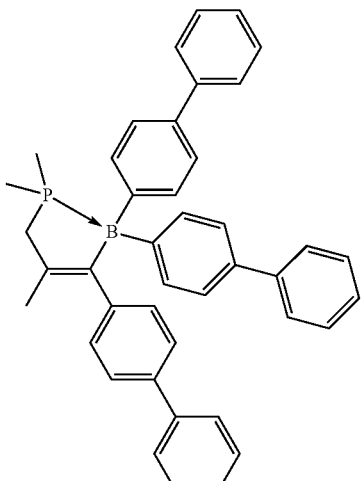
[Chemical Formula 107]
(L-30)
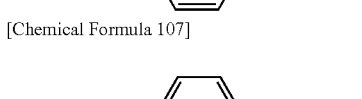
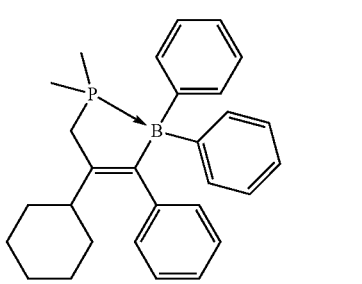
(L-31)
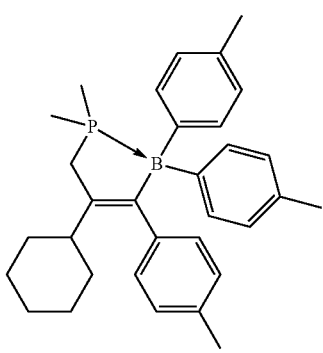
(L-32)
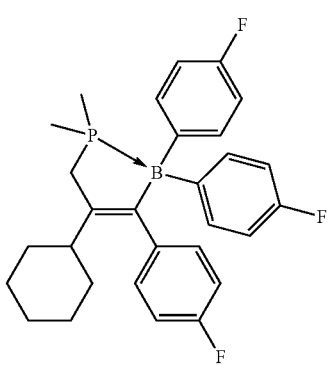

(L-33)
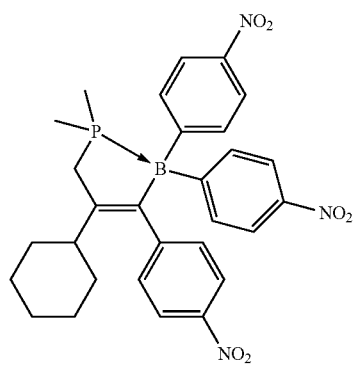
(L-34)
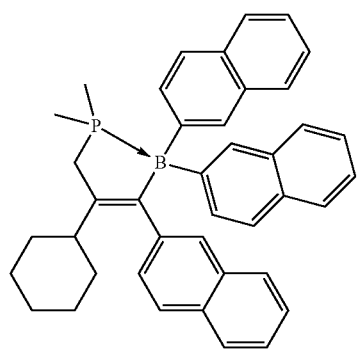
(L-35)
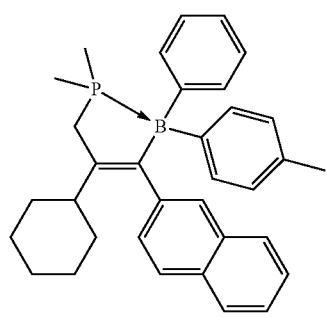
(L-36)
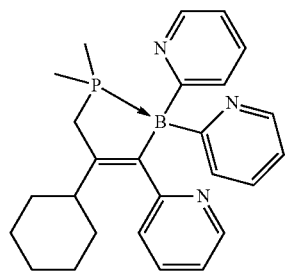
(L-37)
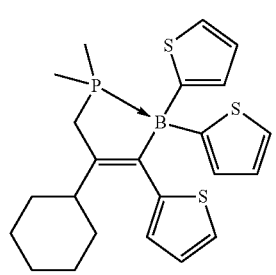
(L-38)
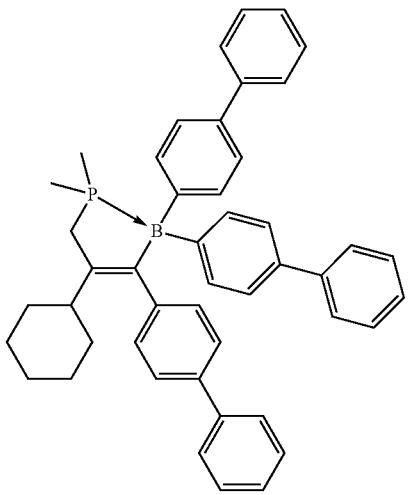
[Chemical Formula 108]
(L-39)
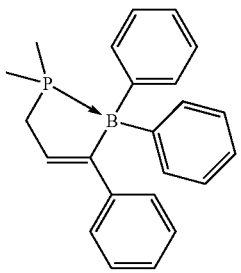
(L-40)
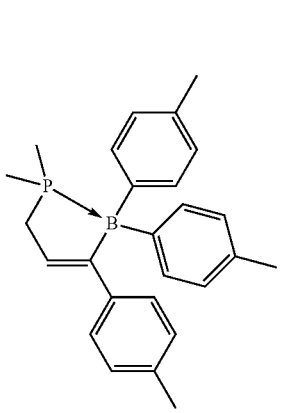
(L-41)
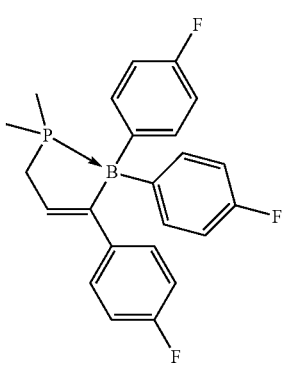

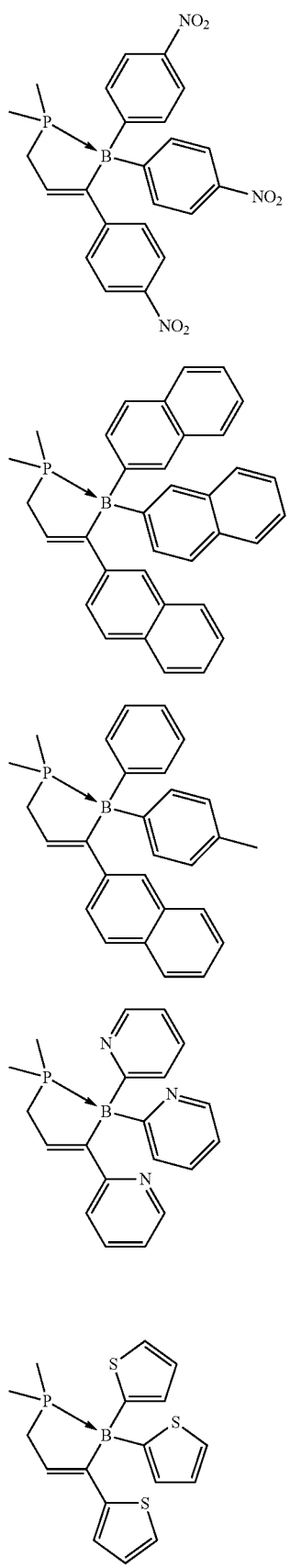
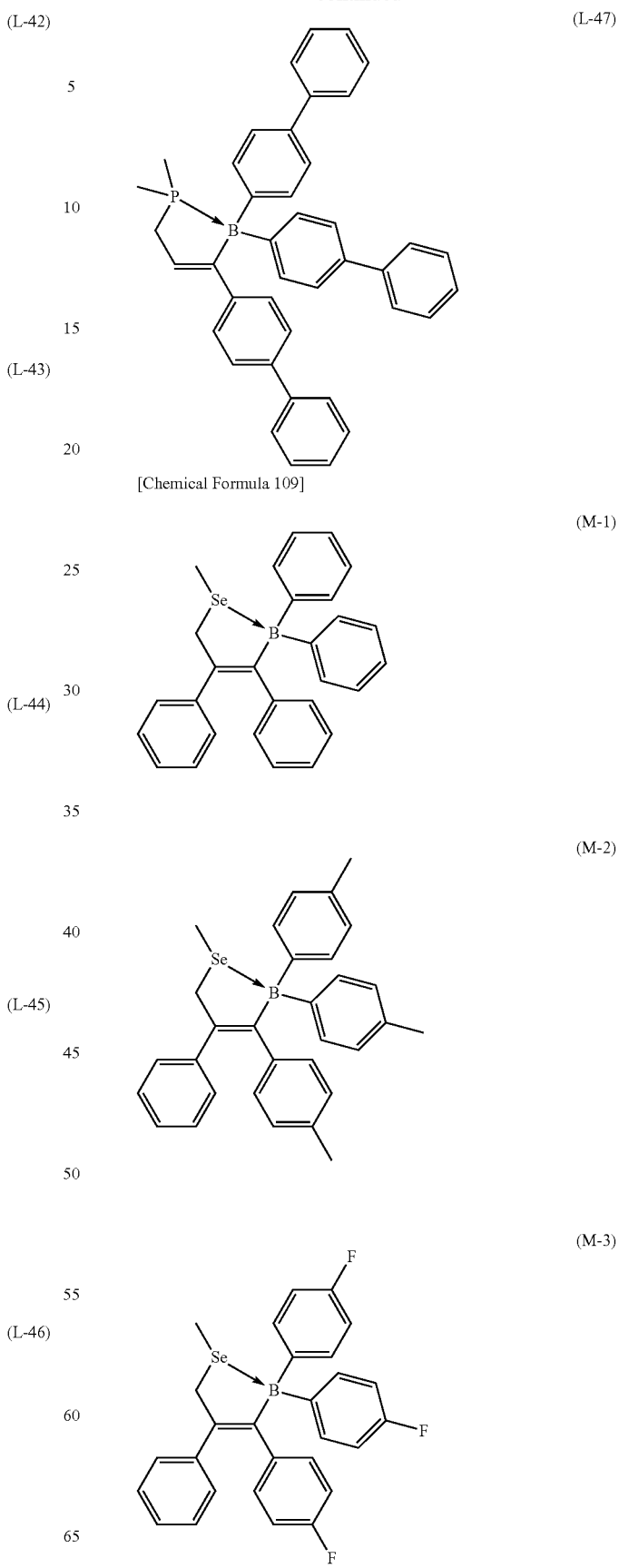
[Chemical Formula 109]

(M-4)
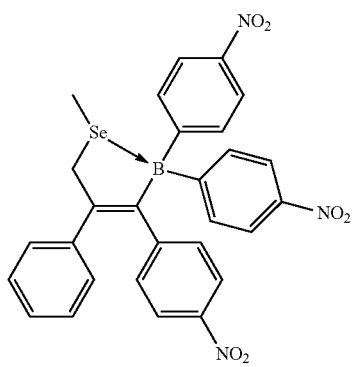
(M-5)
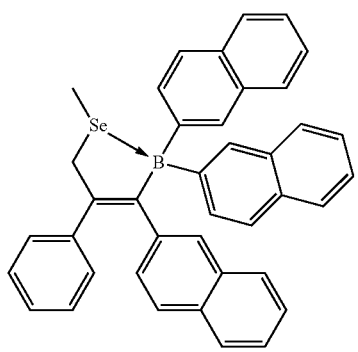
(M-6)
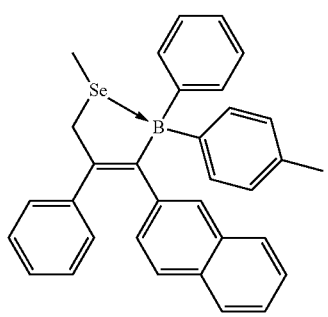
(M-7)
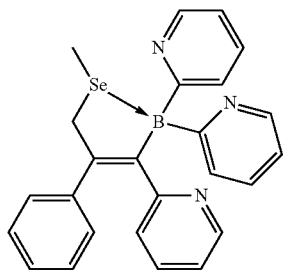
(M-8)
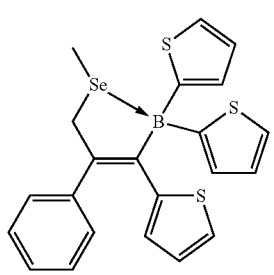
(M-9)
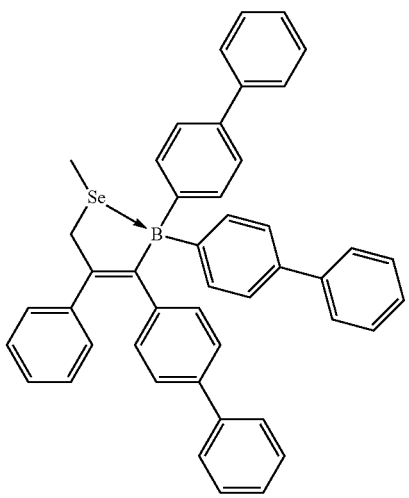
(M-10)
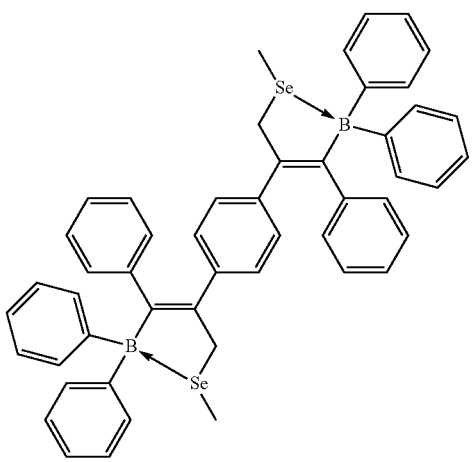
(M-11)
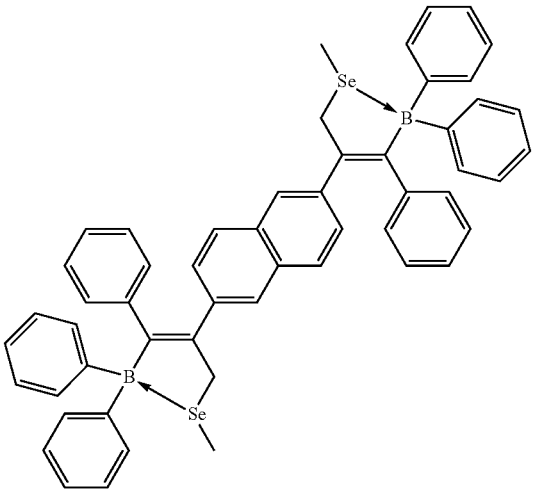

-continued
[Chemical Formula 110]
(M-12)
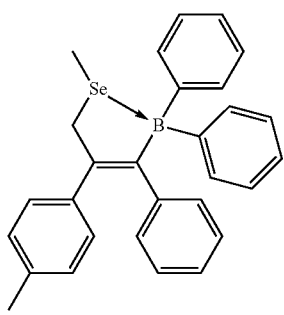
(M-13)
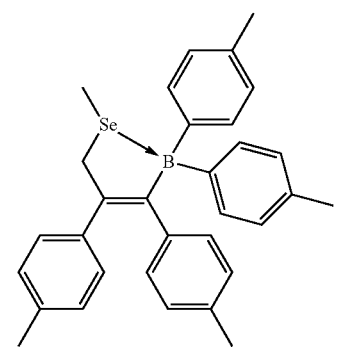
(M-14)
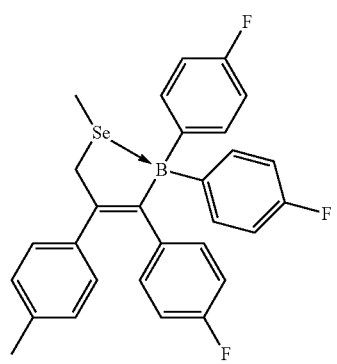
(M-15)
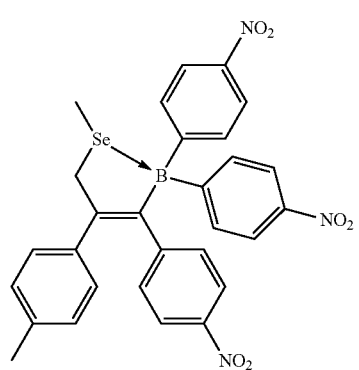
-continued
(M-16)
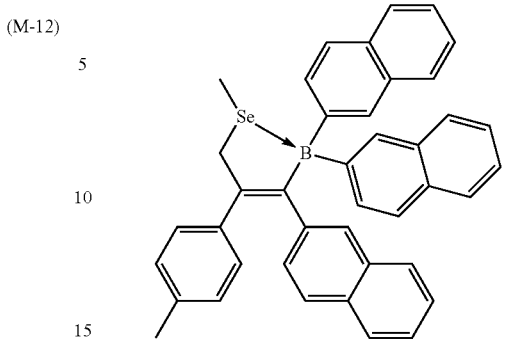
(M-17)
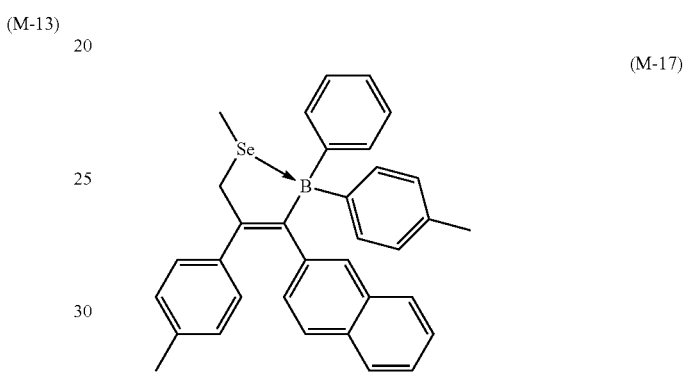
(M-18)
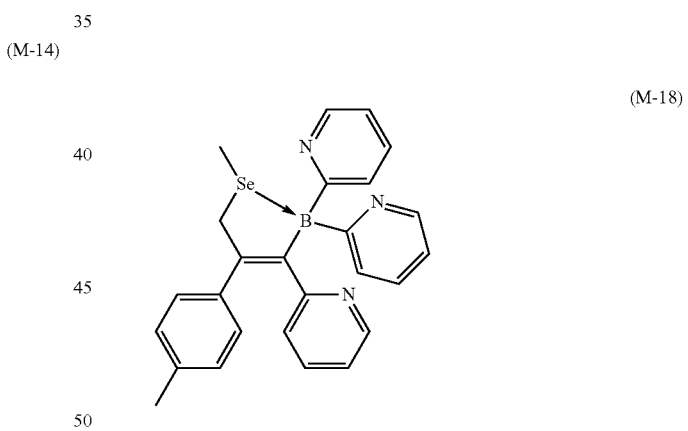
(M-19)
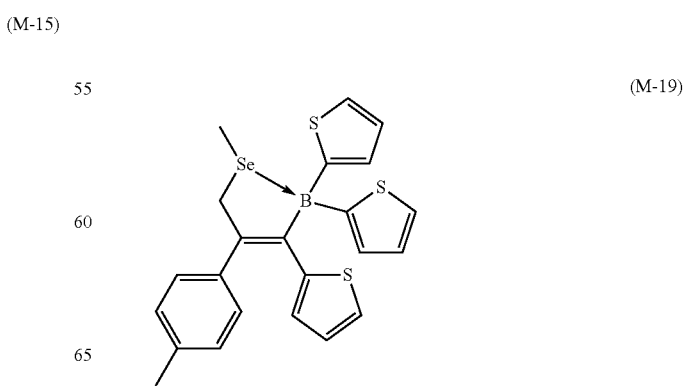

(M-20)
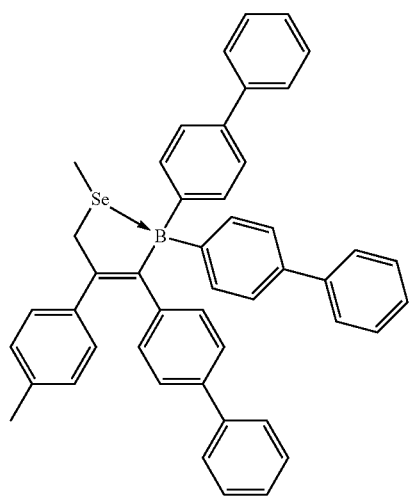
[Chemical Formula 111]
(M-21)
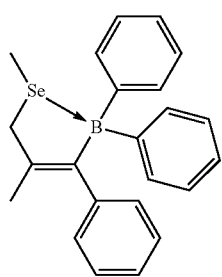
(M-22)
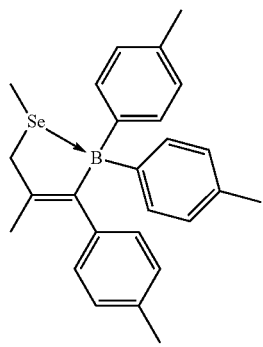
(M-23)
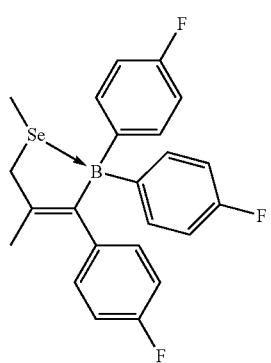
(M-24)
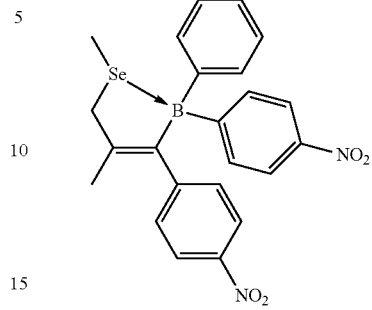
(M-25)
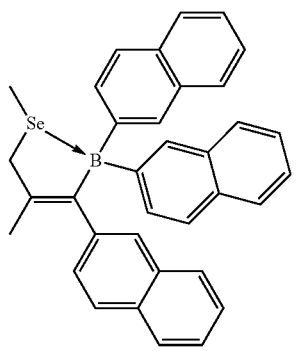
(M-26)
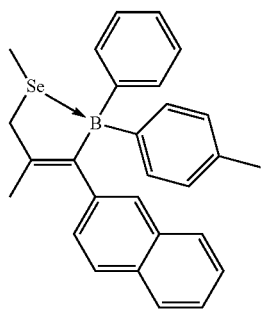
(M-27)
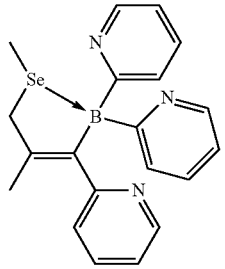
(M-28)
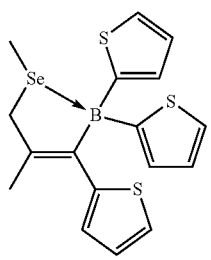

(M-29)
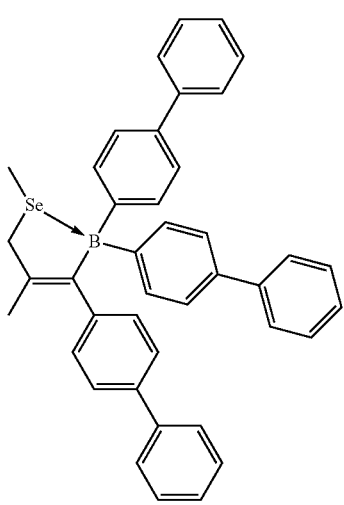
[Chemical Formula 112]
(M-30)
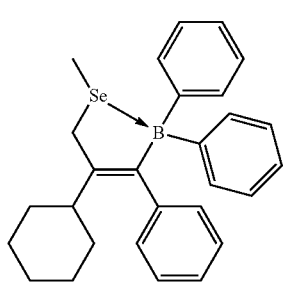
(M-31)
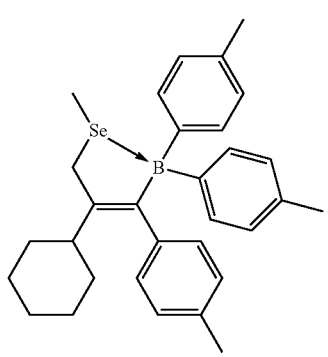
(M-32)
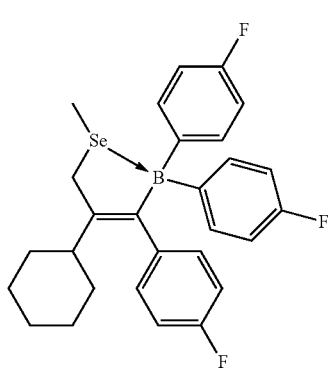
(M-33)
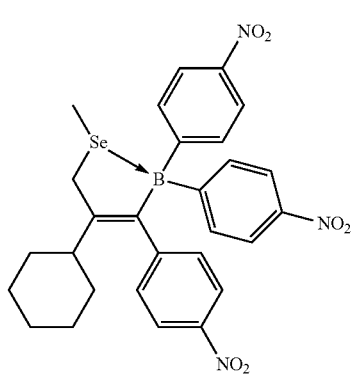
(M-34)
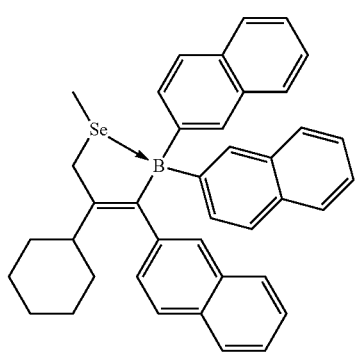
(M-35)
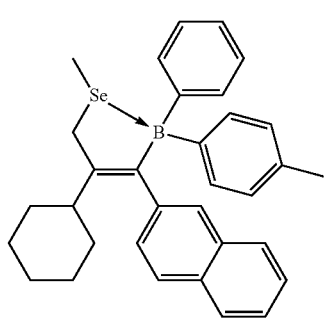
(M-36)
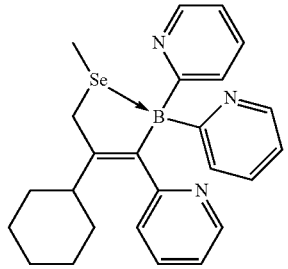
(M-37)
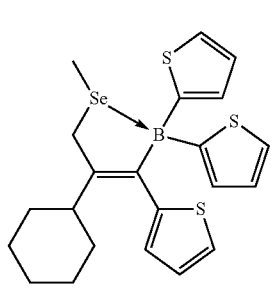

-continued
(M-38)
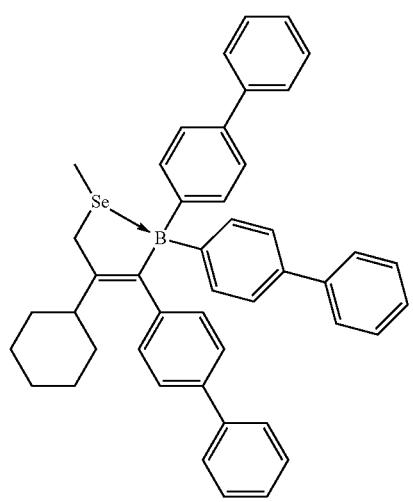
[Chemical Formula 113]
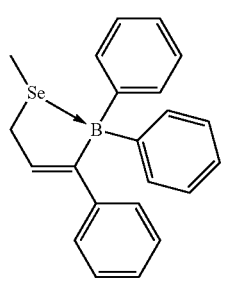
(M-39)
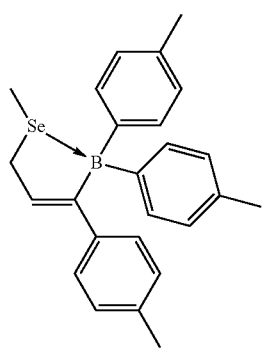
(M-40)
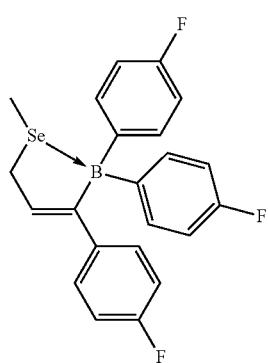
(M-41)
-continued
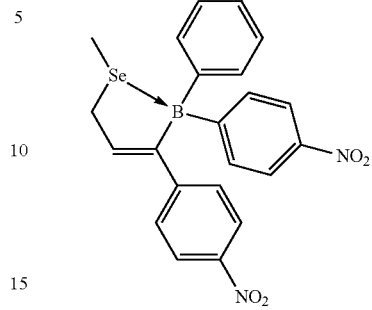
(M-42)
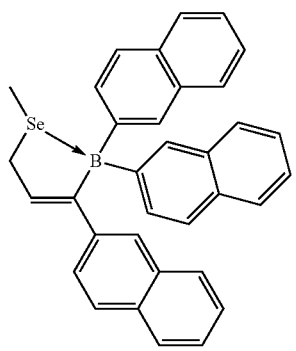
(M-43)
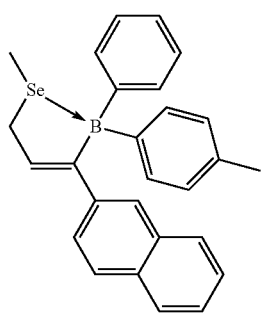
(M-44)
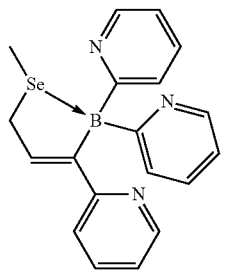
(M-45)
(M-46)

(M-47)

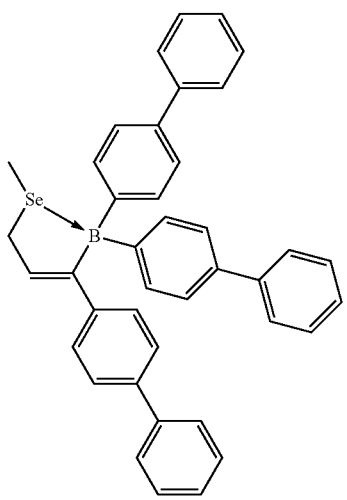

<<Processes for Producing Novel Boron Compounds I>>

The novel boron compounds I of the present invention can be produced with high efficiency in a simple and easy manner by the production process (1), (2), (3), (4), or (5) as described below. In addition, their more specific boron compounds can be produced with high efficiency in a simple and easy manner by the production processes (1-1) to (1-5), production processes (2-1) to (2-17), production processes (3-1) to (3-2), production processes (4-1) to (4-3), or production processes (5-1) to (5-4) as described below.

<Production Process (1)>

One of the novel boron compounds I of the present invention, i.e., a boron compound of the following formula (1):

[Chemical Formula 114]

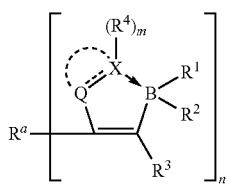 (1)

wherein $R^1$, $R^2$, and $R^3$ are the same or different from each other and are each independently an aryl group or a heterocyclic group, each of which optionally has at least one substituent group, or any two of $R^1$, $R^2$, and $R^3$ are combined with each other to form a ring; $R^4$ is a hydrogen atom or a substituent group; m is an integer of from 0 to 2; when m is 2, plurally occurring $R^4$'s are the same or different from each other; Q is a linking group; X is a nitrogen atom, an oxygen atom, a sulfur atom, a phosphorus atom, or a selenium atom; a dashed half arc indicates that Q and X may be part of a common ring; dashed and solid lines between Q and X indicate a single or double bond; an arrow directed from X to B indicates a coordinate bond; $R^a$ is hydrogen or a monovalent, divalent, trivalent, or tetravalent organic framework; n is an integer of from 1 to 4; and when n is an integer of from 2 to 4, plurally occurring $R^1$'s, $R^2$'s, $R^3$'s, m's, Q's, X's, dashed half arcs, and dashed and solid lines between Q and X are the same or different from each other, respectively, can be produced by reacting a boron compound of the following formula (4):

[Chemical Formula 115]

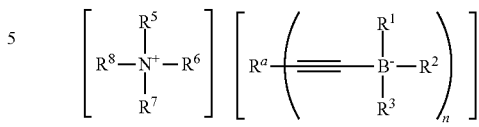 (4)

wherein $R^1$, $R^2$, $R^3$, $R^a$, and n have the same meanings as in the above formula (1); when n is an integer of from 2 to 4, plurally occurring $R^1$'s, $R^2$'s, and $R^3$'s are the same or different from each other; and $R^5$, $R^6$, $R^7$, and $R^8$ are the same or different from each other and are each independently a hydrogen atom or a substituent group, with a compound of the following formula (5):

[Chemical Formula 116]

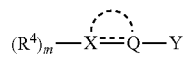 (5)

wherein $R^4$, m, Q, X, a dashed half arc, and dashed and solid lines between Q and X have the same meanings as in the above formula (1); when m is 2, plurally occurring $R^4$'s are the same or different from each other; and Y is a fluorine atom, a chlorine atom, a bromine atom, or an iodine atom, in the presence of a catalyst containing at least one metal element selected from the group consisting of palladium, platinum, and nickel.

The amount of the compound of the above formula (5) to be used may preferably be not smaller than 0.5×n mol and not larger than 2.0×n mol, more preferably not smaller than 0.65×n mol and not larger than 1.5×n mol, and still more preferably not smaller than 0.8×n mol and not larger than 1.25×n mol, relative to 1 mol of the boron compound of the above formula (4). When the amount of the compound of the above formula (5) to be used is too small, a lack of the compound of the above formula (5) may occur, resulting in a decrease in the yield of the final product. In contrast, when the amount of the compound of the above formula (5) to be used is too great, an excess of the compound of the above formula (5) may occur, resulting in an increase in the production cost. In this connection, n is the number of boron-containing ring moieties (i.e., moieties in brackets) bonded to the monovalent, divalent, trivalent, or tetravalent organic framework as indicated by $R^d$ in the above formula (1), and is an integer of from 1 to 4.

The catalyst contains at least one metal element selected from the group consisting of palladium, platinum, and nickel. Among these metal elements, palladium and platinum may be preferred.

Examples of the catalyst may include, but are not limited to, complexes containing metal elements as described above. Specific examples of the catalyst may include, but are not limited to, tris(dibenzylideneacetone)dipalladium chloroform complex ($Pd_2dba_3 \cdot CHCl_3$), tetrakis(triphenylphosphine)palladium, bis(tri-tert-butylphosphine)palladium (Pd($P^tBu_3$)$_2$), bis(tricyclohexylphosphine)palladium, bis(1,5-cyclooctadiene)platinum, and bis(1,5-cyclooctadiene)nickel. These catalysts may be used alone, or two or more kinds thereof may be used in combination. Among these catalysts, tris(dibenzylideneacetone)dipalladium chloroform complex ($Pd_2dba_3 \cdot CHCl_3$) may be preferred.

The amount of the catalyst to be used may preferably be not smaller than 0.001 mol and not larger than 0.2 mol, more preferably not smaller than 0.005 mol and not larger than 0.15 mol, and still more preferably not smaller than 0.01 mol and not larger than 0.1 mol, relative to 1 mole of the boron compound of the above formula (4). When the amount of the catalyst to be used is too small, the reaction rate may be slow, so that the reaction cannot quickly proceed. In contrast, when the amount of the catalyst to be used is too great, the catalyst may be used more than necessary, resulting in an increase in the production cost.

In the above reaction, a stabilizer may be used in addition to the catalyst. Examples of the stabilizer may include, but are not limited to, triphenylphosphine, tri(o-tolyl)phosphine (P(o-tol)$_3$), tri(2-furyl)phosphine, tri-tert-butylphosphine, trimethylphosphine, dimethylphenylphosphine, diphenylmethylphosphine, tricyclohexylphosphine, bis[2-(diphenylphosphino)phenyl]ether (DPEphos; or also called "(oxydi-2,1-phenylene)bis(diphenylphosphine)"), and bipyridine. These stabilizers may be used alone, or two or more kinds thereof may be used in combination. Among these stabilizers, bis[2-(diphenylphosphino)phenyl]ether (DPEphos) may be preferred.

The amount of the stabilizer to be used may preferably be not smaller than 0.01 mol and not larger than 0.3 mol, more preferably not smaller than 0.02 mol and not larger than 0.25 mol, and still more preferably not smaller than 0.03 mol and not larger than 0.2 mol, relative to 1 mol of the boron compound of the above formula (4). When the amount of the stabilizer to be used is too small, the function of the stabilizer cannot sufficiently be exerted, resulting in a decrease in the yield of the final product. In contrast, when the amount of the stabilizer to be used is too great, the stabilizer may be used more than necessary, resulting in an increase in the production cost.

In this connection, when a catalyst containing at least one stabilizer such as phosphine ligand (e.g., tetrakis(triphenylphosphine)palladium, bis(tri-tert-butylphosphine)palladium, bis(tricyclohexylphosphine)palladium) is used, there is no need to use an additional stabilizer.

The above reaction is typically carried out in an organic solvent. Examples of the organic solvent may include, but are not limited to, aromatic hydrocarbons such as benzene, toluene, and xylene, mesitylene; halogenated aromatic hydrocarbons such as chlorobenzene and 1,2-dichlorobenzene; halogenated aliphatic hydrocarbons such as dichloromethane, chloroform, carbon tetrachloride, 1,2-dichloroethane, 1,1,1-trichloroethane, 1,1,2,2-tetrachloroethane, 1,2-dichloroethylene, trichloroethylene, and tetrachloroethylene; alcohols such as methanol, ethanol, isopropyl alcohol, 1-butanol, 2-butanol, isobutyl alcohol, and isopentyl alcohol; esters such as methyl acetate, ethyl acetate, propyl acetate, isopropyl acetate, butyl acetate, isobutyl acetate, pentyl acetate, and isopentyl acetate; ethers such as diethyl ether, 1,4-dioxane, tetrahydrofuran, and methyl phenyl ether (anisole); ketones such as acetone, methyl ethyl ketone, methyl butyl ketone, and methyl isobutyl ketone; glycol ethers (cellosolves) such as ethylene glycol monomethyl ether (methylcellosolve), ethylene glycol monoethyl ether (cellosolve), ethylene glycol monobutyl ether (butylcellosolve), and ethylene glycol monoethyl ether acetate (cellosolve acetate); alicyclic hydrocarbons such as cyclohexane; and aliphatic hydrocarbons such as n-hexane. These organic solvents may be used alone, or two or more kinds thereof may be used in combination. Among these organic solvents, aromatic hydrocarbons such as benzene and toluene may be preferred.

The above reaction may preferably be carried out under an inert gas atmosphere. Examples of the inert gas may include, but are not limited to, nitrogen, helium, and argon. These inert gases may be used alone, or two or more kinds thereof may be used in combination. Among these inert gases, nitrogen and argon may be preferred.

The reaction conditions are not particularly limited, so long as the above reaction can sufficiently proceed under these conditions. For example, the reaction temperature may preferably be from 0° C. to 100° C., more preferably from room temperature to 80° C., and the reaction time may preferably be from 0.5 to 24 hours, more preferably from 1 to 12 hours. The reaction pressure may be normal pressure, reduced pressure, or increased pressure, preferably normal pressure.

After the completion of the reaction, for example, the reaction solution is directly concentrated or evaporated to dryness, or alternatively, water is added to the reaction solution, followed by extraction with an appropriate organic solvent, washing with water and a saturated sodium chloride solution, and then concentration or evaporation to dryness, and if necessary, followed by purification using any of the heretofore known methods, e.g., various kinds of chromatography or recrystallization. Thus, the desired product is obtained.

In the production process (1), the boron compound of the above formula (4), which is a starting material, can be produced by causing acid-base reaction between a 1-alkyne compound of the following formula (42):

[Chemical Formula 117]

(42)

wherein $R^a$ and n have the same meanings as in the above formula (1), and a strong base such as n-butyl lithium or sodium amide, to form a salt, and then reacting this salt with a boron compound of the following formula (43):

[Chemical Formula 118]

(43)

wherein $R^1$, $R^2$, and $R^3$ have the same meanings as in the above formula (1), or with a complex thereof, and further reacting the resultant product with an ammonium salt of the following formula (44):

[Chemical Formula 119]

(44)

wherein $R^5$, $R^6$, $R^7$, and $R^8$ have the same meanings as in the above formula (4); and $T^-$ is a fluoride ion, a chloride ion, a bromide ion, an iodide ion, or a hydroxide ion, to cause cation exchange. In this connection, these reactions are heretofore known (see, e.g., Dietmar Seyferth and Michael A. Weinr, J. Am. Chem. Soc., 1961, 83(17), pp. 3583-3586). The amounts of the starting materials to be used, the type of the organic solvent, the reaction conditions, and others, may appropriately be selected, and are not particularly limited. The 1-alkyne compound of the above formula (42), the boron compound of the above formula (43), and the ammonium salt of the above formula (44), all of which are starting materials, can be produced by any of the heretofore known processes or can be obtained as commercially available products.

In the production process (1), the compound of the above formula (5), which is a starting material, can be produced by any of the heretofore known processes or can be obtained as commercially available products.

<Production Processes (1-1) to (1-3)>

In the above formulas (1) and (5), Q and X may preferably be part of a common ring, and it may be more preferred that the above common ring is a pyridine ring, a quinoline ring, or a thiophene ring, X is the nitrogen atom of the pyridine ring or the quinoline ring, or the sulfur atom of the thiophene ring, and m is 0. That is, a preferred boron compound of the following formula (27):

[Chemical Formula 120]

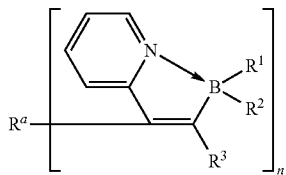

(27)

wherein $R^1$, $R^2$, $R^3$, $R^a$, and n have the same meanings as in the above formula (1); when n is an integer of from 2 to 4, plurally occurring $R^1$'s, $R^2$'s, and $R^3$'s are the same or different from each other, respectively; the pyridine ring optionally has at least one substituent group; and an arrow directed from N to B indicates a coordinate bond, can be produced by reacting a boron compound of the following formula (4):

[Chemical Formula 121]

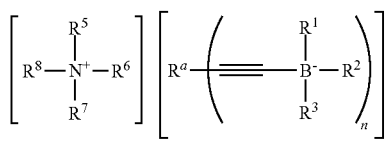

(4)

wherein $R^1$, $R^2$, $R^3$, $R^a$, and n have the same meanings as in the above formula (1); when n is an integer of from 2 to 4, plurally occurring $R^1$'s, $R^2$'s, and $R^3$'s are the same or different from each other, respectively; and $R^5$, $R^6$, $R^7$, and $R^8$ are the same or different from each other and are each independently a hydrogen atom or a substituent group, with a compound of the following formula (45):

[Chemical Formula 122]

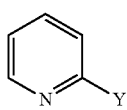

(45)

wherein Y has the same meaning as in the above formula (5); and the pyridine ring optionally has at least one substituent group, in the presence of a catalyst containing at least one metal element selected from the group consisting of palladium, platinum, and nickel (hereinafter referred to sometimes as the "production process (1-1)").

Further, a preferred boron compound of the following formula (28):

[Chemical Formula 123]

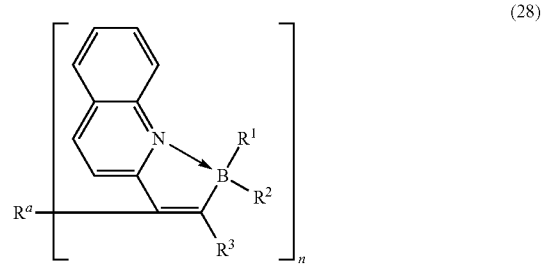

(28)

wherein $R^1$, $R^2$, $R^3$, $R^a$, and n have the same meanings as in the above formula (1); when n is an integer of from 2 to 4, plurally occurring $R^1$'s, $R^2$'s, and $R^3$'s are the same or different from each other, respectively; the quinoline ring optionally has at least one substituent group; and an arrow directed from N to B indicates a coordinate bond, can be produced by reacting a boron compound of the following formula (4):

[Chemical Formula 124]

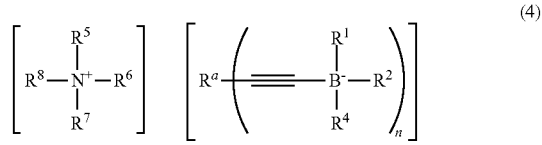

(4)

wherein $R^1$, $R^2$, $R^3$, $R^a$, and n have the same meanings as in the above formula (1); when n is an integer of from 2 to 4, plurally occurring $R^1$'s, $R^2$'s, and $R^3$'s are the same or different from each other, respectively; and $R^5$, $R^6$, $R^7$, and $R^8$ are the same or different from each other and are each independently a hydrogen atom or a substituent group, with a compound of the following formula (46):

[Chemical Formula 125]

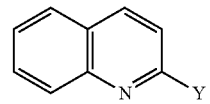

(46)

wherein Y has the same meaning as in the above formula (5); and the quinoline ring optionally has at least one substituent group, in the presence of a catalyst containing at least one metal element selected from the group consisting of palladium, platinum, and nickel (hereinafter referred to sometimes as the "production process (1-2)").

Further, a preferred boron compound of the following formula (29):

[Chemical Formula 126]

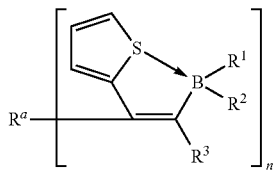

(29)

wherein $R^1$, $R^2$, $R^3$, $R^a$, and n have the same meanings as in the above formula (1); when n is an integer of from 2 to 4, plurally occurring $R^1$'s, $R^2$'s, and $R^3$'s are the same or different from each other, respectively; the thiophene ring optionally has at least one substituent group; and an arrow directed from S to B indicates a coordinate bond, can be produced by reacting a boron compound of the following formula (4):

[Chemical Formula 127]

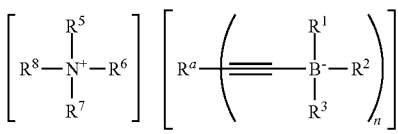

(4)

wherein $R^1$, $R^2$, $R^3$, $R^a$, and n have the same meanings as in the above formula (1); when n is an integer of from 2 to 4, plurally occurring $R^1$'s, $R^2$'s, and $R^3$'s are the same or different from each other, respectively; and $R^5$, $R^6$, $R^7$, and $R^8$ are the same or different from each other and are each independently a hydrogen atom or a substituent group, with a compound of the following formula (47):

[Chemical Formula 128]

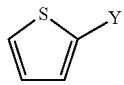

(47)

wherein Y has the same meaning as in the above formula (5); and the thiophene ring optionally has at least one substituent group, in the presence of a catalyst containing at least one metal element selected from the group consisting of palladium, platinum, and nickel (hereinafter referred to sometimes as the "production process (1-3)").

In the production process (1-1), (1-2), or (1-3), the amounts of the starting materials to be used, the types and amounts of the catalyst and the stabilizer to be used, the types of the organic solvent and the inert gas, the reaction conditions, the post-treatments after the completion of the reaction, and others, are similar to those of the production process (1); however, the compound of the above formula (5) should be read as the compound of the above formula (45), (46), or (47).

In the production process (1-1), (1-2), or (1-3), the boron compound of the above formula (4), which is a starting material, can be produced by the process as described above. The compound of the above formula (45), (46), or (47), which is a starting material, can be produced by any of the heretofore known processes or can be obtained as commercially available products.

<Production Process (1-4)>

In the above formulas (1) and (5), it may be preferred that Q is a methylene group, X is a nitrogen atom, and m is 2. That is, a boron compound of the following formula (30):

[Chemical Formula 129]

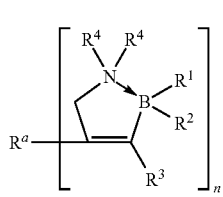

(30)

wherein $R^1$, $R^2$, $R^3$, $R^4$, $R^a$, and n have the same meanings as in the above formula (1); when n is 1, plurally occurring $R^4$'s are the same or different from each other; when n is an integer of from 2 to 4, plurally occurring $R^1$'s, $R^2$'s, $R^3$'s, and $R^4$'s are the same or different from each other, respectively; and an arrow directed from N to B indicates a coordinate bond, can be produced by reacting a boron compound of the following formula (4):

[Chemical Formula 130]

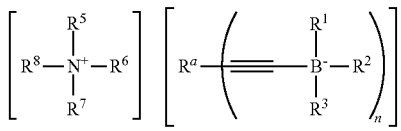

(4)

wherein $R^1$, $R^2$, $R^3$, $R^a$, and n have the same meanings as in the above formula (1); when n is an integer of from 2 to 4, plurally occurring $R^1$'s, $R^2$'s, and $R^3$'s are the same or different from each other, respectively; and $R^5$, $R^6$, $R^7$, and $R^8$ are the same or different from each other and are each independently a hydrogen atom or a substituent group, with a compound of the following formula (48):

[Chemical Formula 131]

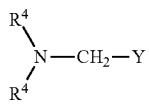

(48)

wherein $R^4$'s have the same meanings as in the above formula (1); plurally occurring $R^4$'s are the same or different from each other; and Y has the same meaning as in the above formula (5), in the presence of a catalyst containing at least one metal element selected from the group consisting of palladium, platinum, and nickel (hereinafter referred to sometimes as the "production process (1-4)").

In the production process (1-4), the amounts of the starting materials to be used, the types and amounts of the catalyst and the stabilizer to be used, the types of the organic solvent and the inert gas, the reaction conditions, the post-treatments after the completion of the reaction, and others, are similar to those of the production process (1); however; the compound of the above formula (5) should be read as the compound of the above formula (48).

In the production process (1-4), the boron compound of the above formula (4), which is a starting material, can be produced by the process as described above. The compound of the above formula (48), which is a starting material, can be produced by any of the heretofore known processes or can be obtained as commercially available products.

<Production Process (1-5)>

In the above formulas (1) and (5), it may be preferred that Q is a methylene group, X is an oxygen atom, and m is 1. That is, a boron compound of the following formula (31):

[Chemical Formula 132]

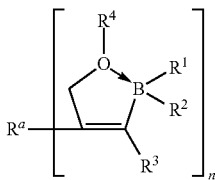
(31)

wherein $R^1$, $R^2$, $R^3$, $R^4$, $R^a$, and n have the same meanings as in the above formula (1); when n is an integer of from 2 to 4, plurally occurring $R^1$'s, $R^2$'s, $R_3$'s, and $R^4$'s are the same or different from each other, respectively; and an arrow directed from O to B indicates a coordinate bond, can be produced by reacting a boron compound of the following formula (4):

[Chemical Formula 133]

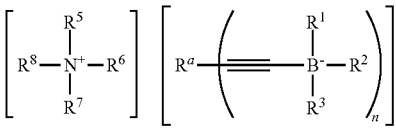
(4)

wherein $R^1$, $R^2$, $R^3$, $R^a$, and n have the same meanings as in the above formula (1); when n is an integer of from 2 to 4, plurally occurring $R^1$'s, $R^2$'s, and $R^3$'s are the same or different from each other, respectively; and $R^5$, $R^6$, $R^7$, and $R^8$ are the same or different from each other and are each independently a hydrogen atom or a substituent group, with a compound of the following formula (49):

[Chemical Formula 134]

$R^4$—O—$CH_2$—Y  (49)

wherein $R^4$ has the same meaning as in the above formula (1); and Y has the same meaning as in the above formula (5), in the presence of a catalyst containing at least one metal element selected from the group consisting of palladium, platinum, and nickel (hereinafter referred to sometimes as the "production process (1-5)").

In the production process (1-5), the amounts of the starting materials to be used, the types and amounts of the catalyst and the stabilizer to be used, the types of the organic solvent and the inert gas, the reaction conditions, the post-treatments after the completion of the reaction, and others, are similar to those of the production process (1); however, the compound of the above formula (5) should be read as the compound of the above formula (49).

In the production process (1-5), the boron compound of the above formula (4), which is a starting material, can be produced by the process as described above. The compound of the above formula (49), which is a starting material, can be produced by any of the heretofore known processes or can be obtained as commercially available products.

<Production Process (2)>

Among the novel boron compounds I of the present invention, a boron compound of the following formula (6):

[Chemical Formula 135]

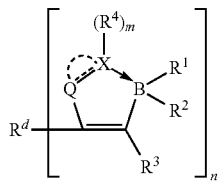
(6)

wherein $R^1$, $R^2$, and $R^3$ are the same or different from each other and are each independently an aryl group or a heterocyclic group, each of which optionally has at least one substituent group, or any two of $R^1$, $R^2$, and $R^3$ are combined with each other to form a ring; $R^4$ is a hydrogen atom or a substituent group; m is an integer of from 0 to 2; when m is 2, plurally occurring $R^4$'s are the same or different from each other; Q is a linking group; X is a nitrogen atom, an oxygen atom, a sulfur atom, a phosphorus atom, or a selenium atom; a dashed half arc indicates that Q and X may be part of a common ring; dashed and solid lines between Q and X indicate a single or double bond; an arrow directed from X to B indicates a coordinate bond; $R^d$ is a monovalent, divalent, trivalent, or tetravalent organic framework; n is an integer of from 1 to 4; and when n is an integer of from 2 to 4, plurally occurring $R^1$'s, $R^2$'s, $R^3$'s, $R^4$'s, m's, Q's, X's, dashed half arcs, and dashed and solid lines between Q and X are the same or different from each other, respectively, can be produced by reacting a boron compound of the following formula (7):

[Chemical Formula 136]

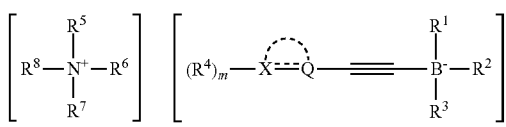
(7)

wherein $R^1$, $R^2$, $R^3$, $R^4$, m, Q, X, a dashed half arc, and dashed and solid lines between Q and X have the same meanings as in the above formula (6); when m is 2, plurally occurring $R^4$'s are the same or different from each other; and $R^5$, $R^6$, $R^7$, and $R^8$ are the same or different from each other and are each independently a hydrogen atom or a substituent group, with a compound of the following formula (8):

[Chemical Formula 137]

$R^d$—(Y)$_n$  (8)

wherein $R^d$ and n have the same meanings as in the above formula (6); Y is a fluorine atom, a chlorine atom, a bromine atom, or an iodine atom; and when n is an integer of from 2 to 4, plurally occurring Y's are the same or different from each other, in the presence of a catalyst containing at least one metal element selected from the group consisting of palladium, platinum, and nickel (hereinafter referred to sometimes as the "production process (2)").

The amount of the compound of the above formula (8) to be used may preferably be not smaller than 0.5/n mol and not larger than 2.0/n mol, more preferably not smaller than 0.65/n mol and not larger than 1.5/n mol, and still more preferably not smaller than 0.8/n mol and not larger than 1.25/n mol, relative to 1 mole of the boron compound of the above formula (7). When the amount of the compound of the above formula (8) to be used is too small, a lack of the compound of the above formula (8) may occur, resulting in a decrease in the yield of the final product. In contrast, when the amount of the compound of the above formula (8) to be used is too great, an excess of the compound of the above formula (8) may occur, resulting in an increase in the production cost. In this connection, n is the number of boron-containing ring moieties (i.e., moieties in brackets) boned to the monovalent, divalent, trivalent, or tetravalent organic framework as indicated by $R^d$ in the above formula (6), and is an integer of from 1 to 4.

The catalyst contains at least one metal element selected from the group consisting of palladium, platinum, and nickel. Among these metal elements, palladium and platinum may be preferred.

Examples of the catalyst may include, but are not limited to, complexes containing metal elements as described above. Specific examples of the catalyst may include, but are not limited to, tris(dibenzylideneacetone)dipalladium chloroform complex ($Pd_2dba_3\cdot CHCl_3$), tetrakis(triphenylphosphine)palladium, bis(tri-tert-butylphosphine)palladium (Pd($P^tBu_3$)$_2$), bis(tricyclohexylphosphine)palladium, bis(1,5-cyclooctadiene)platinum, and bis(1,5-cyclooctadiene)nickel. These catalysts may be used alone, or two or more kinds thereof may be used in combination. Among these catalysts, tris(dibenzylideneacetone)dipalladium chloroform complex ($Pd_2dba_3\cdot CHCl_3$) may be preferred.

The amount of the catalyst to be used may preferably be not smaller than 0.001 mol and not larger than 0.2 mol, more preferably not smaller than 0.005 mol and not larger than 0.15 mol, and still more preferably not smaller than 0.01 mol and not larger than 0.1 mol, relative to 1 mole of the boron compound of the above formula (7). When the amount of the catalyst to be used is too small, the reaction rate may be slow, so that the reaction cannot quickly proceed. In contrast, when the amount of the catalyst to be used is too great, the catalyst may be used more than necessary, resulting in an increase in the production cost.

In the above reaction, a stabilizer may be used in addition to the catalyst. Examples of the stabilizer may include, but are not limited to, triphenylphosphine, tri(o-tolyl)phosphine (P(o-tol)$_3$), tri(2-furyl)phosphine, tri-tert-butylphosphine, trimethylphosphine, dimethylphenylphosphine, diphenylmethylphosphine, tricyclohexylphosphine, bis[2-(diphenylphosphino)phenyl]ether (DPEphos; or also called "(oxydi-2,1-phenylene)bis(diphenylphosphine)"), and bipyridine. These stabilizers may be used alone, or two or more kinds thereof may be used in combination. Among these stabilizers, tri(o-tolyl)phosphine (P(o-tol)$_3$) may be preferred.

The amount of the stabilizer to be used may preferably be not smaller than 0.01 mol and not larger than 0.3 mol, more preferably not smaller than 0.02 mol and not larger than 0.25 mol, and still more preferably not smaller than 0.03 mol and not larger than 0.2 mol, relative to 1 mol of the boron compound of the above formula (7). When the amount of the stabilizer is too small, the function of the stabilizer cannot sufficiently be exerted, resulting in a decrease in the yield of the final product. In contrast, when the amount of the stabilizer to be used is too great, the stabilizer may be used more than necessary, resulting in an increase in the production cost.

In this connection, when a catalyst containing at least one stabilizer such as phosphine ligand (e.g., tetrakis(triphenylphosphine)palladium, bis(tri-tert-butylphosphine)palladium, bis(tricyclohexylphosphine)palladium) is used, there is no need to use an additional stabilizer.

The above reaction is typically carried out in an organic solvent. Examples of the organic solvent may include, but are not limited to, aromatic hydrocarbons such as benzene, toluene, xylene, and mesitylene; halogenated aromatic hydrocarbons such as chlorobenzene and 1,2-dichlorobenzene; halogenated aliphatic hydrocarbons such as dichloromethane, chloroform, carbon tetrachloride, 1,2-dichloroethane, 1,1,1-trichloroethane, 1,1,2,2-tetrachloroethane, 1,2-dichloroethylene, trichloroethylene, and tetrachloroethylene; alcohols such as methanol, ethanol, isopropyl alcohol, 1-buthanol, 2-buthanol, isobutyl alcohol, and isopentyl alcohol; esters such as methyl acetate, ethyl acetate, propyl acetate, isopropyl acetate, butyl acetate, isobutyl acetate, pentyl acetate, and isopentyl acetate; ethers such as diethyl ether, 1,4-dioxane, tetrahydrofuran, and methyl phenyl ether (anisole); ketones such as acetone, methyl ethyl ketone, methyl butyl ketone, and methyl isobutyl ketone; glycol ethers (cellosolves) such as ethylene glycol monomethyl ether (methylcellosolve), ethylene glycol monoethyl ether (cellosolve), ethylene glycol monobutyl ether (butylcellosolve), and ethylene glycol monoethyl ether acetate (cellosolve acetate); alicyclic hydrocarbons such as cyclohexane; and aliphatic hydrocarbons such as n-hexane. These organic solvents may be used alone, or two or more kinds thereof may be used in combination. Among these organic solvents, there may be preferred halogenated aliphatic hydrocarbons such as dichloromethane and 1,2-dichloroethane, and ethers such as tetrahydrofuran.

The above reaction may preferably be carried out under an inert gas atmosphere. Examples of the inert gas may include, but are not limited to, nitrogen, helium, and argon. These inert gases may be used alone, or two or more kinds thereof may be used in combination. Among these inert gases, nitrogen and argon may be preferred.

The reaction conditions are not particularly limited, so long as the above reaction can sufficiently proceed under these conditions. For example, the reaction temperature may preferably be from 0° C. to 100° C., more preferably from room temperature to 80° C., and the reaction time may preferably be from 0.5 to 24 hours, more preferably from 1 to 12 hours. The reaction pressure may be normal pressure, reduced pressure, or increased pressure, preferably normal pressure.

After the completion of the reaction, for example, the reaction solution is directly concentrated or evaporated to dryness, or alternatively, water is added to the reaction solution, followed by extraction with an appropriate organic solvent, washing with water and a saturated sodium chloride solution, and then concentration or evaporation to dryness, and if necessary, followed by purification using any of the heretofore known methods, e.g., various kinds of chromatography or recrystallization. Thus, the desired product is obtained.

In the production process (2), the boron compound of the above formula (7), which is a starting material, can be produced by causing acid-base reaction between a 1-alkyne compound of the following formula (50):

[Chemical Formula 138]

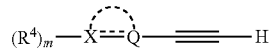

(50)

wherein $R^4$, m, Q, X, a dashed half arc, and dashed and solid lines between Q and X have the same meanings as in the above formula (6); and when m is 2, plurally occurring $R^4$'s are the same or different from each other, and a strong base such as n-butyl lithium or sodium amide, to form a salt, and then reacting this salt with a boron compound of the following formula (51):

[Chemical Formula 139]

(51)

wherein $R^1$, $R^2$, and $R^3$ have the same meanings as in the above formula (6), or with a complex thereof, and further reacting the resultant product with an ammonium salt of the following formula (52):

[Chemical Formula 140]

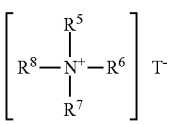
(52)

wherein $R^5$, $R^6$, $R^7$, and $R^8$ have the same meanings as in the above formula (7); and $T^-$ is a fluoride ion, a chloride ion, a bromide ion, an iodide ion, or a hydroxide ion, to cause cation exchange. In this connection, these reactions are heretofore known (see, e.g., Dietmar Seyferth and Michael A. Weinr, J. Am. Chem. Soc., 1961, 83(17), pp. 3583-3586). The amounts of the starting materials to be used, the type of the organic solvent, the reaction conditions, and others, may appropriately be selected, and are not particularly limited. The 1-alkyne compound of the above formula (50), the boron compound of the above formula (51), and the ammonium salt of the above formula (52), all of which are starting materials, can be produced by any of the heretofore known processes or can be obtained as commercially available products.

In the production process (2), the compound of the above formula (8), which is a starting material, can be produced by any of the heretofore known processes or can be obtained as commercially available products.

<Production Processes (2-1) to (2-3)>

In the above formulas (6) and (7), Q and X may preferably be part of a common ring, and it may be more preferred that the above common ring is a pyridine ring, a quinoline ring, or a thiophene ring, X is the nitrogen atom of the pyridine ring or the quinoline ring, or the sulfur atom of the thiophene ring, and m is 0. That is, a preferred boron compound of the following formula (53):

[Chemical Formula 141]

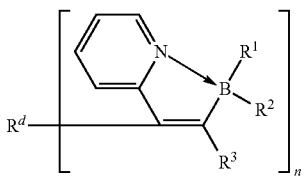
(53)

wherein $R^1$, $R^2$, $R^3$, $R^d$, and n have the same meanings as in the above formula (6); when n is an integer of from 2 to 4, plurally occurring $R^1$'s, $R^2$'s, and $R^3$'s are the same or different from each other, respectively; the pyridine ring optionally has at least one substituent group; and an arrow directed from N to B indicates a coordinate bond, can be produced by reacting a boron compound of the following formula (54):

[Chemical Formula 142]

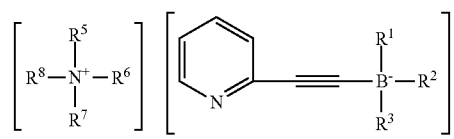
(54)

wherein $R^1$, $R^2$, and $R^3$ have the same meanings as in the above formula (6); the pyridine ring optionally has at least one substituent group; and $R^5$, $R^6$, $R^7$, and $R^8$ have the same meanings as in the above formula (7), with a compound of the following formula (8):

[Chemical Formula 143]

$$R^d\text{---}(Y)_n \quad (8)$$

wherein $R^d$ and n have the same meanings as in the above formula (6); Y is a fluorine atom, a chlorine atom, a bromine atom, or an iodine atom; and when n is an integer of from 2 to 4, plurally occurring Y's are the same or different from each other, in the presence of a catalyst containing at least one metal element selected from the group consisting of palladium, platinum, and nickel (hereinafter referred to sometimes as the "production process (2-1)").

Further, a preferred boron compound of the following formula (55):

[Chemical Formula 144]

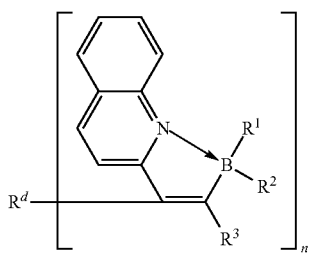
(55)

wherein $R^1$, $R^2$, $R^3$, $R^d$, and n have the same meanings as in the above formula (6); when n is an integer of from 2 to 4, plurally occurring $R^1$'s, $R^2$'s, and $R^3$'s are the same or different from each other, respectively; the quinoline ring optionally has at least one substituent group; and an arrow directed from N to B indicates a coordinate bond, can be produced by reacting a boron compound of the following formula (56):

[Chemical Formula 145]

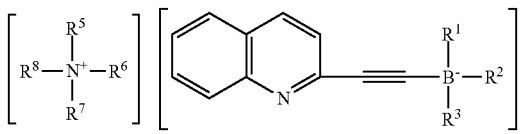
(56)

wherein $R^1$, $R^2$, and $R^3$ have the same meanings as in the above formula (6); the quinoline ring optionally has at least one substituent group; and $R^5$, $R^6$, $R^7$, and $R^8$ have the same meanings as in the above formula (7), with a compound of the following formula (8):

[Chemical Formula 146]

$$R^d\text{—}(Y)_n \qquad (8)$$

wherein $R^d$ and n have the same meanings as in the above formula (6); Y is a fluorine atom, chlorine atom, bromine atom, or iodine atom; and when n is an integer of from 2 to 4, plurally occurring Y's are the same or different from each other, in the presence of a catalyst containing at least one metal element selected from the group consisting of palladium, platinum, and nickel (hereinafter referred to sometimes as the "production process (2-2)").

Further, a preferred boron compound of the following formula (57):

[Chemical Formula 147]

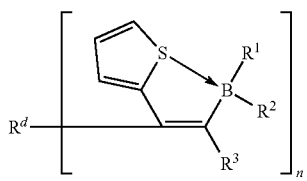

(57)

wherein $R^1$, $R^2$, $R^3$, $R^d$, and n have the same meanings as in the above formula (6); when n is an integer of from 2 to 4, plurally occurring $R^1$'s, $R^2$'s, and $R^3$'s are the same or different from each other, respectively; the thiophene ring optionally has at least one substituent group; and an arrow directed from S to B indicates a coordinate bond, can be produced by reacting a boron compound of the following formula (58):

[Chemical Formula 148]

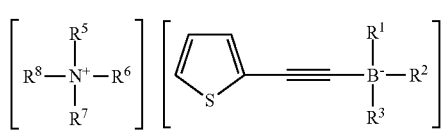

(58)

wherein $R^1$, $R^2$, and $R^3$ have the same meanings as in the above formula (6); the thiophene ring optionally has at least one substituent group; and $R^5$, $R^6$, $R^7$, and $R^8$ have the same meanings as in the above formula (7), with a compound of the following formula (8):

[Chemical Formula 149]

$$R^d\text{—}(Y)_n \qquad (8)$$

wherein $R^d$ and n have the same meanings as in the above formula (6); Y is a fluorine atom, a chlorine atom, a bromine atom, or an iodine atom; and when n is an integer of from 2 to 4, plurally occurring Y's are the same or different from each other, in the presence of a catalyst containing at least one metal element selected from the group consisting of palladium, platinum, and nickel (hereinafter referred to sometimes as the "production process (2-3)").

In the production process (2-1), (2-2), or (2-3), the amounts of the starting materials to be used, the types and amounts of the catalyst and the stabilizer to be used, the types of the organic solvent and the inert gas, the reaction conditions, the post-treatments after the completion of the reaction, and others, are similar to those of the production process (2); however, the boron compound of the above formula (7) should be read as the boron compound of the above formula (54), (56), or (58).

In the production process (2-1), (2-2), or (2-3), the boron compound of the above formula (54), (56), or (58), which is a starting material, can be produced in accordance with the production process for the boron compound of the above formula (7). The compound of the above formula (8), which is a starting material, can be produced by any of the heretofore known processes or can be obtained as commercially available products.

<Production Process (2-4)>

In the above formulas (6) and (7), it may be preferred that Q is a methylene group, X is a nitrogen atom, and m is 2. That is, a preferred boron compound of the following formula (59):

[Chemical Formula 150]

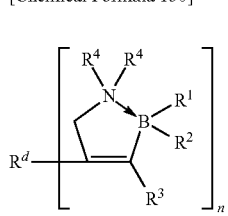

(59)

wherein $R^1$, $R^2$, $R^3$, $R^4$, $R^d$, and n have the same meanings as in the above formula (6); when n is 1, plurally occurring $R^4$'s are the same or different from each other; when n is an integer of from 2 to 4, plurally occurring $R^1$'s, $R^2$'s, $R^3$'s, and $R^4$'s are the same or different from each other, respectively; and an arrow directed from N to B indicates a coordinate bond, can be produced by reacting a boron compound of the following formula (60):

[Chemical Formula 151]

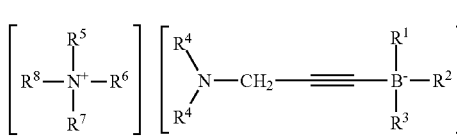

(60)

wherein $R^1$, $R^2$, $R^3$, and $R^4$ have the same meanings as in the above formula (6); plurally occurring $R^4$'s are the same or different from each other; and $R^5$, $R^6$, $R^7$, and $R^8$ have the same meanings as in the above formula (7), with a compound of the following formula (8):

[Chemical Formula 152]

$$R^d\text{—}(Y)_n \qquad (8)$$

wherein $R^d$ and n have the same meanings as in the above formula (6); Y is a fluorine atom, a chlorine atom, a bromine atom, or an iodine atom; and when n is an integer of from 2 to 4, plurally occurring Y's are the same or different from each other, in the presence of a catalyst containing at least one metal element selected from the group consisting of palladium, platinum, and nickel (hereinafter referred to sometimes as the "production process (2-4)").

In the production process (2-4), the amounts of the starting materials to be used, the types and amounts of the catalyst and the stabilizer to be used, the types of the organic solvent and the inert gas, the reaction conditions, the post-treatments after the completion of the reaction, and others, are similar to those of the production process (1); however, the boron compound of the above formula (7) should be read as the boron compound of the above formula (60).

In the production process (2-4), the boron compound of the above formula (60), which is a starting material, can be produced in accordance with the production process for the boron compound of the above formula (7). The compound of the above formula (8), which is a starting material, can be produced by any of the heretofore known processes or can be obtained as commercially available products.

<Production Process (2-5)>

Further, in the above formulas (6) and (7), it may be preferred that Q is a methylene group, X is an oxygen atom, and m is 1. That is, a preferred boron compound of the following formula (61):

[Chemical Formula 153]

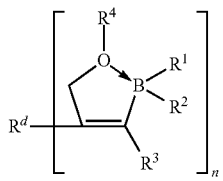

(61)

wherein $R^1$, $R^2$, $R^3$, $R^4$, $R^d$, and n have the same meanings as in the above formula (6); when n is an integer of from 2 to 4, plurally occurring $R^1$'s, $R^2$'s, $R^3$'s, and $R^4$'s are the same or different from each other, respectively; and an arrow directed from O to B indicates a coordinate bond, can be produced by reacting a boron compound of the following formula (62):

[Chemical Formula 154]

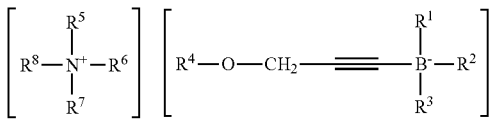

(62)

wherein $R^1$, $R^2$, $R^3$, and $R^4$ have the same meanings as in the above formula (6); and $R^5$, $R^6$, $R^7$, and $R^8$ have the same meanings as in the above formula (7), with a compound of the following formula (8):

[Chemical Formula 155]

  $R^d$—$(Y)_n$ (8)

wherein $R^d$ and n have the same meanings as in the above formula (6); Y is a fluorine atom, a chlorine atom, a bromine atom, or an iodine atom; and when n is an integer of from 2 to 4, plurally occurring Y's are the same or different from each other, in the presence of a catalyst containing at least one metal element selected from the group consisting of palladium, platinum, and nickel (hereinafter referred to sometimes as the "production process (2-5)").

In the production process (2-5), the amounts of the starting materials to be used, the types and amounts of the catalyst and the stabilizer to be used, the types of the organic solvent and the inert gas, the reaction conditions, the post-treatments after the completion of the reaction, and others, are similar to those of the production process (1); however, the boron compound of the above formula (7) should be read as the boron compound of the above formula (62).

In the production process (2-5), the boron compound of the above formula (62), which is a starting material, can be produced can be produced in accordance with the production process for the boron compound of the above formula (7). The compound of the above formula (8), which is a starting material, can be produced by any of the heretofore known processes or can be obtained as commercially available products.

<Production Process (2-6)>

Among the boron compounds of the above formula (6), a preferred boron compound of the following formula (9):

[Chemical Formula 156]

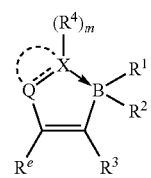

(9)

wherein $R^1$, $R^2$, $R^3$, $R^4$, m, Q, X, a dashed half arc, dashed and solid lines between Q and X, and an arrow directed from X to B have the same meanings as in the above formula (6); when m is 2, plurally occurring $R^4$'s are the same or different from each other; and $R^e$ is a monovalent organic framework, can be produced by reacting a boron compound of the following formula (7):

[Chemical Formula 157]

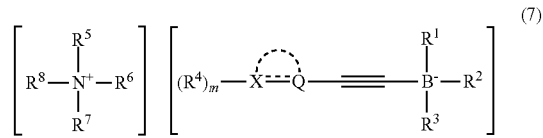

(7)

wherein $R^1$, $R^2$, $R^3$, $R^4$, m, Q, X, a dashed half arc, and dashed and solid lines between Q and X have the same meanings as in the above formula (6); when m is 2, plurally occurring $R^4$'s are the same or different from each other; and $R^5$, $R^6$, $R^7$, and $R^8$ are the same or different from each other and are each independently a hydrogen atom or a substituent group, with a compound of the above formula (8) wherein $R^d$ is $R^e$ which indicates a monovalent organic framework and n is 1, i.e., a compound of the following formula (63):

[Chemical Formula 158]

  $R^e$—Y (63)

wherein $R^e$ has the same meaning as in the above formula (9); and Y has the same meaning as in the above formula (8), in the presence of a catalyst containing at least one metal element selected from the group consisting of palladium, platinum, and nickel (hereinafter referred to sometimes as the "production process (2-6)").

In the production process (2-6), the amounts of the starting materials to be used, the types and amounts of the catalyst and the stabilizer to be used, the types of the organic solvent and the inert gas, the reaction conditions, the post-treatments after the completion of the reaction, and others, are similar to those of the production process (1); however, the amounts of the starting materials to be used, and the amounts of the catalyst and the stabilizer to be used, have values determined when the variable n is 1, and the compound of the above formula (8) should be read as the compound of the above formula (63).

In the production process (2-6), the boron compound of the above formula (7), which is a starting material, can be produced by the process as described above. The compound of the above formula (63), which is a starting material, can be produced by any of the heretofore known processes or can be obtained as commercially available products.

<Production Process (2-7)>

Further, among the boron compounds of the above formula (6), a preferred boron compound of the following formula (3):

[Chemical Formula 159]

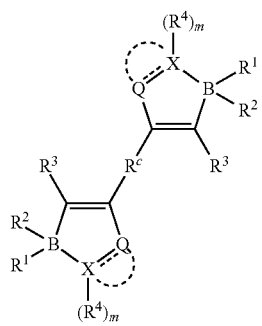

(3)

wherein $R^1$, $R^2$, $R^3$, $R^4$, m, Q, X, dashed half arcs, dashed and solid lines between Q and X, and arrows directed from X to B have the same meanings as in the above formula (6); $R^c$ is a divalent organic framework; and plurally occurring $R^1$'s, $R^2$'s, $R^3$'s, $R^4$'s, m's, Q's, X's, dashed half arcs, and dashed and solid lines between Q and X are the same or different from each other, respectively, can be produced by reacting a boron compound of the following formula (7):

[Chemical Formula 160]

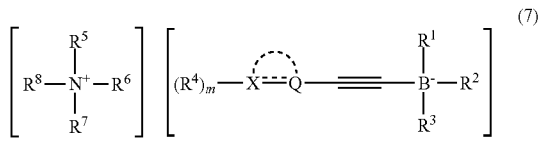

(7)

wherein $R^1$, $R^2$, $R^3$, $R^4$, m, Q, X, a dashed half arc, and dashed and solid lines between Q and X have the same meanings as in the above formula (6); when m is 2, plurally occurring $R^4$'s are the same or different from each other; and $R^5$, $R^6$, $R^7$, and $R^8$ are the same or different from each other and are each independently a hydrogen atom or a substituent group, with a compound of the above formula (8) wherein $R^d$ is $R^c$ which indicates a divalent organic framework and n is 2, i.e., a compound of the following formula (64):

[Chemical Formula 161]

Y—$R^c$—Y    (64)

wherein $R^c$ has the same meaning as in the above formula (3); Y has the same meaning as in the above formula (8); and plurally occurring Y's are the same or different from each other, in the presence of a catalyst containing at least one metal element selected from the group consisting of palladium, platinum, and nickel (hereinafter referred to sometimes as the "production process (2-7)").

In the production process (2-7), the amounts of the starting materials to be used, the types and amounts of the catalyst and the stabilizer to be used, the types of the organic solvent and the inert gas, the reaction conditions, the post-treatments after the completion of the reaction, and others, are similar to those of the production process (1); however, the amounts of the starting materials to be used, and the amounts of the catalyst and the stabilizer to be used, have values determined when the variable n is 2, and the compound of the above formula (8) should be read as the compound of the above formula (64).

In the production process (2-7), the boron compound of the above formula (7), which is a starting material, can be produced by the process as described above. The compound of the above formula (64), which is a starting material, can be produced by any of the heretofore known processes or can be obtained as commercially available products.

<Production Processes (2-8) to (2-10)>

In the above formula (9), Q and X may preferably be part of a common ring, and it may be more preferred that the above common ring is a pyridine ring, a quinoline ring, or a thiophene ring, X is the nitrogen atom of the pyridine ring or the quinoline ring, or the sulfur atom of the thiophene ring, and m is 0. That is, a preferred boron compound of the following formula (65):

[Chemical Formula 162]

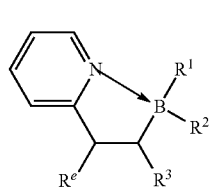

(65)

wherein $R^1$, $R^2$, and $R^3$ have the same meanings as in the above formula (6); the pyridine ring optionally has at least one substituent group; an arrow directed from N to B indicates a coordinate bond; and $R^e$ has the same meaning as in the above formula (9), can be produced by reacting a boron compound of the following formula (54):

[Chemical Formula 163]

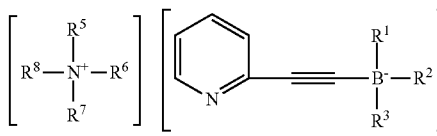

(54)

wherein $R^1$, $R^2$, and $R^3$ have the same meanings as in the above formula (6); the pyridine ring optionally has at least one substituent group; and $R^5$, $R^6$, $R^7$, and $R^8$ have the same meanings as in the above formula (7), with a compound of the following formula (63):

[Chemical Formula 164]

$R^e$—Y    (63)

wherein $R^e$ has the same meaning as in the above formula (9); and Y has the same meaning as in the above formula (8), in the presence of a catalyst containing at least one metal element selected from the group consisting of palladium, platinum, and nickel (hereinafter referred to sometimes as the "production process (2-8)").

Further, a preferred boron compound of the following formula (66):

[Chemical Formula 165]

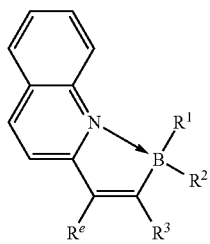

(66)

wherein $R^1$, $R^2$, and $R^3$ have the same meanings as in the above formula (6); the quinoline ring optionally has at least one substituent group; an arrow directed from N to B indicates a coordinate bond; and $R^e$ has the same meaning as in the above formula (9), can be produced by reacting a boron compound of the following formula (56):

[Chemical Formula 166]

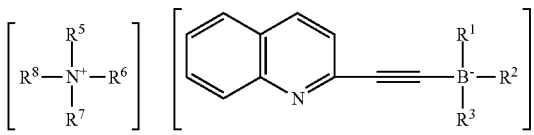

(56)

wherein $R^1$, $R^2$, and $R^3$ have the same meanings as in the above formula (6); the quinoline ring optionally has at least one substituent group; and $R^5$, $R^6$, $R^7$, and $R^8$ have the same meanings as in the above formula (7), with a compound of the following formula (63):

[Chemical Formula 167]

$R^e$—Y      (63)

wherein $R^e$ has the same meaning as in the above formula (9); and Y has the same meaning as in the above formula (8), in the presence of a catalyst containing at least one metal element selected from the group consisting of palladium, platinum, and nickel (hereinafter referred to sometimes as the "production process (2-9)").

Further, a preferred boron compound of the following formula (67):

[Chemical Formula 168]

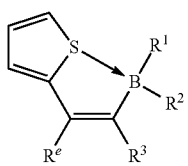

(67)

wherein $R^1$, $R^2$, and $R^3$ have the same meanings as in the above formula (6); the thiophene ring optionally has at least one substituent group; an arrow directed from S to B indicates a coordinate bond; and $R^e$ has the same meaning as in the above formula (9), can be produced by reacting a boron compound of the following formula (58):

[Chemical Formula 169]

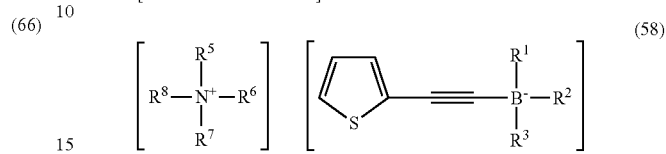

(58)

wherein $R^1$, $R^2$, and $R^3$ have the same meanings as in the above formula (6); the thiophene ring optionally has at least one substituent group; and $R^5$, $R^6$, $R^7$, and $R^8$ have the same meanings as in the above formula (7), with a compound of the following formula (63):

[Chemical Formula 170]

$R^e$—Y      (63)

wherein $R^e$ has the same meaning as in the above formula (9); and Y has the same meaning as in the above formula (8), in the presence of a catalyst containing at least one metal element selected from the group consisting of palladium, platinum, and nickel (hereinafter referred sometimes to as the "production process (2-10)").

In the production process (2-8), (2-9), or (2-10), the amounts of the starting materials to be used, the types and amounts of the catalyst and the stabilizer to be used, the types of the organic solvent and the inert gas, the reaction conditions, the post-treatments after the completion of the reaction, and others, are similar to those of the production process (2); however, the amounts of the starting materials to be used, and the amounts of the catalyst and the stabilizer to be used, have values determined when the variable n is 1, and the boron compound of the above formula (7) should be read as the boron compound of the above formula (54), (56), or (58), and the compound of the above formula (8) should be read as the compound of the above formula (63).

In the production process (2-8), (2-9), or (2-10), the boron compound of the above formula (54), (56), or (58), which is a starting material, can be produced in accordance with the production process for the boron compound of the above formula (7). The compound of the above formula (63), which is a starting material, can be produced by any of the heretofore known processes or can be obtained as commercially available products.

<Production Processes (2-11) to (2-13)>

In the above formula (3), Q and X may preferably be part of a common ring, and it may be more preferred that the above common ring is a pyridine ring, a quinoline ring, or a thiophene ring, X is the nitrogen atom of the pyridine ring or the quinoline ring, or the sulfur atom of the thiophene ring, and m is 0. That is, a preferred boron compound of the following formula (68):

[Chemical Formula 171]

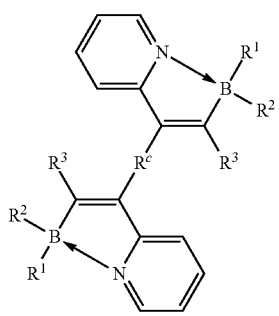

(68)

wherein $R^1$, $R^2$, and $R^3$ have the same meanings as in the above formula (6); plurally occurring $R^1$'s, $R^2$'s, and $R^3$'s are the same or different from each other, respectively; the pyridine ring optionally has at least one substituent group; and $R^c$ has the same meaning as in the above formula (3), can be produced by reacting a boron compound of the following formula (54):

[Chemical Formula 172]

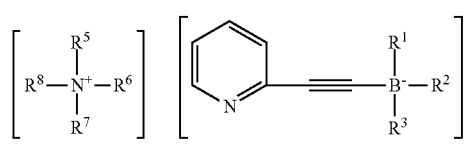

(54)

wherein $R^1$, $R^2$, and $R^3$ have the same meanings as in the above formula (6); the pyridine ring optionally has at least one substituent group; and $R^5$, $R^6$, $R^7$, and $R^8$ have the same meanings as in the above formula (7), with a compound of the following formula (64):

[Chemical Formula 173]

Y—$R^c$—Y     (64)

wherein $R^c$ has the same meaning as in the above formula (3); Y has the same meaning as in the above formula (8); and plurally occurring Y's are the same or different from each other, in the presence of a catalyst containing at least one metal element selected from the group consisting of palladium, platinum, and nickel (hereinafter referred to sometimes as the "production process (2-11)").

Further, a preferred boron compound of the following formula (69):

[Chemical Formula 174]

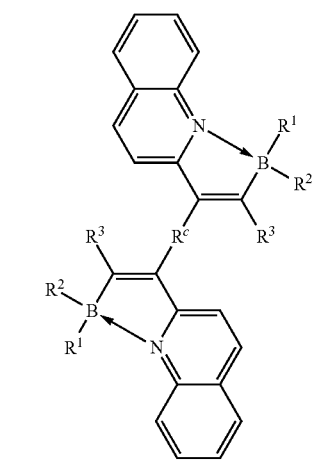

(69)

wherein $R^1$, $R^2$, and $R^3$ have the same meanings as in the above formula (6); plurally occurring $R^1$'s, $R^2$'s, and $R^3$'s are the same or different from each other, respectively; the quinoline ring optionally has at least one substituent group; and $R^e$ has the same meaning as in the above formula (3), can be produced by reacting a boron compound of the following formula (56):

[Chemical Formula 175]

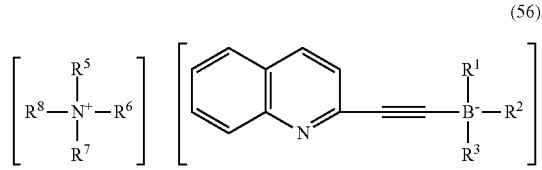

(56)

wherein $R^1$, $R^2$, and $R^3$ have the same meanings as in the above formula (6); the quinoline ring optionally has at least one substituent group; and $R^5$, $R^6$, $R^7$, and $R^8$ have the same meanings as in the above formula (7), with a compound of the following formula (64):

[Chemical Formula 176]

Y—$R^c$—Y     (64)

wherein $R^c$ has the same meaning as in the above formula (3); Y has the same meaning as in the above formula (8); and plurally occurring Y's are the same or different from each other, in the presence of a catalyst containing at least one metal element selected from the group consisting of palladium, platinum, and nickel (hereinafter referred to sometimes as the "production process (2-12)").

Further, a preferred boron compound of the following formula (70):

[Chemical Formula 177]

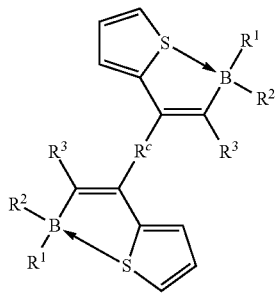

(70)

wherein $R^1$, $R^2$, and $R^3$ have the same meanings as in the above formula (6); plurally occurring $R^1$'s, $R^2$'s, and $R^3$'s are the same or different from each other, respectively; the thiophene ring optionally has at least one substituent group; and $R^c$ has the same meaning as in the above formula (3), can be produced by reacting a boron compound of the following formula (58):

[Chemical Formula 178]

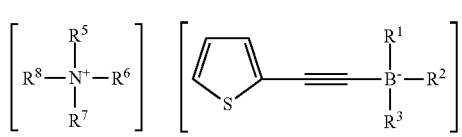

(58)

wherein $R^1$, $R^2$, and $R^3$ have the same meanings as in the above formula (6); the thiophene ring optionally has at least one substituent group; and $R^5$, $R^6$, $R^7$, and $R^8$ have the same meanings as in the above formula (7), with a compound of the following formula (64):

[Chemical Formula 179]

Y—$R^c$—Y (64)

wherein $R^c$ has the same meaning as in the above formula (3); Y has the same meaning as in the above formula (8); and plurally occurring Y's are the same or different from each other, in the presence of a catalyst containing at least one metal element selected from the group consisting of palladium, platinum, and nickel (hereinafter referred to sometimes as the "production process (2-13)").

In the production process (2-11), (2-12), or (2-13), the amounts of the starting materials to be used, the types and amounts of the catalyst and the stabilizer to be used, the types of the organic solvent and the inert gas, the reaction conditions, the post-treatments after the completion of the reaction, and others, are similar to those of the production process (2); however, the amounts of the starting materials to be used, and the amounts of the catalyst and the stabilizer to be used, have values determined when the variable n is 2, and the above formula (7) should be read as the boron compound of the above formula (54), (56), or (58), and the compound of the above formula (8) should be read as the compound of the above formula (64).

In the production process (2-11), (2-12), or (2-13), the boron compound of the above formula (54), (56), or (58), which is a starting material, can be produced in accordance with the production process for the boron compound of the above formula (7). The compound of the above formula (64), which is a starting material, can be produced by any of the heretofore known processes or can be obtained as commercially available products.

<Production Processes (2-14) and (2-15)>

In the above formula (9) or (3), it may be preferred that Q is a methylene group, X is a nitrogen atom, and m is 2. That is, a preferred boron compound of the following formula (71):

[Chemical Formula 180]

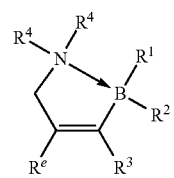

(71)

wherein $R^1$, $R^2$, $R^3$, and $R^4$ have the same meanings as in the above formula (6); plurally occurring $R^4$'s are the same or different from each other; an arrow directed from N to B indicates a coordinate bond; and $R^e$ has the same meaning as in the above formula (9), can be produced by reacting a boron compound of the following formula (60):

[Chemical Formula 181]

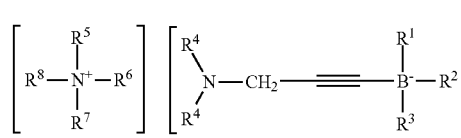

(60)

wherein $R^1$, $R^2$, $R^3$, and $R^4$ have the same meanings as in the above formula (6); plurally occurring $R^4$'s are the same or different from each other; and $R^5$, $R^6$, $R^7$, and $R^8$ have the same meanings as in the above formula (7), with a compound of the following formula (63):

[Chemical Formula 182]

$R^e$—Y (63)

wherein $R^e$ has the same meaning as in the above formula (9); and Y has the same meaning as in the above formula (8), in the presence of a catalyst containing at least one metal element selected from the group consisting of palladium, platinum, and nickel (hereinafter referred to sometimes as the "production process (2-14)").

Further, a preferred boron compound of the following formula (72):

[Chemical Formula 183]

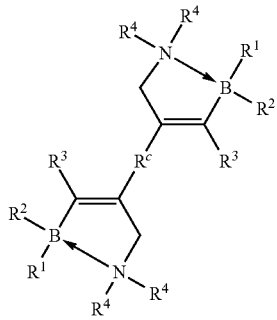

(72)

wherein $R^1$, $R^2$, $R^3$, and $R^4$ have the same meanings as in the above formula (6); plurally occurring $R^1$'s, $R^2$'s, $R^3$'s, and $R^4$'s are the same or different from each other, respectively; an arrow directed from N to B indicates a coordinate bond; and $R^c$ has the same meaning as in the above formula (3), can be produced by reacting a boron compound of the following formula (60):

[Chemical Formula 184]

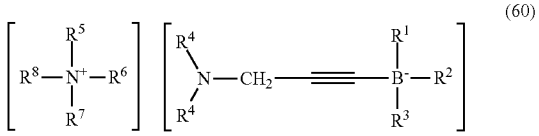

(60)

wherein $R^1$, $R^2$, $R^3$, and $R^4$ have the same meanings as in the above formula (6); plurally occurring $R^4$'s are the same or different from each other; and $R^5$, $R^6$, $R^7$, and $R^8$ have the same meanings as in the above formula (7), with a compound of the following formula (64):

[Chemical Formula 185]

 Y—$R^c$—Y (64)

wherein $R^c$ has the same meaning as in the above formula (3); Y has the same meaning as in the above formula (8); and plurally occurring Y's are the same or different from each other, in the presence of a catalyst containing at least one metal element selected from the group consisting of palladium, platinum, and nickel (hereinafter referred to sometimes as the "production process (2-15)").

In the production process (2-14) or (2-15), the amounts of the starting materials to be used, the types and amounts of the catalyst and the stabilizer to be used, the types of the organic solvent and the inert gas, the reaction conditions, the post-treatments after the completion of the reaction, and others, are similar to those of the production process (2); however, the amounts of the starting materials to be used, and the amounts of the catalyst and the stabilizer to be used, have values determined when the variable n is 1 or 2, and the boron compound of the above formula (7) should be read as the boron compound of the above formula (60), and the compound of the above formula (8) should be read as the compound of the above formula (63) or (64).

In the production process (2-14) or (2-15), the boron compound of the above formula (60), which is a starting material, can be produced in accordance with the production process for the boron compound of the above formula (7). The compound of the above formula (63) or (64), which is a starting material, can be produced by any of the heretofore known processes or can be obtained as commercially available products.

<Production Processes (2-16) and (2-17)>

In the above formula (9) or (3), it may be preferred that Q is a methylene group, X is an oxygen atom, and m is 1. That is, a preferred boron compound of the following formula (73):

[Chemical Formula 186]

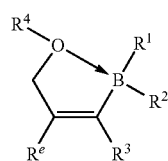

(73)

wherein $R^1$, $R^2$, $R^3$, and $R^4$ have the same meanings as in the above formula (6); an arrow directed from O to B indicates a coordinate bond; and $R^e$ has the same meaning as in the above formula (9), can be produced by reacting a boron compound of the following formula (62):

[Chemical Formula 187]

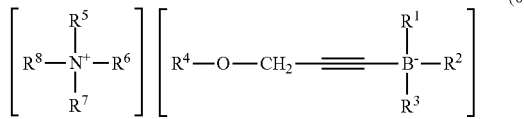

(62)

wherein $R^1$, $R^2$, $R^3$, and $R^4$ have the same meanings as in the above formula (6); and $R^5$, $R^6$, $R^7$, and $R^8$ have the same meanings as in the above formula (7), with a compound of the following formula (63):

[Chemical Formula 188]

 $R^e$—Y (63)

wherein $R^e$ has the same meaning as in the above formula (9); and Y has the same meaning as in the above formula (8), in the presence of a catalyst containing at least one metal element selected from the group consisting of palladium, platinum, and nickel (hereinafter referred to sometimes as the "production process (2-16)").

Further, a preferred boron compound of the following formula (74):

[Chemical Formula 189]

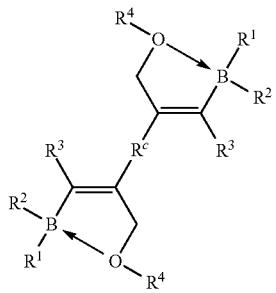

(74)

wherein $R^1$, $R^2$, $R^3$, and $R^4$ have the same meanings as in the above formula (6); plurally occurring $R^1$'s, $R^2$'s, $R^3$'s, and $R^4$'s are the same or different from each other, respectively; an arrow directed from O to B indicates a coordinate bond; and $R^c$ has the same meaning as in the above formula (3), can be produced by reacting a boron compound of the following formula (62):

[Chemical Formula 190]

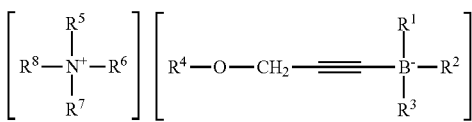

(62)

wherein $R^1$, $R^2$, $R^3$, and $R^4$ have the same meanings as in the above formula (6); and $R^5$, $R^6$, $R^7$, and $R^8$ have the same meanings as in the above formula (7), with a compound of the following formula (64):

[Chemical Formula 191]

Y—$R^c$—Y (64)

wherein $R^c$ has the same meaning as in the above formula (3); Y has the same meaning as in the above formula (8); and plurally occurring Y's are the same or different from each other, in the presence of a catalyst containing at least one metal element selected from the group consisting of palladium, platinum, and nickel (hereinafter referred to sometimes as the "production process (2-17)").

In the production process (2-16) or (2-17), the amounts of the starting materials to be used, the types and amounts of the catalyst and the stabilizer to be used, the types of the organic solvent and the inert gas, the reaction conditions, the post-treatments after the completion of the reaction, and others, are similar to those of the production process (2); however, the amounts of the starting materials to be used, and the amounts of the catalyst and the stabilizer to be used, have values determined when the variable n is 1 or 2, and the boron compound of the above formula (7) should be read as the boron compound of the above formula (62), and the compound of the above formula (8) should be read as the compound of the above formula (63) or (64).

In the production process (2-16) or (2-17), the boron compound of the above formula (62), which is a starting material, can be produced in accordance with the production process for the boron compound of the above formula (7). The compound of the above formula (63) or (64), which is a starting material, can be produced by any of the heretofore known processes or can be obtained as commercially available products.

<Production Process (3)>

Among the novel boron compounds I of the present invention, a boron compound of the following formula (11):

[Chemical Formula 192]

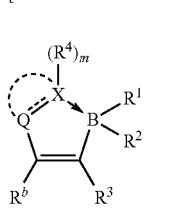

(11)

wherein $R^1$, $R^2$, and $R^3$ are the same or different from each other and are each independently an aryl group or a heterocyclic group, each of which optionally has at least one substituent group, or any two of $R^1$, $R^2$, and $R^3$ are combined with each other to form a ring; $R^4$ is a hydrogen atom or a substituent group; m is an integer of from 0 to 2; when m is 2, plurally occurring $R^4$'s are the same or different from each other; Q is a linking group; X is a nitrogen atom, an oxygen atom, a sulfur atom, a phosphorus atom, or a selenium atom; a dashed half arc indicates that Q and X may be part of a common ring; dashed and solid lines between Q and X indicate a single or double bond; an arrow directed from X to B indicates a coordinate bond; and $R^b$ is hydrogen or a monovalent organic framework, can be produced by reacting a boron compound of the following formula (12):

[Chemical Formula 193]

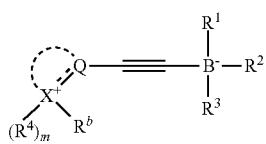

(12)

wherein $R^1$, $R^2$, $R^3$, $R^4$, $R^b$, m, Q, X, a dashed half arc, and dashed and solid lines between Q and X have the same meanings as in the above formula (11); and when m is 2, plurally occurring $R^4$'s are the same or different from each other, in the presence of a catalyst containing at least one metal element selected from the group consisting of palladium, platinum, and nickel (hereinafter referred to sometimes as the "production process (3)").

The amount of the boron compound of the above formula (12) may appropriately be adjusted depending on the required amount of the final product, and although it is not particularly limited, for example, it may preferably be not smaller than 0.01 mmol and not larger than 2 mmol, more preferably not smaller than 0.05 mmol and not larger than 1 mmol, and still more preferably not smaller than 0.1 mmol and not larger than 0.5 mmol, per 1 mL of the organic solvent. When the amount of the boron compound of the above formula (12) to be used is too small, the reaction efficiency may be poor, resulting in a decrease in the productivity. In contrast, when the amount of the boron compound of the above formula (12) to be used is too great, as the case may be, the boron compound of the above formula (12) is less soluble in the organic solvent, resulting in a decrease in the yield.

The catalyst contains at least one metal element selected from the group consisting of palladium, platinum, and nickel. Among these metal elements, palladium and platinum may be preferred.

Examples of the catalyst may include, but are not limited to, complexes containing metal elements as described above. Specific examples of the catalyst may include, but are not limited to, tris(dibenzylideneacetone)dipalladium chloroform complex ($Pd_2dba_3.CHCl_3$), tetrakis(triphenylphosphine)palladium, bis(tri-tert-butylphosphine)palladium (Pd($P^tBu_3$)$_2$), bis(tricyclohexylphosphine)palladium, bis(1,5-cyclooctadiene)platinum, and bis(1,5-cyclooctadiene)nickel. These catalysts may be used alone, or two or more kinds thereof may be used in combination. Among these catalysts, tris(dibenzylideneacetone)dipalladium chloroform complex ($Pd_2dba_3.CHCl_3$) may be preferred.

The amount of the catalyst to be used may preferably not smaller than 0.001 mol and not larger than 0.2 mol, more preferably not smaller than 0.005 mol and not larger than 0.15 mol, and still more preferably not smaller than 0.01 mol and not larger than 0.1 mol, relative to 1 mol of the boron compound of the above formula (12). When the amount of the catalyst to be used is too small, the reaction rate may be slow, so that the reaction cannot quickly proceed. In contrast, when the amount of the catalyst to be used is too great, the catalyst may be used more than necessary, resulting in an increase in the production cost.

In the above reaction, a stabilizer may be used in addition to the catalyst. Examples of the stabilizer may include, but are not limited to, triphenylphosphine, tri(o-tolyl)phosphine (P(o-tol)$_3$), tri(2-furyl)phosphine, tri-tert-butylphosphine, trimethylphosphine, dimethylphenylphosphine, diphenylmethylphosphine, tricyclohexylphosphine, bis[2-(diphenylphosphino)phenyl]ether (DPEphos; or also called "(oxydi-2,1-phenylene)bis(diphenylphosphine)"), and bipyridine. These stabilizers may be used alone, or two or more kinds thereof may be used in combination. Among these stabilizers, tri(o-tolyl)phosphine (P(o-tol)$_3$) may be preferred.

The amount of the stabilizer to be used may preferably be not smaller than 0.01 mol and not larger than 0.3 mol, more preferably not smaller than 0.02 mol and not larger than 0.25 mol, and still more preferably not smaller than 0.03 mol and not larger than 0.2 mol, relative to 1 mol of the boron compound of the above formula (12). When the amount of the stabilizer to be used is too small, the function of the stabilizer cannot sufficiently be exerted, resulting in a decrease in the yield. In contrast, when the amount of the stabilizer to be used is too great, the stabilizer may be used more than necessary, resulting in an increase in the production cost.

In this connection, when a catalyst containing at least one stabilizer such as phosphine ligand (e.g., tetrakis(triphenylphosphine)palladium, bis(tri-tert-butylphosphine)palladium, bis(tricyclohexylphosphine)palladium) is used, there is no need to use an additional stabilizer.

The above reaction is typically carried out in an organic solvent. Examples of the organic solvent may include, but are not limited to, aromatic hydrocarbons such as benzene, toluene, xylene, and mesitylene; halogenated aromatic hydrocarbons such as chlorobenzene and 1,2-dichlorobenzene; halogenated aliphatic hydrocarbons such as dichloromethane, chloroform, carbon tetrachloride, 1,2-dichloroethane, 1,1,1-trichloroethane, 1,1,2,2-tetrachloroethane, 1,2-dichloroethylene, trichloroethylene, and tetrachloroethylene; alcohols such as methanol, ethanol, isopropyl alcohol, 1-buthanol, 2-buthanol, isobutyl alcohol, and isopentyl alcohol; esters such as methyl acetate, ethyl acetate, propyl acetate, isopropyl acetate, butyl acetate, isobutyl acetate, pentyl acetate, and isopentyl acetate; ethers such as diethyl ether, 1,4-dioxane, tetrahydrofuran, and methyl phenyl ether (anisole); ketones such as acetone, methyl ethyl ketone, methyl butyl ketone, and methyl isobutyl ketone; glycol ethers (cellosolves) such as ethylene glycol monomethyl ether (methylcellosolve), ethylene glycol monoethyl ether (cellosolve), ethylene glycol monobutyl ether (butylcellosolve), and ethylene glycol monoethyl ether acetate (cellosolve acetate); alicyclic hydrocarbons such as cyclohexane, cyclohexanone, methylcyclohexanone, cyclohexanol, and methylcyclohexanol; and aliphatic hydrocarbons such as n-hexane. These organic solvents may be used alone, or two or more kinds thereof may be used in combination. Among these organic solvents, there may be preferred halogenated aliphatic hydrocarbons such as dichloromethane and 1,2-dichloroethane, and ethers such as tetrahydrofuran.

The above reaction may preferably be carried out under an inert gas atmosphere. Examples of the inert gas may include, but are not limited to, nitrogen, helium, and argon. These inert gases may be used alone, or two or more kinds thereof may be used in combination. Among these inert gases, nitrogen and argon may be preferred.

The reaction conditions are not particularly limited, so long as the above reaction can sufficiently proceed under these conditions. For example, the reaction temperature may preferably be from 0° C. to 100° C., more preferably from room temperature to 80° C., and the reaction time may preferably be from 0.5 to 24 hours, more preferably from 1 to 12 hours. The reaction pressure may be normal pressure, reduced pressure, or increased pressure, preferably normal pressure.

After the completion of the reaction, for example, the reaction solution is directly concentrated or evaporated to dryness, or alternatively, water is added to the reaction solution, followed by extraction with an appropriate organic solvent, washing with water and a saturated sodium chloride solution, and then concentration or evaporation to dryness, and if necessary, followed by purification using any of the heretofore known methods, e.g., various kinds of chromatography or recrystallization. Thus, the desired product is obtained.

In the production process (3), the boron compound of the above formula (12), which is a starting material, can be produced by causing acid-base reaction between a 1-alkyne compound of the following formula (75):

[Chemical Formula 194]

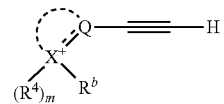

(75)

wherein $R^4$, m, Q, X, a dashed half arc, and dashed and solid lines between Q and X have the same meanings as in the above formula (11); when m is 2, plurally occurring $R^4$'s are the same or different from each other; and $R^b$ has the same meaning as in the above formula (12), and a strong base such as n-butyl lithium or sodium amide, to form a salt of the 1-alkyne compound, and then reacting this salt with a boron compound of the following formula (43):

[Chemical Formula 195]

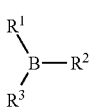

(43)

wherein $R^1$, $R^2$, and $R^3$ have the same meanings as in the above formula (11), or with a complex thereof, to cause cation exchange. In this connection, these reactions are heretofore known (see, e.g., Dietmar Seyferth and Michael A. Weiner, J. Am. Chem. Soc., 1961, 83(17), pp. 3583-3586). The amounts of the starting materials to be used, the type of the organic solvent, the reaction conditions, and others, may appropriately be selected, and are not particularly limited. The 1-alkyne compound of the above formula (75), which is a starting material, can be produced by any of the heretofore known processes or can be obtained as commercially available products.

<Production Processes (3-1) and (3-2)>

In the above formulas (11) and (12), Q and X may preferably be part of a common ring, and it may be more preferred that the above common ring is a pyridine ring, a quinoline ring, or a thiophene ring, X is the nitrogen atom of the pyridine ring or the quinoline ring, or the sulfur atom of the thiophene ring, and m is 0. That is, a preferred boron compound of the following formula (76):

[Chemical Formula 196]

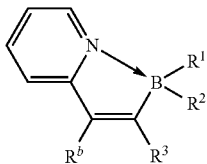

(76)

wherein $R^1$, $R^2$, and $R^3$ have the same meanings as in the above formula (11); the pyridine ring optionally has at least one substituent group; an arrow directed from N to B indicates a coordinate bond; and $R^b$ has the same meaning as in the above formula (12), can be produced by reacting a boron compound of the following formula (77):

[Chemical Formula 197]

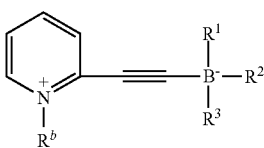

(77)

wherein $R^1$, $R^2$, and $R^3$ have the same meanings as in the above formula (11); and $R^b$ has the same meaning as in the above formula (12), in the presence of a catalyst containing at least one metal element selected from the group consisting of palladium, platinum, and nickel (hereinafter referred to sometimes as the "production process (3-1)").

Further, a preferred boron compound of the following formula (78):

[Chemical Formula 198]

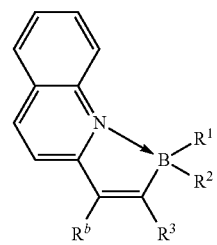

(78)

wherein $R^1$, $R^2$, and $R^3$ have the same meanings as in the above formula (11); the quinoline ring optionally has at least one substituent group; an arrow directed from N to B indicates a coordinate bond; and $R^b$ has the same meaning as in the above formula (12), can be produced by reacting a boron compound of the following formula (79):

[Chemical Formula 199]

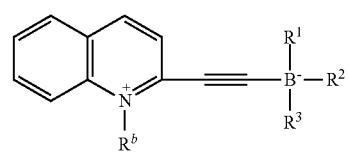

(79)

wherein $R^1$, $R^2$, and $R^3$ have the same meanings as in the above formula (11); the quinoline ring optionally has at least one substituent group; and $R^b$ has the same meaning as in the above formula (12), in the presence of a catalyst containing at least one metal element selected from the group consisting of palladium, platinum, and nickel (hereinafter referred sometimes to as the "production process (3-2)").

In the production process (3-1) or (3-2), the amounts of the starting materials to be used, the types and amounts of the catalyst and the stabilizer to be used, the types of the organic solvent and the inert gas, the reaction conditions, the post-treatments after the completion of the reaction, and others, are similar to those of the production process (3); however, the boron compound of the above formula (12) should be read as the boron compound of the above formula (77) or (79).

In the production process (3-1) or (3-2), the boron compound of the above formula (77) or (79), which is a starting material, can be produced in accordance with the production process for the boron compound of the above formula (12).

<Production Process (4)>

Among the novel boron compounds I of the present invention, a boron compound of the following formula (13):

[Chemical Formula 200]

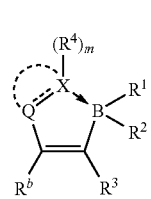

(13)

wherein $R^1$, $R^2$, and $R^3$ are the same or different from each other and are each independently an aryl group or a heterocyclic group, each of which optionally has at least one substituent group, or alternatively, $R^1$ and $R^2$ are combined with each other to form a ring; $R^4$ is a hydrogen atom or a substituent group; m is an integer of from 0 to 2; when m is 2, plurally occurring $R^4$'s are the same or different from each other; Q is a linking group; X is a nitrogen atom, an oxygen atom, a sulfur atom, a phosphorus atom, or a selenium atom; a dashed half arc indicates that Q and X may be part of a common ring; dashed and solid lines between Q and X indicate a single or double bond; an arrow directed from X to B indicates a coordinate bond; and $R^b$ is hydrogen or a monovalent organic framework, can be produced by reacting a lithium compound which is produced by causing an organic lithium compound to act on a compound of the following formula (14):

[Chemical Formula 201]

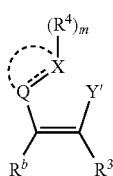

(14)

wherein $R^3$, $R^4$, m, Q, X, a dashed half arc, dashed and solid lines between Q and X, and $R^b$ have the same meanings as in the above formula (13); when m is 2, plurally occurring $R^4$'s are the same or different from each other; and Y' is a chlorine atom, a bromine atom, or an iodine atom, with a boron compound of the following formula (15):

[Chemical Formula 202]

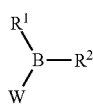

(15)

wherein $R^1$ and $R^2$ have the same meanings as in the above formula (13); and W is a fluorine atom, a chlorine atom, a bromine atom, an iodine atom, an alkoxy group, or an aryloxy group (hereinafter referred to sometimes as the "production process (4)").

Examples of the organic lithium compound to be used in the above reaction may include, but are not limited to, n-butyl lithium, sec-butyl lithium, and tert-butyl lithium. These organic lithium compounds may be used alone, or two or more kinds thereof may be used in combination. Among these organic lithium compounds, n-butyl lithium may be preferred.

The amount of the organic lithium compound to be used may preferably be not smaller than 0.5 mol and not larger than 2.0 mol, more preferably not smaller than 0.65 mol and not larger than 1.5 mol, and still more preferably not smaller than 0.8 mol and not larger than 1.2 mol, relative to 1 mol of the compound of the above formula (14). When the amount of the organic lithium compound to be used is too small, a lack of the organic lithium compound may occur, resulting in a decrease in the yield of the final product. In contrast, when the amount of the organic lithium compound to be used is too great, an excess of the amount of the organic lithium compound to be used may occur, so that the organic lithium compound reacts with the boron compound of the above formula (15), resulting in a decrease in the yield of the final product or an increase in the production cost.

The amount of the boron compound of the above formula (15) to be used may preferably be not smaller than 0.5 mol and not larger than 2.0 mol, more preferably not smaller than 0.65 mol and not larger than 1.5 mol, and still more preferably not smaller than 0.8 mol and not larger than 1.2 mol, relative to 1 mol of the compound of the above formula (14). When the amount of the boron compound of the above formula (15) to be used is too small, a lack of the boron compound of the above formula (15) may occur, resulting in a decrease in the yield of the final product. In contrast, when the amount of the boron compound of the above formula (15) to be used is too great, an excess of the boron compound of the above formula (15) may occur, resulting in an increase in the production cost.

The above reaction is typically carried out in an organic solvent. Examples of the organic solvent may include, but are not limited to, ethers such as diethyl ether, tetrahydrofuran, 1,4-dioxane, and methyl phenyl ether (anisole); aliphatic hydrocarbons such as n-hexane; alicyclic hydrocarbons such as cyclohexane; and aromatic hydrocarbons such as benzene, toluene, xylene, and mesitylene. These organic solvents may be used alone, or two or more kinds thereof may be used in combination. Among these organic solvents, ethers such as diethyl ether and tetrahydrofuran may be preferred.

The above reaction may preferably be carried out under an inert gas atmosphere. Examples of the inert gas may include, but are not limited to, nitrogen, helium, and argon. These inert gases may be used alone, or two or more kinds thereof may be used in combination. Among these inert gases, nitrogen and argon may be preferred.

The reaction conditions are not particularly limited, so long as the above reaction can sufficiently proceed under these conditions. For example, in the step of allowing the organic lithium compound to act on the compound of the above formula (14), the reaction temperature may preferably be from −150° C. to 50° C., more preferably from −100° C. to 0° C., and the reaction time may preferably be from 0.5 to 10 hours, more preferably from 1 to 3 hours. The reaction pressure may be normal pressure, reduced pressure, or increased pressure, preferably normal pressure. In the step of reacting the resultant lithium compound with the boron compound of the above formula (15), the reaction temperature may preferably from 0° C. to 100° C., more preferably from 10° C. to 50° C., and the reaction time may preferably be from 5 to 30 hours, more preferably from 12 to 24 hours. The reaction pressure may be normal pressure, reduced pressure, or increased pressure, preferably normal pressure.

After the completion of the reaction, for example, the reaction solution is directly concentrated or evaporated to dryness, or alternatively, water is added to the reaction solution, followed by extraction with an appropriate organic solvent, washing with water and a saturated sodium chloride solution, and then concentration or evaporation to dryness, and if necessary, followed by purification using any of the heretofore known methods, e.g., various kinds of chromatography or recrystallization. Thus, the desired product is obtained.

In the production process (4), the compound of the above formula (14), which is a starting material, can be produced by casing organomellation reaction of an acetylene compound of the following formula (80):

[Chemical Formula 203]

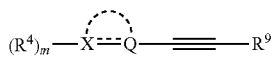
(80)

wherein $R^4$, m, Q, X, a dashed half arc, and dashed and solid lines between Q and X have the same meanings as in the above formula (13); and $R^9$ is a silyl group, a germyl group, or a stannyl group, with a metal hydride (e.g., diisobutylaluminum hydride, biscyclopentadienyl zirconium chloride hydride, catechol borane) or trialkyl aluminum, followed by metal exchange reaction with zinc chloride, copper chloride, or the like, to produce a vinyl metal compound of the following formula (81):

[Chemical Formula 204]

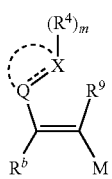
(81)

wherein $R^4$, m, Q, X, a dashed half arc, dashed and solid lines between Q and X, and $R^b$ have the same meanings as in the above formula (13); when m is 2, plurally occurring $R^4$'s are the same or different from each other; $R^9$ has the same meaning as in the above formula (80); and M is a metal atom, and then reacting the resultant vinylmetal compound with an organic halogen compound of the following formula (82):

[Chemical Formula 205]

  $R^3$—Z (82)

wherein $R^3$ has the same meaning as in the above formula (13); and Z is a fluorine atom, a chlorine atom, a bromine atom, an iodine atom, or a trifluoromethane-sulfonyloxy group, in the presence of a catalyst containing palladium or nickel, and then allowing a halogenating agent (e.g., N-iodosuccinimide, N-bromosuccinimide, bromine, iodine) to act on the resultant product to replace the substituent group $R^9$ with a halogen atom (Y). In this connection, these reactions are heretofore known (see, e.g., J. Org. Chem., 1995, pp. 3276-3277; and J. Am. Chem. Soc., 1986, pp. 3402-3408). The amounts of the starting materials to be used, the type of the organic solvent, the reaction conditions, and others, may appropriately be selected, and are not particularly limited. The above metal exchange reaction with zinc chloride, copper chloride, or the like, is not necessarily required.

The boron compound of the above formula (15), which is a starting material, can be produced by any of the heretofore known processes or can be obtained as commercially available products.

<Production Processes (4-1) to (4-3)>

In the above formulas (13) and (14), Q and X may preferably be part of a common ring, and it may be more preferred that the above common ring is a pyridine ring, a quinoline ring, or a thiophene ring, X is the nitrogen atom of the pyridine ring or the quinoline ring, or the sulfur atom of the thiophene ring, and m is 0. That is, a preferred boron compound of the following formula (83):

[Chemical Formula 206]

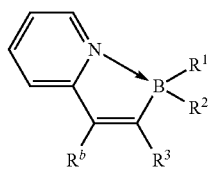
(83)

wherein $R^1$, $R^2$, $R^3$, and $R^b$ have the same meanings as in the above formula (13); the pyridine ring optionally has at least one substituent group; and an arrow directed from N to B indicates a coordinate bond, can be produced by reacting a lithium compound which is produced by allowing an organic lithium compound to act on a compound of the following formula (84):

[Chemical Formula 207]

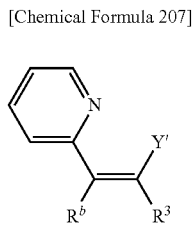
(84)

wherein $R^3$ and $R^b$ have the same meanings as in the above formula (13); the pyridine ring optionally has at least one substituent group; and Y' is a chlorine atom, a bromine atom, or an iodine atom, with a boron compound of the following formula (15):

[Chemical Formula 208]

(15)

wherein $R^1$ and $R^2$ have the same meanings as in the above formula (13); and W is a fluorine atom, a chlorine atom, a bromine atom, an iodine atom, an alkoxy group, or an aryloxy group (hereinafter referred to sometimes as the "production process (4-1)").

Further, a preferred boron compound of the following formula (85):

[Chemical Formula 209]

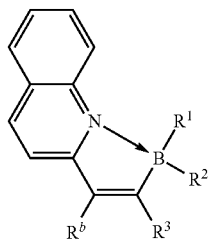
(85)

wherein $R^1$, $R^2$, $R^3$, and $R^b$ have the same meanings as in the above formula (13); the quinoline ring optionally has at least one substituent group; and an arrow directed from N to B indicates a coordinate bond, can be produced by reacting a lithium compound which is produced by allowing an organic lithium compound to act on a compound of the following formula (86):

[Chemical Formula 210]

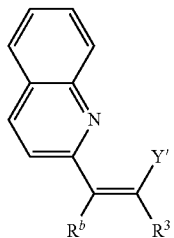

(86)

wherein $R^3$ and $R^b$ have the same meanings as in the above formula (13); the quinoline ring optionally has at least one substituent group; and Y' is a chlorine atom, a bromine atom, or an iodine atom, with a boron compound of the following formula (15):

[Chemical Formula 211]

(15)

wherein $R^1$ and $R^2$ have the same meanings as in the above formula (13); and W is a fluorine atom, a chlorine atom, a bromine atom, an iodine atom, an alkoxy group, or an aryloxy group (hereinafter referred to sometimes as the "production process (4-2)").

Further, a preferred boron compound of the following formula (87):

[Chemical Formula 212]

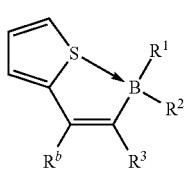

(87)

wherein $R^1$, $R^2$, $R^3$, and $R^b$ have the same meanings as in the above formula (13); the thiophene ring optionally has at least one substituent group; and an arrow directed from S to B indicates a coordinate bond, can be produced by reacting a lithium compound which is produced by allowing an organic lithium compound to act on a compound of the following formula (88):

[Chemical Formula 213]

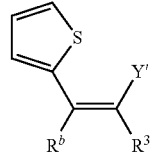

(88)

wherein $R^3$ and $R^b$ have the same meanings as in the above formula (13); the thiophene ring optionally has at least one substituent group; and Y' is a chlorine atom, a bromine atom, or an iodine atom, with a boron compound of the following formula (15):

[Chemical Formula 214]

(15)

wherein $R^1$ and $R^2$ have the same meanings as in the above formula (13); and W is a fluorine atom, a chlorine atom, a bromine atom, an iodine atom, an alkoxy group, or an aryloxy group (hereinafter referred to sometimes as the "production process (4-3)").

In the production process (4-1), (4-2), or (4-3), the amounts of the starting materials to be used, the type and amount of the organic lithium compound to be used, the types of the organic solvent and the inert gas, the reaction conditions, the post-treatments after the completion of the reaction, and others, are similar to those of the production process (4); however, the compound of the above formula (14) should be read as the compound of the above formula (84), (86), or (88).

In the production process (4-1), (4-2), or (4-3), the compound of the above formula (84), (86), or (88), which is a starting material, can be produced in accordance with the production process for the compound of the above formula (14). The boron compound of the above formula (15), which is a starting material, can be produced by any of the heretofore known processes or can be obtained as commercially available products.

<Production Process (5)>

One of the novel boron compounds I of the present invention, i.e., a boron compound of the following formula (1):

[Chemical Formula 215]

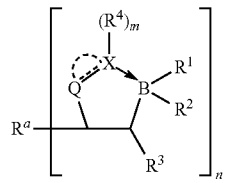

(1)

wherein $R^1$, $R^2$, and $R^3$ are the same or different from each other and are each independently an aryl group or a heterocyclic group, each of which optionally has at least one substituent group, or any two of $R^1$, $R^2$, and $R^3$ are combined with each other to form a ring; $R^4$ is a hydrogen atom or a substituent group; m is an integer of from 0 to 2; when m is 2, plurally occurring R⁴'s are the same or different from each other; Q is a linking group; X is a nitrogen atom, an oxygen atom, a sulfur atom, a phosphorus atom, or a selenium atom; a dashed half arc indicates that Q and X may be part of a common ring; dashed and solid lines between Q and X indicate a single or double bond; an arrow directed from X to B indicates a coordinate bond; $R^a$ is hydrogen or a monovalent, divalent, trivalent, or tetravalent organic framework; n is an integer of from 1 to 4; and when n is an integer of from 2 to 4, plurally occurring R¹'s, R²'s, R³'s, R⁴'s, m's, Q's, X's, dashed half arcs, and dashed and solid lines between Q and X are the same or different from each other, respectively, can be produced by reacting a boron compound of the following formula (4):

[Chemical Formula 216]

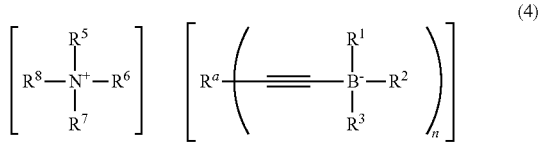

(4)

wherein $R^1$, $R^2$, $R^3$, $R^a$, and n have the same meanings as in the above formula (1); when n is an integer of from 2 to 4, plurally occurring R¹'s, R²'s, and R³'s are the same or different from each other; and $R^5$, $R^6$, $R^7$, and $R^8$ are the same or different from each other and are each independently a hydrogen atom or a substituent group, with a compound of the following formula (16):

[Chemical Formula 217]

(16)

wherein $R^4$, m, Q, X, a dashed half arc, and dashed and solid lines between Q and X have the same meanings as in the above formula (1); when m is 2, plurally occurring R⁴'s are the same or different from each other; and Tf is a trifluoromethanesulfonyl group, in the presence of a catalyst containing at least one metal element selected from the group consisting of palladium, platinum, and nickel.

In this connection, the trifluoromethanesulfonyl group as indicated by Tf is one of the strongest electron-withdrawing groups, which is also called a trifuryl group, and means $-SO_2CF_3$.

The amount of the compound of the above formula (16) to be used may preferably be not smaller than 0.5×n mol and not larger than 2.0×n mol, more preferably not smaller than 0.65×n mol and not larger than 1.5×n mol, and still more preferably not smaller than 0.8×n mol and not larger than 1.25×n mol, relative to 1 mol of the boron compound of the above formula (4). When the amount of the compound of the above formula (16) to be used is too small, a lack of the compound of the above formula (16) may occur, resulting in a decrease in the yield of the final product. In contrast, when the amount of the compound of the above formula (16) to be used is too great, an excess of the compound of the above formula (16) may occur, resulting in an increase in the production cost. In this connection, n is the number of boron-containing ring moieties (i.e., moieties in brackets) bonded to the hydrogen or the monovalent, divalent, trivalent, or tetravalent organic framework as indicated by $R^a$ in the above formula (1), and is an integer of from 1 to 4.

The catalyst contains at least one metal element selected from the group consisting of palladium, platinum, and nickel. Among these metal elements, palladium and platinum may be preferred.

Examples of the catalyst may include, but are not limited to, complexes containing metal elements as described above. Specific examples of the catalyst may include, but are not limited to, tris(dibenzylideneacetone)dipalladium chloroform complex ($Pd_2dba_3 \cdot CHCl_3$), tetrakis(triphenylphosphine)palladium, bis(tri-tert-butylphosphine)palladium (Pd($P^tBu_3$)$_2$), bis(tricyclohexylphosphine)palladium, bis(1,5-cyclooctadiene)platinum, and bis(1,5-cyclooctadiene)nickel. These catalysts may be used alone, or two or more kinds thereof may be used in combination. Among these catalysts, tris(dibenzylideneacetone)dipalladium chloroform complex ($Pd_2dba_3 \cdot CHCl_3$) may be preferred.

The amount of the catalyst to be used may preferably be not smaller than 0.001 mol and not larger than 0.2 mol, more preferably not smaller than 0.005 mol and not larger than 0.15 mol, and still more preferably not smaller than 0.01 mol and not larger than 0.1 mol, relative to 1 mol of the boron compound of the above formula (4). When the amount of the catalyst to be used is too small, the reaction rate may be slow, so that the reaction cannot quickly proceed. In contrast, when the amount of the catalyst to be used is too great, the catalyst may be used more than necessary, resulting in an increase in the production cost.

In the above reaction, a stabilizer may be used in addition to the catalyst. Examples of the stabilizer may include, but are not limited to, triphenylphosphine, tri(o-tolyl)phosphine (P(o-tol)$_3$), tri(2-furyl)phosphine, tri-tert-butylphosphine, trimethylphosphine, dimethylphenylphosphine, diphenylmethylphosphine, tricyclohexylphosphine, bis[2-(diphenylphosphino)phenyl]ether (DPEphos; or also called "(oxydi-2,1-phenylene)bis(diphenylphosphine)"), and bipyridine. These stabilizers may be used alone, or two or more kinds thereof may be used in combination. Among these stabilizers, bis[2-(diphenylphosphino)phenyl]ether (DPEphos) may be preferred.

The amount of the stabilizer to be used may preferably be not smaller than 0.01 mol and not larger than 0.3 mol, more preferably not smaller than 0.02 mol and not larger than 0.25 mol, and still more preferably not smaller than 0.03 mol and not larger than 0.2 mol, relative to 1 mol of the boron compound of the above formula (4). When the amount of the stabilizer to be used is too small, the function of the stabilizer cannot sufficiently be exerted, resulting in a decrease in the yield of the final product. In contrast, when the amount of the stabilizer to be used is too great, the stabilizer may be used more than necessary, resulting in an increase in the production cost.

In this connection, when a catalyst containing at least one stabilizer such as phosphine ligand (e.g., tetrakis(triphenylphosphine)palladium, bis(tri-tert-butylphosphine)palladium, bis(tricyclohexylphosphine)palladium) is used, there is no need to use an additional stabilizer.

The above reaction is typically carried out in an organic solvent. Examples of the organic solvent may include, but are not limited to, aromatic hydrocarbons such as benzene, toluene, xylene, and mesitylene; halogenated aromatic hydrocarbons such as chlorobenzene and 1,2-dichlorobenzene; halo genated aliphatic hydrocarbons such as dichloromethane, chloroform, carbon tetrachloride, 1,2-dichloroethane, 1,1,1-trichloroethane, 1,1,2,2-tetrachloroethane, 1,2-dichloroethylene, trichloroethylene, and tetrachloroethylene; alcohols such as methanol, ethanol, isopropyl alcohol, 1-buthanol, 2-buthanol, isobutyl alcohol, and isopentyl alcohol; esters such as methyl acetate, ethyl acetate, propyl acetate, isopropyl acetate, butyl acetate, isobutyl acetate, pentyl acetate, and isopentyl acetate; ethers such as diethyl ether, 1,4-dioxane, tetrahydrofuran, and methyl phenyl ether (anisole); ketones such as acetone, methyl ethyl ketone, methyl butyl ketone, and methyl isobutyl ketone; glycol ethers (cellosolves) such as ethylene glycol monomethyl ether (methylcellosolve), ethylene glycol monoethyl ether (cellosolve), ethylene glycol monobutyl ether (butylcellosolve), and ethylene glycol monoethyl ether acetate (cellosolve acetate); alicyclic hydrocarbons such as cyclohexane; aliphatic hydrocarbons such as n-hexane; and nitriles such as acetonitrile. These organic solvents may be used alone, or two or more kinds thereof may be used in combination. Among these organic solvents, aromatic hydrocarbons such as benzene and toluene may be preferred.

The above reaction may preferably be carried out under an inert gas atmosphere. Examples of the inert gas may include, but are not limited to, nitrogen, helium, and argon. These inert gases may be used alone, or two or more kinds thereof may be used in combination. Among these inert gases, nitrogen and argon may be preferred.

The reaction conditions are not particularly limited, so long as the above reaction can sufficiently proceeds under these conditions. For example, the reaction temperature may preferably be from 0° C. to 100° C., more preferably from room temperature to 80° C., and the reaction time may preferably be from 0.5 to 24 hours, more preferably from 1 to 12 hours. The reaction pressure may be normal pressure, reduced pressure, or increased pressure, preferably normal pressure.

After the completion of the reaction, for example, the reaction solution is directly concentrated or evaporated to dryness, or alternatively, water is added to the reaction solution, followed by extraction with an appropriate organic solvent, washing with water and a saturated sodium chloride solution, and then concentration or evaporation to dryness, and if necessary, followed by purification using any of the heretofore known methods, e.g., various kinds of chromatography or recrystallization. Thus, the desired product is obtained.

In the production process (5), the boron compound of the above formula (4), which is a starting material, can be produced by the process as described in the production process (1).

In the production process (5), the compound of the above formula (16), which is a starting material, can be produced by any of the heretofore known processes or can be obtained as commercially available products.

<Production Processes (5-1) to (5-4)>

In the above formulas (1) and (16), Q and X may preferably be part of a common ring, and it may be more preferred that the above common ring is a pyridine ring, a quinoline ring, a phenanthridine ring, or a thiophene ring, X is the nitrogen atom of the pyridine ring, quinoline ring, or phenanthridine ring, or the sulfur atom of the thiophene ring, and m is 0. That is, a preferred boron compound of the following formula (27):

[Chemical Formula 218]

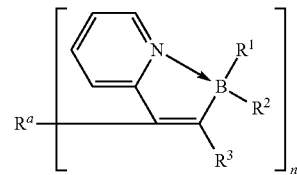

(27)

wherein $R^1$, $R^2$, $R^3$, $R^a$, and n have the same meanings as in the above formula (1); when n is an integer of from 2 to 4, plurally occurring $R^1$'s, $R^2$'s, and $R^3$'s are the same or different from each other, respectively; the pyridine ring optionally has at least one substituent group; and an arrow directed from N to B indicates a coordinate bond, can be produced by reacting a boron compound of the following formula (4):

[Chemical Formula 219]

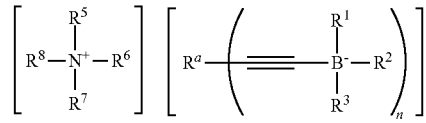

(4)

wherein $R^1$, $R^2$, $R^3$, $R^a$, and n have the same meanings as in the above formula (1); when n is an integer of from 2 to 4, plurally occurring $R^1$'s, $R^2$'s, and $R^3$'s are the same or different from each other, respectively; and $R^5$, $R^6$, $R^7$, and $R^8$ are the same or different from each other and are each independently a hydrogen atom or a substituent group, with a compound of the following formula (89):

[Chemical Formula 220]

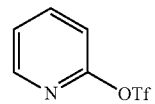

(89)

wherein Tf has the same meaning as, in the above formula (16), in the presence of a catalyst containing at least one metal element selected from the group consisting of palladium, platinum, and nickel (hereinafter referred to sometimes as the "production process (5-1)").

Further, a preferred boron compound of the following formula (28):

[Chemical Formula 221]

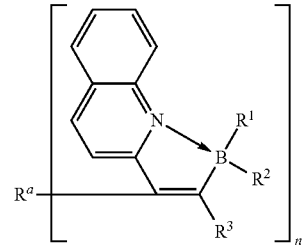

(28)

wherein $R^1$, $R^2$, $R^3$, $R^a$, and n have the same meanings as in the above formula (1); when n is an integer of from 2 to 4, plurally occurring $R^1$'s, $R^2$'s, and $R^3$'s are the same or different from each other, respectively; the quinoline ring optionally has at least one substituent group; and an arrow directed from N to B indicates a coordinate bond, can be produced by reacting a boron compound of the following formula (4):

[Chemical Formula 222]

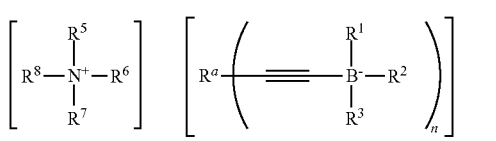

(4)

wherein $R^1$, $R^2$, $R^3$, $R^a$, and n have the same meanings as in the above formula (1); when n is an integer of from 2 to 4, plurally occurring $R^1$'s, $R^2$'s, and $R^3$'s are the same or different from each other, respectively; and $R^5$, $R^6$, $R^7$, and $R^8$ are the same or different from each other and are each independently a hydrogen atom or a substituent group, with a compound of the following formula (90):

[Chemical Formula 223]

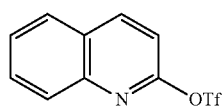

(90)

wherein Tf has the same meaning as in the above formula (16), in the presence of a catalyst containing at least one metal element selected from the group consisting of palladium, platinum, and nickel (hereinafter referred to sometimes as the "production process (5-2)").

Further, a preferred boron compound of the following formula (91):

[Chemical Formula 224]

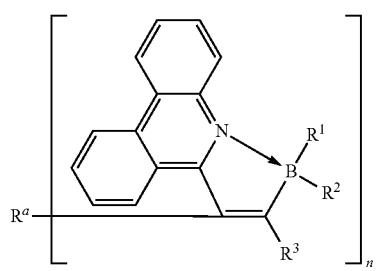

(91)

wherein $R^1$, $R^2$, $R^3$, $R^a$, and n have the same meanings as in the above formula (1); when n is an integer of from 2 to 4, plurally occurring $R^1$'s, $R^2$'s, and $R^3$s are the same or different from each other, respectively; the phenanthridine ring optionally has at least one substituent group; and an arrow directed from N to B indicates a coordinate bond, can be produced by reacting a boron compound of the following formula (4):

[Chemical Formula 225]

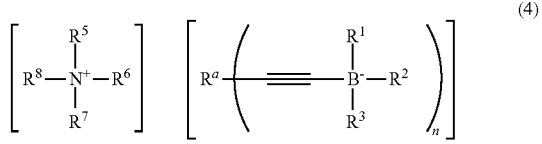

(4)

wherein $R^1$, $R^2$, $R^3$, $R^a$, and n have the same meanings as in the above formula (1); when n is an integer of from 2 to 4, plurally occurring $R^1$'s, $R^2$'s, and $R^3$'s are the same or different from each other, respectively; and $R^5$, $R^6$, $R^7$, and $R^8$ are the same or different from each other and are each independently a hydrogen atom or a substituent group, with a compound of the following formula (92):

[Chemical Formula 226]

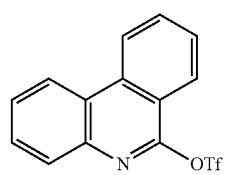

(92)

wherein Tf has the same meaning as in the above formula (16), in the presence of a catalyst containing at least one metal element selected from the group consisting of palladium, platinum, and nickel (hereinafter referred to sometimes as the "production process (5-3)").

Further, a preferred boron compound of the following formula (29):

[Chemical Formula 227]

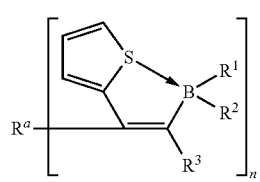

(29)

wherein $R^1$, $R^2$, $R^3$, $R^a$, and n have the same meanings as in the above formula (1); when n is an integer of from 2 to 4, plurally occurring $R^1$'s, $R^2$'s, and $R^3$'s are the same or different from each other, respectively; the thiophene ring optionally has at least one substituent group; and an arrow directed from S to B indicates a coordinate bond, can be produced by reacting a boron compound of the following formula (4):

[Chemical Formula 228]

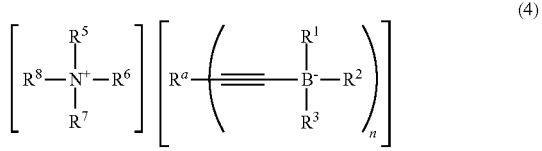

(4)

wherein $R^1$, $R^2$, $R^3$, $R^a$, and n have the same meanings as in the above formula (1); when n is an integer of from 2 to 4, plurally occurring $R^1$'s, $R^2$'s, and $R^3$'s are the same or different from each other, respectively; and $R^5$, $R^6$, $R^7$, and $R^8$ are the same or different from each other and are each independently a hydrogen atom or a substituent group, with a compound of the following formula (93):

[Chemical Formula 229]

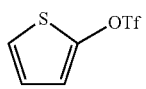

(93)

wherein Tf has the same meaning as in the above formula (16), in the presence of a catalyst containing at least one metal element selected from the group consisting of palladium, platinum, and nickel (hereinafter referred to sometimes as the "production process (5-4)").

In the production process (5-1), (5-2), (5-3), or (5-4), the amounts of the starting materials to be used, the types and amounts of the catalyst and the stabilizer to be used, the types of the organic solvent and the inert gas, the reaction conditions, the post-treatments after the completion of the reaction, and others, are similar to those of the production process (5); however, the compound of the above formula (16) should be read as the compound of the above formula (89), (90), (92), or (93).

In the production process (5-1), (5-2), (5-3), or (5-4), the boron compound of the above formula (4), which is a starting material, can be produced by the process as described in the production process (1). The compound of the above formula (89), (90), (92), or (93), which is a starting material, can be produced by any of the heretofore processes or can be obtained as commercially available products.

Novel Boron Compounds II

The novel boron compounds II according to the present invention are boron compounds of the following formula (17):

[Chemical Formula 230]

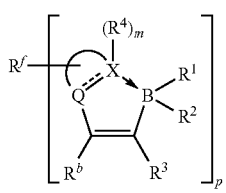

(17)

wherein $R^1$, $R^2$, and $R^3$ are the same or different from each other and are each independently an aryl group or a heterocyclic group, each of which optionally has at least one substituent group, or any two of $R^1$, $R^2$, and $R^3$ are combined with each other to form a ring; $R^4$ is a hydrogen atom or a substituent group; m is an integer of from 0 to 2; when m is 2, plurally occurring $R^4$'s are the same or different from each other; Q is a linking group; X is a nitrogen atom, an oxygen atom, a sulfur atom, a phosphorus atom, or a selenium atom; a solid half arc indicates that Q and X are part of a common ring; dashed and solid lines between Q and X indicate a single or double bond; an arrow directed from X to B indicates a coordinate bond; $R^b$ is hydrogen or a monovalent organic framework; $R^f$ is a p-valent organic framework; p is an integer of from 2 to 6; and plurally occurring $R^1$'s, $R^2$'s, $R^3$'s, m's, Q's, X's, solid half arcs, dashed and solid lines between Q and X, and $R^b$'s are the same or different from each other, respectively.

In the above formula (17), examples of the "aryl group" in the aryl group which optionally has at least one substituent group, as indicated by $R^1$, $R^2$, or $R^3$, may include, but are not limited to, phenyl group, biphenylyl group (e.g., 4-biphenylyl group), naphthyl group (e.g., 2-naphthyl group), tetrahydronaphthyl group (e.g., 5,6,7,8-tetrahydronaphthalen-2-yl group), indenyl group (e.g., 1H-inden-5-yl group), and indanyl group (e.g., indan-5-yl group). Among these aryl groups, phenyl group, biphenylyl group (e.g., 4-biphenylyl group), and naphthyl group (e.g., 2-naphthyl group) may be preferred.

Examples of the "heterocyclic group" in the heterocyclic group which optionally has at least one substituent group, as indicated by $R^1$, $R^2$, or $R^3$, may include, but are not limited to, pyrrolyl group (e.g., 2-pyrrolyl group), pyridyl group (e.g., 2-pyridyl group), quinolyl group (e.g., 2-quinolyl group), piperidinyl group (e.g., 4-piperidinyl group), piperidino group, furyl group (e.g., 2-furyl group), and thienyl group (e.g., 2-thienyl group). Among these heterocyclic groups, pyridyl group (e.g., 2-pyridyl group) and thienyl group (e.g., 2-thienyl group) may be preferred.

Examples of the "substituent group" in the aryl group and in the heterocyclic group, both of which optionally have at least one substituent group, may include, but are not limited to, halogen atom (e.g., fluorine atom, chlorine atom, bromine atom, and iodine atom), haloalkyl group (e.g., fluoromethyl group, difluoromethyl group, trifluoromethyl group), straight or branched chain alkyl group having from 1 to 4 carbon atoms (e.g., methyl group, ethyl group, propyl group, isopropyl group, butyl group, isobutyl group, tert-butyl group), cyclic alkyl group having from 5 to 7 carbon atoms (e.g., cyclopentyl group, cyclohexyl group), straight or branched chain alkoxy group having from 1 to 8 carbon atoms (e.g., methoxy group, ethoxy group, propoxy group, isopropoxy group, butoxy group, isobutoxy group, tert-butoxy group, pentyloxy group, hexyloxy group, heptyloxy group, octyloxy group), hydroxy group, nitro group, cyano group, amino group, mono- or di-alkylamino group in which each alkyl group has from 1 to 4 carbon atoms (e.g., methylamino group, ethylamino group, dimethylamino group, diethylamino group), acyl group (e.g., acetyl group, propionyl group, butyryl group), alkenyl group having from 2 to 6 carbon atoms (e.g., vinyl group, 1-propenyl group, allyl group), alkynyl group having from 2 to 6 carbon atoms (e.g., ethynyl group, 1-propynyl group, propargyl group), phenyl group, substituted phenyl group (e.g., 4-fluorophenyl group, 4-chlorophenyl group, 4-methylphenyl group (i.e., p-tolyl group), 4-methoxyphenyl group, 4-nitrophenyl group), carbamoyl group, and N,N-dialkylcarbamoyl group (e.g., N,N-dimethylcarbamoyl group, N,N-diethylcarbamoyl group, N,N-dipropylcarbamoyl group).

Alternatively, any two of $R^1$, $R^2$, and $R^3$ may be combined with each other to form a ring. Examples of such a ring may include, but are not limited to: as a result of the combination of $R^1$ and $R^2$, borole ring, benzoborole ring, dibenzoborole ring, 1,4-dihydroborinine ring, 1,4-dihydrobenzo[b]borinine ring, 5,10-dihydro-dibenzo[b,e]borinine ring, 4H-1,4-oxaborinine ring, 4H-benzo[b][1,4]oxaborinine ring, 10H-dibenzo[b,e][1,4]oxaborinine ring, 1,4-dihydro-1,4-azaborinine ring, 1,4-dihydrobenzo[b][1,4]azaborinine ring, and 5,10-dihydrodibenzo[b,e][1,4]azaborinine ring; as a result of the combination of $R^1$ and $R^3$, 5,6-dihydrodibenzo[b,d]borinine ring; and these rings having at least one substituent group. In the above formula (17), examples of the substituent group as indicated by $R^4$ may include, but are not limited to, the substituent groups described above as the "substituent groups" in the aryl group and in the heterocyclic group, both of which optionally have at least one substituent group.

In the above formula (17), m is the number of substituent groups $R^4$ bonded to X, and is an integer of from 0 to 2, depending on the valence of X, whether the bond between Q and X is a single or double bond, whether or not Q and X are part of a common ring, and others. In this connection, when m is 2, plurally occurring $R^4$'s are the same or different from each other.

In the above formula (17), examples of the linking group as indicated by Q may include, but are not limited to, =C<, =CH—, —CH<, —CH$_2$—, —CH$_2$CH$_2$—, (e.g., -(1,2-C$_6$H$_4$)—, —C$_{10}$H$_6$— (e.g., -(1,2-C$_{10}$H$_6$)—, —CO—, —CS—, —CH$_2$N<, and —CH$_2$N=. Among these linking groups, =C<, —CH$_2$—; and —CH$_2$CH$_2$— may be preferred.

In the above formula (17), X is a nitrogen atom, an oxygen atom, a sulfur atom, a phosphorus atom, or a selenium atom. Among these atoms, a nitrogen atom and an oxygen atom may be preferred.

In the above formula (17), examples of the common ring of Q and X, as indicated by the dashed half arc, may include, but are not limited to, pyrrole ring, pyridine ring, indole ring, isoindole ring, quinoline ring, isoquinoline ring, phenanthridine ring, pyrazine ring, triazine ring, furan ring, pyran ring, benzofuran ring, isobenzofuran ring, chromene ring, isochromene ring, phosphindole ring, isophosphindole ring, phosphinoline ring, isophosphinoline ring, thiophene ring, thiopyran ring, thiochromene ring, isothiochromene ring, selenophene ring, selenopyran ring, selenochromene ring, and isoselenochromene ring. These rings optionally have at least one substituent group. Among these rings, pyridine ring, quinoline ring, phenanthridine ring, furan ring, and thiophene ring may be preferred.

In the above formula (17), examples of the monovalent organic framework as indicated by $R^b$ may include, but are not limited to, methyl group, ethyl group, propyl group, isopropyl group, cyclohexyl group, phenyl group, 4-methylphenyl group (i.e., tolyl group), and naphthyl group (e.g., 2-naphthyl group).

In the above formula (17), examples of the divalent organic framework as indicated by $R^f$ may include, but are not limited to, methylene group, ethylene group, trimethylene group, propylene group, phenylene group (e.g., 1,4-phenylene group), and naphthylene group (e.g., 2,6-naphthylene group). Examples of the trivalent organic framework as indicated by $R^f$ may include, but are not limited to, methanetriyl group, ethanetriyl group (e.g., ethane-1,1,2-triyl group), propanetriyl group (e.g., propane-1,2,3-triyl group), benzenetriyl group (e.g., benzene-1,3,5-triyl group), and naphthalenetriyl group (e.g., a naphthalene-1,4,6-triyl group. Examples of the tetravalent organic framework as indicated by $R^f$ may include, but are not limited to, methanetetrayl group, ethanetetrayl group (e.g., ethane-1,1,2,2-tetrayl group), propanetetrayl group (e.g., propane-1,1,2,3-tetrayl group), benzenetetrayl group (e.g., benzene-1,2,4,5-tetrayl group), and naphthalenetetrayl group (e.g., naphthalene-1,4,5,8-tetrayl group). Examples of the pentavalent organic framework as indicated by $R^f$ may include, but are not limited to, ethanepentayl group (e.g., ethane-1,1,1,2,2,-pentayl group), propanepentayl group (e.g., propane-1,1,1,2,3-pentayl group), benzenepentayl group (e.g., benzene-1,2,3,4,5-pentayl group), and naphthalenepentayl group (e.g., naphthalene-1,2,4,5,8-pentayl group). Examples of the hexavalent organic framework as indicated by $R^f$ may include, but are not limited to, ethanehexayl group, propanehexayl group (e.g., propane-1,1,1,2,2,3-hexayl group), benzenehexayl group, and naphthalenehexayl group (e.g., naphthalene-1,2,3,4,5,8-hexayl group).

In the above formula (17), p is the number of boron-containing ring moieties (i.e., moieties in brackets) which are bonded to the divalent, trivalent, tetravalent, pentavalent, or hexavalent organic framework as indicated by $R^f$, and p is an integer of from 2 to 6. In this connection, plurally occurring $R^1$'s, $R^2$'s, $R^3$'s, m's, Q's, X's, dashed half arcs, and dashed and solid lines between Q and X are the same or different from each other, respectively.

In the above formula (17), Q and X may preferably be part of a common ring, and it may be more preferred that the above common ring is a pyridine ring, a quinoline ring, a phenanthridine ring, or a thiophene ring, X is the nitrogen atom of the pyridine ring, quinoline ring, or phenanthridine ring, or the sulfur atom of the thiophene ring, and m is 0. That is, boron compounds of the following formulas (96), (97), (98), and (99) may be preferred:

[Chemical Formula 231]

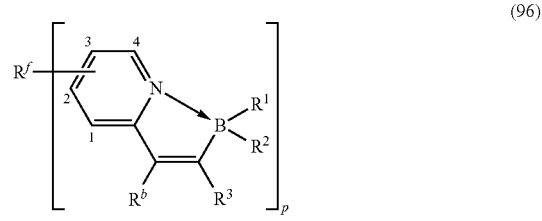

(96)

wherein $R^1$, $R^2$, $R^3$, $R^b$, $R^f$, and p have the same meanings as in the above formula (17); plurally occurring $R^1$'s, $R^2$'s, $R^3$'s, and $R^b$'s are the same or different from each other, respectively; $R^f$ may be bonded to any position of the pyridine ring; the numerals on the carbon atoms of the pyridine ring indicate positions where $R^f$ can be bonded to the pyridine ring; and an arrow directed from N to B indicates a coordinate bond;

[Chemical Formula 232]

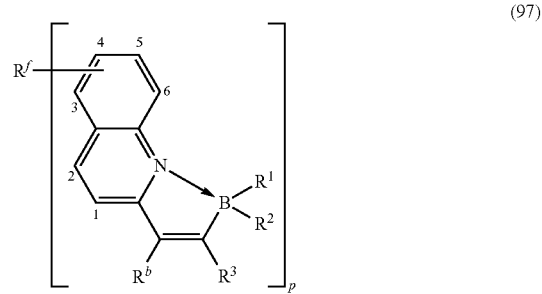

(97)

wherein $R^1$, $R^2$, $R^3$, $R^b$, $R^f$, and p have the same meanings as in the above formula (17); plurally occurring $R^1$'s, $R^2$'s, $R^3$'s, and $R^b$'s are the same or different from each other, respectively; $R^f$ may be bonded to any position of the quinoline ring; the numerals on the carbon atoms of the quinoline ring indicate positions where $R^f$ can be bonded to the quinoline ring; and an arrow directed from N to B indicates a coordinate bond;

[Chemical Formula 233]

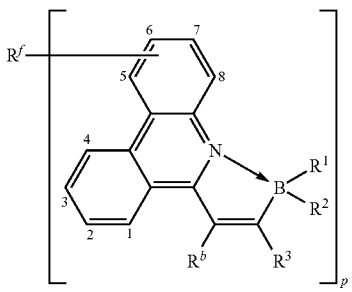

(98)

wherein $R^1$, $R^2$, $R^3$, $R^b$, $R^f$, and p have the same meanings as in the above formula (17); plurally occurring $R^1$'s, $R^2$'s, $R^3$'s, and $R^b$'s are the same or different from each other, respectively; $R^f$ may be bonded to any position of the phenanthridine ring; the numerals on the carbon atoms of the phenanthridine ring indicate positions where $R^f$ can be bonded to the phenanthridine ring; and an arrow directed from N to B indicates a coordinate bond; and

[Chemical Formula 234]

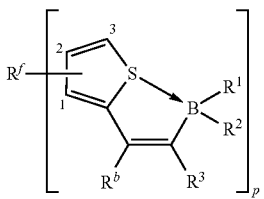

(99)

wherein $R^1$, $R^2$, $R^3$, $R^b$, $R^f$, and p have the same meanings as in the above formula (17); plurally occurring $R^1$'s, $R^2$'s, $R^3$'s, and $R^b$'s are the same or different from each other, respectively; $R^f$ may be bonded to any position of the thiophene ring; the numerals on the carbon atoms of the thiophene ring indicate positions where $R^f$ can be bonded to the thiophene ring; and an arrow directed from S to B indicates a coordinate bond.

In the above formulas (96), (97), (98), and (99), the p-valent organic framework as indicated by $R^f$ may be bonded to any position of each of the pyridine ring, quinoline ring, phenanthridine ring, and thiophene ring, respectively. Although not particularly limited, the p-valent organic framework as indicated by $R^f$ may preferably be bonded to one position selected from the 1-position, 2-position, and 3-position of the pyridine ring, one position selected from the 2-position, 3-position, 4-position, and 5-position of the quinoline ring, one position selected from the 2-position, 3-position, 6-position, and 7-position of the phenanthridine ring, or the 3-position of the thiophene ring, depending on the value of the variable p.

The variable p may usually be an integer of from 2 to 6, preferably an integer of from 2 to 4, and more preferably an integer of 2 or 3. That is, among the boron compounds of the above formula (17), boron compounds of the following formulas (18) and (19) may be preferred:

[Chemical Formula 235]

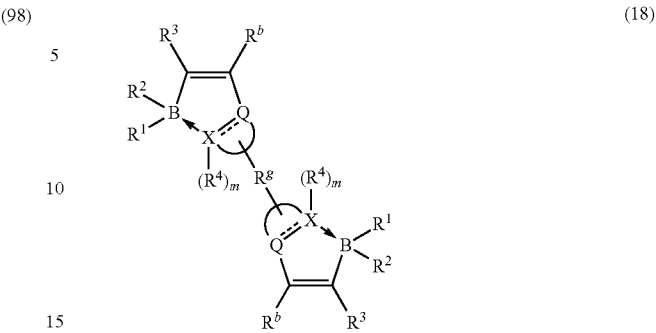

(18)

wherein $R^1$, $R^2$, $R^3$, $R^4$, m, Q, X, a solid half arc, dashed and solid lines between Q and X, an arrow directed from X to B, and Rb have the same meanings as in the above formula (17); $R^g$ is a divalent organic framework; plurally occurring $R^1$'s, $R^2$'s, $R^3$'s, m's, Q's, X's, solid half arcs, dashed and solid lines between Q and X, and $R^b$'s are the same or different from each other, respectively; and

[Chemical Formula 236]

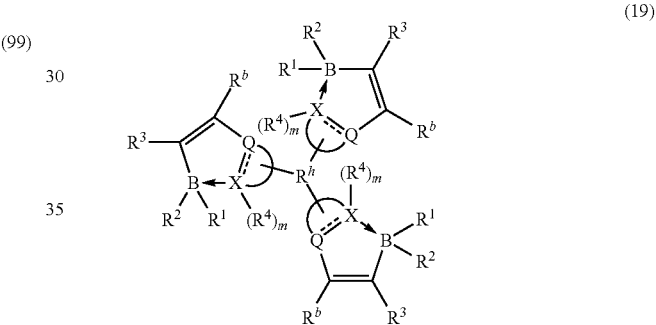

(19)

wherein $R^1$, $R^2$, $R^3$, $R^4$, m, Q, X, a solid half arc, dashed and solid lines between Q and X, an arrow directed from X to B, and $R^b$ have the same meanings as in the above formula (17); $R^h$ is a trivalent organic framework; plurally occurring $R^1$'s, $R^2$'s, $R^3$'s, m's, Q's, X's, solid half arcs, dashed and solid lines between Q and X, and $R^b$'s are the same or different from each other, respectively.

In the above formula (18), examples of the divalent organic framework as indicated by $R^g$ may include, but are not limited to, methylene group, ethylene group, trimethylene group, propylene group, phenylene group (e.g., 1,4-phenylene group), and naphthylene group (e.g., 2,6-naphthylene group).

In the above formula (19), examples of the trivalent organic framework as indicated by $R^h$ may include, but are not limited to, methanetriyl group, ethanetriyl group (e.g., ethane-1,1,2-triyl group), propanetriyl group (e.g., propane-1,2,3-triyl group), benzenetriyl group (e.g., benzene-1,3,5-triyl group), and naphthalenetriyl group (e.g., naphthalene-1,4,6-triyl group).

In the above formula (18), Q and X may preferably be part of a common ring, and it may be more preferred that the above common ring is a pyridine ring, a quinoline ring, a phenanthridine ring, or a thiophene ring, X is the nitrogen atom of the pyridine ring, quinoline ring, or phenanthridine ring, or the sulfur atom of the thiophene ring, and m is 0. That is, boron compounds of the following formulas (100), (101), (102), and (103) may be preferred:

[Chemical Formula 237]

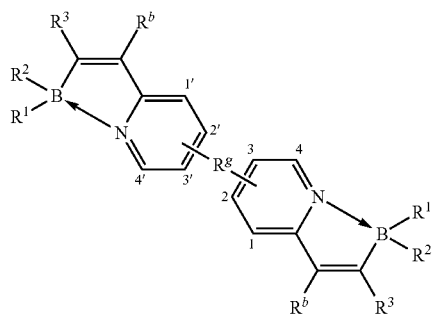

(100)

wherein $R^1$, $R^2$, $R^3$, and $R^b$ have the same meanings as in the above formula (17); plurally occurring $R^1$'s, $R^2$'s, $R^3$'s, and $R^b$'s are the same or different from each other, respectively; $R^g$ has the same meaning as in the above formula (18); $R^g$ may be bonded to any position of the pyridine ring; the numerals on the carbon atoms of the pyridine ring indicate positions where $R^g$ can be bonded to the pyridine ring; and an arrow directed from N to B indicates a coordinate bond;

[Chemical Formula 238]

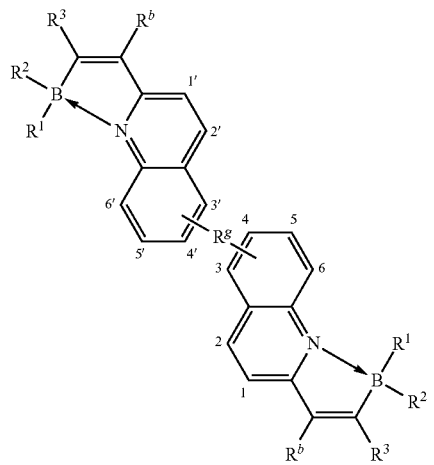

(101)

wherein $R^1$, $R^2$, $R^3$, and $R^b$ have the same meanings as in the above formula (17); plurally occurring $R^1$'s, $R^2$'s, $R^3$'s, and $R^b$'s are the same or different from each other, respectively; $R^g$ has the same meaning as in the above formula (18); $R^g$ may be bonded to any position of the quinoline ring; the numerals on the carbon atoms of the quinoline ring indicate positions where $R^g$ can be bonded to the quinoline ring; and an arrow directed from N to B indicates a coordinate bond;

[Chemical Formula 239]

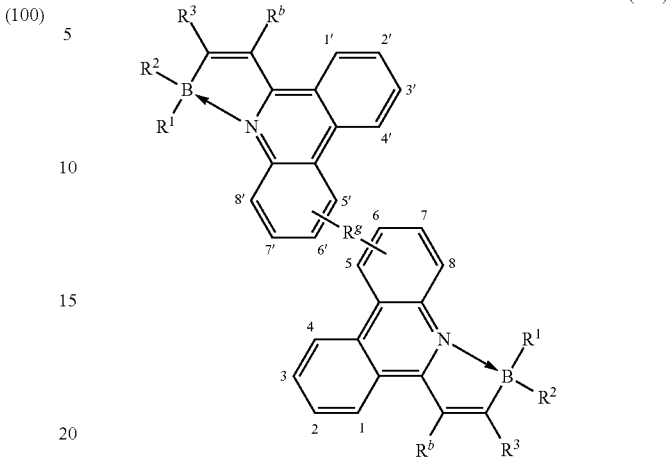

(102)

wherein $R^1$, $R^2$, $R^3$, and $R^b$ have the same meanings as in the above formula (17); plurally occurring $R^1$'s, $R^2$'s, $R^3$'s, and $R^b$'s are the same or different from each other, respectively; $R^g$ has the same meaning as in the above formula (18); $R^g$ may be bonded to any position of the phenanthridine ring; the numerals on the carbon atoms of the phenanthridine ring indicate positions where $R^g$ can be bonded to the phenanthridine ring; and an arrow directed from N to B indicates a coordinate bond; and

[Chemical Formula 240]

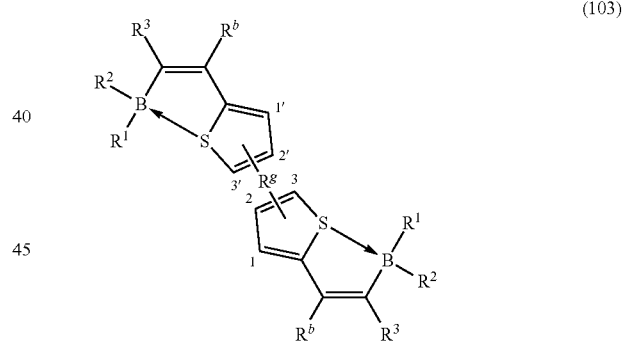

(103)

wherein $R^1$, $R^2$, $R^3$, and $R^b$ have the same meanings as in the above formula (17); plurally occurring $R^1$'s, $R^2$'s, $R^3$'s, and $R^b$'s are the same or different from each other, respectively; $R^g$ has the same meaning as in the above formula (18); $R^g$ may be bonded to any position of the thiophene ring; the numerals on the carbon atoms of the thiophene ring indicate positions where $R^g$ can be bonded to the thiophene ring; and an arrow directed from S to B indicates a coordinate bond.

In the above formulas (100), (101), (102), and (103), the divalent organic framework as indicated by $R^g$ may be bonded to any position of each of the pyridine ring, quinoline ring, phenanthridine ring, and thiophene ring. Although not particularly limited, the divalent organic framework as indicated by $R^g$ may preferably be bonded to one position selected from the 1-position, 2-position, and 3-position of one pyridine ring, and one position selected from the 1'-position, 2'-position, and 3'-position of the other pyridine ring, or one position selected from the 2-position, 3-position, 4-position, and 5-position of one quinoline ring, and one position selected from the 2'-position, 3'-position, 4'-position, and 5'-position of the other quinoline ring, or one position selected from the 2-position, 3-position, 6-position, and 7-position of one phenanthridine ring, and one position selected from the 2'-position, 3'-position, 6'-position, and 7'-position of the other phenanthridine ring, or the 3-position of one thiophene ring and 3'-position of the other thiophene ring.

In the above formula (19), Q and X may preferably be part of a common ring, and it may be more preferred that the above common ring is a pyridine ring, a quinoline ring, a phenanthridine ring, or a thiophene ring, X is the nitrogen atom of the pyridine ring, quinoline ring, or phenanthridine ring, or the sulfur atom of the thiophene ring, and m is 0. That is, boron compounds of the following formulas (104), (105), (106), and (107) may be preferred:

[Chemical Formula 241]

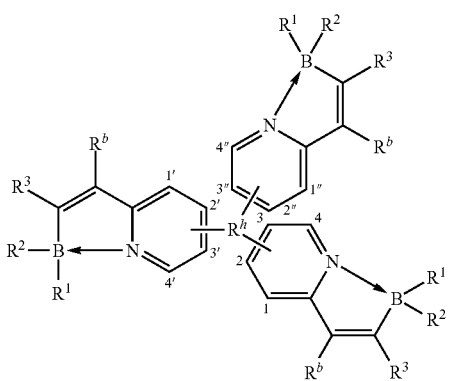

(104)

wherein $R^1$, $R^2$, $R^3$, and $R^b$ have the same meanings as in the above formula (17); plurally occurring $R^1$'s, $R^2$'s, $R^3$'s, and $R^b$'s are the same or different from each other, respectively; $R^h$ has the same meaning as in the above formula (19); $R^h$ may be bonded to any position of the pyridine ring; the numerals on the carbon atoms of the pyridine ring indicate positions where $R^h$ can be bonded to the pyridine ring; and an arrow directed from N to B indicates a coordinate bond;

[Chemical Formula 242]

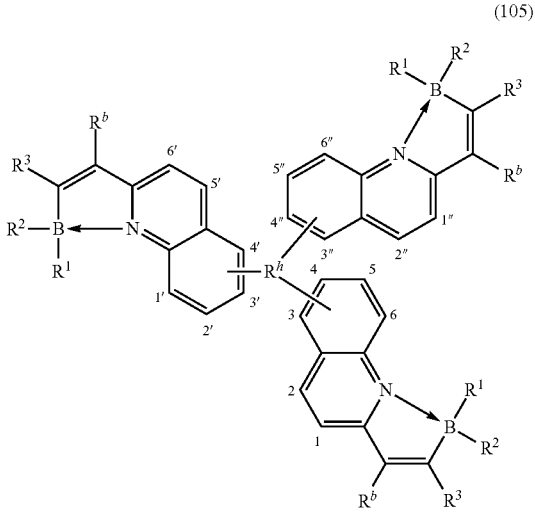

(105)

wherein $R^1$, $R^2$, $R^3$, and $R^b$ have the same meanings as in the above formula (17); plurally occurring $R^1$'s, $R^2$'s, $R^3$'s, and $R^b$'s are the same or different from each other, respectively; $R^h$ has the same meaning as in the above formula (19); $R^h$ may be bonded to any position of the quinoline ring; the numerals on the carbon atoms of the quinoline ring indicate positions where $R^h$ can be bonded to the quinoline ring; and an arrow directed from N to B indicates a coordinate bond;

[Chemical Formula 243]

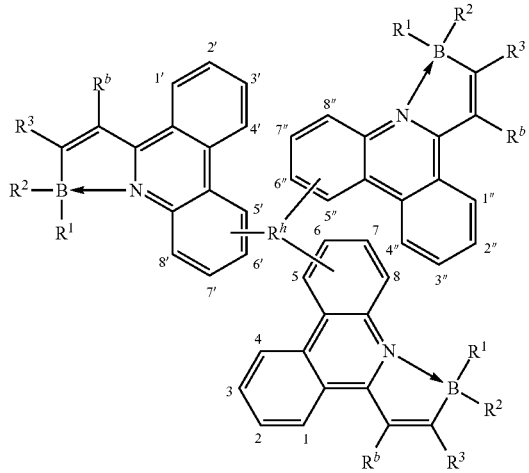

(106)

wherein $R^1$, $R^2$, $R^3$, and $R^b$ have the same meanings as in the above formula (17); plurally occurring $R^1$'s, $R^2$'s, $R^3$'s, and $R^b$'s are the same or different from each other, respectively; $R^h$ has the same meaning as in the above formula (19); $R^h$ may be bonded to any position of the phenanthridine ring; the numerals on the carbon atoms of the phenanthridine ring indicate positions where $R^h$ can be bonded to the phenanthridine ring; and an arrow directed from N to B indicates a coordinate bond; and

[Chemical Formula 244]

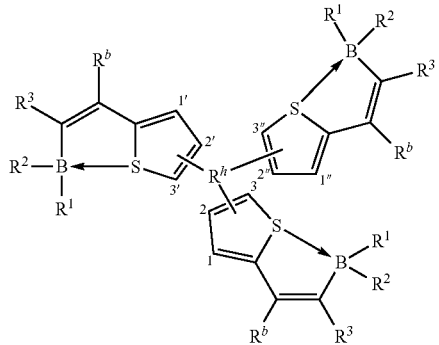

(107)

wherein $R^1$, $R^2$, $R^3$, and $R^b$ have the same meanings as in the above formula (17); plurally occurring $R^1$'s, $R^2$'s, $R^3$'s, and $R^h$'s are the same or different from each other, respectively; $R^h$ has the same meaning as in the above formula (19); $R^h$ may be bonded to any position of the thiophene ring; the numerals on the carbon atoms of the thiophene ring indicate positions where $R^h$ can be bonded to the thiophene ring; and an arrow directed from S to B indicates a coordinate bond.

In the above formulas (104), (105), (106), and (107), the trivalent organic framework as indicated by $R^h$ may be bonded to any position of each of the pyridine ring, quinoline ring, phenanthridine ring, and thiophene ring. Although not particularly limited, the trivalent organic framework as indicated by $R^h$ may preferably be bonded to one position selected from the 1-position, 2-position, and 3-position of the first pyridine ring, one position selected from the 1'-position, 2'-position, and 3'-position of the second pyridine ring, and one position selected from the 1"-position, 2"-position, and 3"-position of the third pyridine ring, or one position selected from the 2-position, 3-position, 4-position, and 5-position of the first quinoline ring, one position selected from the 2'-position, 3'-position, 4'-position, and 5'-position of the second quinoline ring, and one position selected from the 2"-position, 3"-position, 4"-position, and 5"-position of the third quinoline ring, or one position selected from the 2-position, 3-position, 6-position, and 7-position of the first phenanthridine ring, one position selected from the 2'-position, 3'-position, 6'-position, and 7'-position of the second phenanthridine ring, and one position selected from the 2"-position, 3"-position, 6"-position, and 7"-position of the third phenanthridine ring, or the 3-position of the first thiophene ring, the 3'-position of the second thiophene ring, and the 3"-position of the third thiophene ring.

<<Processes for Producing Novel Boron Compounds II>>

The novel boron compounds II of the present invention can be produced with high efficiency in a simple and easy manner by the production process (6) as described below. In addition, their more specific boron compounds can be produced with high efficiency in a simple and easy manner by the production processes (6-1) to (6-4) as described below.

<Production Process (6)>

One of the novel boron compounds II of the present invention, i.e., a boron compound of the following formula (17):

[Chemical Formula 245]

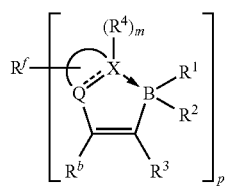

(17)

wherein $R^1$, $R^2$, and $R^3$ are the same or different from each other and are each independently an aryl group or a heterocyclic group, each of which optionally has at least one substituent group, or any two of $R^1$, $R^2$, and $R^3$ are combined with each other to form a ring; $R^4$ is a hydrogen atom or a substituent group; m is an integer of from 0 to 2; when m is 2, plurally occurring $R^4$'s are the same or different from each other; Q is a linking group; X is a nitrogen atom, an oxygen atom, a sulfur atom, a phosphorus atom, or a selenium atom; a solid half arc indicates that Q and X are part of a common ring; dashed and solid lines between Q and X indicate a single or double bond; an arrow directed from X to B indicates a coordinate bond; $R^b$ is hydrogen or a monovalent organic framework; $R^f$ is a p-valent organic framework; p is an integer of from 2 to 6; and plurally occurring $R^1$'s, $R^2$'s, $R^3$'s, m's, Q's, X's, solid half arcs, dashed and solid lines between Q and X, and $R^b$'s are the same or different from each other, respectively, can be produced by reacting a boron compound of the following formula (20):

[Chemical Formula 246]

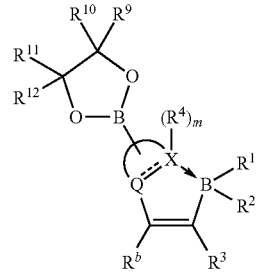

(20)

wherein $R^1$, $R^2$, $R^3$, $R^4$, m, Q, X, a solid half arc, dashed and solid lines between Q and X, an arrow directed from X to B, and $R^b$ have the same meanings as in the above formula (17); when m is 2, plurally occurring $R^4$'s are the same or different from each other; $R^9$, $R^{10}$, $R^{11}$, and $R^{12}$ are the same or different from each other and are each independently a hydrogen atom or a substituent group, with a compound of the following formula (21):

[Chemical Formula 247]

$$R^f-(Y'')_p \quad (21)$$

wherein $R^f$ and p have the same meanings as in the above formula (17); Y" is a fluorine atom, a chlorine atom, a bromine atom, an iodine atom, or a trifluoromethanesulfonyloxy group; and plurally occurring Y"'s are the same or different from each other, in the presence of a catalyst containing at least one metal element selected from the group consisting of palladium, platinum, and nickel.

The amount of the compound of the above formula (21) to be used may preferably be not smaller than 0.5/p mol and not larger than 2.0/p mol, more preferably not smaller than 0.65/p mol and not larger than 1.5/p mol, and still more preferably not smaller than 0.8/p mol and not larger than 1.25/p mol, relative to 1 mol of the compound of the above formula (20). When the amount of the compound of the above formula (21) to be used is too small, a lack of the compound of the above formula (21) may occur, resulting in a decrease in the yield of the final product. In contrast, when the amount of the compound of the above formula (21) to be used is too great, an excess of the compound of the above formula (21) may occur, resulting in an increase in the production cost. In this connection, p is the number of boron-containing ring moieties (i.e., moieties in brackets) bonded to the divalent, trivalent, tetravalent, pentavalent, or hexavalent organic framework as indicated by $R^f$ in the above formula (17), and is an integer of from 2 to 6.

The catalyst contains at least one metal element selected from the group consisting of palladium, platinum, and nickel. Among these metal elements, palladium and platinum may be preferred.

Examples of the catalyst may include, but are not limited to, complexes containing metal elements as described above. Specific examples of the catalyst may include, but are not limited to, tris(dibenzylideneacetone)dipalladium chloroform complex ($Pd_2dba_3 \cdot CHCl_3$), tetrakis(triphenylphosphine)palladium ($Pd(PPh_3)_4$), bis(tri-tert-butylphosphine)palladium ($Pd(P^tBu_3)_2$), bis(tricyclohexylphosphine)

palladium, palladium acetate, palladium chloride, dichlorobis(triphenylphosphine)palladium, dichloro[1,1'-bis(diphenylphosphino)-ferrocene]palladium(II), dichlorobis(acetonitrile)palladium, dichlorobis(benzonitrile)palladium, and dichloro[1,2-bis(diphenylphosphino)ethane]palladium. These catalysts may be used alone, or two or more kinds thereof may be used in combination. Among these catalysts, bis(tri-tert-butylphosphine)palladium ($Pd(P^tBu_3)_2$) may be preferred.

The amount of the catalyst to be used may preferably be not smaller than 0.001 mol and not larger than 0.2 mol, more preferably not smaller than 0.005 mol and not larger than 0.15 mol, and still more preferably not smaller than 0.01 mol and not larger than 0.1 mol, relative to 1 mol of the boron compound of the above formula (20). When the amount of the catalyst to be used is too small, the reaction rate may be slow, so that the reaction cannot quickly proceed. In contrast, when the amount of the catalyst to be used is too great, the catalyst may be used more than necessary, resulting in an increase in the production cost.

In the above reaction, a stabilizer may be used in addition to the catalyst. Examples of the stabilizer may include, but are not limited to, triphenylphosphine, tri(o-tolyl)phosphine ($P(o-tol)_3$), tri(2-furyl)phosphine, 1,1'-bis(diphenylphosphino)ferrocene, 1,2-bis(diphenylphosphino)ethane, tri-tert-butylphosphine, tricyclohexylphosphine, diphenylmethylphosphine, and 2-(di-tert-butylphosphino)biphenyl. These stabilizers may be used alone, or two or more kinds thereof may be used in combination. Among these stabilizers, tri-tert-butylphosphine may be preferred.

The amount of the stabilizer to be used may preferably be not smaller than 0.01 mol and not larger than 0.3 mol, more preferably not smaller than 0.02 mol and not larger than 0.25 mol, and still more preferably not smaller than 0.03 mol and not larger than 0.2 mol, relative to 1 mol of the boron compound of the above formula (20). When the amount of the stabilizer to be used is too small, the function of the stabilizer cannot sufficiently be exerted, resulting in a decrease in the yield of the final product. In contrast, when the amount of the stabilizer to be used is too great, the stabilizer may be used more than necessary, resulting in an increase in the production cost.

In this connection, when a catalyst containing at least one stabilizer such as phosphine ligand (e.g., tetrakis(triphenylphosphine)palladium, bis(tri-tert-butylphosphine)palladium, bis(tricyclohexylphosphine)palladium) is used, there is no need to use an additional stabilizer.

The above reaction is typically carried out in an organic solvent. Examples of the organic solvent may include, but are not limited to, aromatic hydrocarbons such as benzene, toluene, xylene, and mesitylene; halogenated aromatic hydrocarbons such as chlorobenzene and 1,2-dichlorobenzene; halogenated aliphatic hydrocarbons such as dichloromethane, chloroform, carbon tetrachloride, 1,2-dichloroethane, 1,1,1-trichloroethane, 1,1,2,2-tetrachloroethane, 1,2-dichloroethylene, trichloroethylene, and tetrachloroethylene; alcohols such as methanol, ethanol, isopropyl alcohol, 1-butanol, 2-butanol, isobutyl alcohol, and isopentyl alcohol; esters such as methyl acetate, ethyl acetate, propyl acetate, isopropyl acetate, butyl acetate, isobutyl acetate, pentyl acetate, and isopentyl acetate; ethers such as diethyl ether, 1,4-dioxane, tetrahydrofuran, and methyl phenyl ether (anisole); ketones such as acetone, methyl ethyl ketone, methyl butyl ketone, and methyl isobutyl ketone; glycol ethers (cellosolves) such as ethylene glycol monomethyl ether (methylcellosolve), ethylene glycol monoethyl ether (cellosolve), ethylene glycol monobutyl ether (butylcellosolve), and ethylene glycol monoethyl ether acetate (cellosolve acetate); alicyclic hydrocarbons such as cyclohexane; aliphatic hydrocarbons such as n-hexane; nitriles such as acetonitrile; and aprotic polar solvents such as dimethylformamide, dimethylacetamide, and N-methyl-2-pyrrolidone. These organic solvents may be used alone, or two or more kinds thereof may be used in combination. Among these organic solvents, ethers such as 1,4-dioxane and tetrahydrofuran, may be preferred.

In this connection, when a water-miscible solvent is used as the organic solvent, water may be mixed therein. The ratio of the water to be mixed may appropriately be adjusted depending on the solubility of the starting materials in the mixed solvent and others, and is not particularly limited.

When the above reaction is carried out in a mixed solvent of an organic solvent and water, the pH of the reaction system may preferably be increased to be high using, for example, a base such as a hydroxide or a carbonate of an alkali metal, such as sodium hydroxide or potassium hydroxide. In this case, the amount of the base to be used may appropriately be adjusted depending on the amounts of the starting materials to be used and others, and is not particularly limited.

The above reaction may preferably be carried out under an inert gas atmosphere. Examples of the inert gas may include, but are not limited to, nitrogen, helium, and argon. These inert gases may be used alone, or two or more kinds thereof may be used in combination. Among these inert gases, nitrogen and argon may be preferred.

The reaction conditions are not particularly limited, so long as the above reaction can sufficiently proceed under these conditions. For example, the reaction temperature may preferably be from 0° C. to 150° C., more preferably from room temperature to 100° C., and the reaction time may preferably be from 0.5 to 24 hours, more preferably from 1 to 12 hours. The reaction pressure may be normal pressure, reduced pressure, or increased pressure, preferably normal pressure.

After the completion of the reaction, for example, the reaction solution is directly concentrated or evaporated to dryness, or alternatively, water is added to the reaction solution, followed by extraction with an appropriate organic solvent, washing with water and a saturated sodium chloride solution, and then concentration or evaporation to dryness, and if necessary, followed by purification using any of the heretofore known methods, e.g., various kinds of chromatography or recrystallization. Thus, the desired product is obtained.

In the production process (6), the compound of the above formula (20), which is a starting material, can be produced by the production process (1) wherein m is 0, Q and X are part of a common ring, a dioxaborolanyl group is bonded to any position of the ring, $R^a$ is $R^b$, and n is 1.

In the production process (6), the compound of the above formula (21), which is a starting material, can be produced by any of the heretofore known methods or can be obtained as commercially available products.

<Production Process (6-1)>

Among the boron compounds of the above formula (17), a preferred boron compound of the following formula (18):

[Chemical Formula 248]

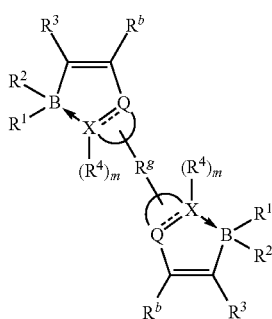

(18)

wherein $R^1$, $R^2$, $R^3$, $R^4$, m, Q, X, a solid half arc, dashed and solid lines between Q and X, an arrow directed from X to B, and $R^b$ have the same meanings as in the above formula (17); $R^g$ is a divalent organic framework; plurally occurring $R^1$'s, $R^2$'s, $R^3$'s, $R^4$'s, m's, Q's, X's, solid half arcs, dashed and solid lines between Q and X, and $R^b$'s are the same or different from each other, respectively, can be produced by reacting a boron compound of the following formula (20):

[Chemical Formula 249]

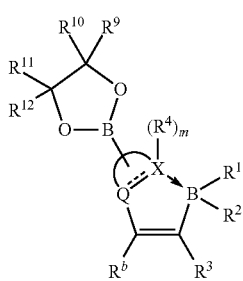

(20)

wherein $R^1$, $R^2$, $R^3$, $R^4$, m, Q, X, a solid half arc, dashed and solid lines between Q and X, an arrow directed from X to B, and $R^b$ have the same meanings as in the above formula (17); when m is 2, plurally occurring $R^4$'s are the same or different from each other; and $R^9$, $R^{10}$, $R^{11}$, and $R^{12}$ are the same or different from each other and are each independently a hydrogen atom or a substituent group, with a compound of the above formula (21) wherein $R^f$ is $R^g$ which indicates a divalent organic framework and p is 2, i.e., a compound of the following formula (108):

[Chemical Formula 250]

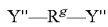 (108)

wherein $R^g$ has the same meaning as in the above formula (18); Y" has the same meaning as in the above formula (21); and plurally occurring Y"'s are the same or different from each other, in the presence of a catalyst containing at least one metal element selected from the group consisting of palladium, platinum, and nickel (hereinafter referred to sometimes as the "production process (6-1)").

In the production process (6-1), the amounts of the starting materials to be used, the types and amounts of the catalyst and the stabilizer to be used, the types of the organic solvent and the inert gas, the reaction conditions, the post-treatments after the completion of the reaction, and others are similar to those of the production process (6); however, the amounts of the starting materials to be used, and the amounts of the catalyst and the stabilizer to be used, have values determined when the variable p is 2, and the compound of the above formula (21) should be read as the compound of the above formula (108).

In the production process (6-1), the compound of the above formula (20), which is a starting material, can be produced by the above production process. The compound of the above formula (108), which is a starting material, can be produced by any of the heretofore known methods or can be obtained as commercially available products.

<Production Process (6-2)>

Among the boron compounds of the above formula (17), a preferred boron compound of the following formula (19):

[Chemical Formula 251]

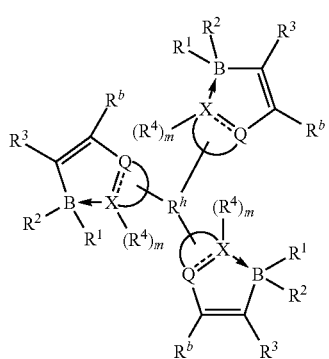

(19)

wherein $R^1$, $R^2$, $R^3$, $R^4$, m, Q, X, a solid half arc, dashed and solid lines between Q and X, an arrow directed from X to B, and $R^b$ have the same meanings as in the above formula (17); $R^h$ is a trivalent organic framework; plurally occurring $R^1$'s, $R^2$'s, $R^3$'s, $R^4$'s, m's, Q's, X's, solid half arcs, dashed and solid lines between Q and X, and $R^b$'s are the same or different from each other, respectively, can be produced by reacting a boron compound of the above formula (20) with a compound of the above formula (21) wherein $R^f$ is $R^h$ which indicates a trivalent organic framework and p is 3, i.e., a compound of the following formula (109):

[Chemical Formula 252]

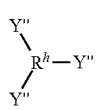

(109)

wherein $R^h$ has the same meaning as in the above formula (19); Y" has the same meaning as in the above formula (21); and plurally occurring Y"'s are the same or different from each other, in the presence of a catalyst containing at least one metal element selected from the group consisting of palladium, platinum, and nickel (hereinafter referred to sometimes as the "production process (6-2)").

In the production process (6-2), the amounts of the starting materials to be used, the types and amounts of the catalyst and the stabilizer to be used, the types of the organic solvent and the inert gas, the reaction conditions, the post-treatments after the completion of the reaction, and others are similar to those of the production process (6); however, the amounts of the starting materials to be used, and the amounts of the catalyst and the stabilizer to be used have values determined when the variable p is 3, and the compound of the above formula (21) should be read as the compound of the above formula (109).

In the production process (6-2), the compound of the above formula (20), which is a starting material, can be produced by the above production process. The compound of the above formula (109), which is a starting material, can be produced by any of the heretofore known methods or can be obtained as commercially available products.

<Production Processes (6-3) to (6-6)>

In the above formula (17), Q and X are part of a common ring, and it may be preferred that the above common ring is a pyridine ring, a quinoline ring, a phenanthridine ring, or a thiophene ring, X is the nitrogen atom of the pyridine ring, quinoline ring, or phenanthridine ring, or the sulfur atom of the thiophene ring, and m is 0. That is, a preferred boron compound of the following formula (96):

[Chemical Formula 253]

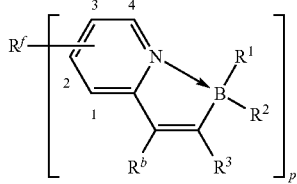

(96)

wherein $R^1$, $R^2$, $R^3$, $R^b$, $R^f$, and p have the same meanings as in the above formula (17); plurally occurring $R^1$'s, $R^2$'s, $R^3$'s, and $R^b$'s are the same or different from each other, respectively; $R^f$ may be bonded to any position of the pyridine ring; the numerals on the carbon atoms of the pyridine ring indicate positions where $R^f$ can be bonded to the pyridine ring; and an arrow directed from N to B indicates a coordinate bond, can be produced by reacting a boron compound of the following formula (110):

[Chemical Formula 254]

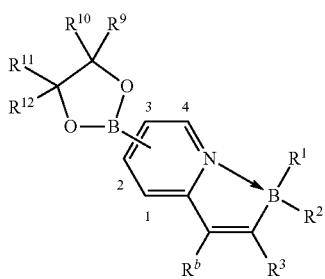

(110)

wherein $R^1$, $R^2$, $R^3$, and $R^b$ have the same meanings as in the above formula (17); the numerals on the carbon atoms of the pyridine ring indicate positions where the dioxaborolanyl group can be bonded to the pyridine ring; an arrow directed from N to B indicates a coordinate bond; and $R^9$, $R^{10}$, $R^{11}$, and $R^{12}$ are the same or different from each other and are each independently a hydrogen atom or a substituent group, with a compound of the following formula (21):

[Chemical Formula 255]

(21)

wherein $R^f$ and p have the same meanings as in the above formula (17); Y" is a fluorine atom, a chlorine atom, a bromine atom, an iodine atom, or a trifluoromethanesulfonyl group; and plurally occurring Y"'s are the same or different from each other, in the presence of a catalyst containing at least one metal element selected from the group consisting of palladium, platinum, and nickel (hereinafter referred to sometimes as the "production process (6-3)").

Further, a preferred boron compound of the following formula (97):

[Chemical Formula 256]

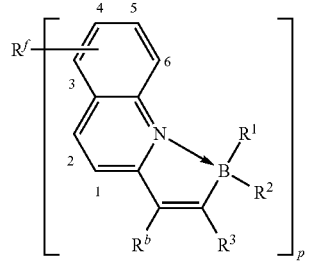

(97)

wherein $R^1$, $R^2$, $R^3$, $R^b$, $R^f$, and p have the same meanings as in the above formula (17); plurally occurring $R^1$'s, $R^2$'s, $R^3$'s, and $R^b$'s are the same or different from each other, respectively; $R^f$ may be bonded to any position of the quinoline ring; the numerals on the carbon atoms of the quinoline ring indicate positions where $R^f$ can be bonded to the quinoline ring; and an arrow directed from N to B indicates a coordinate bond, can be produced by reacting a boron compound of the following formula (111):

[Chemical Formula 257]

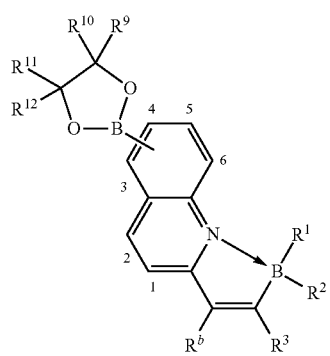

(111)

wherein $R^1$, $R^2$, $R^3$, and $R^b$ have the same meanings as in the above formula (17); the numerals on the carbon atoms of the quinoline ring indicate positions where the dioxaborolanyl group can be bonded to the quinoline ring; an arrow directed from N to B indicates a coordinate bond; and $R^9$, $R^{10}$, $R^{11}$, and $R^{12}$ are the same or different from each other and are each independently a hydrogen atom or a substituent group, with a compound of the following formula (21):

[Chemical Formula 258]

(21)

wherein R$^f$ and p have the same meanings as in the above formula (17); Y''' is a fluorine atom, a chlorine atom, a bromine atom, an iodine atom, or a trifluoromethanesulfonyloxy group; and plurally occurring Y'''s are the same or different from each other, in the presence of a catalyst containing at least one metal element selected from the group consisting of palladium, platinum, and nickel (hereinafter referred to sometimes as the "production process (6-4)").

Further, a preferred boron compound of the following formula (98):

[Chemical Formula 259]

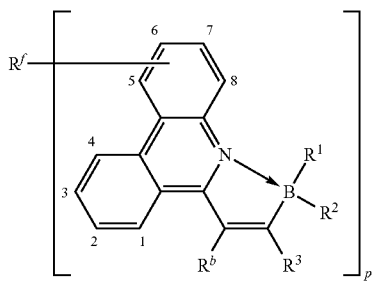
(98)

wherein R$^1$, R$^2$, R$^3$, R$^b$, R$^f$, and p have the same meanings as in the above formula (17); plurally occurring R$^1$'s, R$^2$'s, R$^3$'s, and R$^b$'s are the same or different from each other, respectively; R$^f$ may be bonded to any position of the phenanthridine ring; the numerals on the carbon atoms of the phenanthridine ring indicate positions where R$^f$ can be bonded to the phenanthridine ring; and an arrow directed from N to B indicates a coordinate bond, can be produced by reacting a boron compound of the following formula (112):

[Chemical Formula 260]

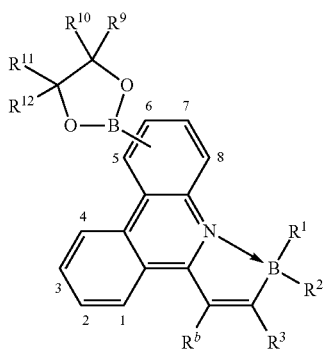
(112)

wherein R$^1$, R$^2$, R$^3$, and R$^b$ have the same meanings as in the above formula (17); the numerals on the carbon atoms of the phenanthridine ring indicate positions where the dioxaborolanyl group can be bonded to the phenanthridine ring; an arrow directed from N to B indicates a coordinate bond; and R$^9$, R$^{10}$, R$^{11}$, and R$^{12}$ are the same or different from each other and are each independently a hydrogen atom or a substituent group, with a compound of the following formula (21):

[Chemical Formula 261]

(21)

wherein R$^f$ and p have the same meanings as in the above formula (17); Y''' is a fluorine atom, a chlorine atom, a bromine atom, an iodine atom, or a trifluoromethanesulfonyloxy group; and plurally occurring Y'''s are the same or different from each other, in the presence of a catalyst containing at least one metal element selected from the group consisting of palladium, platinum, and nickel (hereinafter referred to sometimes as the "production process (6-5)").

Further, a preferred boron compound of the following formula (99):

[Chemical Formula 262]

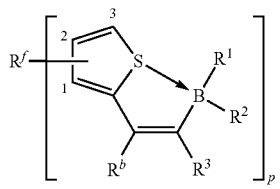
(99)

wherein R$^1$, R$^2$, R$^3$, R$^b$, R$^f$, and p have the same meanings as in the above formula (17); plurally occurring R$^1$'s, R$^2$'s, R$^3$'s, and R$^b$'s are the same or different from each other, respectively; R$^f$ may be bonded to any position of the thiophene ring; the numerals on the carbon atoms of the thiophene ring indicate positions where R$^f$ can be bonded to the thiophene ring; an arrow directed from S to B indicates a coordinate bond; and R$^9$, R$^{10}$, R$^{11}$, and R$^{12}$ are the same or different from each other and are each independently a hydrogen atom or a substituent group, can be produced by reacting a boron compound of the following formula (113):

[Chemical Formula 263]

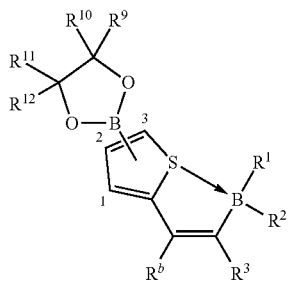
(113)

wherein R$^1$, R$^2$, R$^3$, and R$^b$ have the same meanings as in the above formula (17); the numerals on the carbon atoms of the thiophene ring indicate positions where the dioxaborolanyl group can be bonded to the thiophene ring; an arrow directed from S to B indicates a coordinate bond; and R$^9$, R$^{10}$, R$^{11}$, and R$^{12}$ are the same or different from each other and are each independently a hydrogen atom or a substituent group, with a compound of the following formula (21):

[Chemical Formula 264]

(21)

wherein $R^f$ and p have the same meanings as in the above formula (17); Y''' is a fluorine atom, a chlorine atom, a bromine atom, an iodine atom, or a trifluoromethanesulfonyloxy group; and plurally occurring Y'''s are the same or different from each other, in the presence of a catalyst containing at least one metal element selected from the group consisting of palladium, platinum, and nickel (hereinafter referred to sometimes as the "production process (6-6)").

In the above formulas (96), (97), (98), and (99), the p-valent organic framework as indicated by $R^f$ may be bonded to any position of each of the pyridine ring, quinoline ring, phenanthridine ring, and thiophene ring. Although not particularly limited, the p-valent organic framework as indicated by $R^f$ may preferably be bonded to one position selected from the 1-position, 2-position, and 3-position of the pyridine ring, one position selected from the 2-position, 3-position, 4-position, and 5-position of the quinoline ring, one position selected from the 2-position, 3-position, 6-position, and 7-position of the phenanthridine ring, or the 3-position of the thiophene ring.

In the above formulas (110), (111), (112), and (113), the dioxaborolanyl group may be bonded to any position of each of the pyridine ring, quinoline ring, phenanthridine ring, and thiophene ring. Although not particularly limited, the dioxaborolanyl group may preferably be bonded to one position selected from the 1-position, 2-position, and 3-position of the pyridine ring, one position selected from the 2-position, 3-position, 4-position, and 5-position of the quinoline ring, one position selected from the 2-position, 3-position, 6-position, and 7-position of the phenanthridine ring, or the 3-position of the thiophene ring.

In the production process (6-3), (6-4), (6-5), or (6-6), the amounts of the starting materials to be used, the types and amounts of the catalyst and the stabilizer to be used, the types of the organic solvent and the inert gas, the reaction conditions, the post-treatments after the completion of the reaction, and others are similar to those of the production process (6); however, the compound of the above formula (20) should be read as the boron compound of the above formula (110), (111), (112), or (113).

In the production process (6-3), (6-4), (6-5), or (6-6), the boron compound of the above formula (110), (111), (112), or (113), which is a starting material, can be produced in accordance with the production process for the compound of the above formula (20). The compound of the above formula (21), which is a starting material, can be produced by any of the heretofore known methods or can be obtained as commercially available products.

<Production Processes (6-7) to (6-10)>

In the above formula (18), Q and X are part of a common ring, and it may be preferred that the above common ring is a pyridine ring, a quinoline ring, a phenanthridine ring, or a thiophene ring, X is the nitrogen atom of the pyridine ring, quinoline ring, or phenanthridine ring, or the sulfur atom of the thiophene ring, and m is 0. That is, a preferred boron compound of the following formula (100):

[Chemical Formula 265]

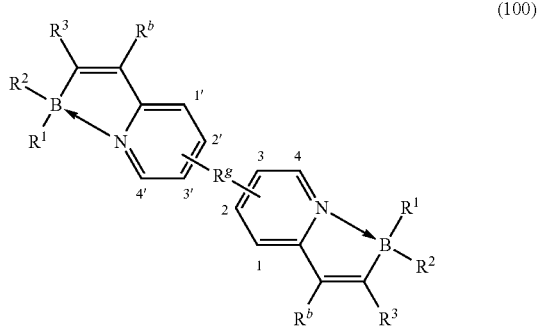

(100)

wherein $R^1$, $R^2$, $R^3$, and $R^b$ have the same meanings as in the above formula (17); plurally occurring $R^1$'s, $R^2$'s, $R^3$'s, and $R^b$'s are the same or different from each other, respectively; $R^g$ has the same meaning as in the above formula (18); $R^g$ may be bonded to any position of the pyridine ring; the numerals on the carbon atoms of the pyridine ring indicate positions where $R^g$ can be bonded to the pyridine ring; the pyridine ring optionally has at least one substituent group; and an arrow directed from N to B indicates a coordinate bond, can be produced by reacting a boron compound of the following formula (110):

[Chemical Formula 266]

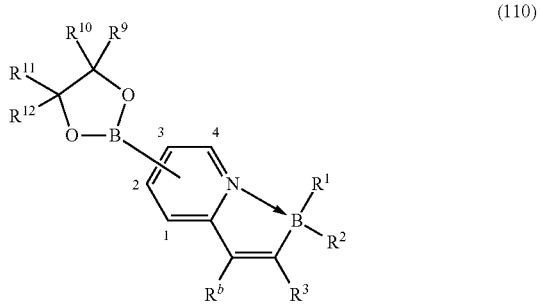

(110)

wherein $R^1$, $R^2$, $R^3$, and $R^b$ have the same meanings as in the above formula (17); the numerals on the carbon atoms of the pyridine ring indicate positions where the dioxaborolanyl group can be bonded to the pyridine ring; an arrow directed from N to B indicates a coordinate bond; and $R^9$, $R^{10}$, $R^{11}$, and $R^{12}$ are the same or different from each other and are each independently a hydrogen atom or a substituent group, with a compound of the following formula (108):

[Chemical Formula 267]

(108)

wherein $R^g$ has the same meaning as in the above formula (18); Y''' has the same meaning as in the above formula (21); and plurally occurring Y'''s are the same or different from each other, in the presence of a catalyst containing at least one metal element selected from the group consisting of palladium, platinum, and nickel (hereinafter referred to sometimes as the "production process (6-7)").

Further, a preferred boron compound of the following formula (101):

[Chemical Formula 268]

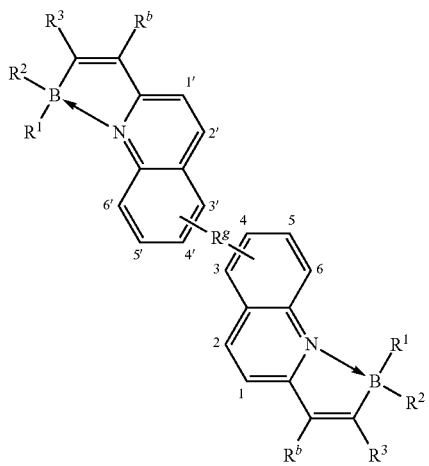

(101)

wherein $R^1$, $R^2$, $R^3$, and $R^b$ have the same meanings as in the above formula (17); plurally occurring $R^1$'s, $R^2$'s, $R^3$'s, and $R^b$'s are the same or different from each other, respectively; $R^g$ has the same meaning as in the above formula (18); $R^g$ may be bonded to any position of the quinoline ring; the numerals on the carbon atoms of the quinoline ring indicate positions where $R^g$ can be bonded to the quinoline ring; the quinoline ring optionally has at least one substituent group; and an arrow directed from N to B indicates a coordinate bond, can be produced by reacting a boron compound of the following formula (111):

[Chemical Formula 269]

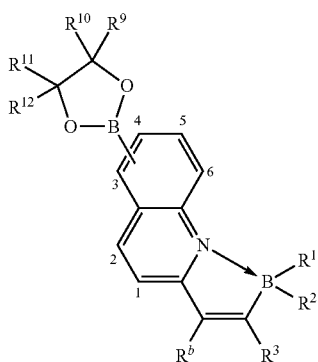

(111)

wherein $R^1$, $R^2$, $R^3$, and $R^b$ have the same meanings as in the above formula (17); the numerals on the carbon atoms of the quinoline ring indicate positions where the dioxaborolanyl group can be bonded to the quinoline ring; an arrow directed from N to B indicates a coordinate bond; and $R^9$, $R^{10}$, $R^{11}$, and $R^{12}$ are the same or different from each other and are each independently a hydrogen atom or a substituent group, with a compound of the following formula (108):

[Chemical Formula 270]

Y''—$R^g$—Y''    (108)

wherein $R^g$ has the same meaning as in the above formula (18); Y'' has the same meaning as in the above formula (21); and plurally occurring Y'''s are the same or different from each other, in the presence of a catalyst containing at least one metal element selected from the group consisting of palladium, platinum, and nickel (hereinafter referred to sometimes as the "production process (6-8)").

Further, a preferred boron compound of the following formula (102):

[Chemical Formula 271]

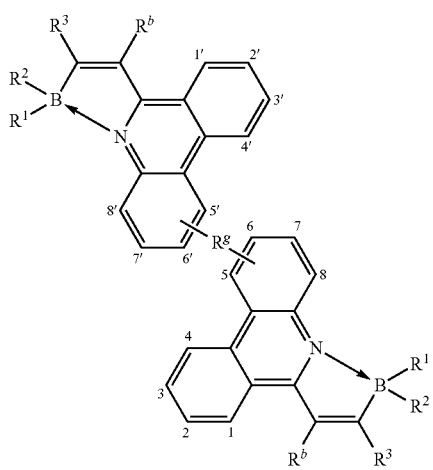

(102)

wherein $R^1$, $R^2$, $R^3$, and $R^b$ have the same meanings as in the above formula (17); plurally occurring $R^1$'s, $R^2$'s, $R^3$'s, and $R^b$'s are the same or different from each other, respectively; $R^g$ has the same meaning as in the above formula (18); $R^g$ may be bonded to any position of the phenanthridine ring; the numerals on the carbon atoms of the phenanthridine ring indicate positions where $R^g$ can be bonded to the phenanthridine ring; the phenanthridine ring optionally has at least one substituent group; and an arrow directed from N to B indicates a coordinate bond, can be produced by reacting a boron compound of the following formula (112):

[Chemical Formula 272]

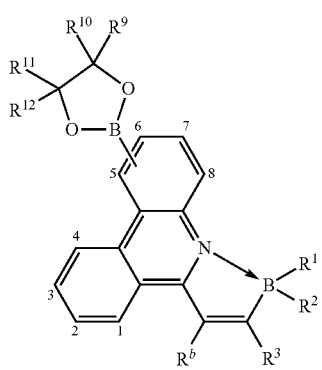

(112)

wherein $R^1$, $R^2$, $R^3$, and $R^b$ have the same meanings as in the above formula (17); the numerals on the carbon atoms of the phenanthridine ring indicate positions where the dioxaborolanyl group can be bonded to the phenanthridine ring; an arrow directed from N to B indicates a coordinate bond; and $R^9$, $R^{10}$, $R^{11}$, and $R^{12}$ are the same or different from each other and are each independently a hydrogen atom or a substituent group, with a compound of the following formula (108):

[Chemical Formula 273]

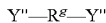
(108)

wherein $R^g$ has the same meaning as in the above formula (18); Y'' has the same meaning as in the above formula (21); and plurally occurring Y'''s are the same or different from each other, in the presence of a catalyst containing at least one metal element selected from the group consisting of palladium, platinum, and nickel (hereinafter referred sometimes to as the "production process (6-9)").

Further, a preferred boron compound of the following formula (103):

[Chemical Formula 274]

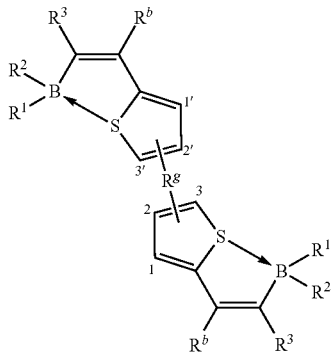
(103)

wherein $R^1$, $R^2$, $R^3$, and $R^b$ have the same meanings as in the above formula (17); plurally occurring $R^1$'s, $R^2$'s, $R^3$'s, and $R^b$'s are the same or different from each other, respectively; $R^g$ has the same meaning as in the above formula (18); $R^g$ may be bonded to any position of the thiophene ring; the numerals on the carbon atoms of the thiophene ring indicate positions where $R^g$ can be bonded to the thiophene ring; the thiophene ring optionally has at least one substituent group; and an arrow directed from S to B indicates a coordinate bond, can be produced by reacting a boron compound of the following formula (113):

[Chemical Formula 275]

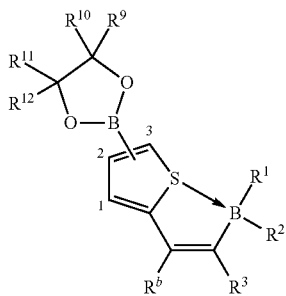
(113)

wherein $R^1$, $R^2$, $R^3$, and $R^b$ have the same meanings as in the above formula (17); the numerals on the carbon atoms of the thiophene ring indicate positions where the dioxaborolanyl group can be bonded to the thiophene ring; an arrow directed from S to B indicates a coordinate bond; and $R^9$, $R^{10}$, $R^{11}$, and $R^{12}$ are the same or different from each other and are each independently a hydrogen atom or a substituent group, with a compound of the following formula (108):

[Chemical Formula 276]

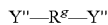
(108)

wherein $R^g$ has the same meaning as in the above formula (18); Y'' has the same meaning as in the above formula (21); and plurally occurring Y'''s are the same or different from each other, in the presence of a catalyst containing at least one metal element selected from the group consisting of palladium, platinum, and nickel (hereinafter referred to sometimes as the "production process (6-10)").

In the above formulas (100), (101), (102), and (103), the divalent organic framework as indicated by $R^g$ may be bonded to any position of each of the pyridine ring, quinoline ring, phenanthridine ring, and thiophene ring. Although not particularly limited, the divalent organic framework as indicated by $R^g$ may preferably be bonded to one position selected from the 1-position, 2-position, and 3-position of one pyridine ring, and one position selected from the 1'-position, 2'-position, and 3'-position of the other pyridine ring, or one position selected from the 2-position, 3-position, 4-position, and 5-position of one quinoline ring, and one position selected from the 2'-position, 3'-position, 4'-position, and 5'-position of the other quinoline ring, or one position selected from the 2-position, 3-position, 6-position, and 7-position of one phenanthridine ring, and one position selected from the 2'-position, 3'-position, 6'-position, and 7'-position of the other phenanthridine ring, or the 3-position of one thiophene ring and 3'-position of the other thiophene ring.

In the above formulas (110), (111), (112), and (113), the dioxaborolanyl group may be bonded to any position of each of the pyridine ring, quinoline ring, phenanthridine ring, and thiophene ring. Although not particularly limited, the dioxaborolanyl group may preferably be bonded to one position selected from the 1-position, 2-position, and 3-position of the pyridine ring, one position selected from the 2-position, 3-position, 4-position, and 5-position of the quinoline ring, one position selected from the 2-position, 3-position, 6-position, and 7-position of the phenanthridine ring, or the 3-position of the thiophene ring.

In the production process (6-7), (6-8), (6-9), or (6-10), the amounts of the starting materials to be used, the types and amounts of the catalyst and the stabilizer to be used, the types of the organic solvent and the inert gas, the reaction conditions, the post-treatments after the completion of the reaction, and others are similar to those of the production process (6); however, the amounts of the starting materials to be used, and the amounts of the catalyst and the stabilizer to be used have values determined when the variable p is 2, the compound of the above formula (20) should be read as the boron compound of the above formula (110), (111), (112), or (113), and the compound of the above formula (21) should be read as the compound of the above formula (108).

In the production process (6-7), (6-8), (6-9), or (6-10), the boron compound of the above formula (110), (111), (112), or (113), which is a starting material, can be produced in accordance with the production process for the compound of the above formula (20). The compound of the above formula (108), which is a starting material, can be produced by any of the heretofore known methods or can be obtained as commercially available products.

<Production Processes (6-11) to (6-14)>

In the above formula (19), Q and X are part of a common ring, and it may be preferred that the above common ring is a pyridine ring, a quinoline ring, a phenanthridine ring, or a thiophene ring, X is the nitrogen atom of the pyridine ring, quinoline ring, or phenanthridine ring, or the sulfur atom of the thiophene ring, and m is 0. That is, a preferred boron compound of the following formula (104):

[Chemical Formula 277]

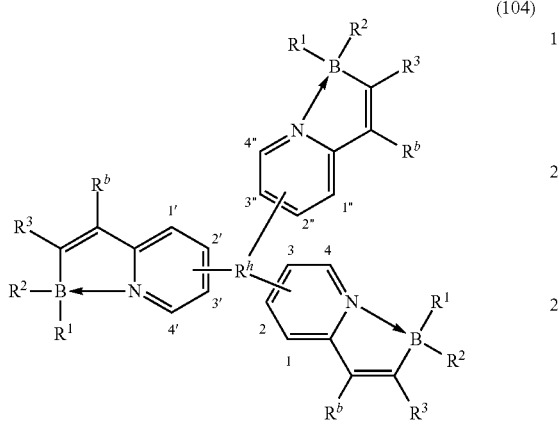

(104)

wherein $R^1$, $R^2$, $R^3$, and $R^b$ have the same meanings as in the above formula (17); plurally occurring $R^1$'s, $R^2$'s, $R^3$'s, and $R^b$'s are the same or different from each other, respectively; $R^h$ has the same meaning as in the above formula (19); $R^h$ may be bonded to any position of the pyridine ring; the numerals on the carbon atoms of the pyridine ring indicate positions where $R^h$ can be bonded to the pyridine ring; the pyridine ring optionally has at least one substituent group; and an arrow directed from N to B indicates a coordinate bond, can be produced by reacting a boron compound of the following formula (110):

[Chemical Formula 278]

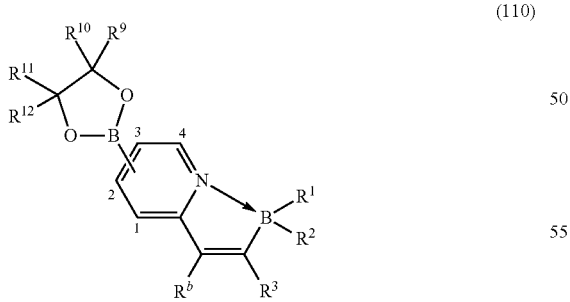

(110)

wherein $R^1$, $R^2$, $R^3$, and $R^b$ have the same meanings as in the above formula (17); the numerals on the carbon atoms of the pyridine ring indicate positions where the dioxaborolanyl group can be bonded to the pyridine ring; an arrow directed from N to B indicates a coordinate bond; and $R^9$, $R^{10}$, $R^{11}$, and $R^{12}$ are the same or different from each other and are each independently a hydrogen atom or a substituent group, with a compound of the following formula (109):

[Chemical Formula 279]

(109)

wherein $R^h$ has the same meaning as in the above formula (19); Y'" has the same meaning as in the above formula (21); and plurally occurring Y'"s are the same or different from each other, in the presence of a catalyst containing at least one metal element selected from the group consisting of palladium, platinum, and nickel (hereinafter referred to sometimes as the "production process (6-11)").

Further, a preferred boron compound of the following formula (105):

[Chemical Formula 280]

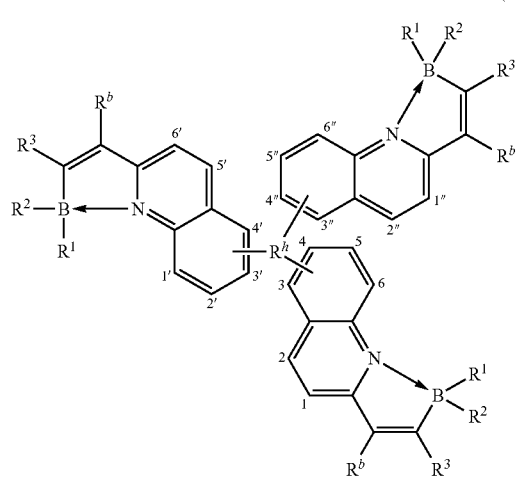

(105)

wherein $R^1$, $R^2$, $R^3$, and $R^b$ have the same meanings as in the above formula (17); plurally occurring $R^1$'s, $R^2$'s, $R^3$'s, and $R^b$'s are the same or different from each other, respectively; $R^h$ has the same meaning as in the above formula (19); $R^h$ may be bonded to any position of the quinoline ring; the numerals on the carbon atoms of the quinoline ring indicate positions where $R^h$ can be bonded to the quinoline ring; the quinoline ring optionally has at least one substituent group; and an arrow directed from N to B indicates a coordinate bond, can be produced by reacting a boron compound of the following formula (111):

[Chemical Formula 281]

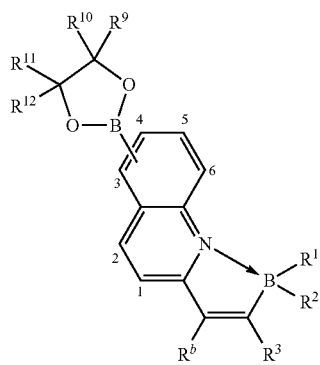

(111)

wherein $R^1$, $R^2$, $R^3$, and $R^b$ have the same meanings as in the above formula (17); the numerals on the carbon atoms of the quinoline ring indicate positions where the dioxaborolanyl group can be bonded to the quinoline ring; an arrow directed from N to B indicates a coordinate bond; and $R^9$, $R^{10}$, $R^{11}$, and $R^{12}$ are the same or different from each other and are each independently a hydrogen atom or a substituent group, with a compound of the following formula (109):

[Chemical Formula 282]

(109)

wherein $R^h$ has the same meaning as in the above formula (19); Y'' has the same meaning as in the above formula (21); and plurally occurring Y'''s are the same or different from each other, in the presence of a catalyst containing at least one metal element selected from the group consisting of palladium, platinum, and nickel (hereinafter referred to sometimes as the "production process (6-12)").

Further, a preferred boron compound of the following formula (106):

[Chemical Formula 283]

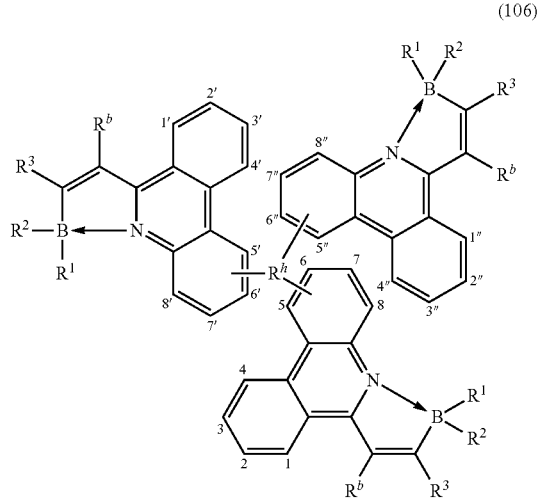

(106)

wherein $R^1$, $R^2$, $R^3$, and $R^b$ have the same meanings as in the above formula (17); plurally occurring $R^1$'s, $R^2$'s, $R^3$'s, and $R^b$'s are the same or different from each other, respectively; $R^h$ has the same meaning as in the above formula (19); $R^h$ may be bonded to any position of the phenanthridine ring; the numerals on the carbon atoms of the phenanthridine ring indicate positions where $R^h$ can be bonded to the phenanthridine ring; the phenanthridine ring optionally has at least one substituent group; and an arrow directed from N to B indicates a coordinate bond, can be produced by reacting a boron compound of the following formula (112):

[Chemical Formula 284]

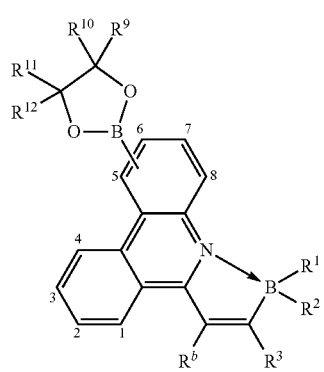

(112)

wherein $R^1$, $R^2$, $R^3$, and $R^b$ have the same meanings as in the above formula (17); the numerals on the carbon atoms of the phenanthridine ring indicate positions where the dioxaborolanyl group can be bonded to the phenanthridine ring; an arrow directed from N to B indicates a coordinate bond; and $R^9$, $R^{10}$, $R^{11}$, and $R^{12}$ are the same or different from each other and are each independently a hydrogen atom or a substituent group, with a compound of the following formula (109):

[Chemical Formula 285]

(109)

wherein $R^h$ has the same meaning as in the above formula (19); Y'' has the same meaning as in the above formula (21); and plurally occurring Y'''s are the same or different from each other, in the presence of a catalyst containing at least one metal element selected from the group consisting of palladium, platinum, and nickel (hereinafter referred to sometimes as the "production process (6-13)").

Further, a preferred boron compound of the following formula (107):

[Chemical Formula 286]

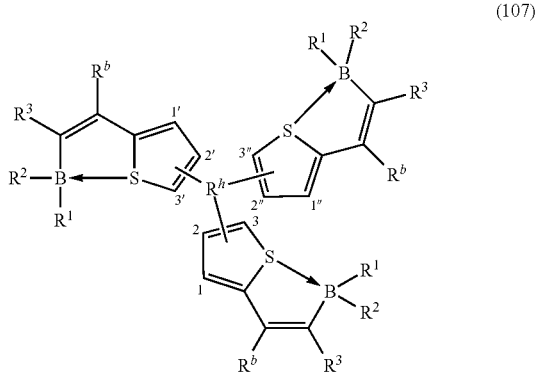

(107)

wherein $R^1$, $R^2$, $R^3$, and $R^b$ have the same meanings as in the above formula (17); plurally occurring $R^1$'s, $R^2$'s, $R^3$'s, and $R^b$'s are the same or different from each other, respectively; $R^h$ has the same meaning as in the above formula (19); $R^h$ may be bonded to any position of the thiophene ring; the numerals on the carbon atoms of the thiophene ring indicate positions where $R^h$ can be bonded to the thiophene ring; the thiophene ring optionally has at least one substituent group; and an arrow directed from S to B indicates a coordinate bond, can be produced by reacting a boron compound of the following formula (113):

[Chemical Formula 287]

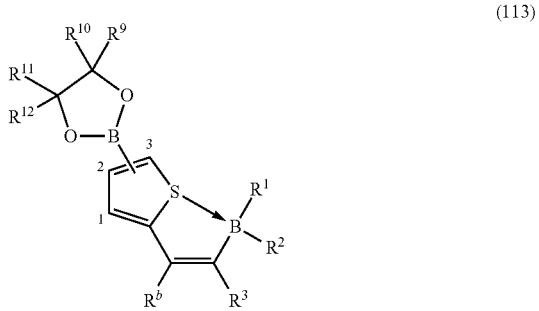

(113)

wherein $R^1$, $R^2$, $R^3$, and $R^b$ have the same meanings as in the above formula (17); the numerals on the carbon atoms of the thiophene ring indicate positions where the dioxaborolanyl group can be bonded to the thiophene ring; an arrow directed from S to B indicates a coordinate bond; and $R^9$, $R^{10}$, $R^{11}$, and $R^{12}$ are the same or different from each other and are each independently a hydrogen atom or a substituent group, with a compound of the following formula (109):

[Chemical Formula 288]

(109)

wherein $R^h$ has the same meaning as in the above formula (19); Y" has the same meaning as in the above formula (21); and plurally occurring Y"'s are the same or different from each other, in the presence of a catalyst containing at least one metal element selected from the group consisting of palladium, platinum, and nickel (hereinafter referred to sometimes as the "production process (6-14)").

In the above formulas (104), (105), (106), and (107), the trivalent organic framework as indicated by $R^h$ may be bonded to any position of each of the pyridine ring, quinoline ring, phenanthridine ring, and thiophene ring. Although not particularly limited, the trivalent organic framework as indicated by $R^h$ may preferably be bonded to one position selected from the 1-position, 2-position, and 3-position of the first pyridine ring, one position selected from the 1'-position, 2'-position, and 3'-position of the second pyridine ring, and one position selected from the 1"-position, 2"-position, and 3"-position of the third pyridine ring, or one position selected from the 2-position, 3-position, 4-position, and 5-position of the first quinoline ring, one position selected from the 2'-position, 3'-position, 4'-position, and 5'-position of the second quinoline ring, and one position selected from the 2"-position, 3"-position, 4"-position, and 5"-position of the third quinoline ring, or one position selected from the 2-position, 3-position, 6-position, and 7-position of the first phenanthridine ring, one position selected from the 2'-position, 3'-position, 6'-position, and 7'-position of the second phenanthridine ring, and one position selected from the 2"-position, 3"-position, 6"-position, and 7"-position of the third phenanthridine ring, or the 3-position of the first thiophene ring, the 3'-position of the second thiophene ring, and 3"-position of the third thiophene ring.

In the above formulas (110), (111), (112), and (113), the dioxaborolanyl group may be bonded to any position of each of the pyridine ring, quinoline ring, phenanthridine ring, and thiophene ring. Although not particularly limited, the dioxaborolanyl group may preferably be bonded to one position selected from the 1-position and 3-position of the pyridine ring, one position selected from the 2-position, 4-position, and 5-position of the quinoline ring, one position selected from the 2-position, 3-position, 6-position, and 7-position of the phenanthridine ring, or the 3-position of the thiophene ring.

In the production process (6-11), (6-12), (6-13), or (6-14), the amounts of the starting materials to be used, the types and amounts of the catalyst and the stabilizer to be used, the types of the organic solvent and the inert gas, the reaction conditions, the post-treatments after the completion of the reaction, and others are similar to those of the production process (6); however, the amounts of the starting materials to be used, and the amounts of the catalyst and the stabilizer to be used have values determined when the variable p is 3, and the compound of the above formula (20) should be read as the boron compound of the above formula (110), (111), (112), or (113), and the compound of the above formula (21) should be read as the compound of the above formula (109).

In the production process (6-11), (6-12), (6-13), or (6-14), the boron compound of the above formula (110), (111), (112), or (113), which is a starting material, can be produced in accordance with the production process for the compound of the above formula (20). The compound of the above formula (109), which is a starting material, can be produced by any of the heretofore known methods or can be obtained as commercially available products.

Novel Boron Compounds III

The novel boron compounds III according to the present invention are boron compounds of the following formula (22):

[Chemical Formula 289]

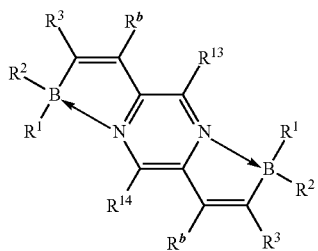

(22)

wherein $R^1$, $R^2$, and $R^3$ are the same or different from each other and are each independently an aryl group or a heterocyclic group, each of which optionally has at least one substituent group, or any two of $R^1$, $R^2$, and $R^3$ are combined with each other to form a ring; an arrow directed from N to B indicates a coordinate bond; $R^b$ is hydrogen or a monovalent organic framework; and $R^{13}$ and $R^{14}$ are the same or different from each other and are each independently a hydrogen atom or a substituent group.

In the above formula (22), examples of the "aryl group" in the aryl group which optionally has at least one substituent group, as indicated by $R^1$, $R^2$, or $R^3$, may include, but are not limited to, phenyl group, biphenylyl group (e.g., 4-biphenylyl group), naphthyl group (e.g., 2-naphthyl group), tetrahydronaphthyl group (e.g., 5,6,7,8-tetrahydronaphthalen-2-yl group), indenyl group (e.g., 1H-inden-5-yl group), and indanyl group (e.g., indan-5-yl group). Among these aryl groups, phenyl group, biphenylyl group (e.g., 4-biphenylyl group), and naphthyl group (e.g., 2-naphthyl group) may be preferred.

Examples of the "heterocyclic group" in the heterocyclic group which optionally has at least one substituent group, as indicated by $R^1$, $R^2$, or $R^3$, may include, but are not limited to, pyrrolyl group (e.g., 2-pyrrolyl group), pyridyl group (e.g., 2-pyridyl group), quinolyl group (e.g., 2-quinolyl group), piperidinyl group (e.g., 4-piperidinyl group), piperidino group, furyl group (e.g., 2-furyl group), and thienyl group (e.g., 2-thienyl group). Among these heterocyclic groups, pyridyl group (e.g., 2-pyridyl group) and thienyl group (e.g., 2-thienyl group) may be preferred.

Examples of the "substituent group" in the aryl group and the heterocyclic group, both of which optionally have at least one substituent group, may include, but are not limited to, halogen atom (e.g., fluorine atom, chlorine atom, bromine atom, and iodine atom), haloalkyl group (e.g., fluoromethyl group, difluoromethyl group, trifluoromethyl group), straight or branched chain-alkyl group having from 1 to 4 carbon atoms (e.g., methyl group, ethyl group, propyl group, isopropyl group, butyl group, isobutyl group, tert-butyl group), cyclic alkyl group having from 5 to 7 carbon atoms (e.g., cyclopentyl group, cyclohexyl group), straight or branched chain alkoxy group having from 1 to 8 carbon atoms (e.g., methoxy group, ethoxy group, propoxy group, isopropoxy group, butoxy group, isobutoxy group, tert-butoxy group, pentyloxy group, hexyloxy group, heptyloxy group, octyloxy group), hydroxy group, nitro group, cyano group, amino group, mono- or di-alkylamino group in which each alkyl group has from 1 to 4 carbon atoms (e.g., methylamino group, ethylamino group, dimethylamino group, diethylamino group), acyl group (e.g., acetyl group, propionyl group, butyryl group), alkenyl group having from 2 to 6 carbon atoms (e.g., vinyl group, 1-propenyl group, allyl group), alkynyl group having from 2 to 6 carbon atoms (e.g., ethynyl group, 1-propynyl group, propargyl group), phenyl group, substituted phenyl group (e.g., 4-fluorophenyl group, 4-chlorophenyl group, 4-methylphenyl group (i.e., p-tolyl group), 4-methoxyphenyl group, 4-nitrophenyl group), carbamoyl group, and N,N-dialkylcarbamoyl group (e.g., N,N-dimethylcarbamoyl group, N,N-diethylcarbamoyl group, N,N-dipropylcarbamoyl group).

Alternatively, any two of $R^1$, $R^2$, and $R^3$ may be combined with each other to form a ring. Examples of such a ring may include, but are not limited to: as a result of the combination of $R^1$ and $R^2$, borole ring, benzoborole ring, dibenzoborole ring, 1,4-dihydroborinine ring, 1,4-dihydrobenzo[b]borinine ring, 5,10-dihydro-dibenzo[b,e]borinine ring, 4H-1,4-oxaborinine ring, 4H-benzo[b][1,4]oxaborinine ring, 10H-dibenzo[b,e][1,4]oxaborinine ring, 1,4-dihydro-1,4-azaborinine ring, 1,4-dihydrobenzo[b][1,4]azaborinine ring, and 5,10-dihydrodibenzo[b,e][1,4]azaborinine ring; as a result of the combination of $R^1$ and $R^3$, 5,6-dihydrodibenzo[b,d]borinine ring; and these rings having at least one substituent group. In the above formula (22), examples of the substituent group as indicated by $R^{13}$ or $R^{14}$ may include, but are not limited to, the substituent groups described above as the "substituent group" in the aryl group and the heterocyclic group, both of which optionally have at least one substituent group.

In the above formula (22), examples of the monovalent organic framework as indicated by $R^b$ may include, but are not limited to, methyl group, ethyl group, propyl group, isopropyl group, cyclohexyl group, phenyl group, 4-methylphenyl group (i.e., tolyl group), and naphthyl group (e.g., 2-naphthyl group).

In the above formula (22), it may be preferred that $R^{13}$ and $R^{14}$ are methyl groups, $R^1$, $R^2$, and $R^3$ are biphenylyl groups, and $R^b$ is a hydrogen atom.

<<Process for Producing Novel Boron Compounds III>>

The novel boron compounds III of the present invention can be produced with high efficiency in a simple and easy manner by the production process (7) as described below.

<Production Process (7)>

One of the novel boron compounds III of the present invention, i.e., a boron compound of the following formula (22):

[Chemical Formula 290]

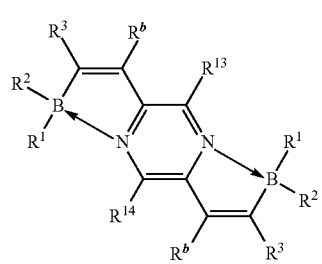

(22)

wherein $R^1$, $R^2$, and $R^3$ are the same or different from each other and are each independently an aryl group or a heterocyclic group, each of which optionally has at least one substituent group, or any two of $R^1$, $R^2$, and $R^3$ are combined with each other to form a ring; an arrow directed from N to B indicates a coordinate bond; $R^b$ is hydrogen or a monovalent organic framework; $R^{13}$ and $R^{14}$ are the same or different from each other and are each independently a hydrogen atom or a substituent group, can be produced by reacting a boron compound of the following formula (23):

[Chemical Formula 291]

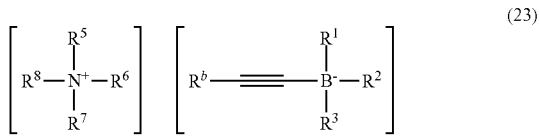
(23)

wherein $R^1$, $R^2$, $R^3$, and $R^b$ have the same meanings as in the above formula (22); and $R^5$, $R^6$, $R^7$, and $R^8$ are the same or different from each other and are each independently a hydrogen atom or a substituent group, with a compound of the following formula (24):

[Chemical Formula 292]

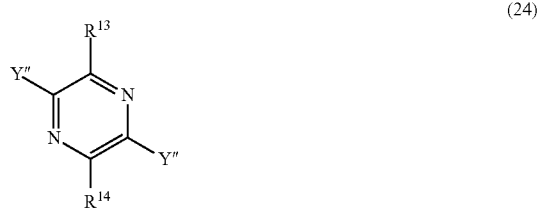
(24)

wherein $R^{13}$ and $R^{14}$ have the same meanings as in the above formula (22); Y" is a fluorine atom, a chlorine atom, a bromine atom, an iodine atom, or a trifluoromethanesulfonyloxy group; and plurally occurring Y"'s are the same or different from each other, in the presence of a catalyst containing at least one metal element selected from the group consisting of palladium, platinum, and nickel (hereinafter referred to sometimes as the "production process (7)").

The amount of the compound of the above formula (24) to be used may preferably be not smaller than 0.2 mol and not larger than 1.0 mol, more preferably not smaller than 0.3 mol and not larger than 0.8 mol, and still more preferably not smaller than 0.4 mol and not larger than 0.6 mol, relative to 1 mol of the boron compound of the above formula (23). When the amount of the compound of the above formula (24) to be used is too small, a lack of the compound of the above formula (24) may occur, resulting in a decrease in the yield of the final product. In contrast, when the amount of the compound of the above formula (24) to be used is too great, an excess of the compound of the above formula (24) may occur, resulting in an increase in the production cost.

The catalyst contains at least one metal element selected from the group consisting of palladium, platinum, and nickel. Among these metal elements, palladium and platinum may be preferred.

Examples of the catalyst may include, but are not limited to, complexes containing metal elements as described above. Specific examples of the catalyst may include, but are not limited to, tris(dibenzylideneacetone)dipalladium chloroform complex ($Pd_2dba_3.CHCl_3$), tetrakis(triphenylphosphine)palladium, bis(tri-tert-butylphosphine)palladium (Pd($P^tBu_3$)$_2$), bis(tricyclohexylphosphine)palladium, bis(1,5-cyclooctadiene)platinum, and bis(1,5-cyclooctadiene)nickel. These catalysts may be used alone, or two or more kinds thereof may be used in combination. Among these catalysts, tris(dibenzylideneacetone)dipalladium chloroform complex ($Pd_2dba_3.CHCl_3$) may be preferred.

The amount of the catalyst to be used may preferably be not smaller than 0.001 mol and not larger than 0.2 mol, more preferably not smaller than 0.005 mol and not larger than 0.15 mol, and still more preferably not smaller than 0.01 mol and not larger than 0.1 mol, relative to 1 mol of the boron compound of the above formula (23). When the amount of the catalyst to be used is too small, the reaction rate may be slow, so that the reaction cannot quickly proceed. In contrast, when the amount of the catalyst to be used is too great, the catalyst may be used more than necessary, resulting in an increase in the production cost.

In the above reaction, a stabilizer may be used in addition to the catalyst. Examples of the stabilizer may include, but are not limited to, triphenylphosphine, tri(o-tolyl)phosphine (P(o-tol)$_3$), tri(2-furyl)phosphine, tri-tert-butylphosphine, trimethylphosphine, dimethylphenylphosphine, diphenylmethylphosphine, tricyclohexylphosphine, bis[2-(diphenylphosphino)phenyl]ether (DPEphos; or also called "(oxydi-2,1-phenylene)bis(diphenylphosphine)"), and bipyridine. These stabilizers may be used alone, or two or more kinds thereof may be used in combination. Among these stabilizers, bis[2-(diphenylphosphino)phenyl]ether (DPEphos) may be preferred.

The amount of the stabilizer to be used may preferably be not smaller than 0.01 mol and not larger than 0.3 mol, more preferably not smaller than 0.02 mol and not larger than 0.25 mol, and still more preferably not smaller than 0.03 mol and not larger than 0.2 mol, relative to 1 mol of the boron compound of the above formula (23). When the amount of the stabilizer to be used is too small, the function of the stabilizer cannot sufficiently be exerted, resulting in a decrease in the yield of the final product. In contrast, when the amount of the stabilizer to be used is too great, the stabilizer may be used more than necessary, resulting in an increase in the production cost.

In this connection, when a catalyst containing at least one stabilizer such as phosphine ligand (e.g., tetrakis(triphenylphosphine)palladium, bis(tri-tert-butylphosphine)palladium, bis(tricyclohexylphosphine)palladium) is used, there is no need to use an additional stabilizer.

The above reaction is typically carried out in an organic solvent. Examples of the organic solvent may include, but are not limited to, aromatic hydrocarbons such as benzene, toluene, xylene, and mesitylene; halogenated aromatic hydrocarbons such as chlorobenzene and 1,2-dichlorobenzene; halogenated aliphatic hydrocarbons such as dichloromethane, chloroform, carbon tetrachloride, 1,2-dichloroethane, 1,1,1-trichloroethane, 1,1,2,2-tetrachloroethane, 1,2-dichloroethylene, trichloroethylene, and tetrachloroethylene; alcohols such as methanol, ethanol, isopropyl alcohol, 1-butanol, 2-butanol, isobutyl alcohol, and isopentyl alcohol; esters such as methyl acetate, ethyl acetate, propyl acetate, isopropyl acetate, butyl acetate, isobutyl acetate, pentyl acetate, and isopentyl acetate; ethers such as diethyl ether, 1,4-dioxane, tetrahydrofuran, and methylphenyl ether (anisole); ketones such as acetone, methyl ethyl ketone, methyl butyl ketone, and methyl isobutyl ketone; glycol ethers (cellosolves) such as ethylene glycol monomethyl ether (methylcellosolve), ethylene glycol monoethyl ether (cellosolve), ethylene glycol monobutyl ether (butylcellosolve), and ethylene glycol monoethyl ether acetate (cellosolve acetate); alicyclic hydrocarbons such as cyclohexane; aliphatic hydrocarbons such as n-hexane; and nitriles such as acetonitrile. These organic solvents may be used alone, or two or more kinds thereof may be used in combination. Among these organic solvents, aromatic hydrocarbons such as benzene and toluene may be preferred.

The above reaction may preferably be carried out under an inert gas atmosphere. Examples of the inert gas may include, but are not limited to, nitrogen, helium, and argon. These inert gases may be used alone, or two or more kinds thereof may be used in combination. Among these inert gases, nitrogen and argon may be preferred.

The reaction conditions are not particularly limited, so long as the above reaction can sufficiently proceed under these conditions. For example, the reaction temperature may preferably be from 0° C. to 100° C., more preferably from room temperature to 80° C., and the reaction time may preferably be from 0.5 to 24 hours, more preferably from 1 to 12 hours. The reaction pressure may be normal pressure, reduced pressure, or increased pressure, preferably normal pressure.

After the completion of the reaction, for example, the reaction solution is directly concentrated or evaporated to dryness, or alternatively, water is added to the reaction solution, followed by extraction with an appropriate organic solvent, washing with water and a saturated sodium chloride solution, and then concentration or evaporation to dryness, and if necessary, followed by purification using any of the heretofore known methods, e.g., various kinds of chromatography or recrystallization. Thus, the desired product is obtained.

In the production process (7), the boron compound of the above formula (23), which is a starting material, can be produced in accordance with the production process for the boron compound of the above formula (4).

In the production process (7), the compound of the above formula (24), which is a starting material, can be produced by any of the heretofore known methods or can be obtained as commercially available products.

In the above formulas (22) and (24), $R^{13}$ and $R^{14}$ may preferably be methyl groups. In the above formula (24), Y" may preferably be a bromine atom. In the above formulas (22) and (23), $R^1$, $R^2$, and $R^3$ may preferably be biphenylyl groups, and $R^b$ may preferably be a hydrogen atom.

Novel Boron Compounds IV

The novel boron compounds IV according to the present invention are boron compounds of the following formula (25):

[Chemical Formula 293]

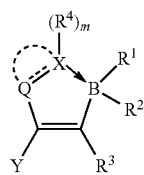

(25)

wherein $R^1$, $R^2$, and $R^3$ are the same or different from each other and are each independently an aryl group or a heterocyclic group, each of which optionally has at least one substituent group, or any two of $R^1$, $R^2$, and $R^3$ are combined with each other to form a ring; $R^4$ is a hydrogen atom or a substituent group; m is an integer of from 0 to 2; when m is 2, plurally occurring $R^4$'s are the same or different from each other; Q is a linking group; X is a nitrogen atom, an oxygen atom, a sulfur atom, a phosphorus atom, or a selenium atom; a dashed half arc indicates that Q and X may be part of a common ring; dashed and solid lines between Q and X indicate a single or double bond; an arrow directed from X to B indicates a coordinate bond; and Y is a fluorine atom, a chlorine atom, a bromine atom, or an iodine atom.

In the above formula (25), examples of the "aryl group" in the aryl group which optionally has at least one substituent group, as indicated by $R^1$, $R^2$, or $R^3$, may include, but are not limited to, phenyl group, biphenylyl group (e.g., 4-biphenylyl group), naphthyl group (e.g., 2-naphthyl group), tetrahydronaphthyl group (e.g., 5,6,7,8-tetrahydronaphthalen-2-yl group), indenyl group (e.g., 1H-inden-5-yl group), and indanyl group (e.g., indan-5-yl group). Among these aryl groups, phenyl group, biphenylyl group (e.g., 4-biphenylyl group), and naphthyl group (e.g., 2-naphthyl group) may be preferred.

Examples of the "heterocyclic group" in the heterocyclic group which optionally has at least one substituent group, as indicated by $R^1$, $R^2$, or $R^3$, may include, but are not limited to, pyrrolyl group (e.g., 2-pyrrolyl group), pyridyl group (e.g., 2-pyridyl group), quinolyl group (e.g., 2-quinolyl group), piperidinyl group (e.g., 4-piperidinyl group), piperidino group, furyl group (e.g., 2-furyl group), and thienyl group (e.g., 2-thienyl group). Among these heterocyclic groups, pyridyl group (e.g., 2-pyridyl group), and thienyl group (e.g., 2-thienyl group) may be preferred.

Examples of the "substituent group" in the aryl group and the heterocyclic group, both of which optionally have at least one substituent group, may include, but are not limited to, a halogen atom (e.g., fluorine atom, chlorine atom, bromine atom, and iodine atom), haloalkyl group (e.g., fluoromethyl group, difluoromethyl group, trifluoromethyl group), straight or branched chain alkyl group having from 1 to 4 carbon atoms (e.g., methyl group, ethyl group, propyl group, isopropyl group, butyl group, isobutyl group, tert-butyl group), cyclic alkyl group having from 5 to 7 carbon atoms (e.g., cyclopentyl group, cyclohexyl group), straight or branched chain alkoxy group having from 1 to 8 carbon atoms (e.g., methoxy group, ethoxy group, propoxy group, isopropoxy group, butoxy group, isobutoxy group, tert-butoxy group, pentyloxy group, hexyloxy group, heptyloxy group, octyloxy group), hydroxy group, nitro group, cyano group, amino group, mono- or di-alkylamino group in which each alkyl group has from 1 to 4 carbon atoms (e.g., methylamino group, ethylamino group, dimethylamino group, diethylamino group), acyl group (e.g., acetyl group, propionyl group, butyryl group), alkenyl group having from 2 to 6 carbon atoms (e.g., vinyl group, 1-propenyl group, allyl group), alkynyl group having from 2 to 6 carbon atoms (e.g., ethynyl group, 1-propynyl group, propargyl group), phenyl group, substituted phenyl group (e.g., 4-fluorophenyl group, 4-chlorophenyl group, 4-methylphenyl group (i.e., p-tolyl group), 4-methoxyphenyl group, 4-nitrophenyl group), carbamoyl group, and N,N-dialkylcarbamoyl group (e.g., N,N-dimethylcarbamoyl group, N,N-diethylcarbamoyl group, N,N-dipropylcarbamoyl group).

Alternatively, any two of $R^1$, $R^2$, and $R^3$ may be combined with each other to form a ring. Examples of such a ring may include, but are not limited to: as a result of the combination of $R^1$ and $R^2$, borole ring, benzoborole ring, dibenzoborole ring, 1,4-dihydroborinine ring, 1,4-dihydrobenzo[b]borinine ring, 5,10-dihydro-dibenzo[b,e]borinine ring, 4H-1,4-oxaborinine ring, 4H-benzo[b][1,4]oxaborinine ring, 10H-dibenzo[b,e][1,4]oxaborinine ring, 1,4-dihydro-1,4-azaborinine ring, 1,4-dihydrobenzo[b][1,4]azaborinine ring, and 5,10-dihydrodibenzo[b,e][1,4]azaborinine ring; as a result of the combination of $R^1$ and $R^3$, 5,6-dihydrodibenzo[b,d]borinine ring; and these rings having at least one substituent group. In the above formula (25), examples of the substituent group as indicated by $R^4$ may include, but are not limited to, the substituent groups described above as the "substituent group" in the aryl group and the heterocyclic group, both of which optionally have at least one substituent group.

In the above formula (25), m is the number of substituent groups R4 attached to X, and is an integer of from 0 to 2, depending on the valence of X, whether the bond between Q and X is a single or double bond, whether or not Q and X are part of a common ring, or others. In this connection, when m is 2, plurally occurring $R^4$'s are the same or different from each other.

In the above formula (25), examples of the linking group as indicated by Q may include, but are not limited to, =C<, =CH—, —CH<, —CH$_2$—, —CH$_2$CH$_2$—, —C$_6$H$_4$— (e.g., -(1,2-C$_6$H$_4$), —C$_{10}$H$_6$— (e.g., -(1,2-C$_{10}$H$_6$), —CO—, —CS—, —CH$_2$N<, and —CH$_2$N=. Among these linking groups, =C<, —CH$_2$—, and —CH$_2$CH$_2$— may be preferred.

In the above formula (25), X is a nitrogen atom, an oxygen atom, a sulfur atom, a phosphorus atom, or a selenium atom. Among these atoms, a nitrogen atom and an oxygen atom may be preferred.

In the above formula (25), examples of the common ring of Q and X, as indicated by the dashed half arc, may include, but are not limited to, pyrrole ring, pyridine ring, indole ring, isoindole ring, quinoline ring, isoquinoline ring, phenanthridine ring, pyrazine ring, triazine ring, furan ring, pyran ring, benzofuran ring, isobenzofuran ring, chromene ring, isochromene ring, phosphindole ring, isophosphindole ring, phosphinoline ring, isophosphinoline ring, thiophene ring, thiopyran ring, thiochromene ring, isothiochromene ring, selenophene ring, selenopyran ring, selenochromene ring, and isoselenochromene ring; however, 1,3-benzodithiol ring is excluded. These rings optionally have at least one substituent group. Among these rings, pyridine ring, quinoline ring, phenanthridine ring, furan ring, and thiophene ring may be preferred.

In the above formula (25), Q and X may preferably be part of a common ring, and it may be more preferred that the above common ring is a pyridine ring, a quinoline ring, a phenanthridine ring, or a thiophene ring, X is the nitrogen atom of the pyridine ring, quinoline ring, or phenanthridine ring, or the sulfur atom of the thiophene ring, and m is 0. That is, boron compounds of the following formulas (114), (115), (116), and (117) may be preferred:

[Chemical Formula 294]

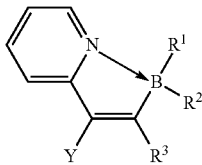

(114)

wherein $R^1$, $R^2$, $R^3$, and Y have the same meanings as in the above formula (25); the pyridine ring optionally has at least one substituent group; and an arrow directed from N to B indicates a coordinate bond;

[Chemical Formula 295]

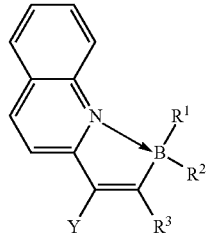

(115)

wherein $R^1$, $R^2$, $R^3$, and Y have the same meanings as in the above formula (25); the quinoline ring optionally has at least one substituent group; and an arrow directed from N to B indicates a coordinate bond;

[Chemical Formula 296]

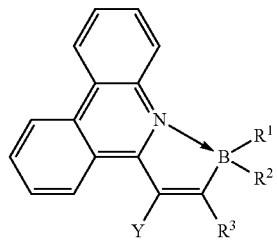

(116)

wherein $R^1$, $R^2$, $R^3$, and Y have the same meanings as in the above formula (25); the phenanthridine ring optionally has at least one substituent group; and an arrow directed from N to B indicates a coordinate bond; and

[Chemical Formula 297]

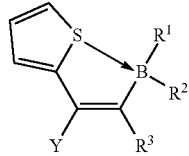

(117)

wherein $R^1$, $R^2$, $R^3$, and Y have the same meanings as in the above formula (25); the thiophene ring optionally has at least one substituent group; and an arrow directed from S to B indicates a coordinate bond.

In the above formula (25), it may be preferred that Q is a methylene group, X is a nitrogen atom, and m is 2. That is, a boron compound of the following formula (118) may be preferred:

[Chemical Formula 298]

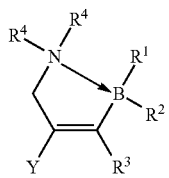
(118)

wherein $R^1$, $R^2$, $R^3$, $R^4$, and Y have the same meanings as in the above formula (25); plurally occurring $R^4$'s are the same or different from each other; and an arrow directed from N to B indicates a coordinate bond.

Further, in the above formula (25), it may be preferred that Q is a methylene group, X is an oxygen atom, and m is 1. That is, a boron compound of the following formula (119) may be preferred:

[Chemical Formula 299]

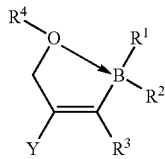
(119)

wherein $R^1$, $R^2$, $R^3$, $R^4$, and Y have the same meanings as in the above formula (25); and an arrow directed from O to B indicates a coordinate bond.

<<Processes for Producing Novel Boron Compounds IV>>

The novel boron compounds IV of the present invention can be produced with high efficiency in a simple and easy manner by the production process (8) as described below. In addition, their more specific boron compounds can be produced with high efficiency in a simple and easy manner by the production processes (8-1) to (8-6) as described below.

<Production Process (8)>

One of the novel boron compounds IV of the present invention, i.e., a boron compound of the following formula (25):

[Chemical Formula 300]

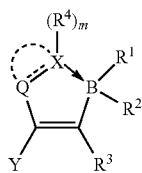
(25)

wherein $R^1$, $R^2$, and $R^3$ are the same or different from each other and are each independently an aryl group or a heterocyclic group, each of which optionally has at least one substituent group, or any two of $R^1$, $R^2$, and $R^3$ are combined with each other to form a ring; $R^4$ is a hydrogen atom or a substituent group; m is an integer of from 0 to 2; when m is 2, plurally occurring $R^4$'s are the same or different from each other; Q is a linking group; X is a nitrogen atom, an oxygen atom, a sulfur atom, a phosphorus atom, or a selenium atom; a dashed half arc indicates that Q and X may be part of a common ring; dashed and solid lines between Q and X indicate a single or double bond; an arrow directed from X to B indicates a coordinate bond; and Y is a fluorine atom, a chlorine atom, a bromine atom, or an iodine atom, can be produced by reacting a boron compound of the following formula (120):

[Chemical Formula 301]

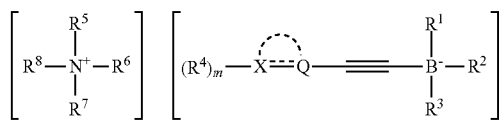
(120)

wherein $R^1$, $R^2$, $R^3$, $R^4$, Q, X, a dashed half arc, and dashed and solid lines between Q and X have the same meanings as in the above formula (25); when m is 2, plurally occurring $R^4$'s are the same or different from each other; and $R^5$, $R^6$, $R^7$, and $R^8$ are the same or different from each other and are each independently a hydrogen atom or a substituent group, with a halogenating agent (hereinafter referred to sometimes as the "production process (8)").

The halogenating agent may appropriately be selected from the heretofore known halogenating agents, depending on the type of the halogen atom as indicated by Y in the above formula (25), and is not particularly limited. In particular, when Y is a fluorine atom in the above formula (25), examples of the fluorinating agent may include, but are not limited to, 1-chloromethyl-4-fluoro-1,4-diazonia-bicyclo[2,2,2]octane-bis(tetrafluoroborate) (available from Air Products and Chemicals, Inc., the product name: "SelectFluor (registered trade name)") of the following formula (121):

[Chemical Formula 302]

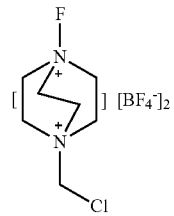
(121)

and bis(2-methoxyethyl)aminosulfur trifluoride (available from Air Products and Chemicals, Inc., the product name: "Deoxo-Fluor (registered trade name)") of the following formula (122):

[Chemical Formula 303]

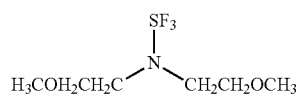
(122)

Among these fluorinating agents, 1-chloromethyl-4-fluoro-1,4-diazonia-bicyclo[2,2,2]octane-bis(tetrafluoroborate) (available from Air Products and Chemicals, Inc., the product name: "SelectFluor (registered trade name)") of the above formula (121) may be preferred.

The amount of the halogenating agent to be used may preferably be not smaller than 0.2 mol and not larger than 2.0 mol, more preferably not smaller than 0.4 mol and not larger than 1.8 mol, and still more preferably not smaller than 0.6 mol and not larger than 1.6 mol, relative to 1 mol of the boron compound of the above formula (120). When the amount of the halogenating agent to be used is too small, a lack of the halogenating agent may occur, resulting in a decrease in the yield of the final product. In contrast, when the amount of the halogenating agent to be used is too great, an excess of the halogenating agent may occur, resulting in an increase in the production cost.

The above reaction is typically carried out in an organic solvent. Examples of the organic solvent may include, but are not limited to, aromatic hydrocarbons such as benzene, toluene, xylene, and mesitylene; halogenated aromatic hydrocarbons such as chlorobenzene and 1,2-dichlorobenzene; halogenated aliphatic hydrocarbons such as dichloromethane, chloroform, carbon tetrachloride, 1,2-dichloroethane, 1,1,1-trichloroethane, 1,1,2,2-tetrachloroethane, 1,2-dichloroethylene, trichloroethylene, and tetrachloroethylene; alcohols such as methanol, ethanol, isopropyl alcohol, 1-butanol, 2-butanol, isobutyl alcohol, and isopentyl alcohol; esters such as methyl acetate, ethyl acetate, propyl acetate, isopropyl acetate, butyl acetate, isobutyl acetate, pentyl acetate, and isopentyl acetate; ethers such as diethyl ether, 1,4-dioxane, tetrahydrofuran, and methyl phenyl ether (anisole); ketones such as acetone, methyl ethyl ketone, methyl butyl ketone, and methyl isobutyl ketone; glycol ethers (cellosolves) such as ethylene glycol monomethyl ether (methylcellosolve), ethylene glycol monoethyl ether (cellosolve), ethylene glycol monobutyl ether (butylcellosolve), and ethylene glycol monoethyl ether acetate (cellosolve acetate); alicyclic hydrocarbons such as cyclohexane; aliphatic hydrocarbons such as n-hexane; nitriles such as acetonitrile; and aprotic polar solvents such as dimethylformamide and dimethyl sulfoxide. These organic solvents may be used alone, or two or more kinds thereof may be used in combination. Among these organic solvents, nitriles such as acetonitrile may be preferred.

The above reaction may preferably be carried out under an inert gas atmosphere. Examples of the inert gas may include, but are not limited to, nitrogen, helium, and argon. These inert gases may be used alone, or two or more kinds thereof may be used in combination. Among these inert gases, nitrogen and argon may be preferred.

The reaction conditions are not particularly limited, so long as the above reaction can sufficiently proceed under these conditions. For example, the reaction temperature may preferably be from 0° C. to 100° C., more preferably from room temperature to 80° C., and the reaction time may preferably be from 0.5 to 24 hours, more preferably from 1 to 12 hours. The reaction pressure may be normal pressure, reduced pressure, or increased pressure, preferably normal pressure.

After the completion of the reaction, for example, the reaction solution is directly concentrated or evaporated to dryness, or alternatively, water is added to the reaction solution, followed by extraction with an appropriate organic solvent, washing with water and a saturated sodium chloride solution, and then concentration or evaporation to dryness, and if necessary, followed by purification using any of the heretofore known methods, e.g., various kinds of chromatography or recrystallization. Thus, the desired product is obtained.

In the production process (8), the boron compound of the above formula (120), which is a starting material, can be produced in accordance with the production process for the boron compound of the above formula (7).

<Production Processes (8-1) to (8-4)>

In the above formulas (25) and (120), Q and X may preferably be part of a common ring, and it may be more preferred that the above common ring is a pyridine ring, a quinoline ring, or a thiophene ring, X is the nitrogen atom of the pyridine ring or quinoline ring, or the sulfur atom of the thiophene ring, and m is 0. That is, a boron compound of the following formula (114):

[Chemical Formula 304]

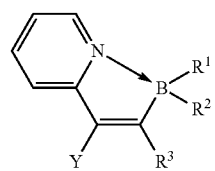

(114)

wherein $R^1$, $R^2$, $R^3$, and Y have the same meanings as in the above formula (25); the pyridine ring optionally has at least one substituent group; and an arrow directed from N to B indicates a coordinate bond, can be produced by reacting a boron compound of the following formula (123):

[Chemical Formula 305]

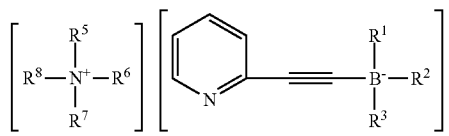

(123)

wherein $R^1$, $R^2$, and $R^3$ have the same meanings as in the above formula (25); the pyridine ring optionally has at least one substituent group; and $R^5$, $R^6$, $R^7$, and $R^8$ have the same meanings as in the above formula (120), with a halogenating agent (hereinafter referred to sometimes as the "production process (8-1)").

Further, a boron compound of the following formula (115):

[Chemical Formula 306]

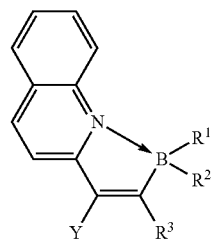

(115)

wherein $R^1$, $R^2$, $R^3$, and Y have the same meanings as in the above formula (25); the quinoline ring optionally has at least one substituent group; and an arrow directed from N to B indicates a coordinate bond, can be produced by reacting a boron compound of the following formula (124):

[Chemical Formula 307]

(124)

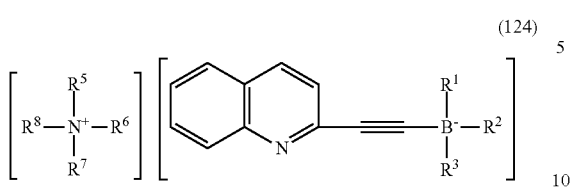

wherein $R^1$, $R^2$, and $R^3$ have the same meanings as in the above formula (25); the quinoline ring optionally has at least one substituent group; and $R^5$, $R^6$, $R^7$, and $R^8$ have the same meanings as in the above formula (120), with a halogenating agent (hereinafter referred to sometimes as the "production process (8-2)").

Further, a boron compound of the following formula (116):

[Chemical Formula 308]

(116)

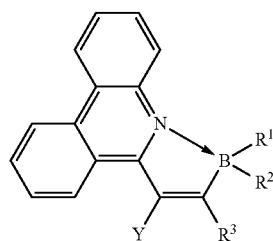

wherein $R^1$, $R^2$, $R^3$, and Y have the same meanings as in the above formula (25); the phenanthridine ring optionally has at least one substituent group; and an arrow directed from N to B indicates a coordinate bond, can be produced by reacting a boron compound of the following formula (125):

[Chemical Formula 309]

(125)

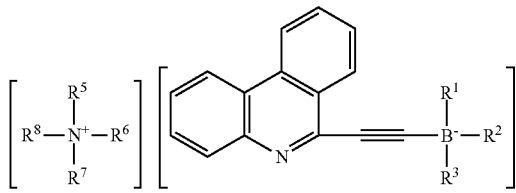

wherein $R^1$, $R^2$, and $R^3$ have the same meanings as in the above formula (25); the phenanthridine ring optionally has at least one substituent group; and $R^5$, $R^6$, $R^7$, and $R^8$ have the same meanings as in the above formula (120), with a halogenating agent (hereinafter referred to sometimes as the "production process (8-3)").

Further, a boron compound of the following formula (117):

[Chemical Formula 310]

(117)

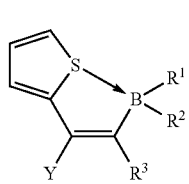

wherein $R^1$, $R^2$, $R^3$, and Y have the same meanings as in the above formula (25); the thiophene ring optionally has at least one substituent group; and an arrow directed from S to B indicates a coordinate bond, can be produced by reacting a boron compound of the following formula (126):

[Chemical Formula 311]

(126)

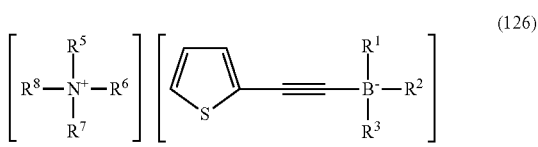

wherein $R^1$, $R^2$, and $R^3$ have the same meanings as in the above formula (25); the thiophene ring optionally has at least one substituent group; and $R^5$, $R^6$, $R^7$, and $R^8$ have the same meanings as in the above formula (120), with a halogenating agent (hereinafter referred to sometimes as the "production process (8-4)").

In the production processes (8-1) to (8-4), the amounts of the starting materials and the halogenating agent to be used, the types of the organic solvent and the inert gas, the reaction conditions, the post-treatments after the completion of the reaction, and others are similar to those of the production process (8); however, the boron compound of the above formula (120) should be read as the boron compound of the above formula (123), (124), (125), or (126).

In the production processes (8-1) to (8-4), the boron compound of the above formula (123), (124), (125), or (126), which is a starting material, can be produced in accordance with the production process for the boron compound of the above formula (7).

<Production Process (8-5)>

In the above formulas (25) and (120), it may be preferred that Q is a methylene group, X is a nitrogen atom, and m is 2. That is, a boron compound of the following formula (118):

[Chemical Formula 312]

(118)

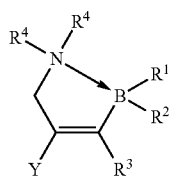

wherein $R^1$, $R^2$, $R^3$, $R^4$, and Y have the same meanings as in the above formula (25); plurally occurring $R^4$'s are the same or different from each other; and an arrow directed from N to B indicates a coordinate bond, can be produced by reacting a boron compound of the following formula (127):

[Chemical Formula 313]

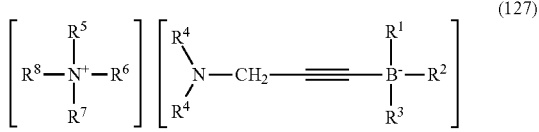

(127)

wherein $R^1$, $R^2$, $R^3$, and $R^4$ have the same meanings as in the above formula (25); plurally occurring $R^4$'s are the same or different from each other; and $R^5$, $R^6$, $R^7$, and $R^8$ have the same meanings as in the above formula (120), with a halogenating agent (hereinafter referred to sometimes as the "production process (8-5)").

In the production process (8-5), the amounts of the starting materials and the halogenating agent to be used, the types of the organic solvent and the inert gas, the reaction conditions, the post-treatments after the completion of the reaction, and others are similar to those of the production process (8); however, the boron compound of the above formula (120) should be read as the boron compound of the above formula (127).

In the production process (8-5), the boron compound of the above formula (127), which is a starting material, can be produced in accordance with the production process for the boron compound of the above formula (7).

<Production Process (8-6)>

In the above formulas (25) and (120), it may be preferred that Q is a methylene group, X is an oxygen atom, and m is 1. That is, a boron compound of the following formula (119):

[Chemical Formula 314]

(119)

wherein $R^1$, $R^2$, $R^3$, $R^4$, and Y have the same meanings as in the above formula (25); and an arrow directed from O to B indicates a coordinate bond, can be produced by reacting a boron compound of the following formula (128):

[Chemical Formula 315]

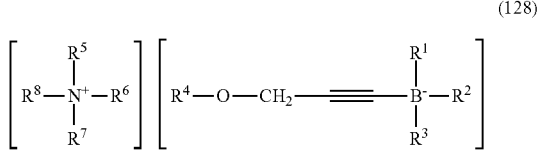

(128)

wherein $R^1$, $R^2$, $R^3$, and $R^4$ have the same meanings as in the above formula (25); and $R^5$, $R^6$, $R^7$, and $R^8$ have the same meanings as in the above formula (120), with a halogenating agent (hereinafter referred to sometimes as the "production process (8-6)").

In the production process (8-6), the amounts of the starting materials and the halogenating agent to be used, the types of the organic solvent and the inert gas, the reaction conditions, the post-treatments after the completion of the reaction, and others are similar to those of the production process (8); however, the boron compound of the above formula (120) should be read as the boron compound of the above formula (128).

In the production process (8-5), the boron compound of the above formula (128), which is a starting material, can be produced in accordance with the production process for the boron compound of the above formula (7).

<<Applications of Novel Boron Compounds I to IV>>

The novel boron compounds I to IV of the present invention have novel molecular structures which are quite different from those of the heretofore known boron compounds, and are useful as light-emitting materials, electron-transport materials, electron-injection materials, hole-blocking materials, or organic semiconductor materials, depending on their characteristics. Therefore, when the novel boron compounds I to IV of the present invention are used for various functional electronic devices, the functional electronic devices obtained have excellent electrical characteristics.

In addition, the novel boron compounds I to IV of the present invention are useful as organic semiconductor materials for solar cells, film capacitors, gate insulating films of CMOS and other devices, interlayer insulating films for impedance matching in high-frequency circuit boards, base substrates of planar (film) antennas, lens materials, protective layers of optical recording disk media, thin film optical filters, optical fibers, optical waveguides, optical adhesives; optical sealing materials, and other applications.

<<Functional Electronic Devices>>

The functional electronic devices of the present invention each comprises any of the boron compounds of the above formula (1), (2), (3), (15), (16), (17), (20), or (23), or any of their more specific boron compounds, as a light-emitting material, an electron-transport material, or a hole-blocking material. In this connection, examples of the functional electronic devices may include, but are not limited to, organic light-emitting diode (OLED) devices and organic thin film transistors.

Among the functional electronic devices of the present invention, organic light-emitting diode (OLED) devices each usually has a single-layer structure in which an anode, a light-emitting layer, and a cathode are successively formed on a transparent substrate; a double-layer structure in which an anode, a light-emitting hole-transport layer, an electron-transport layer, and a cathode are successively formed on a transparent substrate; a double-layer structure in which an anode, a hole-transport layer, a light-emitting electron-transport layer, and a cathode are successively formed on a transparent substrate; a triple-layer structure in which an anode, a hole-transport layer, a light-emitting layer, an electron-transport layer, and a cathode are successively formed on a transparent substrate; or any other structure. The respective layers in these structures have the following functions. The light-emitting layer (including the light-emitting hole-transport layer and the light-emitting electron-transport layer) is a portion of determining the emission color of the organic light-emitting diode (OLED) device, and particularly in display applications, the light-emitting layer is required to produce emission color corresponding to one of the three primary colors (red (R), green (G), and blue (B)) with high efficiency.

The hole-transport layer has a function of transporting, to the light-emitting layer, holes injected from the anode. To achieve highly efficient hole injection, the requirements for the hole-transport layer are to be a material having the highest occupied molecular orbital (HOMO) close to the work function of the anode material; to be a material having weak donor properties for efficiently transporting holes; and to not form an intermolecular interaction, such as an excited complex (exciplex) or a charge transfer complex, with the material of the light-emitting layer.

The electron-transport layer has a function of transporting, to the light-emitting layer, electrons injected from the cathode. To achieve highly efficient electron injection, the requirements for the electron-transport layer are to be a material having weak acceptor properties; and to not form an intermolecular interaction, such as an excited complex (exciplex) or a charge transfer complex, with the material of the light-emitting layer.

There are only a limited number of materials for the hole-transport layer or the electron-transport layer, which meet the above multiple requirements. Therefore, in organic light-emitting diode (OLED) devices which have been studied, each transport layer has a subdivided function and each transport layer is formed into a multilayered structure for the purpose of achieving high efficiency of each device and lowering the drive voltage of each device. Examples of the organic light-emitting diode (OLED) device having subdivided electron-transport layers may include one device having an electron-injection layer between the ordinary electron-transport layer (of which primary function is electron transporting) and the cathode, for the primary purpose of efficiently carrying out electron injection; and one device having a hole-blocking layer between the ordinary electron-transport layer and the light-emitting layer, for the primary purpose of preventing holes from leaving the light-emitting layer.

When the functional electronic device of the present invention is an organic light-emitting diode (OLED) device, the boron compound of the above formula (1), (2), (3), (15), (16), (17), (20), or (23), or its more specific boron compound is used, depending on its characteristics, as a light-emitting material for the light-emitting layer, as an electron-transport material for the electron-transport layer, as an electron-injection material for the electron-injection layer, or as a hole-blocking material for the hole-blocking layer.

Among the functional electronic devices of the present invention, organic thin film transistors each usually has a structure in which a gate electrode, a gate insulating film, source/drain electrodes, and an organic semiconductor layer are formed on a substrate. The thin film transistors are classified into the bottom contact type, in which the organic semiconductor layer is formed on the source/drain electrodes, and the top contact type, in which the source/drain electrodes are formed on the organic semiconductor layer. In this connection, examples of the material to be used for the organic semiconductor layer may include p-type semiconductors, which mainly transport holes as carriers, n-type semiconductors, which mainly transport electrons as carriers, and ambipolar semiconductors, which have their both properties.

When the functional electronic device of the present invention is an organic thin film transistor, the boron compound of the above formula (1), (2), (3), (15), (16), (17), (20), or (23), or its more specific boron compound is used as an organic semiconductor material for the organic semiconductor layer, depending on its characteristics.

The functional electronic devices of the present invention have excellent electrical characteristics because any of the boron compounds of the above formula (1), (2), (3), (15), (16), (17), (20), or (23), or any of their more specific boron compounds, is used as a light-emitting material, an electron-transport material, an electron-injection material, a hole-blocking material, or an organic semiconductor material.

EXAMPLES

The present invention will be explained below in detail by reference to Examples, but the present invention is not limited to these Examples. The present invention can be put into practice after appropriate modifications or variations within a range meeting both of the gist described above and below, all of which are included in the technical scope of the present invention.

First, the following will describe methods of measuring physical and chemical properties of starting materials produced in Synthesis Examples and novel boron compounds produced in Examples, as well as methods of measuring fluorescence spectra, fluorescence quantum yields, glass transition temperatures, and HOMO-LUMO levels of the novel boron compounds produced in Examples.

<$^1$H-NMR Spectra>

Each of the starting materials obtained or the boron compounds obtained was dissolved in either of deuterated chloroform, deuterated dichloromethane, deuterated acetonitrile, or deuterated dimethylsulfoxide, and the measurement for the solution was carried out using a high-resolution nuclear magnetic resonance apparatus (product name: Gemini 2000, available from Varian, Inc.; 300 MHz). Chemical shifts on the low-field side from tetramethylsilane were recorded in parts per million (ppm; $\delta$ scale), and were referenced against the hydrogen nucleus of tetramethylsilane ($\delta$=0.00).

<$^{13}$C-NMR Spectra>

Each of the starting materials obtained or the boron compounds obtained was dissolved in either of deuterated chloroform, deuterated dichloromethane, deuterated acetonitrile, or deuterated dimethylsulfoxide, and the measurement for the solution was carried out using a high-resolution nuclear magnetic resonance apparatus (product name: Gemini 2000, available from Varian, Inc.; 75 MHz). Chemical shifts on the low-field side from tetramethylsilane were recorded in parts per million (ppm; $\delta$ scale), and were referenced against the carbon nucleus of the NMR solvent (CDCl$_3$: $\delta$=77.0, CD$_2$Cl$_2$: $\delta$=53.1, CD$_3$CN: $\delta$=1.32, and DMSO-d$_6$: $\delta$=39.52).

<$^{11}$B-NMR Spectra>

Each of the starting materials obtained or the boron compounds obtained was dissolved in either one of deuterated chloroform, deuterated acetonitrile, or deuterated dimethylsulfoxide, and the measurement for the solution was carried out using a high-resolution nuclear magnetic resonance apparatus (product name: Mercury-400, available from Varian, Inc.; 128 MHz). Chemical shifts were recorded in parts per million (ppm; $\delta$ scale) using the boron nucleus ($\delta$=0.00) of boron trifluoride diethyl ether complex as a standard.

<High-Resolution Mass Spectrometry Spectra>

The measurement was carried out by the electron ionization (EI) method or the fast atom bombardment (FAB) method using a high-resolution mass spectrometer (product names: JMS-SX101A, JMS-MS700, and JMS-BU250, all available from JEOL Ltd.).

<Fluorescence Spectra>

Each of the boron compounds obtained was dissolved in dichloromethane resulting in a dilute solution. A fluorescence spectrum was measured using a fluorescence spectrophotometer (product name: FP-777, available from JASCO Corporation). The measurement temperature was set at room temperature, the wavelength of excitation light was set to 280 nm, and the measurement wavelength was set in a range of from 290 to 600 nm. In this connection, as a result of the measurement, the maximum fluorescence wavelength ($\lambda_{PL}$) is shown.

<Fluorescence Quantum Yield>

First, several dichloromethane solutions having different concentrations of each of the boron compounds obtained were prepared. Then, the absorbance of each solution at a wavelength of 280 nm was measured using an ultraviolet-visible spectrophotometer (product name: Model 8453, available from Agilent Technologies, Inc.). In addition, fluorescence intensity (wavenumber integral value) was determined from the fluorescence spectrum of each solution. From the data of absorbance and fluorescence intensity thus obtained, a graph was drawn in which the horizontal axis represents absorbance and the vertical axis represents fluorescence intensity. Similar measurements were carried out for a 0.1 M sulfuric acid solution of 2-aminopyridine and an aqueous tryptophan solution (pH 7.2) as standard samples to draw respective graphs. When $G_S$ is the slope of a graph (upward-sloping straight line) for a certain sample (boron compound), $G_{R1}$ is the slope of a graph for 2-aminopyridine, $G_{R2}$ is the slope of a graph for tryptophan, $n_S$ is the refractive index of dichloromethane, $n_{R1}$ is the refractive index of 0.1 M sulfuric acid, $n_{R2}$ is the refractive index of water, $Y_{R2}$ is the fluorescence quantum yield of 2-aminopyridine (literature value), and $Y_{R2}$ is the fluorescence quantum yield of tryptophan (literature value), the fluorescence quantum yield $Y_S$ of the sample (boron compound) was determined using the following formulas wherein $n_S$=1.4242, $n_{R1}$=1.333, $n_{R2}$=1.333, $Y_{R1}$=0.60, and $Y_{R2}$=0.14.

$$Y_{S1} = Y_{R1} \times \frac{G_S}{G_{R1}} \times \left(\frac{n_S}{n_{R1}}\right)^2 \quad \text{[Numerical Formula 1]}$$

$$Y_{S2} = Y_{R2} \times \frac{G_S}{G_{R2}} \times \left(\frac{n_S}{n_{R2}}\right)^2 \quad \text{[Numerical Formula 2]}$$

$$Y_S = \frac{Y_{S1} + Y_{S2}}{2} \quad \text{[Numerical Formula 3]}$$

<Glass Transition Temperature (Tg)>

About 5 mg of a sample (boron compound) was put in a sealable aluminum pan which was then sealed, and the measurement was carried out using a differential scanning calorimeter (product name: DSC6220, available from Seiko Instruments Inc.). The measurement temperature was set in a range of from 0° C. to 250° C., and the rate of temperature increase (or decrease) was set at 10° C./min. A cycle of temperature increase and decrease was repeated three times. A glass transition temperature (Tg) was determined as a point where a baseline shifted at a temperature-increasing-process portion of the second or third cycle in the DSC curve obtained.

<HOMO-LUMO Level>

In order to study the energy level of the novel boron compounds of the present invention, the highest occupied molecular orbital (HOMO) level and the lowest unoccupied molecular orbital (LUMO) level were measured as follows:

A substrate (available from ASAHI GLASS CO., LTD.; sheet resistance: 10Ω), which had been obtained by forming an indium tin oxide (ITO) film having a thickness of 150 nm on alkali-free glass, was cut into 2 cm×2 cm pieces, and then cleaned in isopropanol using ultrasonic waves for 10 minutes, followed by boil-washing in isopropanol and then drying. Each piece was fixed to a substrate holder of a vacuum deposition apparatus (available from ULVAC, Inc.) which was connected to a glove box having an argon atmosphere. A sample to be measured was placed in a crucible made of quartz. The pressure was reduced to about $1 \times 10^{-3}$ Pa. The sample was deposited to a film thickness of 50 nm. The ionization potential of the sample thin film thus prepared was measured using a complex electron spectrometer (product name: ESCA-5800, available from ULVAC-PHI, INCORPORATED). The measured value was regarded as the HOMO level of the sample.

The absorption spectrum of another sample thin film which was prepared at the same time was measured using a model-8453 ultraviolet-visible spectrophotometer available from Agilent Technologies, Inc. The absorption edge λ (unit: nm) on the long-wavelength side of an absorption peak was read from the spectrum obtained, and an HOMO-LUMO gap (B.G.) was determined by the following formula:

B.G.=1240/λ.

Further, an LUMO level was determined from the HOMO level and the HOMO-LUMO gap (B.G.) obtained above, using the following formula:

LUMO=HOMO−B.G.

The following will describe Synthesis Examples 1 to 13 of the starting materials to be used in Examples regarding the novel boron compounds I of the present invention and their production processes (1) to (4).

Synthesis Example 1

Synthesis of triphenyl(2-pyridinioethynyl)borate of the following formula:

[Chemical Formula 316]

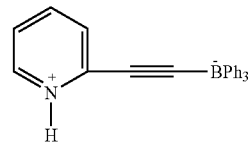

wherein Ph is a phenyl group.

In an argon atmosphere, n-butyl lithium (1.6 M, 1.4 mL, 2.2 mmol) was added dropwise to a tetrahydrofuran solution (8 mL) containing 2-ethynylpyridine (250 mg, 2.4 mmol) at −78° C. The mixture was stirred for 30 minutes while maintaining at −78° C., and triphenylborane pyridine complex (642 mg, 2.0 mmol) was then added thereto, followed by further stirring at room temperature for 1 hour. The reaction was terminated by adding a small amount of methanol, and the solvent was then removed by distillation using a rotary evaporator. The residue obtained was dissolved in methanol, and pyridinium chloride (280 mg, 2.2 mmol) was then added to the solution obtained. The white solid formed was collected by filtration and then washed with tetrahydrofuran and methanol. Thus, triphenyl(2-pyridinioethynyl)borate (390 mg, 1.1 mmol) was obtained in a yield of 56%.

The physical and chemical properties thereof were as follows:

$^1$H-NMR (CD$_3$CN): δ 6.94-7.00 (m, 3H), 7.08-7.12 (m, 6H), 7.37 (d, J=6.9 Hz, 6H), 7.62-7.67 (m, 1H), 7.82-7.85 (m, 1H), 8.28-8.34 (m, 2H);

$^{13}$C-NMR (CD$_3$CN): δ 122.6, 123.9, 127.1, 128.8, 135.2, 142.0, 142.7, 145.9;

$^{11}$B-NMR (CD$_3$CN): δ−6.5;

HRMS (EI) C$_{25}$H$_{20}$BN (M$^+$): theoretical value, 345.1689; experimental value, 345.1692.

Synthesis Example 2

Synthesis of tris(2-naphthyl)(2-pyridinioethynyl)borate of the following formula:

[Chemical Formula 317]

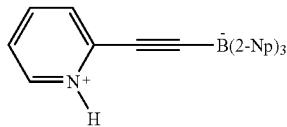

wherein 2-Np is a 2-naphthyl group.

Synthesis was carried out in accordance with Synthesis Example 1, except that triphenylborane pyridine complex was changed to tris(2-naphthyl)borane pyridine complex (945 mg, 2 mmol), followed by washing with dichloromethane. Thus, tris(2-naphthyl)(2-pyridinioethynyl)borate (820 mg, 1.7 mmol) was obtained in a yield of 83%.

The physical and chemical properties thereof were as follows:

$^1$H-NMR (DMSO-$d_6$): δ 7.27-7.33 (m, 6H), 7.58-7.81 (m, 16H), 8.01 (d, J=8.4 Hz, 1H), 8.39 (pseudo t, J=7.8 Hz, 1H), 8.62 (d, J=5.1 Hz, 1H);

$^{11}$B-NMR (DMSO-$d_6$): δ −7.1;

HRMS (EI) $C_{37}H_{26}BN$ (M$^+$): theoretical value, 495.2158; experimental value, 495.2157.

Synthesis Example 3

Synthesis of triphenyl(2-quinolinioethynyl)borate of the following formula:

[Chemical Formula 318]

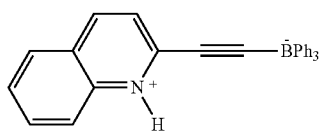

wherein Ph is a phenyl group.

Synthesis was carried out in accordance with Synthesis Example 1, except that 2-ethynylpyridine was changed to 2-ethynylquinoline (363 mg, 2.4 mmol), followed by washing with dichloromethane. Thus, triphenyl(2-quinolinioethynyl)borate (208 mg, 0.53 mmol) was obtained in a yield of 26%.

The physical and chemical properties thereof were as follows:

$^1$H-NMR (DMSO-$d_6$): δ 6.90-6.95 (m, 3H), 7.05 (pseudo t, J=7.2 Hz, 6H), 7.33 (d, J=6.6 Hz, 6H), 7.80-7.85 (m, 1H), 7.94 (d, J=9.0 Hz, 1H), 8.03-8.12 (m, 2H), 8.26 (d, J=8.7 Hz, 1H), 8.94 (d, J=8.7 Hz, 1H);

$^{13}$C-NMR (DMSO-$d_6$): δ 119.8, 122.9, 125.8, 126.0, 128.5, 128.7, 134.1, 137.8, 140.3, 144.4;

$^{11}$B-NMR (DMSO-$d_6$): δ−7.0;

HRMS (EI) $C_{29}H_{22}BN$ (M$^+$): theoretical value, 395.1845; experimental value, 395.1847.

Synthesis Example 4

Synthesis of tetramethylammonium 3-methoxy-1-propynyltriphenylborate of the following formula:

[Chemical Formula 319]

wherein Ph is a phenyl group.

In an argon atmosphere, n-butyl lithium (1.6 M, 3.4 mL, 5.5 mmol) was added dropwise to a tetrahydrofuran solution (20 mL) containing methyl propargyl ether (510 μL, 6 mmol) at −78° C. The mixture was stirred for 30 minutes while maintaining at −78° C., and triphenylborane pyridine complex (1.6 g, 5 mmol) was then added thereto, followed by further stirring at room temperature for 1 hour. The reaction was terminated by adding a small amount of methanol, and the solvent was then removed by distillation using a rotary evaporator. The residue obtained was dissolved in methanol, and tetramethylammonium chloride (600 mg, 5.5 mmol) was then added to the solution obtained. The white solid formed was collected by filtration. Thus, tetramethylammonium 3-methoxy-1-propynyltriphenylborate (1.78 g, 4.6 mmol) was obtained in a yield of 92%.

The physical and chemical properties thereof were as follows:

$^1$H-NMR (CD$_3$CN): δ 2.96 (s, 12H), 3.36 (s, 3H), 4.14 (s, 2H), 6.89 (tt, J=7.4, 1.7 Hz, 3H), 7.00-7.06 (m, 6H), 7.3-7.4 (br, 6H);

$^{13}$C-NMR (CD$_3$CN): δ 56.0, 56.8, 62.1, 123.2, 126.7, 135.3;

HRMS (FAB) $C_{22}H_{20}BO$ [M-N(CH$_3$)$_4$]$^-$: theoretical value, 311.1607; experimental value, 311.1595.

Synthesis Example 5

Synthesis of tetramethylammonium 3-methoxy-1-propynyltris(2-naphthyl)borate of the following formula:

[Chemical Formula 320]

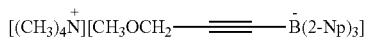

wherein 2-Np is a 2-naphthyl group.

Synthesis and purification were carried out in accordance with Synthesis Example 4, except that triphenylborane pyridine complex was changed to tris(2-naphthyl)borane pyridine complex (2.34 g, 5 mmol). Thus, tetramethylammonium 3-methoxy-1-propynyltris(2-naphthyl)borate (2.43 g, 4.5 mmol) was obtained in a yield of 90%.

The physical and chemical properties thereof were as follows:

$^1$H-NMR (CD$_3$CN): δ 2.72 (s, 12H), 3.47 (s, 3H), 4.27 (s, 2H), 7.27-7.34 (m, 6H), 7.60-7.65 (m, 6H), 7.73-7.78 (m, 6H), 7.87 (s, 3H);

$^{13}$C-NMR (CD$_3$CN): δ 55.8, 56.9, 62.2, 124.1, 125.1, 125.2, 127.9, 132.2, 132.6, 134.3, 135.8;

HRMS (FAB) $C_{34}H_{26}BO$ [M-N(CH$_3$)$_4$]$^-$: theoretical value, 461.2077; experimental value, 461.2073.

Synthesis Example 6

Synthesis of 3-(N,N-dimethylammonio)-1-propynyltriphenylborate of the following formula:

[Chemical Formula 321]

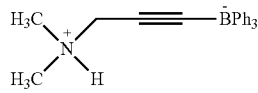

wherein Ph is a phenyl group.

3-(N,N-dimethylammonio)-1-propynyltriphenylborate was synthesized in accordance with Synthesis Example 1, except that 2-ethynylpyridine was changed to 3-(N,N-dimethylamino)-1-propyne.

The physical and chemical properties thereof were as follows:

$^1$H-NMR (CD$_3$CN): δ 2.83 (s, 6H), 3.92 (s, 2H), 6.91-6.97 (m, 3H), 7.05-7.10 (m, 6H), 7.35 (d, J=6.6 Hz, 6H);

$^{13}$C-NMR (CD$_3$CN): δ 42.5, 50.8, 123.6, 126.9, 135.1;

$^{11}$B-NMR (CD$_3$CN): δ −7.0;

HRMS (EI) C$_{23}$H$_{24}$BN (M$^+$): theoretical value, 325.2002; experimental value, 325.2001.

Synthesis Example 7

Synthesis of tris(4-methoxyphenyl){3-(N,N-dimethylammonio)-1-propynyl}borate of the following formula:

[Chemical Formula 322]

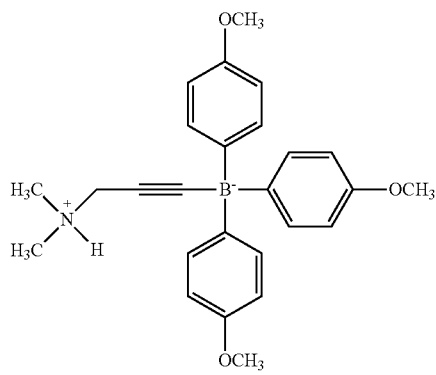

Tris(4-methoxyphenyl){3-(N,N-dimethylammonio)-1-propynyl}borate was synthesized in accordance with Synthesis Example 6, except that triphenylborane pyridine complex was changed to tri(4-methoxyphenyl)borane pyridine complex.

The physical and chemical properties thereof were as follows:

$^1$H-NMR (CD$_3$CN): δ 2.86 (s, 6H), 3.69 (s, 9H), 3.92 (s, 2H), 6.62-6.67 (m, 6H), 7.18 (d, J=8.4 Hz, 6H);

$^{13}$C-NMR (CD$_3$CN): δ 42.6, 50.9, 55.3, 112.5, 125.7, 156.9;

$^{11}$B-NMR (CD$_3$CN): δ−7.8;

HRMS (EI) C$_{26}$H$_{30}$BNO$_3$ (M+): theoretical value, 415.2319; experimental value, 415.2319.

Synthesis Example 8

Synthesis of tris(4-fluorophenyl)-{3-(N,N-dimethylammonio)-1-propynyl}borate of the following formula:

[Chemical Formula 323]

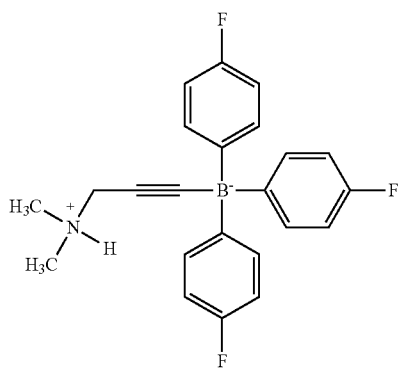

Tris(4-fluorophenyl)-{3-(N,N-dimethylammonio)-1-propynyl}borate was synthesized in accordance with Synthesis Example 6, except that triphenylborane pyridine complex was changed to tris(4-fluorophenyl)borane pyridine complex.

The physical and chemical properties thereof were as follows:

$^1$H-NMR (CD$_3$CN): δ 2.77 (s, 6H), 3.88 (s, 2H), 6.75-6.83 (m, 6H), 7.26 (pseudo t, J=7.5 Hz, 6H);

$^{13}$C-NMR (CD$_3$CN): δ 41.8, 49.5, 113.2 (d, J=18.2 Hz), 136.1 (d, J=6.6 Hz), 161.1 (d, J=235.1 Hz);

$^{11}$B-NMR (CD$_3$CN): δ−7.7;

HRMS (EI) C$_{23}$H$_{21}$BNF$_3$ (M$^+$): theoretical value, 379.1719; experimental value, 379.1715.

Synthesis Example 9

Synthesis of 3-(N,N-dibenzylammonio)-1-propynyltriphenylborate of the following formula:

[Chemical Formula 324]

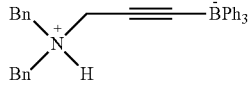

wherein Ph is a phenyl group and Bn is a benzyl group.

3-(N,N-dibenzylammonio)-1-propynyltriphenylborate was synthesized in accordance with Synthesis Example 1, except that 2-ethynylpyridine was changed to 3-(N,N-dibenzylamino)-1-propyne.

The physical and chemical properties thereof were as follows:

$^1$H-NMR (DMSO-d$_6$): δ 3.58 (s, 2H), 4.25-4.45 (m, 4H), 6.88 (t, J=7.2 Hz, 3H), 7.03 (pseudo t, J=7.2 Hz, 6H), 7.36-7.51 (m, 16H);

$^{13}$C-NMR (DMSO-d$_6$): δ 42.3, 55.2, 122.4, 125.7, 128.7, 129.5, 131.1, 134.1;

$^{11}$B-NMR (DMSO-d$_6$): δ −7.4;

HRMS (EI) C$_{35}$H$_{32}$BN (M$^+$): theoretical value, 477.2628; experimental value, 477.2626.

Synthesis Example 10

Synthesis of {2-(N,N-dimethylammonio)phenyl}ethynyltriphenylborate of the following formula:

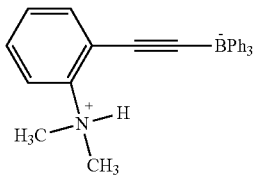

[Chemical Formula 325]

wherein Ph is a phenyl group.

{2-(N,N-dimethylammonio)phenyl}ethynyltriphenylborate was synthesized in accordance with Synthesis Example 1, except that 2-ethynylpyridine was changed to 2-ethynylaniline.

The physical and chemical properties thereof were as follows:

HRMS (EI) $C_{28}H_{26}BN$ (M$^+$): theoretical value, 387.2158; experimental value, 387.2152.

Synthesis Example 11

Synthesis of tris(4-chlorophenyl)pyridinioethynylborate of the following formula:

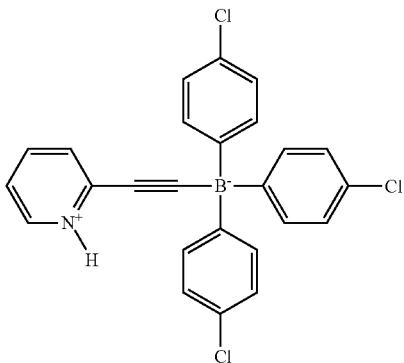

[Chemical Formula 326]

Tris(4-chlorophenyl)pyridinioethynylborate was synthesized in accordance with Synthesis Example 1, except that triphenylborane pyridine complex was changed to tris(4-chlorophenyl)borane pyridine complex.

The physical and chemical properties thereof were as follows:

$^1$H-NMR (CD$_3$CN): δ 7.09-7.14 (m, 6H), 7.30 (d, J=8.1 Hz, 6H), 7.69 (ddd, J=7.7, 6.2, 1.4 Hz, 1H), 7.85 (dd, J=8.6, 1.1 Hz, 1H), 8.31-8.37 (m, 2H);

$^{13}$C-NMR (CD$_3$CN): δ 124.1, 127.1, 129.8, 130.6, 136.5, 141.3, 147.0;

$^{11}$B-NMR (CD$_3$CN): δ−7.1;

HRMS (EI)$C_{25}H_{17}BNCl_3$ (M$^+$): theoretical value, 447.0520; experimental value, 447.0525.

Synthesis Example 12

Synthesis of triphenyl{2-(3-methylpyridinio)ethynyl}borate of the following formula:

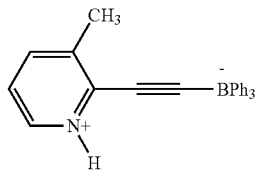

[Chemical Formula 327]

wherein Ph is a phenyl group.

Triphenyl{2-(3-methylpyridinio)ethynyl}borate was synthesized in accordance with Synthesis Example 1, except that 2-ethynylpyridine was changed to 2-ethynyl-3-methylpyridine.

The physical and chemical properties thereof were as follows:

$^1$H-NMR (CD$_3$CN): δ 2.57 (s, 3H), 6.94-7.00 (m, 3H), 7.07-7.13 (m, 6H), 7.38 (d, J=7.2 Hz, 6H), 7.54 (pseudo t, J=6.8 Hz, 1H), 8.14 (d, J=6.0 Hz, 1H), 8.20-8.24 (m, 1H);

$^{13}$C-NMR (CD$_3$CN): δ 19.7, 123.2, 124.0, 127.1, 135.1, 138.3, 140.9, 146.4;

$^{11}$B-NMR (CD$_3$CN): δ−6.3;

HRMS (EI) $C_{26}H_{22}BN$ (M$^+$): theoretical value, 359.1845; experimental value, 359.1839.

Synthesis Example 13

Synthesis of (Z)-(1-(4-methoxyphenyl)-2-(5-methyl-2-thienyl)ethenyl)trimethylsilane of the following formula:

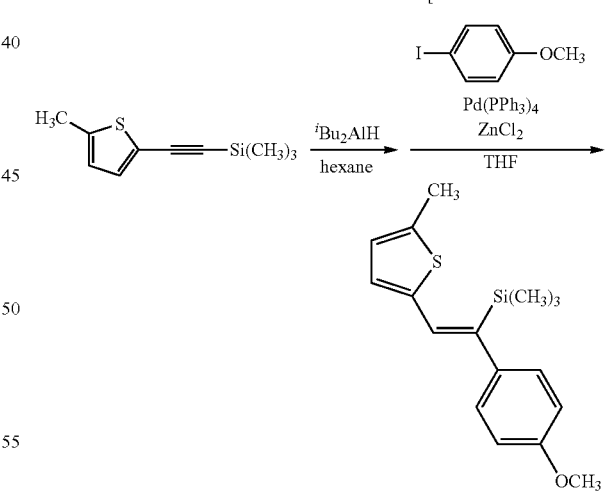

[Chemical Formula 328]

wherein $^i$Bu$_2$AlH is diisobutylaluminum hydride and Pd(PPh$_3$)$_4$ is tetrakis(triphenylphosphine)palladium.

In a nitrogen atmosphere, (5-methyl-2-thienylethynyl)trimethylsilane (1.0 g, 5.2 mmol) was added to a hexane solution (1.0 mol/L) containing diisobutylaluminum (6.0 ml, 6.0 mmol), followed by stirring at room temperature for 24 hours. The mixture was added to a tetrahydrofuran solution, which contained Pd(PPh$_3$)$_4$ (0.3 g, 0.26 mmol), zinc chloride (1.0 g, 7.3 mmol), and p-methoxyiodobenzene (1.7 g, 7.3 mmol), and which had independently been prepared in another container, followed by stirring in an nitrogen atmosphere at 65° C. for 24 hours. The solution obtained was cooled to room temperature, and water was then added thereto, followed by extraction with chloroform. The organic layer was washed with a saturated sodium chloride solution and then dried with magnesium sulfate, followed by filtration. The filtrate was concentrated using a rotary evaporator. The residue was purified by silica gel column chromatography (hexane:ethyl acetate=5:1). Thus, (Z)-(1-(4-methoxyphenyl)-2-(5-methyl-2-thienyl)-ethenyl)trimethylsilane (1.0 g, 3.44 mmol) was obtained in a yield of 66%.

The physical and chemical properties thereof were as follows:

$^1$H-NMR (CDCl$_3$): δ 0.10 (s, 9H), 2.29 (s, 3H), 3.86 (s, 3H), 6.49-6.51 (m, 1H), 6.71 (d, J=3.6 Hz, 1H), 6.90-6.96 (m, 5H).

The following will describe Examples 1 to 18, regarding the novel boron compounds I of the present invention and their production processes (1) to (4), using the starting materials obtained in Synthesis Examples 1 to 13.

Example 1

Synthesis of (E)-2-(2-phenyl-2-diphenylborylethenyl)pyridine by reaction of the following formula:

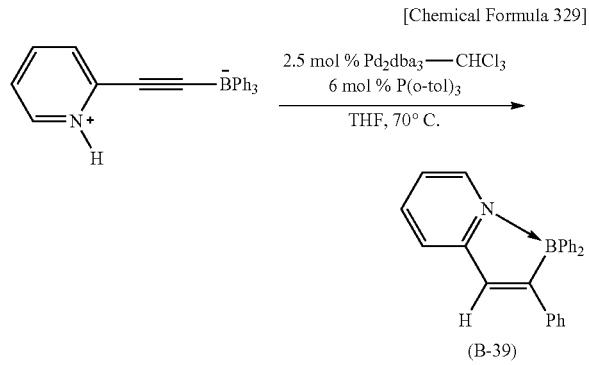

[Chemical Formula 329]

(B-39)

wherein Ph is a phenyl group; dba is a dibenzylideneacetone ligand; o-tol is an o-tolyl group; and an arrow directed from N to B indicates a coordinate bond.

In an argon atmosphere, triphenyl(2-pyridinioethynyl)borate (34.7 mg, 0.10 mmol), tris(dibenzylideneacetone)dipalladium chloroform complex (Pd$_2$dba$_3$·CHCl$_3$) (2.6 mg, 0.0025 mmol), and tri(o-tolyl)phosphine (P(o-tol)$_3$) (1.8 mg, 0.006 mmol) were added to tetrahydrofuran (0.5 mL), followed by stirring at 70° C. for 1 hour. The mixture was concentrated using a rotary evaporator. The residue obtained was purified by silica gel column chromatography (hexane:dichloromethane=1:1). Thus, (E)-2-(2-phenyl-2-diphenylborylethenyl)pyridine (33.8 mg, 0.097 mmol) was obtained in a yield of 97%.

The physical and chemical properties thereof were as follows:

$^1$H-NMR (CDCl$_3$): δ 7.04 (ddd, J=7.2, 6.1, 1.4 Hz, 1H), 7.11-7.31 (m, 14H), 7.48 (pseudo dt, J=8.4, 1.5 Hz, 1H), 7.58-7.61 (m, 2H), 7.79 (ddd, J=8.3, 7.3, 1.6 Hz, 1H), 8.23 (d, J=5.7 Hz, 1H);

$^{13}$C-NMR (CDCl$^3$): δ 119.32, 119.34, 120.9, 125.7, 127.4, 128.0, 128.2, 128.3, 133.6, 138.5, 139.9, 143.0, 160.1;

$^{11}$B-NMR (CDCl$_3$): δ 3.5;

HRMS (EI) C$_{25}$H$_{20}$BN (M$^+$): theoretical value, 345.1689; experimental value, 345.1689.

Example 2

Synthesis of (E)-2-{2-(2-naphthyl)-2-bis(2-naphthyl)borylethenyl}pyridine according to the reaction represented by the following formula:

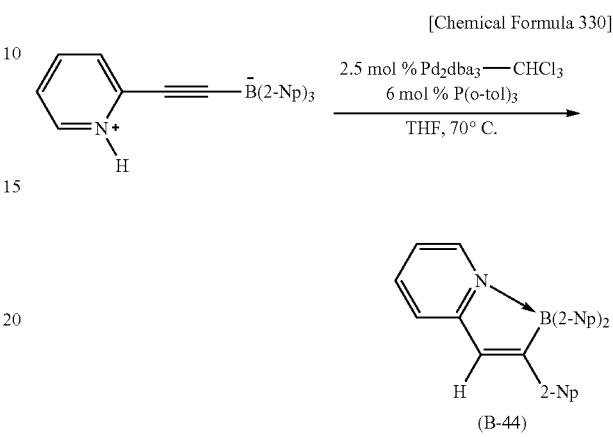

[Chemical Formula 330]

(B-44)

wherein 2-Np is a 2-naphthyl group; dba is a dibenzylideneacetone ligand; o-tol is an o-tolyl group; and an arrow directed from N to B indicates a coordinate bond.

Synthesis and purification were carried out according to Example 1, except that triphenyl(2-pyridinioethynyl)borate was changed to tris(2-naphthyl) (2-pyridinioethynyl)borate (49.5 mg, 0.10 mmol). Thus, (E)-2-{2-(2-naphthyl)-2-bis(2-naphthyl)borylethenyl}pyridine (48.3 mg, 0.097 mmol) was obtained in a yield of 97%.

The physical and chemical properties thereof were as follows:

$^1$H-NMR (CDCl$_3$): δ 7.06 (ddd, J=7.5, 6.0, 1.1 Hz, 1H), 7.28-7.38 (m, 7H), 7.49-7.87 (m, 16H), 8.13 (s, 1H), 8.33 (d, J=5.7 Hz, 1H);

$^{13}$C-NMR (CDCl$_3$): δ 119.4, 119.6, 121.7, 124.7, 125.0, 125.7, 126.0, 126.4, 127.30, 127.34, 127.5, 127.7, 128.6, 128.7, 132.0, 132.4, 132.7, 133.2, 133.3, 133.5, 136.0, 140.1, 143.2, 160.3;

$^{11}$B-NMR (CDCl$_3$): δ 3.9;

HRMS (EI) C$_{37}$H$_{26}$BN (M$^+$): theoretical value, 495.2158; experimental value, 495.2158.

Example 3

Synthesis of (E)-2-(2-phenyl-2-diphenylborylethenyl)quinoline according to the reaction represented by the following formula:

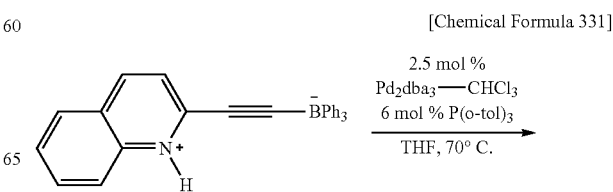

[Chemical Formula 331]

-continued

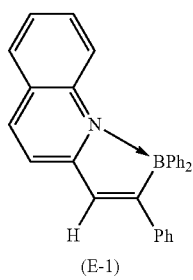

(E-1)

wherein Ph is a phenyl group; dba is a dibenzylideneacetone ligand; o-tol is an o-tolyl group; and an arrow directed from N to B indicates a coordinate bond.

Synthesis and purification were carried out according to Example 1, except that triphenyl(2-pyridinioethynyl)borate was changed to triphenyl(2-quinolinioethynyl)borate (39.6 mg, 0.10 mmol). Thus, (E)-2-(2-phenyl-2-diphenylborylethenyl)quinoline (38.0 mg, 0.96 mmol) was obtained in a yield of 96%.

The physical and chemical properties thereof were as follows:

$^1$H-NMR (CDCl$_3$): δ 7.07-7.16 (m, 7H), 7.18-7.23 (m, 3H), 7.28-7.32 (m, 4H), 7.36-7.45 (m, 4H), 7.70 (d, J=8.7 Hz, 1H), 7.81-7.90 (m, 2H), 8.35 (d, J=8.7 Hz, 1H);

$^{13}$C-NMR (CDCl$_3$): δ 118.2, 122.1, 123.1, 125.3, 125.7, 126.2, 127.3, 128.0, 128.1, 128.3, 128.5, 131.3, 133.2, 139.3, 141.1, 141.5, 161.9;

$^{11}$B-NMR (CDCl$_3$): δ 3.9;

HRMS (EI) C$_{29}$H$_{22}$BN (M$^+$): theoretical value, 395.1845; experimental value, 395.1849.

Example 4

Synthesis of (E)-4-(1-methoxymethyl-2-phenyl-2-diphenylborylethenyl)toluene according to the reaction represented by the following formula:

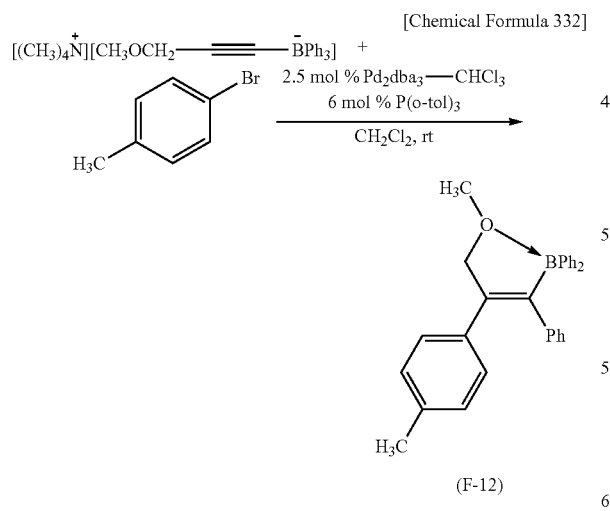

(F-12)

wherein Ph is a phenyl group; dba is a dibenzylideneacetone ligand; o-tol is an o-tolyl group; and an arrow directed from O to B indicates a coordinate bond.

In an argon atmosphere, tetramethylammonium 3-methoxy-1-propynyltriphenylborate (77.0 mg, 0.20 mmol), tris(dibenzylideneacetone)dipalladium chloroform complex (Pd$_2$dba$_3$·CHCl$_3$) (5.2 mg, 0.005 mmol), and tri(o-tolyl)phosphine (P(o-tol)$_3$) (3.6 mg, 0.012 mmol) were added to dichloromethane (0.5 mL), followed by stirring at room temperature for 30 minutes. Then, a dichloromethane solution (0.5 mL) of 4-bromotoluene (34.2 mg, 0.20 mmol) was added to the mixture, followed by further stirring at room temperature for 3 hours. Water was added to the reaction solution, followed by extraction with ethyl acetate. The organic layer was successively washed with water and a saturated sodium chloride solution, followed by concentration using a rotary evaporator. The residue obtained was purified by silica gel column chromatography (hexane:ethyl acetate=20:1). Thus, (E)-4-(1-methoxymethyl-2-phenyl-2-diphenylborylethenyl)toluene (75.2 mg, 0.187 mmol) was obtained in a yield of 93%.

The physical and chemical properties thereof were as follows:

$^1$H-NMR (CDCl$_3$): δ 2.26 (s, 3H), 3.41 (s, 3H), 5.02 (s, 2H), 6.75-6.78 (m, 2H), 6.95-6.98 (m, 7H), 7.21-7.32 (m, 6H), 7.46 (dd, J=8.0, 1.7 Hz, 4H);

$^{13}$C-NMR (CDCl$_3$): δ 21.2, 59.3, 83.4, 125.2, 126.5, 127.2, 127.4, 127.9, 128.4, 128.5, 128.8, 132.3, 134.0, 136.4, 140.2;

HRMS (EI) C$_{29}$H$_{27}$BO (M$^+$): theoretical value, 402.2155; experimental value, 402.2154.

Example 5

Synthesis of (E,E)-1,4-bis(1-methoxymethyl-2-phenyl-2-diphenylborylethenyl)benzene according to the reaction represented by the following formula:

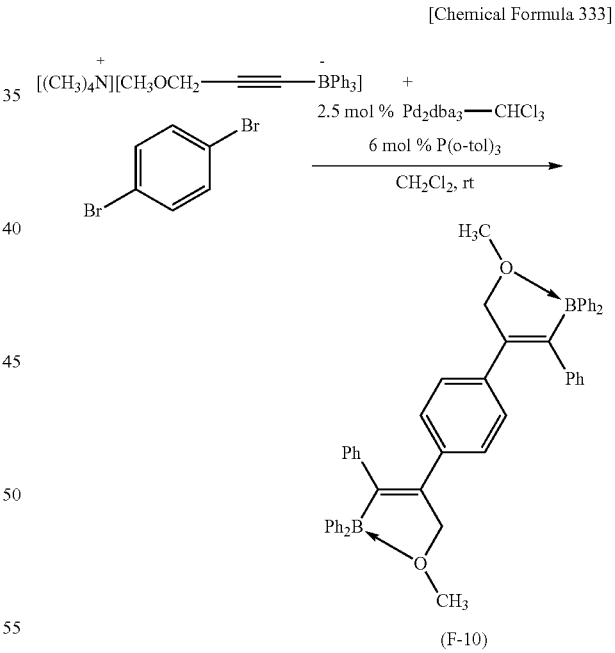

(F-10)

wherein Ph is a phenyl group; dba is a dibenzylideneacetone ligand; o-tol is an o-tolyl group; and an arrow directed from O to B indicates a coordinate bond.

In an argon atmosphere, tetramethylammonium 3-methoxy-1-propynyltriphenylborate (385 mg, 1.0 mmol), tris(dibenzylideneacetone)dipalladium chloroform complex (Pd$_2$dba$_3$·CHCl$_3$) (25.5 mg, 0.025 mmol), and tri(o-tolyl)phosphine (P(o-tol)$_3$) (18.2 mg, 0.06 mmol) were added to dichloromethane (2.5 mL), followed by stirring at room temperature for 30 minutes. Then, a dichloromethane solution (2.5 mL) of 1,4-dibromobenzene (116 mg, 0.50 mmol) was added to the mixture, followed by further stirring at room temperature for 5 hours. Water was added to the reaction solution, followed by extraction with dichloromethane. The organic layer was successively washed with water and a saturated sodium chloride solution, followed by concentration using a rotary evaporator. The residue obtained was purified by silica gel column chromatography (dichloromethane) and recrystallization (dichloromethane-ether). Thus, (E,E)-1,4-bis(1-methoxymethyl-2-phenyl-2-diphenylborylethenyl) benzene (287 mg, 0.41 mmol) was obtained in a yield of 82%.

The physical and chemical properties thereof were as follows:

$^1$H-NMR (CD$_2$Cl$_2$): δ 3.44 (s, 6H), 5.06 (s, 4H), 6.72-6.76 (m, 4H), 6.96-7.01 (m, 10H), 7.20-7.31 (m, 12H), 7.41-7.45 (m, 8H);

$^{13}$C-NMR (CD$_2$Cl$_2$): δ 59.1, 83.0, 125.0, 126.2, 126.8, 127.1, 127.6, 128.0, 128.4, 133.5, 133.7, 140.0;

HRMS (FAB) C$_{50}$H$_{44}$B$_2$O$_2$ (M+): theoretical value, 698.3527; experimental value, 698.3528.

Example 6

Synthesis of (E,E)-1,4-bis{1-methoxymethyl-2-(2-naphthyl)-2-bis(2-naphthyl)borylethenyl}benzene according to the reaction represented by the following formula:

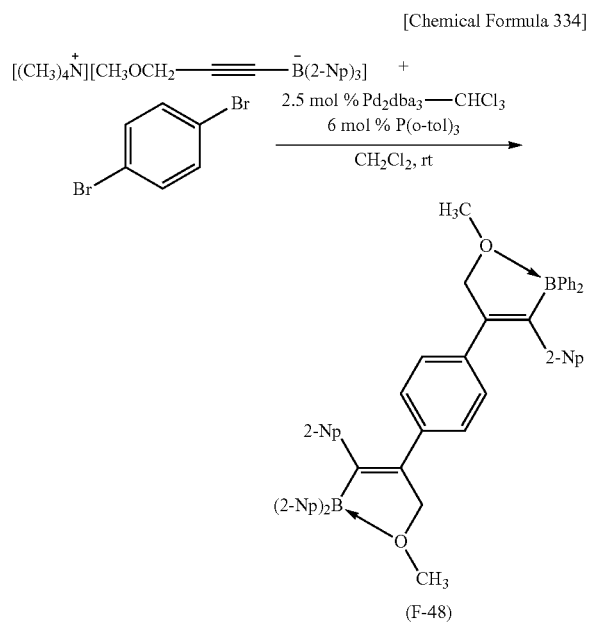

(F-48)

wherein 2-Np is a 2-naphthyl group; dba is a dibenzylideneacetone ligand; o-tol is an o-tolyl group; and an arrow directed from O to B indicates a coordinate bond.

Synthesis and purification were carried out according to Example 5, except that tetramethylammonium 3-methoxy-1-propynyltriphenylborate was changed to tetramethylammonium 3-methoxy-1-propynyltris(2-naphthyl)borate (218 mg, 0.40 mmol). Thus, (E,E)-1,4-bis{1-methoxymethyl-2-(2-naphthyl)-2-bis(2-naphthyl)borylethenyl}benzene (155 mg, 0.16 mmol) was obtained in a yield of 77%.

The physical and chemical properties thereof were as follows:

$^1$H-NMR (CD$_2$Cl$_2$): δ 3.56 (s, 6H), 5.24 (s, 4H), 6.97 (d, J=8.6, 1.7 Hz, 2H), 7.06 (s, 4H), 7.22-7.32 (m, 6H), 7.35-7.50 (m, 12H), 7.60-7.65 (m, 6H), 7.75-7.87 (m, 12H), 8.00 (s, 4H);

HRMS (FAB) C$_{74}$H$_{56}$B$_2$O$_2$ (M+): theoretical value, 996.4539; experimental value, 996.4566.

Example 7

Synthesis of (E,E)-2,6-bis(1-methoxymethyl-2-phenyl-2-diphenylborylethenyl)naphthalene according to the reaction represented by the following formula:

[Chemical Formula 335]

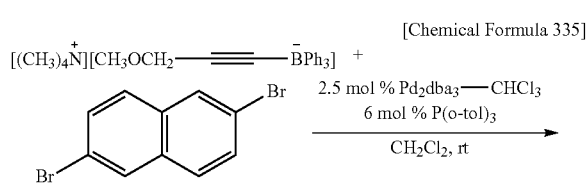

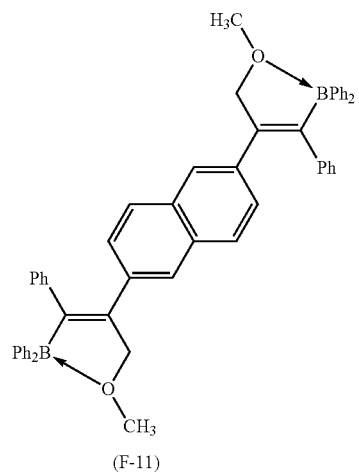

(F-11)

wherein Ph is a phenyl group; dba is a dibenzylideneacetone ligand; o-tol is an o-tolyl group; and an arrow directed from O to B indicates a coordinate bond.

Synthesis and purification were carried out according to Example 5, except that 1,4-dibromobenzene was changed to 2,6-dibromonaphthalene (57.5 mg, 0.20 mmol). Thus, (E,E)-2,6-bis(1-methoxymethyl-2-phenyl-2-diphenylborylethenyl)naphthalene (123.7 mg, 0.17 mmol) was obtained in a yield of 83%.

The physical and chemical properties thereof were as follows:

$^1$H-NMR (CDCl$_3$): δ 3.48 (s, 6H), 5.14 (s, 4H), 6.77-6.80 (m, 4H), 6.96-6.98 (m, 6H), 7.09 (d, J=8.7 Hz, 2H), 7.23-7.33 (m, 12H), 7.41 (d, J=8.7 Hz, 2H), 7.47-7.50 (m, 10H);

$^{13}$C-NMR (CDCl$_3$): δ 59.4, 83.3, 125.5, 125.8, 126.7, 127.2, 127.3, 127.6, 128.4, 128.5, 132.0, 133.1, 134.1, 140.1, 144.6;

HRMS (FAB) C$_{54}$H$_{46}$B$_2$O$_2$ (M+): theoretical value, 748.3684; experimental value, 748.3686.

Example 8

Synthesis of dimethyl {(E)-3-phenyl-3-diphenylboryl-2-propenyl}amine according to the reaction represented by the following formula:

[Chemical Formula 336]

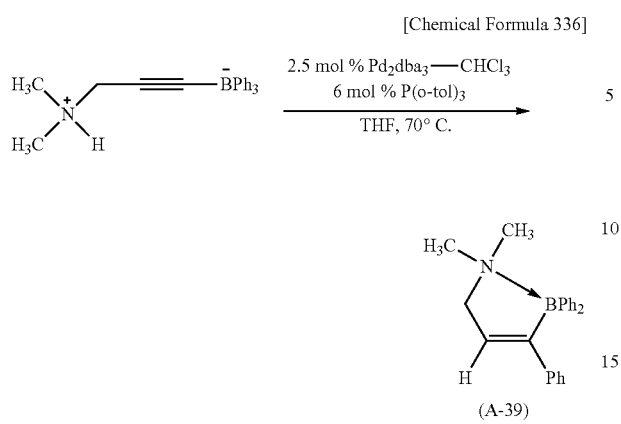

(A-39)

wherein Ph is a phenyl group; dba is a dibenzylideneacetone ligand; o-tol is an o-tolyl group; and an arrow directed from N to B indicates a coordinate bond.

Synthesis and purification were carried out according to Example 1, except, that triphenyl(2-pyridinioethynyl)borate was changed to 3-(N,N-dimethylammonio)-1-propynyltriphenylborate (32.4 mg, 0.10 mmol). Thus, dimethyl{(E)-3-phenyl-3-diphenylboryl-2-propenyl}amine (29.5 mg, 0.091 mmol) was obtained in a yield of 91%.

The physical and chemical properties thereof were as follows:

$^1$H-NMR (CDCl$_3$): δ 2.39 (s, 6H), 3.82 (d, J=2.1 Hz, 2H), 6.18 (t, J=2.0 Hz, 1H), 7.06-7.26 (m, 11H), 7.58 (dd, J=8.1, 1.7 Hz, 4H);

$^{13}$C-NMR (CDCl$_3$): δ 50.1, 70.0, 120.4, 125.8, 125.9, 126.7, 127.2, 127.7, 135.2, 142.2;

$^{11}$B-NMR (CDCl$_3$): δ 6.6;

HRMS (EI) C$_{23}$H$_{24}$BN (M$^+$): theoretical value, 325.2002; experimental value, 325.2003.

Example 9

Synthesis of (E)-3-(4-methoxyphenyl)-3-bis(4-methoxyphenyl)boryl-2-propenyldimethylamine according to the reaction represented by the following formula:

[Chemical Formula 337]

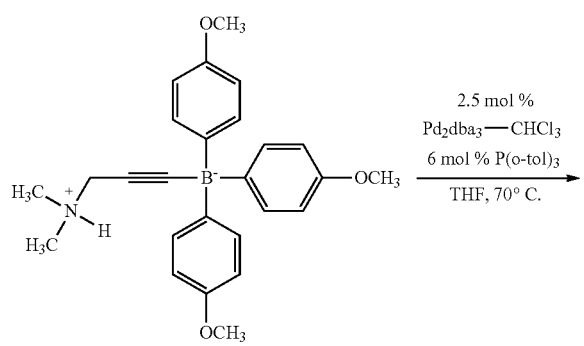

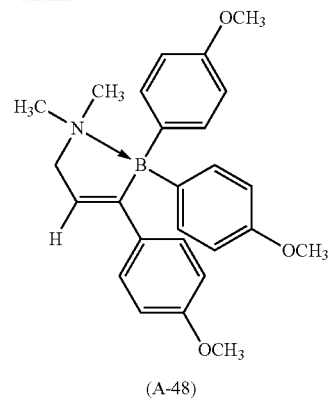

(A-48)

wherein Ph is a phenyl group; dba is a dibenzylideneacetone ligand; o-tol is an o-tolyl group; and an arrow directed from N to B indicates a coordinate bond.

Synthesis and purification were carried out according to Example 1, except that triphenyl(2-pyridinioethynyl)borate was changed to tris(4-methoxyphenyl){3-(N,N-dimethylammonio)-1-propynyl}borate (38.9 mg, 0.10 mmol). Thus, (E)-3-(4-methoxyphenyl)-3-bis(4-methoxyphenyl)boryl-2-propenyldimethylamine (33.2 mg, 0.085 mmol) was obtained in a yield of 85%.

The physical and chemical properties thereof were as follows:

$^1$H-NMR (CDCl$_3$): δ 2.33 (s, 6H), 3.71 (s, 3H), 3.75 (d, J=2.1 Hz, 2H), 3.77 (s, 6H), 6.07 (t, J=2.1 Hz, 1H), 6.67 (d, 8.7 Hz, 2H), 6.80 (d, J=8.7 Hz, 4H), 7.11 (d, J=9.0 Hz, 2H), 7.50 (d, J=8.7 Hz, 4H);

$^{13}$C-NMR (CDCl$_3$): δ 49.9, 54.9, 55.1, 69.7, 112.7, 113.2, 118.2, 127.9, 134.7, 136.3, 157.8;

$^{11}$B-NMR (CDCl$_3$): δ 6.4;

HRMS (EI) C$_{26}$H$_{30}$BNO$_3$ (M+): theoretical value, 415.2319; experimental value, 415.2314.

Example 10

Synthesis of (E)-3-(4-fluorophenyl)-3-bis(4-fluorophenyl)boryl-2-propenyldimethylamine according to the reaction represented by the following formula:

[Chemical Formula 338]

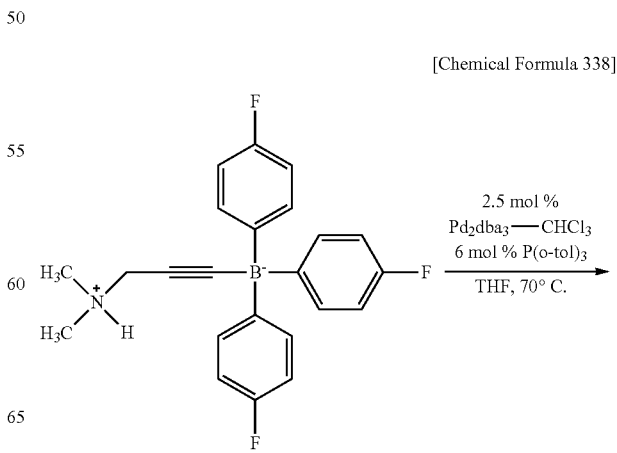

-continued

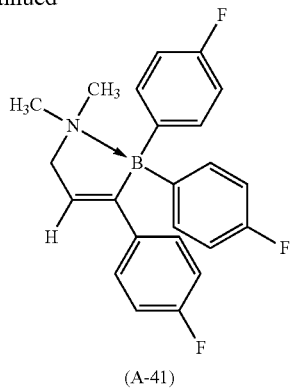

(A-41)

wherein Ph is a phenyl group; dba is a dibenzylideneacetone ligand; o-tol is an o-tolyl group; and an arrow directed from N to B indicates a coordinate bond.

Synthesis and purification were carried out according to Example 1, except that triphenyl(2-pyridinioethynyl)borate was changed to tris(4-fluorophenyl)-{3-(N,N-dimethylammonio)-1-propynyl}borate (42.0 mg, 0.10 mmol). Thus, (E)-3-(4-fluorophenyl)-3-bis(4-fluorophenyl)boryl-2-propenyldimethylamine (38.6 mg, 0.092 mmol) was obtained in a yield of 92%.

The physical and chemical properties thereof were as follows:

$^1$H-NMR (CDCl$_3$): δ 2.35 (s, 6H), 3.79 (d, J=1.8 Hz, 2H), 6.12 (br, 1H), 6.80 (pseudo t, J=8.9 Hz, 2H), 6.93 (pseudo t, J=9.0 Hz, 4H), 7.07 (dd, J=8.7, 5.7 Hz, 2H), 7.48 (dd, J=8.6, 6.3 Hz, 4H);

$^{13}$C-NMR (CDCl$_3$): δ 50.1, 69.9, 114.2 (d, J=18.2 Hz), 114.7 (d, J=21.2 Hz), 120.2 (d, J=1.4 Hz), 128.1 (d, J=8.0 Hz), 136.5 (d, J=6.6 Hz), 137.7 (d, J=2.9 Hz), 161.5 (d, J=242.5 Hz), 161.8 (d, J=243.2 Hz);

$^{11}$B-NMR (CDCl$_3$): δ 5.9;

HRMS (EI) C$_{23}$H$_{21}$BNF$_3$ (M$^+$): theoretical value, 379.1719; experimental value, 379.1722.

Example 11

Synthesis of dibenzyl{(E)-3-phenyl-3-diphenylboryl-2-propenyl}amine by a reaction of the following formula:

[Chemical Formula 339]

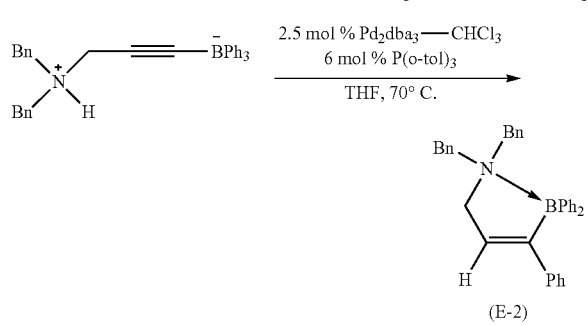

(E-2)

wherein Ph is a phenyl group; Bn is a benzyl group; dba is a dibenzylideneacetone ligand; o-tol is an o-tolyl group; and an arrow directed from N to B indicates a coordinate bond.

Synthesis and purification were carried out as in Example 1, except that triphenyl(2-pyridinioethynyl)borate was changed to 3-(N,N-dibenzylammonio)-1-propynyltriphenylborate (37.1 mg, 0.10 mmol). Thus, dibenzyl{(E)-3-phenyl-3-diphenylboryl-2-propenyl}amine (25.0 mg, 0.067 mmol) was obtained in a yield of 67%.

The physical and chemical properties thereof were as follows:

$^1$H-NMR (CDCl$_3$): δ 3.62 (d, J=2.1 Hz, 2H), 3.8-4.4 (br, 4H), 6.01 (t, J=2.0 Hz, 1H), 6.70-6.73 (m, 4H), 7.06-7.31 (m, 17H), 7.71 (dd, J=8.0, 1.7 Hz, 4H);

$^{13}$C-NMR (CDCl$_3$): δ 59.2, 61.2, 123.0, 125.7, 126.2, 126.6, 127.5, 127.8, 128.1, 128.4, 131.8, 133.4, 135.6, 143.5;

$^{11}$B-NMR (CDCl$_3$): δ 10.3;

HRMS (EI) C$_{35}$H$_{32}$BN (M$^+$): theoretical value, 477.2628; experimental value, 477.2626.

Example 12

Synthesis of dimethyl[2-{(E)-3-phenyl-3-diphenylborylethenyl}phenylamine according to the reaction represented by the following formula:

[Chemical Formula 340]

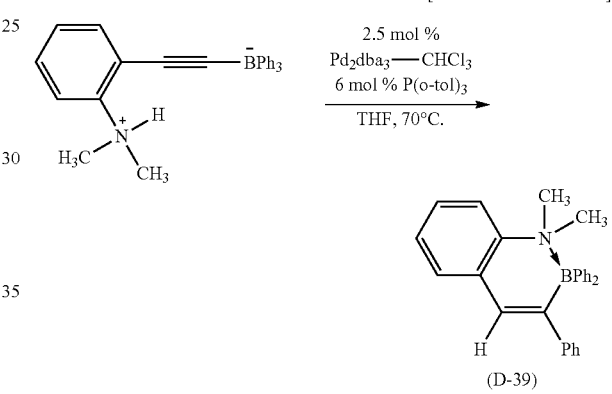

(D-39)

wherein Ph is a phenyl group; dba is a dibenzylideneacetone ligand; o-tol is an o-tolyl group; and an arrow directed from N to B indicates a coordinate bond.

Synthesis and purification were carried out according to Example 1, except that triphenyl(2-pyridinioethynyl)borate was changed to {2-(N,N-dimethyl-ammonio)phenyl}ethynyltriphenylborate (43.4 mg, 0.10 mmol). Thus, dimethyl[2-{(E)-3-phenyl-3-diphenylborylethenyl}phenylamine (43.4 mg, 0.089 mmol) was obtained in a yield of 89%.

The physical and chemical properties thereof were as follows:

$^1$H-NMR (CDCl$_3$): δ 2.83 (s, 6H), 6.95 (s, 1H), 7.02-7.13 (m, 9H), 7.20-7.24 (m, 3H), 7.31-7.34 (m, 3H), 7.55-7.58 (m, 4H);

$^{13}$C-NMR (CDCl$_3$): δ 48.9, 117.9, 125.6, 125.9, 126.6, 126.8, 127.2, 127.4, 128.0, 128.1, 129.7, 133.4, 136.7, 144.7, 147.1;

$^{11}$B-NMR (CDCl$_3$): δ 4.2;

HRMS (EI) C$_{28}$H$_{26}$BN (M$^+$): theoretical value, 386.2158; experimental value, 387.2161.

Example 13

Synthesis of 2-{(E)-2-(4-chlorophenyl)-2-bis(4-chlorophenyl)borylethenyl}pyridine according to the reaction represented by the following formula:

[Chemical Formula 341]

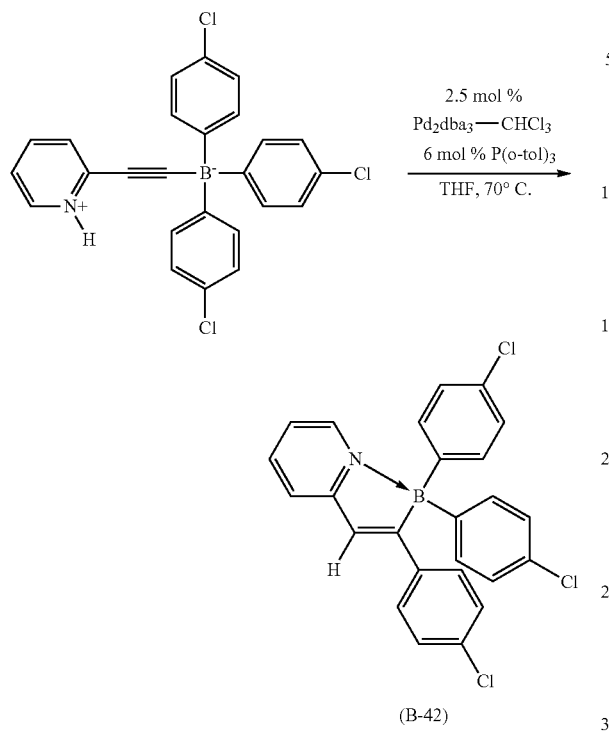

(B-42)

wherein Ph is a phenyl group; dba is a dibenzylideneacetone ligand; o-tol is an o-tolyl group; and an arrow directed from N to B indicates a coordinate bond.

Synthesis and purification were carried out according to Example 1, except that triphenyl(2-pyridinioethynyl)borate was changed to tris(4-chloro-phenyl)pyridinioethynylborate (45.1 mg, 0.10 mmol). Thus, 2-{(E)-2-(4-chlorophenyl)-2-bis(4-chlorophenyl)borylethenyl}pyridine (43.3 mg, 0.096 mmol) was obtained in a yield of 96%.

The physical and chemical properties thereof were as follows:

$^1$H-NMR (CDCl$_3$): δ 7.11-7.22 (m, 12H), 7.45 (d, J=8.4 Hz, 2H), 7.54 (d, J=8.1 Hz, 1H), 7.88 (pseudo dt, J=7.8, 1.2 Hz, 1H), 8.14 (d, J=5.7 Hz, 1H);

$^{13}$C-NMR (CDCl$_3$): δ 119.8, 119.9, 121.5, 127.7, 128.4, 129.3, 132.0, 134.4, 134.8, 136.5, 140.5, 142.7, 159.9;

$^{11}$B-NMR (CDCl$_3$): δ 3.1;

HRMS (EI) C$_{25}$H$_{17}$BNCl$_3$ (M+): theoretical value, 447.0520; experimental value, 447.0517.

Example 14

Synthesis of 3-methyl-2-{(E)-2-diphenylborylethenyl}pyridine according to the reaction represented by the following formula:

[Chemical Formula 342]

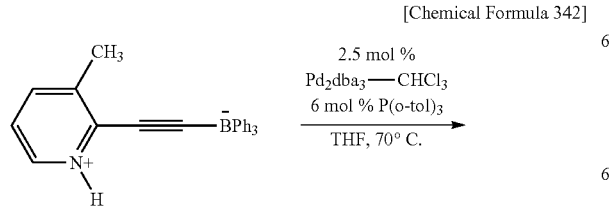

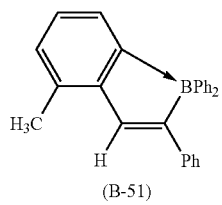

(B-51)

wherein Ph is a phenyl group; dba is a dibenzylideneacetone ligand; o-tol is an o-tolyl group; and an arrow directed from N to B indicates a coordinate bond.

Synthesis and purification were carried out according to Example 1, except that triphenyl(2-pyridinioethynyl)borate was changed to triphenyl{2-(3-methylpyridinio) ethynyl}borate (35.9 mg, 0.10 mmol). Thus, 3-methyl-2-{ (E)-2-diphenylborylethenyl}pyridine (33.0 mg, 0.092 mmol) was obtained in a yield of 92%.

The physical and chemical properties thereof were as follows:

$^1$H-NMR (CDCl$_3$): δ 2.55 (s, 3H), 7.00 (pseudo t, J=6.5 Hz, 1H), 7.10-7.30 (m, 14H), 7.58-7.63 (m, 3H), 8.08 (d, J=5.4 Hz, 1H);

$^{13}$C-NMR (CDCl$_3$): δ 18.1, 119.1, 119.2, 125.6, 127.3, 128.0, 128.19, 128.22, 128.8, 133.6, 138.9, 140.3, 140.5, 159.1;

$^{11}$B-NMR (CDCl$_3$): δ 3.9;

HRMS (EI) C$_{26}$H$_{22}$BN (M$^+$): theoretical value, 359.1845; experimental value, 359.1845.

Example 15

Synthesis of 3-methyl-5-{4,4,5,5-tetramethyl-1,3,2-(2-dioxaborolanyl)}-2-{(E)-2-phenyl-2-diphenylborylethenyl}pyridine according to the reaction represented by the following formula:

[Chemical Formula 343]

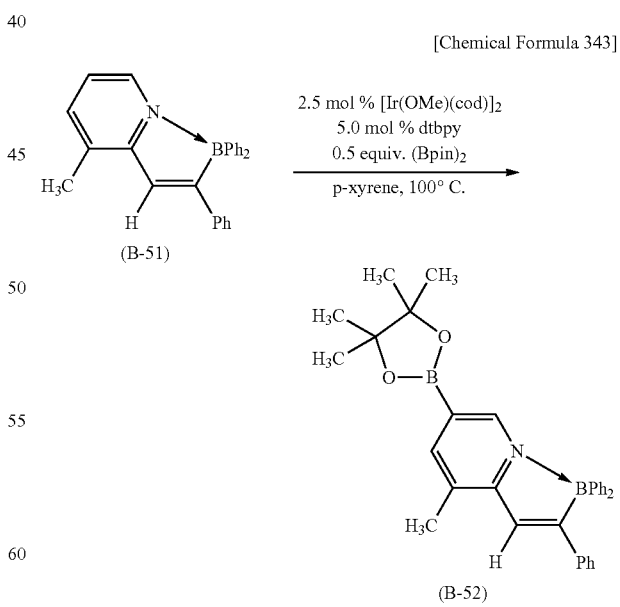

wherein Ph is a phenyl group; Me is a methyl group; cod is 1,5-cyclooctadiene; dtbpy is 4,4'-di(tert-butyl)-2,2'-bipyridine; (Bpin)$_2$ is bis(pinacolato)diboron; and an arrow directed from N to B indicates a coordinate bond.

In an argon atmosphere, 3-methyl-2-{(E)-2-diphenylborylethenyl}pyridine (71.8 mg, 0.20 mmol), bis(pinacolato)diboron ((Bpin)$_2$) (25.38 mg, 0.10 mmol), di-μ-methoxobis(1,5-cyclooctadiene)diiridium ([Ir(OMe)(cod)]$_2$) (3.3 mg, 0.005 mmol), and 4,4'-di(tert-butyl)-2,2'-bipyridine (dtbpy) (2.7 mg, 0.01 mmol) were added to p-xylene (1.0 mL), followed by stirring at 100° C. for 3 hours. The reaction solution was cooled to room temperature, and then applied to a silica gel short column. Further, the reaction solution was purified by gel permeation column chromatography. Thus, 3-methyl-5-{4,4,5,5-tetramethyl-1,3,2-(2-dioxaborolanyl)}-2-{(E)-2-phenyl-2-diphenylborylethenyl}pyridine (79.3 mg, 0.16 mmol) was obtained in a yield of 82%.

The physical and chemical properties thereof were as follows:

$^1$H-NMR (CDCl$_3$): δ 1.27 (s, 12H), 2.53 (s, 3H), 7.11-7.33 (m, 14H), 7.58-7.63 (m, 2H), 7.98 (s, 1H), 8.43 (s, 1H);

$^{13}$C-NMR (CDCl$_3$): δ 17.8, 24.9, 84.4, 119.2, 125.5, 127.3, 127.9, 128.0, 128.3, 128.4, 133.8, 138.7, 146.1, 146.2, 160.8;

$^{11}$B-NMR (CDCl$_3$): δ 3.5, 30.1;

HRMS (EI) C$_{32}$H$_{33}$BNO$_2$ (M$^+$): theoretical value, 485.2697; experimental value, 485.2691.

Example 16

Synthesis of 5-(4-methoxyphenyl)-3-methyl-2-{(E)-2-phenyl-2-diphenylborylethenyl}pyridine according to the reaction represented by the following formula:

[Chemical Formula 344]

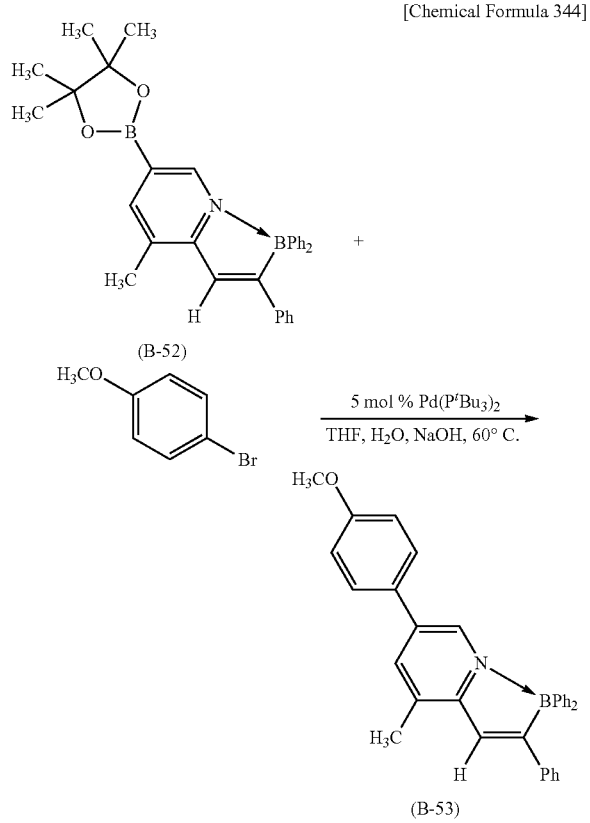

wherein Ph is a phenyl group; $^t$Bu is a tert-butyl group; and an arrow directed from N to B indicates a coordinate bond.

In an argon atmosphere, a tetrahydrofuran solution containing 3-methyl-5-{4,4,5,5-tetramethyl-1,3,2-(2-dioxaborolanyl)}-2-{(E)-2-phenyl-2-diphenylborylethenyl}pyridine (48.5 mg, 0.10 mmol), p-bromoanisole (22.0 mg, 0.12 mmol), bis(tri-tert-butylphosphine)palladium (Pd(P$^t$Bu$_3$)$_2$) (2.6 mg, 0.005 mmol), sodium hydroxide (12.0 mg, 0.30 mmol), and water (5 μL) was stirred at 60° C. for 1 hour. The reaction solution was cooled to room temperature, and water was then added to the reaction solution. The organic layer was separated, and the aqueous layer was extracted with ethyl acetate. The organic layer was collected and successively washed with water and a saturated sodium chloride solution, and then dried by adding magnesium sulfate. The solvent was removed by distillation under reduced pressure, followed by purification by gel permeation column chromatography. As a result, 5-(4-methoxyphenyl)-3-methyl-2-{(E)-2-phenyl-2-diphenylborylethenyl}pyridine (44.0 mg, 0.095 mmol) was obtained in a yield of 95%.

The physical and chemical properties thereof were as follows:

$^1$H-NMR (CDCl$_3$): δ 2.60 (s, 3H), 3.80 (s, 3H), 6.89-6.94 (m, 2H), 7.11-7.26 (m, 10H), 7.31-7.37 (m, 6H), 7.60-7.64 (m, 2H), 7.775-7.784 (m, 1H), 8.26 (d, J=1.8 Hz, 1H);

$^{13}$C-NMR (CDCl$_3$): δ 18.2, 55.4, 114.5, 118.9, 125.6, 127.4, 127.8, 128.0, 128.1, 128.2, 128.3, 128.6, 132.8, 133.7, 138.2, 138.4, 138.9, 157.2, 159.8;

$^{11}$B-NMR (CDCl$_3$): δ 3.9;

HRMS (EI) C$_{33}$H$_{28}$BN (M$^+$): theoretical value, 465.2264; experimental value, 465.2259.

Example 17

Synthesis of (E)-2-(1-methyl-2-phenyl-2-diphenylborylethenyl)pyridine according to the reaction represented by the following formula:

[Chemical Formula 345]

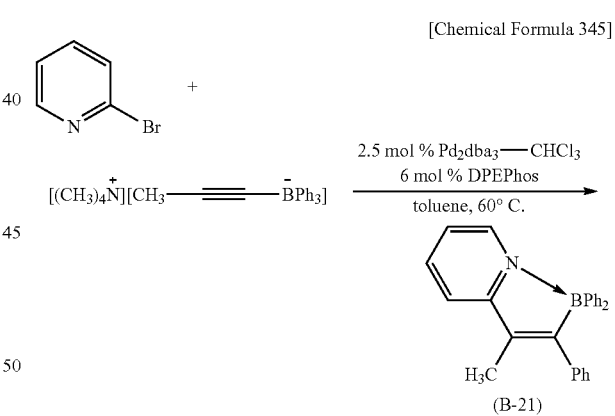

wherein Ph is a phenyl group; dba is a dibenzylideneacetone ligand; DPEphos is bis[2-(diphenylphosphino)phenyl]ether; and an arrow directed from N to B indicates a coordinate bond.

In an argon atmosphere, a toluene solution of tetramethylammonium triphenyl(1-propynyl)borate (35.7 mg, 0.10 mmol), 2-bromopyridine (15.8 mg, 0.1 mmol), tris(dibenzylideneacetone)dipalladium chloroform complex (Pd$_2$dba$_3$.CHCl$_3$), bis[2-(diphenylphosphino)phenyl]ether (2.7 mg, 0.0025 mmol), and bis[2-(diphenylphosphino)phenyl]ether (DPEphos) (3.2 mg, 0.006 mmol) was stirred at 60° C. for 12 hours. The reaction solution was cooled to room temperature, and water was then added thereto. The organic layer was separated, and the aqueous layer was extracted with ethyl acetate. The organic layers were combined and successively washed with water and a saturated, sodium chloride solution, and then dried by adding magnesium sulfate. The solvent was removed by distillation to obtain a crude product. The crude product was purified by silica gel column chromatography (hexane: dichloromethane=1:1). Thus, purified (E)-2-(1-methyl-2-phenyl-2-diphenylborylethenyl)pyridine (27.9 mg, 0.078 mmol) was obtained in a yield of 78%.

The physical and chemical properties thereof were as follows:
$^1$H-NMR (CDCl$_3$): δ 2.18 (s, 3H), 7.03-7.05 (m, 2H), 7.13-7.22 (m, 14H), 7.55 (d, J=8 Hz, 1H), 7.93-7.97 (m, 1H), 8.24 (d, 5.2 Hz, 1H).

Example 18

Synthesis of (E)-(1-(4-methoxyphenyl)-2-(5-methyl-2-thienyl)ethenyl)-bis(2,4,6-trimethylphenyl)borane

[Chemical Formula 346]

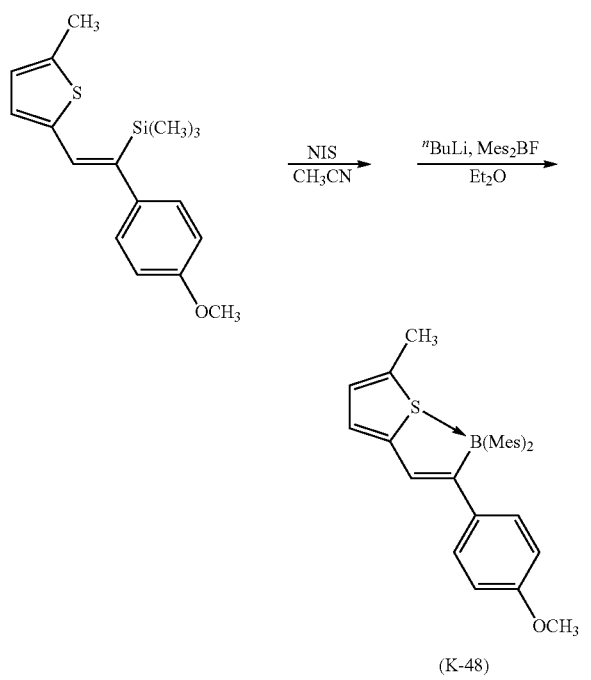

(K-48)

wherein NIS is N-iodosuccinimide; $^n$BuLi is n-butyl lithium; Mes is a 2,4,6-trimethylphenyl group; and an arrow directed from S to B indicates a coordinate bond.

In a nitrogen atmosphere, N-iodosuccinimide (1.1 g, 5.0 mmol) was added to an acetonitrile solution of (Z)-(1-(4-methoxyphenyl)-2-(5-methyl-2-thienyl)-ethenyl)trimethylsilane (0.3 g, 1.0 mmol) at 0° C. The mixture was stirred for 5 hours while maintaining at 0° C., and then applied to an alumina column for concentration. In a nitrogen atmosphere, the residue obtained was dissolved in diethyl ether, and n-butyl lithium (0.9 mL, 1.4 mmol) was added dropwise at −78° C. The mixture was stirred for 1 hour while maintaining at −78° C., and dimesityl boron fluoride (0.37 g, 1.56 mmol) was then added thereto. The mixture was stirred at room temperature for 12 hours, and water was then added thereto, followed by extraction with ethyl acetate. The organic layer was washed with a saturated sodium chloride solution and then dried with magnesium sulfate, followed by filtration. The filtrate was concentrated, and the residue was purified by silica gel column chromatography (dichloromethane) and recrystallization (diethyl ether). Thus, (E)-(1-(4-methoxyphenyl)-2-(5-methyl-2-thienyl)ethenyl)-bis(2,4,6-trimethylphenyl)borane was obtained.

The physical and chemical properties thereof were as follows:
$^1$H-NMR (CDCl$_3$): δ 2.15 (s, 12H), 2.21 (s, 6H), 2.29 (s, 3H), 3.74 (s, 31-1), 6.39-6.40 (m, 1H), 6.63-6.66 (m, 5H), 6.70-6.72 (m, 2H), 7.10-7.26 (m, 3H).

The following will describe Synthesis Examples 14 to 19 of the starting materials to be used in Examples regarding the production process (5) for the novel boron compounds I of the present invention.

Synthesis Example 14

Synthesis of tetramethylammonium triphenylethynylborate of the following formula:

[Chemical Formula 347]

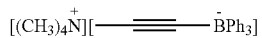

wherein Ph is a phenyl group.

In a nitrogen atmosphere, triphenylborane pyridine complex (15.3 g, 47.5 mmol) was dissolved in tetrahydrofuran (67 mL), and ethynylmagnesium bromide (100 mL, 50.0 mmol) was added dropwise to the solution at room temperature, followed by stirring for 2 hours. The reaction was terminated by adding a small amount of methanol, and the solvent was then removed by distillation using a rotary evaporator. The residue obtained was dissolved in methanol, and tetramethylammonium chloride (5.5 g, 50 mmol) was added to the solution at room temperature, followed by stirring for 1 hour. The white solid formed was collected by filtration and then washed with methanol. Thus, tetramethylammonium triphenylethynylborate (7.0 g, 20.5 mmol) was obtained in a yield of 43%.

The physical and chemical properties thereof were as follows:
$^1$H-NMR (DMSO): δ 2.16 (s, 1H), 3.06 (s, 12H), 6.83 (t, J=6.8 Hz, 6H), 6.95 (t, J=5.6 Hz, 6H), 7.29 (d, J=7.2 Hz, 6H).

Synthesis Example 15

Synthesis of 4-phenyl-2-quinolinyltrifluoromethanesulfonate according to the reaction represented by the following formula:

[Chemical Formula 348]

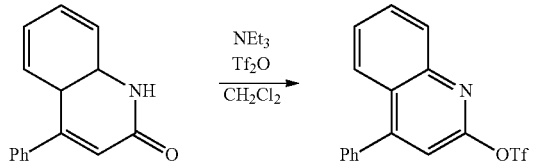

wherein Ph is a phenyl group; Et is an ethyl group; and Tf is a trifluoromethanesulfonyl group.

First, 4-phenyl-2-quinolinone was synthesized according to the process described in Tetrahedron, 2004, 60(13), pp. 2993-3000.

Then, in a nitrogen atmosphere, 4-phenyl-2-quinolinone (16.90 g, 76.4 mmol) was dissolved in methylene chloride (191 mL), and the solution was then cooled to 0° C. To the solution, triethylamine (19.1 mL, 137.5 mmol) and trifluoromethanesulfonic anhydride (14.1 mL, 84.0 mmol) were then successively added, followed by stirring for 1 hour. The reaction was terminated by adding an aqueous sodium hydrogen carbonate solution drop by drop. The reaction solution was extracted with methylene chloride. The organic layer was washed with water and dried with sodium sulfate, followed by filtration. The filtrate was concentrated using a rotary evaporator, and the residue obtained was then purified by silica gel column chromatography (hexane:ethyl acetate=10:1). Thus, 4-phenyl-2-quinolinyltrifluoromethanesulfonate (25.4 g, 71.8 mmol) was obtained in a yield of 94%.

The physical and chemical properties thereof were as follows:

$^1$H-NMR (CDCl$_3$): δ 7.19 (s, 1H), 7.50-7.61 (m, 6H), 7.79-7.83 (m, 1H), 7.95 (d, J=8.2 Hz, 1H), 8.12 (d, J=8.8 Hz, 1H).

Synthesis Example 16

Synthesis of 3',5'-bis(trifluoromethyl)-2-aminobenzophenone according to the reaction represented by the following formula:

[Chemical Formula 349]

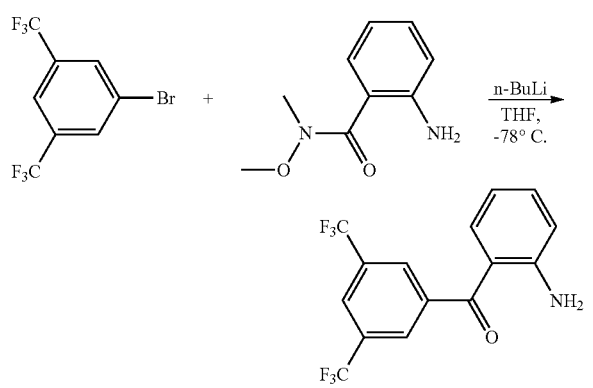

wherein n-Bu is an n-butyl group, and synthesis of 4-{3,5-bis(trifluoromethyl)phenyl}-2-quinolinone according to the reaction represented by the following formula:

[Chemical Formula 350]

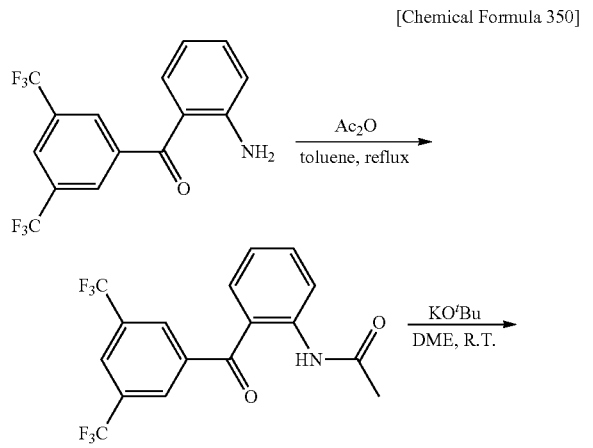

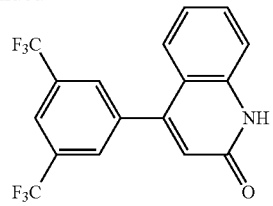

where Ac is an acetyl group; and $^t$Bu is a tert-butyl group; and DME is ethylene glycol dimethyl ether, and synthesis of 4-{3,5-bis(trifluoromethyl)phenyl}-2-quinolinyltrifluoromethanesulfonate according to the reaction represented by the following formula:

[Chemical Formula 351]

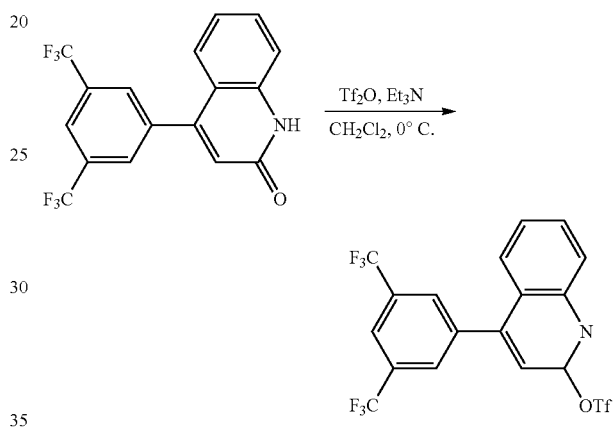

wherein Tf is a trifluoromethanesulfonyl group; and Et is an ethyl group.

First, N-methoxy-N-methyl-anthranilamide was synthesized according to the process described in Org. Chem., 1991, 56(11), pp. 3750-3752.

Then, in a nitrogen atmosphere, N-methoxy-N-methyl-anthranilamide (0.62 g, 3.4 mmol), and 3,5-bis(trifluoromethyl)-1-bromobenzene (1.00 g, 3.4 mmol) were dissolved in tetrahydrofuran (20 mL), followed by stirring at −78° C. To the solution, 1.66 mol/L n-butyl lithium (4.11 mL, 6.8 mmol) was gradually added dropwise, followed by stirring for 30 minutes. The reaction was terminated by adding 1 mol/L hydrochloric acid. The reaction solution was extracted with ethyl acetate. The organic layer was washed with a sodium chloride solution and then dried with magnesium sulfate, followed by filtration. The filtrate was concentrated using a rotary evaporator. The residue was purified by recrystallization (hexane). Thus, 3',5'-bis(trifluoromethyl)-2-aminobenzophenone (1.1 g, 3.3 mmol) was obtained in a yield of 96%.

Further, in a nitrogen atmosphere, 3',5'-bis(trifluoromethyl)-2-aminobenzophenone (1.1 g, 3.3 mmol) was dissolved in toluene (13 mL), and acetic anhydride (0.62 mL, 6.5 mL) was added to the solution at room temperature, followed by stirring while heating and refluxing. The mixture was cooled to room temperature and then concentrated using a rotary evaporator. The residue was dissolved in ethylene glycol dimethyl ether (13 mL), and potassium tert-butoxide (1.5 mL, 13 mmol) was added to the solution at room temperature, followed by stirring for 2 hours. Water was added to the reaction solution, followed by extraction with methylene chloride. The organic layer was dried and then concentrated using a rotary evaporator. The residue was purified by silica gel column chromatography (hexane/ethyl acetate). Thus, 4-{3,5-bis(trifluoromethyl)phenyl}-2-quinolinone (372 mg, 1.04 mmol) was obtained in a yield of 32%.

Further, synthesis and purification were carried out in accordance with Synthesis Example 15, except that 4-phenyl-2-quinolinone was changed to 4-{3,5-bis(trifluoromethyl)phenyl}-2-quinolinone. Thus, 4-{3,5-bis(trifluoromethyl)phenyl}-2-quinolinyltrifluoromethanesulfonate (371 mg, 0.76 mmol) was obtained in a yield of 76%.

The physical and chemical properties thereof were as follows:

$^1$H-NMR (CDCl$_3$): δ 7.23 (s, 1H), 7.65-7.70 (m, 1H), 7.72-7.43 (dd, J=8.4, 1.2 Hz, 1H), 7.87-7.91 (m, 1H), 8.98 (s, 2H), 8.09 (s, 1H), 8.28 (d, J=8.8 Hz, 1H).

Synthesis Example 17

Synthesis of 4-trifluoromethyl-2-quinolinyltrifluoromethanesulfonate according to the reaction represented by the following formula:

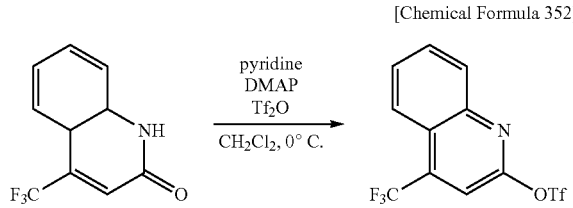

[Chemical Formula 352]

wherein DMAP is N,N-dimethylaminopyridine; and Tf is a trifluoromethanesulfonyl group.

First, 4-trifluoromethyl-2-quinolinone was synthesized according to the process described in Eur. Org. Chem., 2004, 2004(1), pp. 54-63.

Then, in a nitrogen atmosphere, 4-trifluoromethyl-2-quinolinone (3.0 g, 14 mmol) was dissolved in methylene chloride (200 mL), and the solution was cooled to 0° C. To the solution, N,N-dimethylaminopyridine (0.17 g, 1.4 mmol), pyridine (2.0 g, 25 mmol), and trifluoromethanesulfonic anhydride (4.4 g, 16 mmol) were successively added, and the mixture was brought back to room temperature, followed by stirring for 12 hours. The reaction was terminated by adding an aqueous sodium hydrogen carbonate solution to the reaction solution drop by drop, followed by extraction with chloroform. The organic layer was washed with water and then dried with sodium sulfate, followed by filtration. The filtrate was concentrated using a rotary evaporator. Thus, 4-trifluoromethyl-2-quinolinyltrifluoromethanesulfonate (4.48 g, 13.0 mmol) was obtained in a yield of 92%.

The physical and chemical properties thereof were as follows:

$^1$H-NMR (DMSO): δ 7.96-8.00 (m, 1H), 8.07-8.10 (m, 1H), 8.18-8.23 (m, 2H), 8.29 (s, 1H).

Synthesis Example 18

Synthesis of 6-methyl-4-trifluoromethyl-2-quinolinyltrifluoromethanesulfonate according to the reaction represented by the following formula:

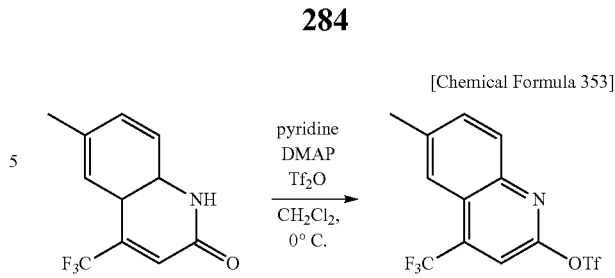

[Chemical Formula 353]

wherein DMAP is N,N-dimethylaminopyridine; and Tf is a trifluoromethanesulfonyl group.

First, 6-methyl-4-trifluoromethyl-2-quinolinone was synthesized according to the process described in Eur. Org. Chem., 2004, 2004(1), pp. 54-63.

Then, synthesis and purification were carried out in accordance with Synthesis Example 16, except that 4-trifluoromethyl-2-quinolinone was changed to 6-methyl-4-trifluoromethyl-2-quinolinone. Thus, 6-methyl-4-trifluoromethyl-2-quinolinyltrifluoromethanesulfonate (7.89 g, 22.0 mmol) was obtained in a yield of 76%.

The physical and chemical properties thereof were as follows:

$^1$H-NMR (CDCl$_3$): δ 2.62 (s, 3H), 7.52 (s, 1H), 7.73-7.75 (m, 1H), 7.93 (s, 1H), 8.03-8.05 (m, 1H).

Synthesis Example 19

Synthesis of 6-phenanthridinone according to the reaction represented by the following formula:

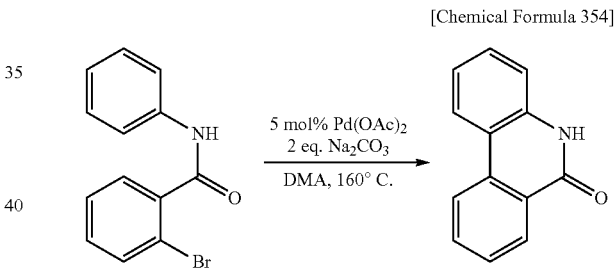

[Chemical Formula 354]

wherein Ac is an acetyl group; and DMA is a dimethylacetamide; and synthesis of 6-phenanthridinyltrifluoromethane sulfonate according to the reaction represented by the following formula:

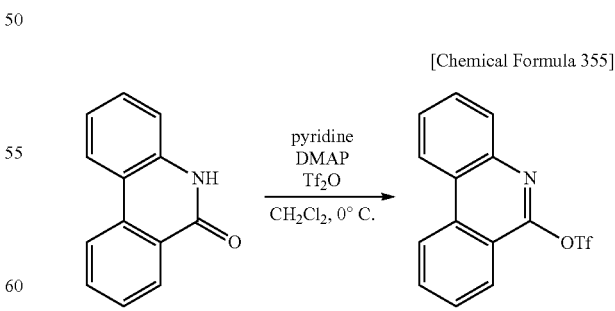

[Chemical Formula 355]

wherein DMAP is N,N-dimethylaminopyridine; and Tf is a trifluoromethanesulfonyl group.

First, 2-bromo-N-phenylbenzamide was synthesized according to the process described in J. Org. Chem., 2006, 71(5), pp. 1802-1808.

Then, in a nitrogen atmosphere, 2-bromo-N-phenylbenzamide (17.3 g, 62.7 mmol), palladium acetate (0.70 g, 3.1 mmol), and sodium carbonate (13.3 g, 125 mmol) were dissolved in dimethylacetamide (300 mL), followed by stirring and heating at 160° C. for 6 hours to cause reaction. The reaction solution was cooled to room temperature and then poured into cooled water, followed by extraction with ethyl acetate. The organic layer was dried with sodium sulfate, followed by filtration. The filtrate was concentrated using a rotary evaporator. The residue was collected by filtration and then successively washed with hexane and water. Thus, 6-phenanthridinone (6.36 g, 32.6 mmol) was obtained in a yield of 52%.

Then, synthesis and purification were carried out in accordance with Synthesis Example 16, except that 4-trifluoromethyl-2-quinolinone was changed to 6-phenanthridinone. Thus, 6-phenanthridinyltrifluoromethane sulfonate (2.95 g, 9.0 mmol) was obtained in a yield of 90%.

The physical and chemical properties thereof were as follows:

$^1$H-NMR (CDCl$_3$): δ 7.72-7.82 (m, 3H), 7.96-8.00 (m, 1H), 8.07-8.10 (m, 1H), 8.23-8.25 (m, 1H), 8.55-8.57 (m, 1H), 8.64-8.66 (m, 1H).

The following will describe Examples 19 to 23, regarding the production process (5) for the novel boron compounds I of the present invention, using the starting materials obtained in Synthesis Examples 14 to 19.

Example 19

Synthesis of (E)-2-(2-phenyl-2-diphenylborylethenyl)-4-phenylquinoline according to the reaction represented by the following formula:

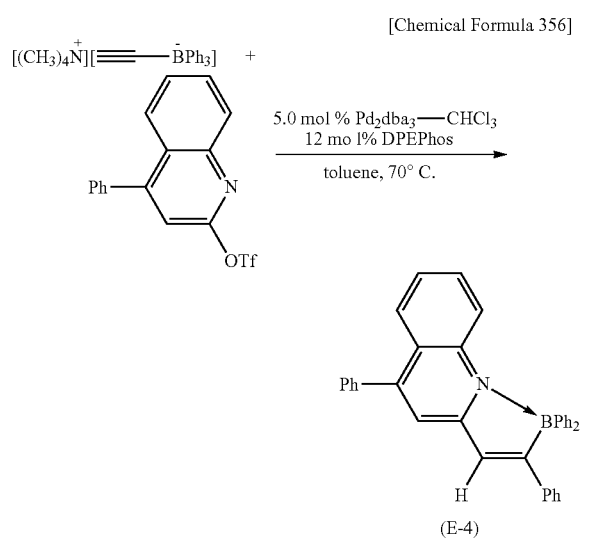

(E-4)

wherein Ph is a phenyl group; Tf is a trifluoromethanesulfonyl group; dba is a dibenzylideneacetone ligand; DPEphos is bis[2-(diphenylphosphino)phenyl]ether; and an arrow directed from N to B indicates a coordinate bond.

In a nitrogen atmosphere, tetramethylammonium triphenylethynylborate (0.5 g, 1.46 mmol), 4-phenyl-2-quinolinyltrifluoromethanesulfonate (0.5 g, 1.61 mmol), tris(dibenzylideneacetone)dipalladium chloroform complex (Pd$_2$dba$_3$.CHCl$_3$) (0.08 g, 0.08 mmol), and bis[2-(diphenylphosphino)phenyl]ether (DPEphos) (0.10 g, 0.19 mmol) were added to toluene (142 mL), followed by stirring at 70° C. The reaction solution was cooled to room temperature and then applied to a silica gel short column (chloroform), followed by concentration using a rotary evaporator. The residue was washed with methanol. Thus, (E)-2-(2-phenyl-2-diphenylborylethenyl)-4-phenylquinoline (446 mg, 0.95 mmol) was obtained in a yield of 65%.

The physical and chemical properties thereof were as follows:

$^1$H-NMR (CDCl$_3$): δ 7.10-7.19 (m, 7H), 7.20-7.23 (m, 3H), 7.32-7.44 (m, 8H), 7.58-7.61 (m, 5H), 7.64 (s, 1H), 7.88 (dd, J=8.2, 1.6, 1.2 Hz, 1H), 7.96 (d, J=8.0 Hz, 1H).

Example 20

Synthesis of (E)-2-(2-phenyl-2-diphenylborylethenyl)-4-{3,5-bis(trifluoromethyl)phenyl}quinoline according to the reaction represented by the following formula:

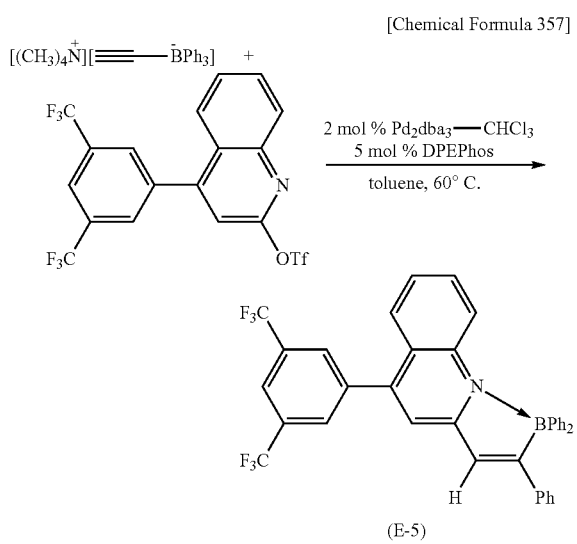

(E-5)

wherein Ph is a phenyl group; Tf is a trifluoromethanesulfonyl group; dba is a dibenzylideneacetone ligand; DPEphos is bis[2-(diphenylphosphino)phenyl]ether; and an arrow directed from N to B indicates a coordinate bond.

In a nitrogen atmosphere, tetramethylammonium triphenylethynylborate (0.31 g, 0.91 mmol), 4-{3,5-bis(trifluoromethyl)phenyl}-2-quinolinyltrifluoromethane-sulfonate (0.37 g, 0.76 mmol), tris(dibenzylideneacetone)dipalladium chloroform complex (Pd$_2$dba$_3$.CHCl$_3$) (0.02 g, 0.2 mmol), and bis[2-(diphenylphosphino)phenyl]ether (DPEphos) (0.02 g, 0.04 mmol) were added to toluene (2.5 mL), followed by stirring at 60° C. The reaction solution was cooled to room temperature and then applied to a silica gel short column (methylene chloride), followed by concentration using a rotary evaporator. The residue was washed with methanol. Thus, (E)-2-(2-phenyl-2-diphenylborylethenyl)-4-{3,5-bis(trifluoromethyl)phenyl}quinoline (302 mg, 0.49 mmol) was obtained in a yield of 65%.

The physical and chemical properties thereof were as follows:

$^1$H-NMR (CDCl$_3$): δ 7.23 (s, 1H), 7.65-7.70 (m, 1H), 7.72-7.43 (dd, J=8.4, 1.2 Hz, 1H), 7.87-7.91 (m, 1H), 8.98 (s, 2H), 8.09 (s, 1H), 8.28 (d, J=8.8 Hz, 1H).

Example 21

Synthesis of (E)-2-(2-phenyl-2-diphenylborylethenyl)-4-trifluoromethylquinoline according to the reaction represented by the following formula:

[Chemical Formula 358]

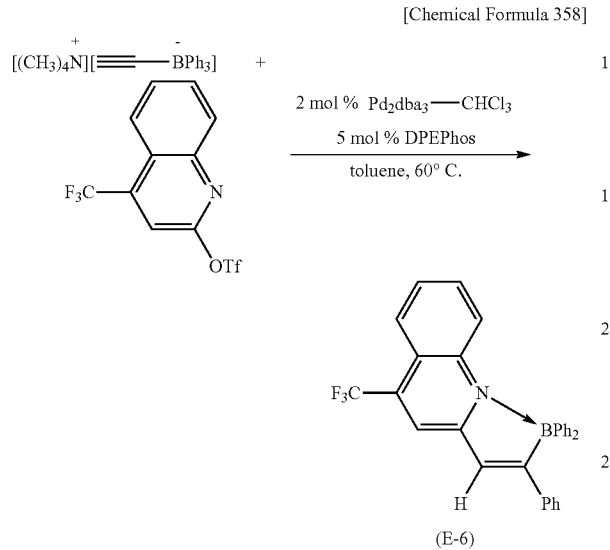

(E-6)

wherein Ph is a phenyl group; Tf is a trifluoromethanesulfonyl group; dba is a dibenzylideneacetone ligand; DPEphos is bis[2-(diphenylphosphino)phenyl]ether; and an arrow directed from N to B indicates a coordinate bond.

In a nitrogen atmosphere, synthesis and purification were carried out in accordance with Example 20, except that 4-{3,5-bis(trifluoromethyl)phenyl}-2-quinolinyltrifluoromethanesulfonate was changed to 4-trifluoromethyl-2-quinolinyltrifluoromethanesulfonate. Thus, (E)-2-(2-phenyl-2-diphenylborylethenyl)-4-trifluoromethylquinoline (4.22 g, 9.1 mmol) was obtained in a yield of 91%.

The physical and chemical properties thereof were as follows:

$^1$H-NMR (CDCl$_3$): δ 7.10-7.17 (m, 6H), 7.20-7.29 (m, 8H), 7.39-7.41 (m, 2H), 7.48-7.54 (m, 2H), 8.00-8.02 (m, 1H), 8.05 (s, 1H), 8.12-8.15 (m, 1H).

Example 22

Synthesis of (E)-2-(2-phenyl-2-diphenylborylethenyl)-4-trifluoromethyl-6-methyl-quinoline according to the reaction represented by the following formula:

[Chemical Formula 359]

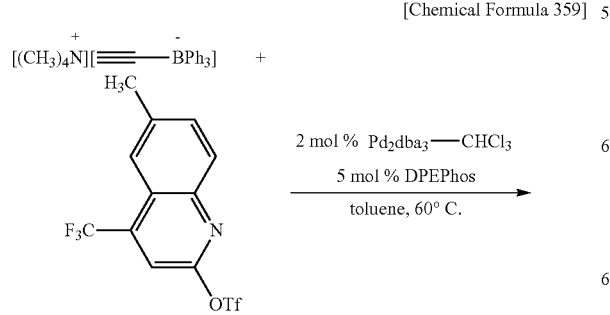

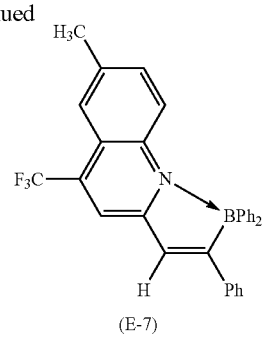

(E-7)

wherein Ph is a phenyl group; Tf is a trifluoromethanesulfonyl group; dba is a dibenzylideneacetone ligand; DPEphos is bis[2-(diphenylphosphino)phenyl]ether; and an arrow directed from N to B indicates a coordinate bond.

Synthesis and purification were carried out in accordance with Example 20, except that 4-{3,5-bis(trifluoromethyl)phenyl}-2-quinolinyltrifluoromethanesulfonate was changed to 6-methyl-4-trifluoromethyl-2-quinolinyltrifluoromethanesulfonate. Thus, (E)-2-(2-phenyl-2-diphenylboryl-ethenyl)-4-trifluoromethyl-6-methyl-quinoline (2.39 g, 5.0 mmol) was obtained in a yield of 90%.

The physical and chemical properties thereof were as follows:

$^1$H-NMR (CDCl$_3$): δ 2.46 (s, 3H), 7.11-7.24 (m, 10H), 7.25-7.29 (m, 4H), 7.30-7.33 (m, 1H), 7.37-7.40 (m, 2H), 7.87-7.90 (m, 2H), 8.01 (s, 1H).

Example 23

Synthesis of (E)-6-(2-phenyl-2-diphenylborylethenyl)phenanthridine according to the reaction represented by the following formula:

[Chemical Formula 360]

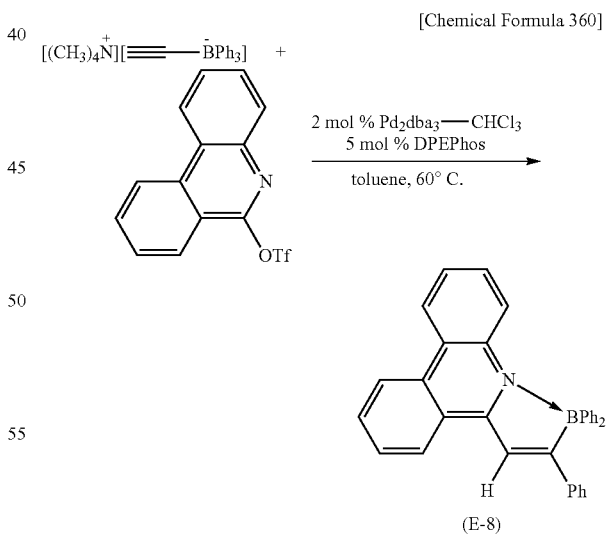

(E-8)

wherein Ph is a phenyl group; Tf is a trifluoromethanesulfonyl group; dba is a dibenzylideneacetone ligand; DPEphos is bis[2-(diphenylphosphino)phenyl]ether; and an arrow directed from N to B indicates a coordinate bond.

Synthesis and purification were carried out in accordance with Example 20, except that 4-{3,5-bis(trifluoromethyl)phenyl}-2-quinolinyltrifluoromethane-sulfonate was changed to 6-phenanthridinyltrifluoromethane sulfonate. Thus, (E)-6-(2-phenyl-2-diphenylborylethenyl)phenanthridine (2.37 g, 5.3 mmol) was obtained in a yield of 82%.

The physical and chemical properties thereof were as follows:

$^1$H-NMR (CDCl$_3$): δ 7.07-7.16 (m, 6H), 7.23-7.26 (m, 3H), 7.34-7.36 (m, 5H), 7.44-7.50 (m, 3H), 7.79 (s, 1H), 7.84-7.87 (m, 1H), 7.96-7.98 (m, 1H), 8.00-8.04 (m, 1H), 8.52-8.54 (m, 1H), 8.64-8.69 (m, 2H).

The following will describe Synthesis Examples 20 to 22 of the starting materials to be used in Examples regarding the novel boron compounds II of the present invention and their production process (6).

Synthesis Example 20

Synthesis of 5-{4,4,5,5-tetramethyl-1,3,2-(2-dioxaborolanyl)}-2-{(E)-2-phenyl-2-diphenylborylethenyl}pyridine as represented by the following formula:

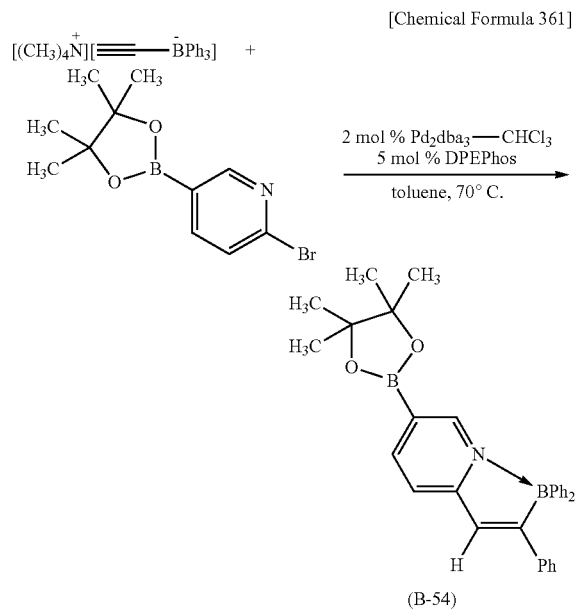

(B-54)

wherein Ph is a phenyl group; dba is a dibenzylideneacetone ligand; DPEphos is bis[2-(diphenylphosphino)phenyl]ether; and an arrow directed from N to B indicates a coordinate bond.

First, 2-bromo-5-{4,4,5,5-tetramethyl-1,3,2-(2-dioxaborolanyl)}pyridine was synthesized according to the process described in J. Org. Chem., 2002, 67(15), pp. 5394-5397.

Then, in a nitrogen atmosphere, 2-bromo-5-{4,4,5,5-tetramethyl-1,3,2-(2-dioxaborolanyl)}pyridine (3.62 g, 12.8 mmol), tetramethylammonium triphenyl-ethynylborate (4.57 g, 13.4 mmol), tris(dibenzylideneacetone)dipalladium chloroform complex (Pd$_2$dba$_3$.CHCl$_3$) (0.25 g, 0.24 mmol), and bis[2-(diphenylphosphino)phenyl]ether (DPEphos) (0.31 g, 0.58 mmol) were added to toluene (64 mL), followed by stirring at 70° C. for 5 hours. The reaction solution was cooled to room temperature and then applied to a silica gel short column (methylene chloride), followed by concentration using a rotary evaporator. The residue was washed with methanol. Thus, 5-{4,4,5,5-tetramethyl-1,3,2-(2-dioxaborolanyl)}-2-{(E)-2-phenyl-2-diphenylborylethenyl}pyridine (4.23 g, 8.98 mmol) was obtained in a yield of 70%.

The physical and chemical properties thereof were as follows:

$^1$H-NMR (CDCl$_3$): δ 1.29 (s, 12H), 7.14-7.25 (m, 10H), 7.31-7.34 (m, 4H), 7.50 (d, J=8 Hz, 1H), 7.59-7.61 (m, 2H), 8.19 (d, J=8 Hz, 1H), 8.57 (s, 1H).

Synthesis Example 21

Synthesis of tetramethylammonium tri(4-methylphenyl) ethynylborate according to the reaction represented by the following formula:

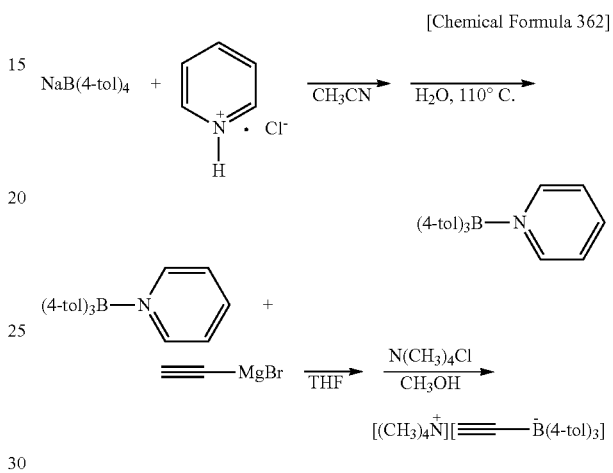

wherein 4-tol is a 4-methylphenyl group.

Sodium tri(4-methylphenyl)borate (6.1 g, 15.4 mmol) was dissolved in acetonitrile, and pyridine hydrochloride (1.86 g, 16.1 mmol) was added thereto, followed by stirring. The solvent was removed using a rotary evaporator. The solid obtained was suspended in water, followed by stirring and heating at 110° C. for 3 hours. The water was removed, followed by drying under a reduced pressure. The residue was purified by recrystallization (methylene chloride-hexane). Thus, tri(4-methylphenyl)borane pyridine complex (3.09 g, 8.51 mmol) was obtained in a yield of 55%.

In a nitrogen atmosphere, tri(4-methylphenyl)borane pyridine complex (3.0 g, 8.3 mmol) was dissolved in tetrahydrofuran (10 mL), and ethynylmagnesium bromide (0.5 M tetrahydrofuran solution, 17.3 mL, 8.7 mmol) was added dropwise thereto at −78° C. The solution was stirred at room temperature for 1 hour, and the reaction was then terminated by adding a small amount of methanol. The solvent was removed using a rotary evaporator. The residue was dissolved in methanol (28 mL), and tetramethylammonium chloride (0.95 g, 8.7 mmol) was added to the solution at room temperature, followed by stirring for 1 hour. The white solid formed was collected by filtration and then washed with methanol. Thus, tetra-methylammonium tri(4-methylphenyl) ethynylborate (2.74 g, 7.15 mmol) was obtained in a yield of 86%.

The physical and chemical properties thereof were as follows:

$^1$H-NMR (CD$_3$CN): δ 2.04 (s, 1H), 2.16 (s, 12H), 2.19 (s, 3H), 6.82 (d, J=7.2 Hz, 6H), 7.20 (d, J=6.4 Hz, 6H).

Synthesis Example 22

Synthesis of 5-{4,4,5,5-tetramethyl-1,3,2-(2-dioxaborolanyl)}-2-{(E)-2-(4-methylphenyl)-2-di(4-methylphenyl) borylethenyl}pyridine according to the reaction represented by the following formula:

[Chemical Formula 363]

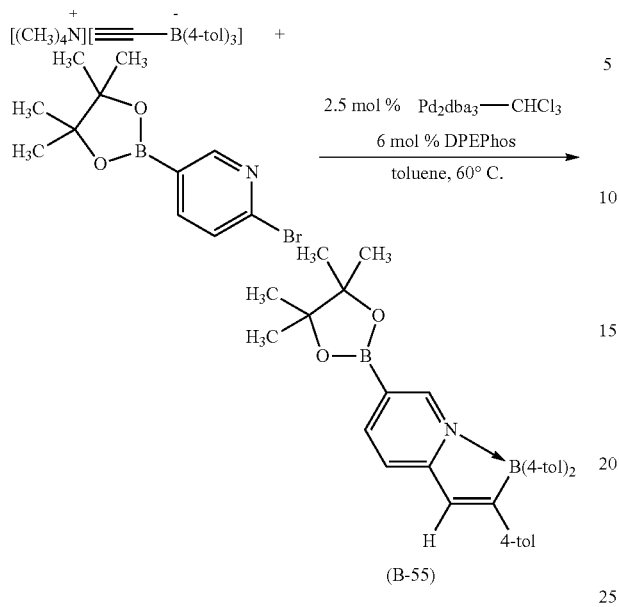

[Chemical Formula 364]

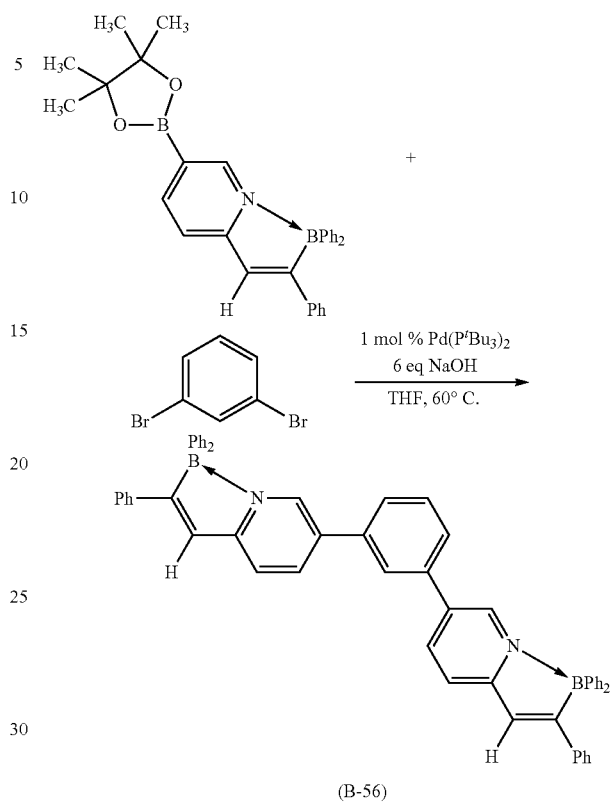

wherein 4-tol is a 4-methylphenyl group; dba is a dibenzylideneacetone ligand; DPEphos is bis[2-(diphenylphosphino)phenyl]ether; and an arrow directed from N to B indicates a coordinate bond.

First, 2-bromo-5-{4,4,5,5-tetramethyl-1,3,2-(2-dioxaborolanyl)}pyridine was synthesized according to the process described in J. Org. Chem., 2002, 67(15), pp. 5394-5397.

Then, in a nitrogen atmosphere, 2-bromo-5-{4,4,5,5-tetramethyl-1,3,2-(2-dioxaborolanyl)}pyridine (2.7 g, 7.0 mmol), tetramethylammonium=tri(4-methyl-phenyl)ethynylborate (1.91 g, 6.7 mmol), tris(dibenzylideneacetone)dipalladium chloroform complex ($Pd_2dba_3 \cdot CHCl_3$) (0.17 g, 0.17 mmol), and bis[2-(diphenyl-phosphino)phenyl]ether (DPEphos) (0.22 g, 0.40 mmol) were added to toluene (34 mL), followed by stirring at 65° C. for 3 hours. The reaction solution was cooled to room temperature, followed by filtration using celite. The filtrate was concentrated using a rotary evaporator, and methanol was then added to the residue. The precipitated solid was collected by filtration and then washed with methanol. Thus, 5-{4,4,5,5-tetramethyl-1,3,2-(2-dioxaborolanyl)}-2-{(E)-2-(4-methylphenyl)-2-di(4-methylphenyl)borylethenyl}pyridine (2.89 g, 5.63 mmol) was obtained in a yield of 84%.

The physical and chemical properties thereof were as follows:

$^1$H-NMR ($CDCl_3$): δ 1.27 (s, 12H), 2.27 (s, 3H), 2.28 (s, 6H), 7.02 (d, J=7.8 Hz, 6H), 7.17 (s, 1H), 7.21 (d, J=7.6 Hz, 4H), 7.44 (dd, J=8.0, 0.8, 0.4 Hz), 7.54 (d, J=8.0 Hz, 2H), 8.13 (dd, J=8.0, 1.2 Hz, 1H), 8.58 (s, 1H).

The following will describe Examples 24 to 30, regarding the novel boron compounds II of the present invention and their production process (6), using the starting materials obtained in Synthesis Examples 20 to 22.

Example 24

Synthesis of 1,3-bis[5-{(E)-2-(2-phenyl-2-diphenyl-borylethenyl)pyridyl}]benzene according to the reaction represented by the following formula:

wherein Ph is a phenyl group; $^t$Bu is a tert-butyl group; and an arrow directed from N to B indicates a coordinate bond.

In a nitrogen atmosphere, 5-{4,4,5,5-tetramethyl-1,3,2-(2-dioxaborolanyl)}-2-{(E)-2-phenyl-2-diphenylborylethenyl}pyridine (2.00 g, 4.24 mmol), 1,3-dibromobenzene (0.50 g, 2.12 mmol), bis(tri-tert-butyl phosphine)palladium ($Pd(P^tBu_3)_2$) (0.02 g, 0.04 mmol), and a 5 mol/L aqueous sodium hydroxide solution (5.1 mL, 25.5 mmol) were added to tetrahydrofuran (42 mL), followed by stirring at 60° C. for 12 hours. The reaction solution was cooled to room temperature, and water was then added thereto, followed by extraction with ethyl acetate. The organic layer was successively washed with 1 N hydrochloric acid, a saturated aqueous sodium hydrogen carbonate solution, and a saturated sodium chloride solution, and then dried with magnesium sulfate, followed by filtration. The solvent was removed using a rotary evaporator. The residue was washed with methanol. Thus, 1,3-bis[5-{(E)-2-(2-phenyl-2-diphenylborylethenyl)pyridyl}]benzene (1.62 g, 2.12 mmol) was obtained in a yield of 100%.

The physical and chemical properties thereof were as follows:

$^1$H-NMR ($CDCl_3$): δ 7.15-7.28 (m, 20H), 7.34-7.36 (m, 8H), 7.40-7.50 (m, 4H), 7.60-7.65 (m, 6H), 8.04 (dd, J=8.4, 2.0 Hz, 2H), 8.45 (d, J=2.0 Hz, 1.6H).

Example 25

Synthesis of 1,4-bis[5-{(E)-2-(2-phenyl-2-diphenyl-borylethenyl)pyridyl}]benzene according to the reaction represented by the following formula:

[Chemical Formula 365]

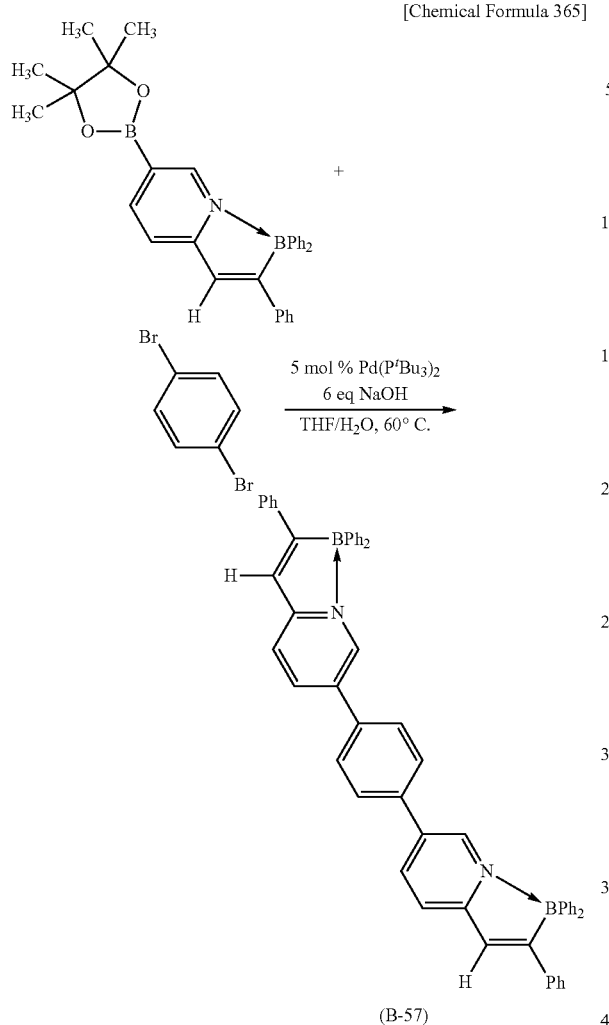

wherein Ph is a phenyl group; $^t$Bu is a tert-butyl group; and an arrow directed from N to B indicates a coordinate bond.

In a nitrogen atmosphere, 5-{4,4,5,5-tetramethyl-1,3,2-(2-dioxaborolanyl)}-2-{(E)-2-phenyl-2-diphenylborylethenyl}pyridine (0.44 g, 0.94 mmol), 1,4-dibromobenzene (0.10 g, 0.42 mmol), bis(tri-tert-butylphosphine)palladium (Pd(P$^t$Bu$_3$)$_2$) (0.024 g, 0.047 mmol), and sodium hydroxide (0.25 g, 6.28 mmol) were added to a mixed solvent of tetrahydrofuran (11 mL) and water (0.1 mL), followed by stirring at 60° C. for 4 hours. The reaction solution was cooled to room temperature and then applied to a silica gel short column (ethyl acetate), followed by concentration using a rotary evaporator. The residue was dissolved in 80 mL of toluene at 80° C. Then, 80 mL of hexane was added to the solution, resulting in the precipitation of yellow solid. The solution was cooled to room temperature, and then the precipitated solid was collected by filtration and washed with methanol. Thus, 1,4-bis[5-{(E)-2-(2-phenyl-2-diphenylborylethenyl)pyridyl}]benzene (0.216 g, 0.28 mmol) was obtained in a yield of 67%.

The physical and chemical properties thereof were as follows:

$^1$H-NMR (CDCl$_3$): δ 7.12-7.25 (m, 20H), 7.33 (dd, J=8.0, 1.6 Hz, 8H), 7.49 (s, 4H), 7.58-7.64 (m, 6H), 8.05 (dd, J=8.4, 2.0 Hz, 2H), 8.46 (d, J=1.6 Hz, 2H).

Example 26

Synthesis of 4,4'-bis[5-{(E)-2-(2-phenyl-2-diphenyl-borylethenyl)pyridyl}]biphenyl according to the reaction represented by the following formula:

[Chemical Formula 366]

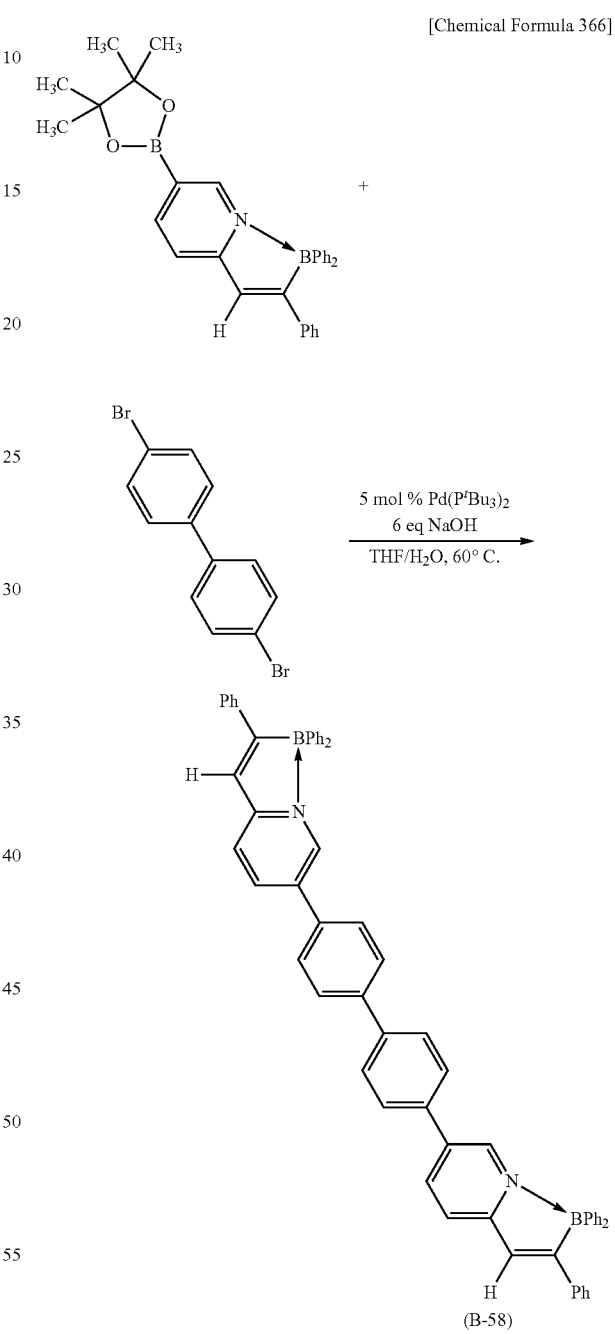

wherein Ph is a phenyl group; $^t$Bu is a tert-butyl group; and an arrow directed from N to B indicates a coordinate bond.

Synthesis and purification were carried out in accordance with Example 25, except that 1,4-dibromobenzene was changed to 4,4'-dibromobiphenyl. Thus, 4,4'-bis[5-{(E)-2-(2-phenyl-2-diphenylborylethenyl)pyridyl}]biphenyl (0.251 g, 0.30 mmol) was obtained in a yield of 65%.

The physical and chemical properties thereof were as follows:

$^1$H-NMR (CDCl$_3$): δ 7.16-7.24 (m, 20H), 7.25-7.36 (dd, J=1.6 Hz, 8H), 7.52 (d, J=8.4 Hz, 4H), 7.58-7.64 (m, 10H), 8.10 (dd, J=8.4, 2.0 Hz, 2H), 8.50 (s, 2H).

Example 27

Synthesis of 1,1-dioctyl-2,7-bis[5-{(E)-2-(2-phenyl-2-diphenylborylethenyl)pyridyl}]fluorene according to the reaction represented by the following formula:

[Chemical Formula 367]

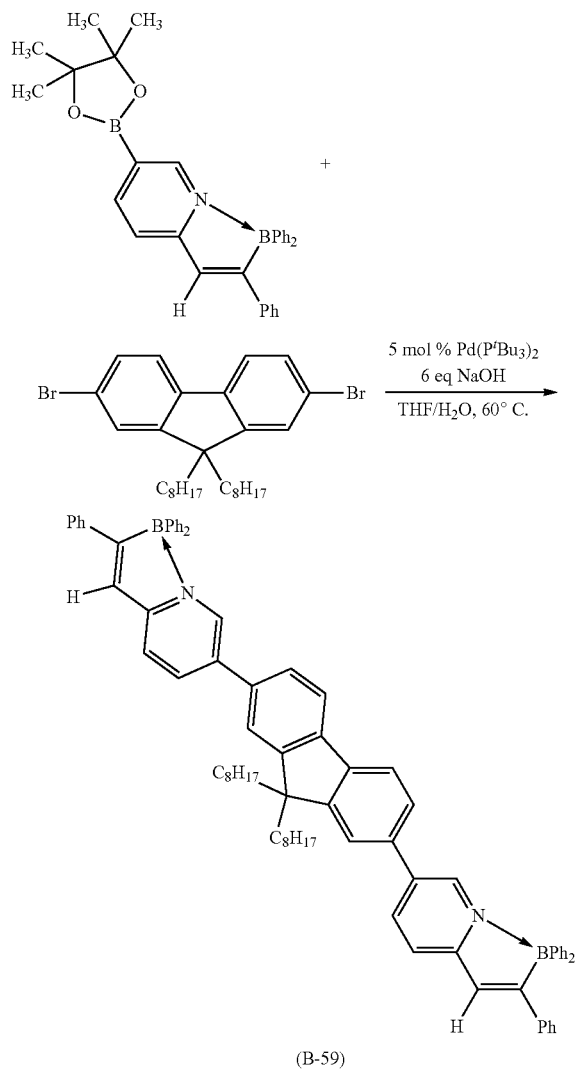

(B-59)

wherein Ph is a phenyl group; $^t$Bu is a tert-butyl group; and an arrow directed from N to B indicates a coordinate bond.

Synthesis and purification were carried out in accordance with Example 25, except that 1,4-dibromobenzene was changed to 1,1-dioctyl-2,7-dibromofluorene. Thus, 1,1-dioctyl-2,7-bis[5-{(E)-2-(2-phenyl-2-diphenyl-borylethenyl)pyridyl}]fluorene (0.190 g, 0.18 mmol) was obtained in a yield of 38%.

The physical and chemical properties thereof were as follows:

$^1$H-NMR (CDCl$_3$): δ 0.62 (m, 4H), 0.79 (t, 7.6 Hz, 6H), 0.96-1.22 (m, 20H), 1.95-2.08 (m, 4H), 7.14-7.30 (m, XH), 7.36-7.34 (m, 12H), 8.12 (dd, J=8.6, 2.2 Hz, 2H), 8.53 (s, 2H).

Example 28

Synthesis of 2,5-bis[5-{(E)-2-(2-phenyl-2-diphenylborylethenyl)pyridyl}]-3-hexylthiophene according to the reaction represented by the following formula:

[Chemical Formula 368]

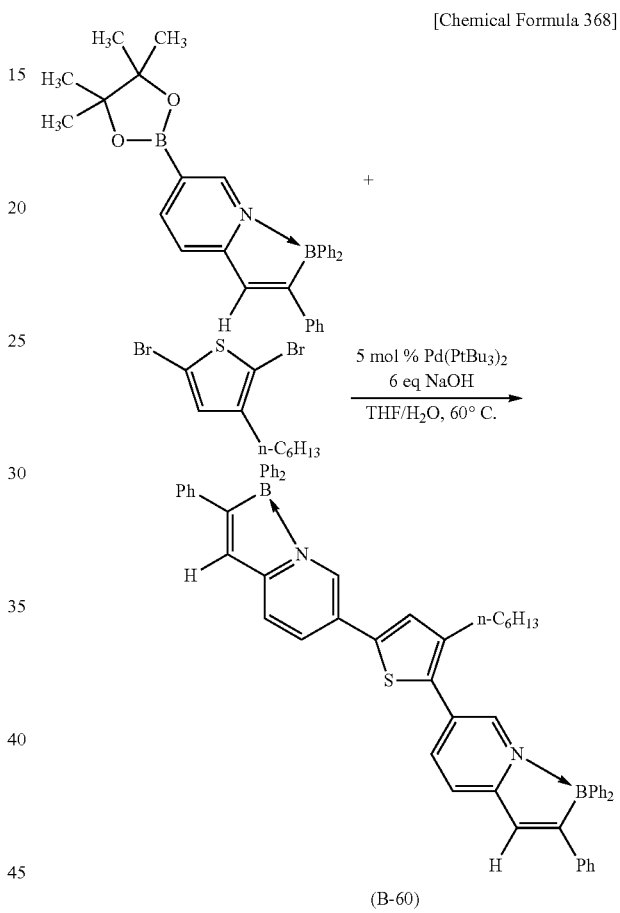

(B-60)

wherein Ph is a phenyl group; $^t$Bu is a tert-butyl group; and an arrow directed from N to B indicates a coordinate bond.

Synthesis and purification were carried out in accordance with Example 25, except that 1,4-dibromobenzene was changed to 2,5-dibromo-3-hexylthiophene. Thus, 2,5-bis[5-{(E)-2-(2-phenyl-2-diphenylborylethenyl)pyridyl}]-3-hexylthiophene (0.385 g, 0.45 mmol) was obtained in a yield of 95%.

The physical and chemical properties thereof were as follows:

$^1$H-NMR (CDCl$_3$): δ 0.86 (t, J=7.6 Hz, 3H), 1.09-1.18 (m, 6H), 1.433 (m, 2H), 2.38 (t, J=8.0 Hz, 2H), 7.04 (s, 1H), 7.12-7.35 (m, 28H), 7.51-7.63 (m, 6H), 7.85 (dd, J=8.4, 2.0 Hz, 1H), 7.89 (dd, J=8.4, 2.0 Hz, 1H), 8.27 (d, J=1.6 Hz, 1H), 8.41 (d, J=2.0 Hz, 1H).

Example 29

Synthesis of 2,6-bis[5-{(E)-2-(2-phenyl-2-diphenylborylethenyl)pyridyl}]-pyridine according to the reaction represented by the following formula:

[Chemical Formula 369]

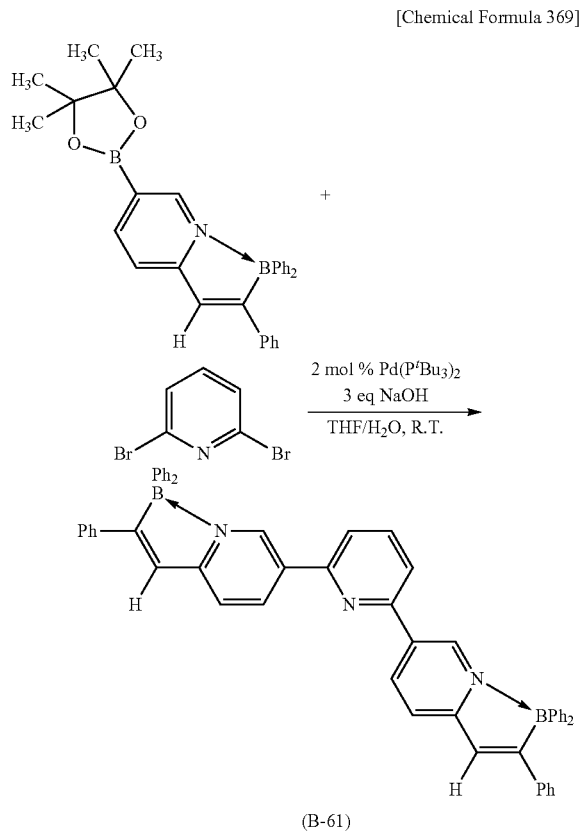

(B-61)

wherein Ph is a phenyl group; $^{t}$Bu is a tert-butyl group; and an arrow directed from N to B indicates a coordinate bond.

In a nitrogen atmosphere, 5-{4,4,5,5-tetramethyl-1,3,2-(2-dioxaborolanyl)}-2-{(E)-2-phenyl-2-diphenylborylethenyl}pyridine (0.50 g, 1.06 mmol), 2,6-dibromopyridine (0.12 g, 0.52 mmol), bis(tri-tert-butylphosphine)palladium (Pd(P$^{t}$Bu$_{3}$)$_{2}$) (0.005 g, 0.01 mmol), and a 5 mol/L aqueous sodium hydroxide solution (0.42 mL, 2.1 mmol) were added to tetrahydrofuran (11 mL), followed by stirring at 60° C. for 12 hours. The reaction solution was cooled to room temperature, and water was then added thereto, followed by extraction with ethyl acetate. The organic layer was successively washed with 1 N hydrochloric acid, a saturated aqueous sodium hydrogen carbonate solution, and a saturated sodium chloride solution, and then dried with magnesium sulfate, followed by filtration. The solvent was removed using a rotary evaporator, and the residue was then washed with methanol. Thus, 5-(4-diphenylaminophenyl)-2-{(E)-2-phenyl-2-diphenylborylethenyl}pyridine (367 mg, 0.48 mmol) was obtained in a yield of 92%.

The physical and chemical properties thereof were as follows:

$^{1}$H-NMR (CDCl$_{3}$): δ 7.11-7.24 (m, 22H), 7.31-7.34 (m, 8H), 7.50 (d, J=8.0 Hz, 2H), 7.60-7.63 (m, 6H), 7.74 (t, J=8.0, 7.6 Hz, 1H), 8.55 (dd, J=8.4, 2.0 Hz, 2H), 8.84 (d, J=2.0 Hz, 2H).

Example 30

Synthesis of 1,3,5-tris[5-{(E)-2-(2-(4-methylphenyl)-2-di(4-methylphenyl)borylethenyl)pyridyl}]benzene according to the reaction represented by the following formula:

[Chemical Formula 370]

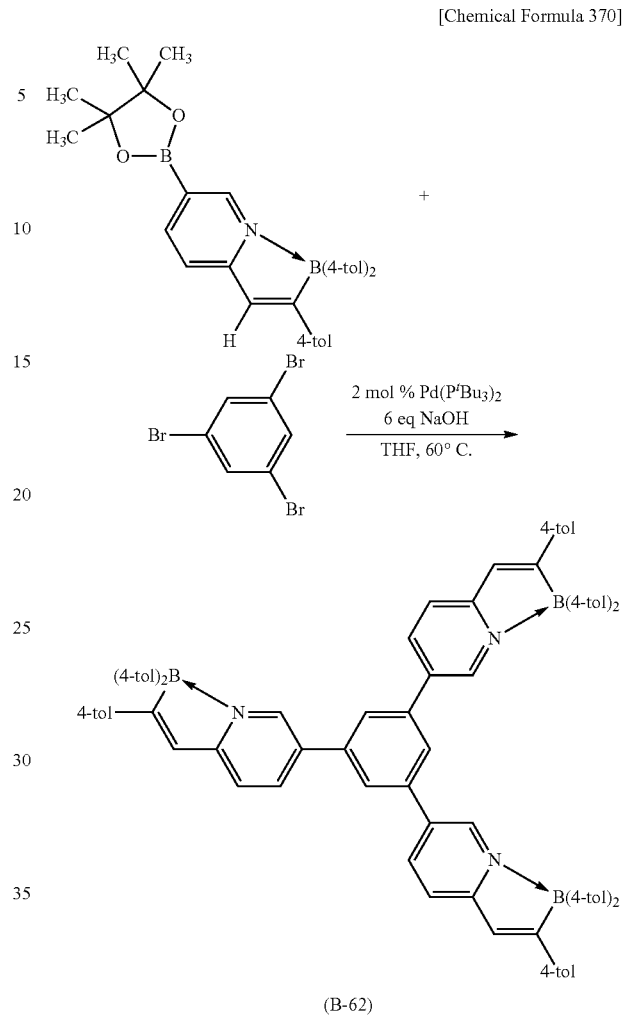

(B-62)

wherein 4-tol is a 4-methylphenyl group; $^{t}$Bu is a tert-butyl group; and an arrow directed from N to B indicates a coordinate bond.

In a nitrogen atmosphere, 5-{4,4,5,5-tetramethyl-1,3,2-(2-dioxaborolanyl)}-2-{(E)-2-(4-methylphenyl)-2-di(4-methylphenyl)borylethenyl}pyridine (0.50 g, 0.97 mmol), 1,3,5-tribromobenzene (0.092 g, 0.29 mmol), bis(tri-tert-butylphosphine)palladium (Pd(P$^{t}$Bu$_{3}$)$_{2}$) (0.010 g, 0.02 mmol), and a 5 mol/L aqueous sodium hydroxide solution (1.2 mL, 5.8 mmol) were added to tetrahydrofuran (10 mL), followed by stirring at 70° C. for 5 hours. The reaction solution was cooled to room temperature, and water was then added thereto, followed by extraction with ethyl acetate. The organic layer was successively washed with 1 N hydrochloric acid, a saturated aqueous sodium hydrogencarbonate solution, and a saturated sodium chloride solution, and then dried with magnesium sulfate, followed by filtration. The solvent was removed using a rotary evaporator, and the residue was then washed with methanol. Thus, 1,3,5-tris[5-{(E)-2-(2-(4-methylphenyl)-2-di(4-methylphenyl)borylethenyl)pyridyl}]benzene (225 mg, 0.18 mmol) was obtained in a yield of 63%.

The physical and chemical properties thereof were as follows:

$^{1}$H-NMR (CDCl$_{3}$): δ 2.27 (s, 6H), 2.29 (s, 3H), 7.00 (d, J=7.6 Hz, 4H), 7.05 (d, J=7.6 Hz, 2H), 7.22-7.24 (m, 5H), 7.39 (s, 1H), 7.55-7.58 (m, 3H), 7.97 (dd, J=8.0, 2.0, 1.6 Hz, 1H), 8.42 (d, J=2.0 Hz, 1H).

The following will describe Synthesis Example 23 of the starting material to be used in Examples regarding the novel boron compounds III of the present invention and their production process (7).

Synthesis Example 23

Synthesis of tetramethylammonium tri(4-biphenylyl)ethynylborate according to the reaction represented by the following formula:

[Chemical Formula 371]

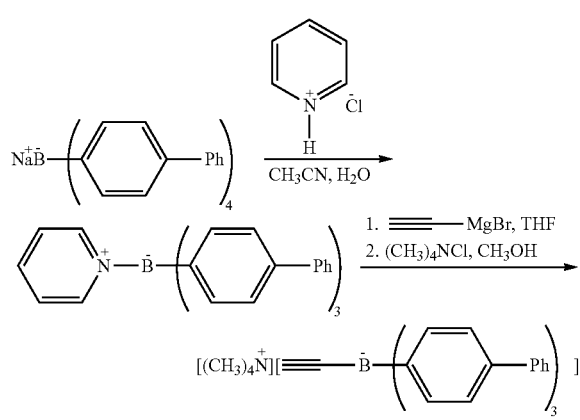

wherein Ph is a phenyl group.

First, sodium tetrakis(4-biphenylyl)borate was obtained according to the process described in Chemistry-A European Journal, 2005, 11, pp. 2071-2080.

Then, sodium tetrakis(4-biphenylyl)borate (9.8 g, 15.1 mmol), acetonitrile (50 mL), and water (100 mL) were placed in an 300-mL recovery flask, and pyridine hydrochloride (2.10 g, 18.2 mmol) was added thereto while stirring at room temperature, followed stirring at room temperature for 1 hour. The acetonitrile was removed using a rotary evaporator. The precipitated solid was recovered by filtration and then dried. The solid obtained was added to toluene, followed by stirring and heating at 100° C. for 4 hours, and then condensation. Chloroform was added to the residue, and insoluble substances were removed by filtration. The filtrate was concentrated again. The residue was purified by recrystallization (hexane-methylene chloride). Thus, tri(4-biphenylyl)borane pyridine complex (5.08 g, 9.24 mmol) was obtained in a yield of 61%.

Further, in a nitrogen atmosphere, tri(4-biphenylyl)borane pyridine complex (5.00 g, 9.1 mmol) was dissolved in tetrahydrofuran (11 mL), and ethynylmagnesium bromide (19 mL, 9.6 mmol) was added dropwise to the solution while cooling at −78° C. After the dropwise addition, the solution was stirred at room temperature for 1 hour. The reaction was terminated by adding a small amount of methanol, and the solvent was then removed using a rotary evaporator. The residue was dissolved in methanol (30 mL), and tetramethylammonium chloride (1.05 g, 9.6 mmol) was added to the solution at room temperature, followed by stirring for 1 hour. The precipitated solid was collected by filtration and then washed with methanol. Thus, tetramethylammonium tri(4-biphenylyl)ethynylborate (4.22 g, 7.41 mmol) was obtained in a yield of 81%.

The physical and chemical properties thereof were as follows:
$^1$H-NMR (CD$_3$CN): δ 3.04 (s, 12H), 7.26 (tt, J=3.6, 3.2, 1.6, 1.2 Hz, 3H), 7.36-7.42 (m, 12H), 7.52 (d, J=7.6 Hz, 6H), 7.60-7.63 (m, 6H).

The following will describe Example 31, regarding the novel boron compounds III of the present invention and their production process (7), using the starting material obtained in Synthesis Example 23.

Example 31

Synthesis of 2,5-bis{(E)-2-(4-biphenylyl)-2-di(4-biphenylyl)borylethenyl}-3,6-dimethylpyrazine according to the reaction represented by the following formula:

[Chemical Formula 372]

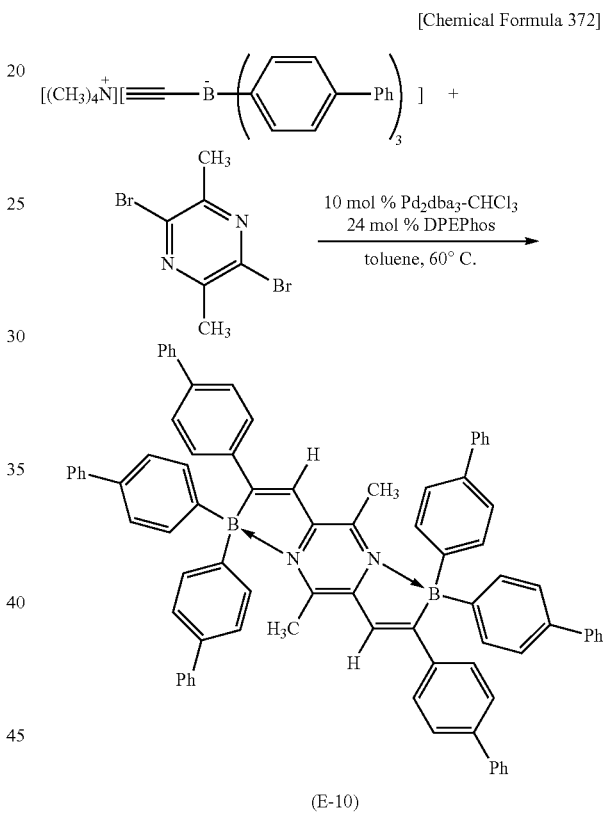

(E-10)

wherein Ph is a phenyl group; dba is a dibenzylideneacetone ligand; DPEphos is bis[2-(diphenylphosphino)phenyl]ether; and an arrow directed from N to B indicates a coordinate bond.

In a nitrogen atmosphere, tetramethylammonium tri(4-biphenylyl)ethynylborate (104 mg, 0.20 mmol), 2,5-dibromo-3,6-dimethylpyrazine (28 mg, 0.1 mmol), tris(dibenzylideneacetone)dipalladium chloroform complex (Pd$_2$dba$_3$.CHCl$_3$) (15.8 mg, 0.01 mmol), and bis[2-(diphenylphosphino)phenyl]ether (DPEphos) (19.3 mg, 0.024 mmol) were added to toluene (1.0 mL), followed by stirring at 60° C. for 12 hours. The mixture was cooled to room temperature, and water was then added thereto, followed by extraction with ethyl acetate. The organic layer was successively washed with water and a saturated sodium chloride solution, and then dried with magnesium sulfate, followed by filtration. The filtrate was concentrated using a rotary evaporator. Methylene chloride was added to the residue obtained, and insoluble substances were removed by filtration, and the filtrate was then concentrated. The residue obtained was purified by silica gel thin-layer chromatography (methylene chloride: hexane=1:1). Thus, 2,5-bis{(E)-2-(4-biphenylyl)-2-di(4-biphenylyl)borylethenyl}-3,6-dimethylpyrazine (39.7 mg, 0.036 mmol) was obtained in a yield of 36%.

The physical and chemical properties thereof were as follows:

$^1$H-NMR (CDCl$_3$): δ 3.68 (s, 6H), 7.17 (s, 1H), 7.28-7.66 (m, 54H).

The following will describe Synthesis Example 24 of the starting material to be used in Examples regarding the novel boron compounds IV of the present invention and their production process (8).

Synthesis Example 24

Synthesis of tetramethylammonium triphenyl(2-pyridinylethynyl)borate according to the reaction represented by the following formula:

[Chemical Formula 373]

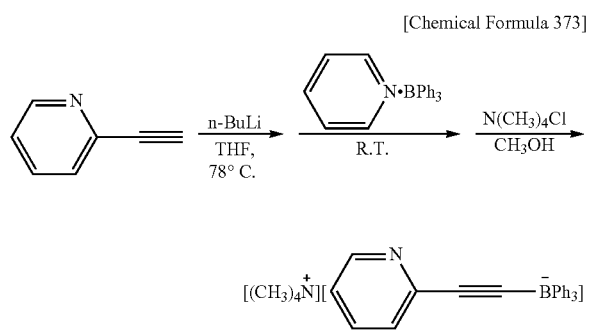

In an argon atmosphere, a tetrahydrofuran (20 ml) solution containing 2-ethynylpyridine (613 mg, 6.0 mmol) dissolved therein was cooled to −78° C., and 1.6 M n-butyl lithium (3.4 ml, 5.5 mmol) was added dropwise thereto, followed by stirring for 30 minutes. Then, triphenylborane pyridine complex was added at once, and the mixture was warmed to room temperature while stirring. The mixture was stirred at room temperature for 1 hour, and the reaction was then terminated by adding several drops of methanol. The solvent was removed using a rotary evaporator. The residue was dissolved in methanol, and tetramethylammonium chloride was added to the solution. The solid formed was collected by filtration and then dried under a reduced pressure. Thus, tetramethylammonium triphenyl(2-pyridinylethynyl)borate (1.86 g, 4.45 mmol) was obtained in a yield of 89%.

The physical and chemical properties thereof were as follows:

$^1$H-NMR (CD$_3$CN): δ 3.0 (s, 12H), 6.89-6.95 (m, 3H), 7.03-7.11 (m, 7H), 7.35 (ddd, J=10.4, 1.2, 0.9 Hz, 1H), 7.41 (d, J=6.9 Hz, 6H), 7.59 (dt, J=1.8, 2.1, 7.5, 7.7 Hz, 1H), 8.44 (ddd, J=4.8, 1.8, 1.2 Hz, 1H).

The following will describe Example 32, regarding the novel boron compounds IV of the present invention and their production process (8), using the starting material obtained in Synthesis Example 24.

Example 32

Synthesis of 2-{(E)-2-phenyl-(1-fluoro-2-diphenylboryl)ethenyl}pyridine by a reaction of the following formula:

[Chemical Formula 374]

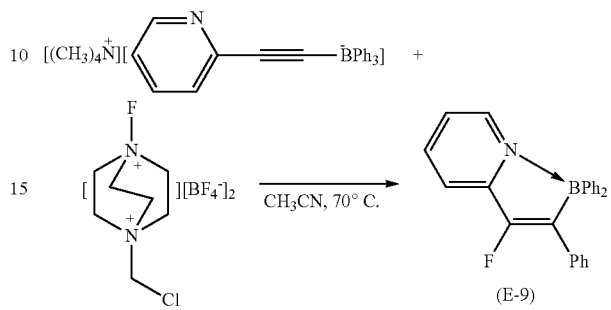

wherein Ph is a phenyl group; and an arrow directed from N to B indicates a coordinate bond.

In a nitrogen atmosphere, tetramethylammonium triphenyl (2-pyridinylethynyl)borate (41.7 mg, 0.1 mmol) was dissolved in acetonitrile (0.5 mL). To the solution, 1-chloromethyl-4-fluoro-1,4-diazonia-bicyclo[2,2,2]octane-bis (tetrafluoroborate) (available from Air Products and Chemicals, Inc., product name: "SelectFluor (registered trade name)") (35.8 mg, 0.1 mmol) was added, followed by stirring at 70° C. for 1 hour. The reaction was terminated by adding water, followed by extraction with ethyl acetate. The organic layer was successively washed with water and a saturated sodium chloride solution, and then dried with magnesium sulfate, followed by filtration. The filtrate was concentrated using a rotary evaporator. The residue obtained was purified by silica gel thin-layer chromatography (methylene chloride: hexane=1:1). Thus, 2-{(E)-2-phenyl-(1-fluoro-2-diphenylboryl)ethenyl}pyridine (7.3 mg, 0.02 mmol) was obtained in a yield of 20%.

The physical and chemical properties thereof were as follows:

$^1$H-NMR (CDCl$_3$): δ 7.02-7.6 (m, 11H), 7.20-7.26 (m, 4H), 7.55 (d, J=7.8 Hz), 7.60 (d, J=8.4, 1.5, 1.2 Hz, 1H), 7.78 (m, 1H), 8.17 (d, J=5.4 Hz, 1H).

<<Evaluation of Characteristics of Novel Boron Compounds>>

The following evaluations were carried out to demonstrate that the novel boron compounds of the present invention are useful as light-emitting materials, electron-transport materials, electron-injection materials, hole-blocking materials, or organic semiconductor materials, depending on their characteristics.

For example, with respect to light-emitting materials, it is particularly preferred that their emission colors typically become any emission colors (wavelengths) of R (red), G (green), and B (blue), for example, when color display is carried out by organic light-emitting diode (OLED) devices or when illumination is carried out by white EL devices. Therefore, in the present invention, the emission color of each light-emitting material was examined by its fluorescence spectrum. In addition, the emission efficiency of each light-emitting material was examined by its fluorescence quantum yields (i.e., the ratio of the number of photons emitted to the number of photons absorbed by the light-emitting material).

Further, in general, functional electronic devices such as organic light-emitting diode (OLED) devices are required not to give: a change in morphology because of an increase in temperature; a formation of pin holes accompanying such a change; a decrease in the emission efficiency of a light-emitting layer; a decrease in the electron mobility at an electron-transport layer; and others, all of which are caused by a change in environmental temperature or a heat generation during operation. Therefore, in the present invention, the possibility of stable operation of each functional electronic device using each light-emitting material was examined by the thermal characteristic (specifically, glass transition temperature) of the light-emitting material. In this connection, a higher glass transition temperature of each light-emitting material is advantageous for the stable operation of each functional electronic device using the light-emitting material.

Further, HOMO-LUMO levels were measured to examine usefulness as electron-transport materials, electron-injection materials, hole-blocking materials, or organic semiconductor materials. Electron transport materials, electron-injection materials, and organic semiconductor materials (particularly, n-type semiconductor materials) are required to have respective low LUMOs (large absolute values of the numerical values indicating the levels). Low LUMO indicates high stability when electrons are accepted. In particular, the electron-injection material used in organic light-emitting diode (OLED) devices may preferably have a LUMO which is represented by the numerical value close to the work function of a material used in the cathode. Typical examples of the material used in the cathode may include Mg (3.7 eV) and Al (4.0 eV) (the numerical value in parentheses is the value of the work function). The hole-blocking materials used in organic light-emitting diode (OLED) devices are required to have respective low HOMOs (large absolute values of the numerical values indicating the levels) so as to prevent the passage of holes leaking from the light-emitting layer. Since tris(8-quinolinol)aluminum complex ($Alq_3$), which is widely used as a light-emitting material or an emission host material, has an HOMO of about 6.0 eV, the hole-blocking material may preferably have a HOMO lower than this value.

First, some of the novel boron compounds produced in Examples were selected, and their fluorescence spectra and fluorescence maximum yields were measured. As a result, boron compound (B-21) had a maximum fluorescence wavelength of 422 nm (blue) and a fluorescence quantum yield of 0.44; boron compound (B-44) had a maximum fluorescence wavelength of 431 nm (blue) and a fluorescence quantum yield of 0.32; and boron compound (E-1) had a maximum fluorescence wavelength of 473 nm (light blue) and a fluorescence quantum yield of 0.26. All of these novel boron compounds emit blue or near-blue fluorescent light (blue is one of the three primary colors of light) at room temperature, and have high fluorescence quantum yields, and further have high emission efficiencies. It can, therefore, be understood that the novel boron compounds of the present invention are useful as, for example, light-emitting materials for the light-emitting layers of organic light-emitting diode (OLED) devices.

Then, some of the novel boron compounds produced in Examples were selected, and their glass transition temperatures were measured. As a result, boron compound (B-21) had a glass transition temperature of 49° C.; boron compound (B-44) had a glass transition temperature of 71° C.; boron compound (E-1) had a glass transition temperature of 76° C.; and boron compound (F-12) had a glass transition temperature of 43° C. All of these novel boron compounds have high glass transition temperatures. It can, therefore, be understood that when the novel boron compounds of the present invention are used as, for example, light-emitting materials for the light-emitting layers of organic light-emitting diode (OLED) devices, the organic light-emitting diode (OLED) devices obtained have the possibility of stably operating against temperature changes.

Then, some of the novel boron compounds produced in Examples were selected, and their HOMO-LUMO levels were measured. As a result, boron compound (B-52) had an HOMO of 6.2 eV, an LUMO of 3.4 eV, and an HOMO-LUMO gap (B.G.) of 2.8 eV; and boron compound (E-1) had an HOMO of 6.8 eV, an LUMO of 4.0 eV, and an HOMO-LUMO gap (B.G.) of 2.8 eV. All of these novel boron compounds have considerably low LUMOs (large absolute values of the numerical values indicating the levels). It can, therefore, be understood that these novel boron compounds are excellent as electron-transport materials, electron-injection materials, and organic semiconductor materials (particularly, n-type semiconductor materials). Further, all of these novel boron compounds have considerably low HOMOs (large absolute values of the numerical values indicating the levels). It can, therefore, be understood that these novel boron compounds are excellent as hole-blocking materials.

<<Fabrication of Functional Electronic Devices>>

As a typical example of the functional electronic devices using the novel boron compounds of the present invention, an organic light-emitting diode (OLED) device was produced.

A substrate (available from ASAHI GLASS CO., LTD.; sheet resistance: 10Ω), which had been obtained by forming an indium tin oxide (ITO) film having a thickness of 150 nm on alkali-free glass, was cut into 29 mm×25 mm pieces, and the ITO portion of each piece was etched to a rectangle having a width of 2 mm. These pieces were cleaned in isopropanol using ultrasonic waves for 10 minutes, followed by boil-washing in isopropanol and then drying. The pieces were subjected to UV-ozone treatment, and then each used as a transparent conductive support substrate.

The transparent conductive support substrate was fixed to a substrate holder of a vacuum deposition apparatus (available from ULVAC, Inc.) which was connected to a glove box having an argon atmosphere. Copper phthalocyanine to be used for forming a hole injection layer was placed in a crucible made of quartz. The pressure was reduced to about $1\times10^{-3}$ Pa, and the copper phthalocyanine was deposited to a film thickness of 10 nm. Then, bis[N-(1-naphthyl)-N-phenyl]benzidine (α-NPD) to be used for forming a hole-transport layer was placed in another crucible. The pressure was reduced to about $1\times10^{-3}$ Pa, and the bis[N-(1-naphthyl)-N-phenyl]benzidine (α-NPD) was deposited to a film thickness of 60 nm. Then, tris(8-quinolinol)aluminum complex ($Alq_3$) to be used for forming a light-emitting layer was placed in another crucible. The pressure was reduced to about $1\times10^{-3}$ Pa. The tris(8-quinolinol)aluminum complex ($Alq_3$) was deposited to a film thickness of 35 nm. Then, either of boron compound (B-52), boron compound (E-1), or tris(8-quinolinol)aluminum complex ($Alq_3$) to be used for forming an electron-transport layer was placed in another crucible, and then deposited to a film thickness of 15 nm after the pressure was reduced to about $1\times10^{-3}$ Pa. Then, magnesium (Mg) and silver (Ag) to be used for forming a counter electrode were placed respectively in separate tungsten boats. The pressure was reduced to about $1\times10^{-3}$ Pa. The magnesium and silver were simultaneously deposited so that the ratio, by volume, of magnesium and silver became about 10:1. At that time, the Mg:Ag electrode was in the shape of a rectangle having a width of 2 mm, and was arranged perpendicular to the ITO electrode. Therefore, the organic light-emitting diode (OLED) device had an emission area of 4 $mm^2$.

A voltage of from 0 to 20 V was applied to the device thus produced, in which the ITO electrode was an anode and the Mg:Ag electrode was a cathode, and light emission luminance was measured. The results are shown in FIG. 1.

As can be seen from FIG. 1, it is understood that the organic light-emitting diode (OLED) devices using the novel boron compounds of the present invention exhibit excellent electrical characteristics. More specifically, when emission start voltage (i.e., voltage at which luminance is larger than 0.1 cd/m$^2$) was compared, it was 13 V in the case where tris(8-quinolinol)aluminum complex (Alq$_3$) was used, whereas it was very lower, at 8 V in the case where boron compound (B-52) was used, and at 7 V in the case where boron compound (E-1) was used. Further, when light emission luminance was compared, both of the latter cases exhibited extremely higher luminance at voltages lower than that in the case where tris(8-quinolinol)aluminum complex (Alq$_3$) was used.

INDUSTRIAL APPLICABILITY

The present invention makes a great contribution in the electronics field because novel boron compounds are useful, depending on their characteristics, as light-emitting materials, electron-transport materials, electron-injection materials, hole-blocking materials, or organic semiconductor materials, and their production processes provide high yield and also are simple and easy, and functional electronic devices using these boron compounds exhibit excellent electric characteristics.

The invention claimed is:

1. A boron compound of the following formula (1):

[Chemical Formula 1]

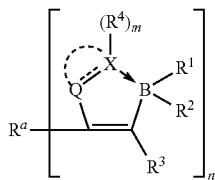

(1)

wherein R$^1$, R$^2$, and R$^3$ are the same or different from each other and are each independently an aryl group or a heterocyclic group, each of which optionally has at least one substituent group, or any two of R$^1$, R$^2$, and R$^3$ are combined with each other to form a ring; R$^4$ is a hydrogen atom or a substituent group; m is an integer of from 0 to 2; when m is 2, plurally occurring R$^4$'s are the same or different from each other; Q is a linking group; X is a nitrogen atom, an oxygen atom, a sulfur atom, a phosphorus atom, or a selenium atom; a dashed half arc indicates that Q and X may be part of a common ring; dashed and solid lines between Q and X indicate a single or double bond; an arrow directed from X to B indicates a coordinate bond; R$^a$ is hydrogen or a monovalent, divalent, trivalent, or tetravalent organic framework; n is an integer of from 1 to 4; and when n is an integer of from 2 to 4, plurally occurring R$^1$'s, R$^2$'s, R$^3$'s, R$^4$'s, m's, Q's, X's, dashed half arcs, and dashed and solid lines between Q and X are the same or different from each other, respectively.

2. The boron compound according to claim 1, which is of the following formula (2):

[Chemical Formula 2]

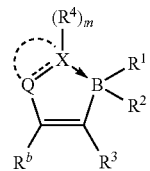

(2)

wherein R$^1$, R$^2$, R$^3$, R$^4$, m, Q, X, a dashed half arc, dashed and solid lines between Q and X, and an arrow directed from X to B have the same meanings in the above formula (1); when m is 2, plurally occurring R$^4$'s are the same or different from each other; and R$^b$ is hydrogen or a monovalent organic framework.

3. The boron compound according to claim 1, which is of the following formula (3):

[Chemical Formula 3]

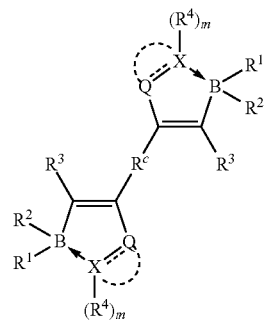

(3)

wherein R$^1$, R$^2$, R$^3$, R$^4$, m, Q, X, a dashed half arc, dashed and solid lines between Q and X, and an arrow directed from X to B have the same meanings in the above formula (1); R$^c$ is a divalent organic framework; and plurally occurring R$^1$'s, R$^2$'s, R$^3$'s, R$^4$'s, m's, Q's, X's, dashed half arcs, and dashed and solid lines between Q and X are the same or different from each other, respectively.

4. The boron compound according to claim 1, wherein Q and X are part of a common ring in the above formula (1), (2), or (3).

5. The boron compound according to claim 4, wherein the above common ring is a pyridine ring, a quinoline ring, or a thiophene ring, X is the nitrogen atom of the pyridine ring or the quinoline ring, or the sulfur atom of the thiophene ring, and m is 0.

6. The boron compound according to claim 1, wherein Q is a methylene group, X is a nitrogen atom, and m is 2 in the above formula (1), (2), or (3).

7. The boron compound according to claim 1, wherein Q is a methylene group, X is an oxygen atom, and m is 1 in the above formula (1), (2), or (3).

8. A process for producing a boron compound of the following formula (1):

[Chemical Formula 4]

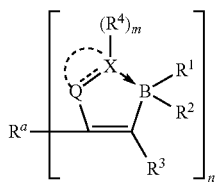
(1)

wherein $R^1$, $R^2$, and $R^3$ are the same or different from each other and are each independently an aryl group or a heterocyclic group, each of which optionally has at least one substituent group, or any two of $R^1$, $R^2$, and $R^3$ are combined with each other to form a ring; $R^4$ is a hydrogen atom or a substituent group; m is an integer of from 0 to 2; when m is 2, plurally occurring $R^4$'s are the same or different from each other; Q is a linking group; X is a nitrogen atom, an oxygen atom, a sulfur atom, a phosphorus atom, or a selenium atom; a dashed half arc indicates that Q and X may be part of a common ring; dashed and solid lines between Q and X indicate a single or double bond; an arrow directed from X to B indicates a coordinate bond; $R^a$ is hydrogen or a monovalent, divalent, trivalent, or tetravalent organic framework; n is an integer of from 1 to 4; and when n is an integer of from 2 to 4, plurally occurring $R^1$'s, $R^2$'s, $R^3$'s, m's, Q's, X's, dashed half arcs, and dashed and solid lines between Q and X are the same or different from each other, respectively, the process comprising reacting a boron compound of the following formula (4):

[Chemical Formula 5]

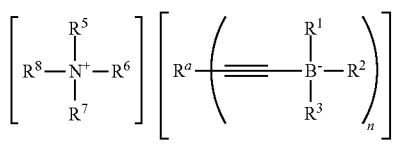
(4)

wherein $R^1$, $R^2$, $R^3$, $R^a$, and n have the same meanings as in the above formula (1); when n is an integer of from 2 to 4, plurally occurring $R^1$'s, $R^2$'s, and $R^3$'s are the same or different from each other, respectively; and $R^5$, $R^6$, $R^7$, and $R^8$ are the same or different from each other and are each independently a hydrogen atom or a substituent group, with a compound of the following formula (5):

[Chemical Formula 6]

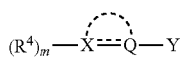
(5)

wherein $R^4$, m, Q, X, a dashed half arc, and dashed and solid lines between Q and X have the same meanings as in the above formula (1); when m is 2, plurally occurring $R^4$'s are the same or different from each other; and Y is a fluorine atom, a chlorine atom, a bromine atom, or an iodine atom, in the presence of a catalyst containing at least one metal element selected from the group consisting of palladium, platinum, and nickel.

9. The production process according to claim 8, wherein Q and X are part of a common ring in the above formulas (1) and (5).

10. The production process according to claim 9, wherein the above common ring is a pyridine ring, a quinoline ring, or a thiophene ring, X is the nitrogen atom of the pyridine ring or the quinoline ring, or the sulfur atom of the thiophene ring, and m is 0.

11. The production process according to claim 8, wherein Q is a methylene group, X is a nitrogen atom, and m is 2 in the above formulas (1) and (5).

12. The production process according to claim 8, wherein Q is a methylene group, X is an oxygen atom, and m is 1 in the above formulas (1) and (5).

13. A functional electronic device comprising a boron compound according to claim 1 to be used as a light-emitting material, an electron-transport material, an electron-injection material, a hole-blocking material, or an organic semiconductor material.

14. A process for producing a boron compound of the following formula (1):

[Chemical Formula 17]

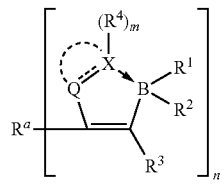
(1)

wherein $R^1$, $R^2$, and $R^3$ are the same or different from each other and are each independently an aryl group or a heterocyclic group, each of which optionally has at least one substituent group, or any two of $R^1$, $R^2$, and $R^3$ are combined with each other to form a ring; $R^4$ is a hydrogen atom or a substituent group; m is an integer of from 0 to 2; when m is 2, plurally occurring $R^4$'s are the same or different from each other; Q is a linking group; X is a nitrogen atom, an oxygen atom, a sulfur atom, a phosphorus atom, or a selenium atom; a dashed half arc indicates that Q and X may be part of a common ring; dashed and solid lines between Q and X indicate a single or double bond; an arrow directed from X to B indicates a coordinate bond; $R^a$ is hydrogen or a monovalent, divalent, trivalent, or tetravalent organic framework; n is an integer of from 1 to 4; and when n is an integer of from 2 to 4, plurally occurring $R^1$'s, $R^2$'s, $R^3$'s, m's, Q's, X's, dashed half arcs, and dashed and solid lines between Q and X are the same or different from each other, respectively, the process comprising reacting a boron compound of the following formula (4):

[Chemical Formula 18]

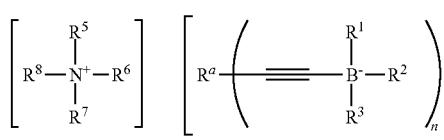
(4)

wherein $R^1$, $R^2$, $R^3$, $R^a$, and n have the same meanings as in the above formula (1); when n is an integer of from 2 to 4, plurally occurring $R^1$'s, $R^2$'s, and $R^3$'s are the same or different from each other, respectively; and $R^5$, $R^6$, $R^7$, and $R^8$ are the same or different from each other and are each independently a hydrogen atom or a substituent group, with a compound of the following formula (16):

[Chemical Formula 19]

(16)

wherein $R^4$, m, Q, X, a dashed half arc, and dashed and solid lines between Q and X have the same meanings as in the above formula (1); when m is 2, plurally occurring $R^4$'s are the same or different from each other; and Tf is a trifluoromethanesulfonyl group, in the presence of a catalyst containing at least one metal element selected from the group consisting of palladium, platinum, and nickel.

15. The production process according to claim 14, wherein and X are part of a common ring in the above formulas (1) and (16).

16. The production process according to claim 15, wherein the above common ring is a pyridine ring, a quinoline ring, a phenanthridine ring, or a thiophene ring, X is the nitrogen atom of the pyridine ring, the quinoline ring, or the phenanthridine ring, or the sulfur atom of the thiophene ring, and m is 0.

* * * * *